United States Patent
Mescher et al.

(10) Patent No.: US 11,179,141 B2
(45) Date of Patent: *Nov. 23, 2021

(54) BIOPSY SYSTEM

(71) Applicant: Devicor Medical Products, Inc., Cincinnati, OH (US)

(72) Inventors: Patrick A. Mescher, Bellbrook, OH (US); John R. Andrisek, Hamilton, OH (US); Edward A. Rhad, Fairfield, OH (US); Kevin M. Fiebig, Cincinnati, OH (US); John S. Ehlert, Cincinnati, OH (US); Kyle P. Moore, Milton, GA (US); Morgan R. Hunter, Cincinnati, OH (US); Jessica Pyzoha Leimbach, Cincinnati, OH (US); Trevor W. V. Speeg, Williamsburg, OH (US); Kathryn M. Dodd, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 447 days.

This patent is subject to a terminal disclaimer.

(21) Appl. No.: 15/910,430

(22) Filed: Mar. 2, 2018

(65) Prior Publication Data

US 2018/0221002 A1  Aug. 9, 2018

Related U.S. Application Data

(63) Continuation of application No. 13/964,202, filed on Aug. 12, 2013, now abandoned, which is a
(Continued)

(51) Int. Cl.
*A61B 10/02* (2006.01)
*A61B 90/98* (2016.01)
*A61B 17/00* (2006.01)

(52) U.S. Cl.
CPC ...... *A61B 10/0266* (2013.01); *A61B 10/0275* (2013.01); *A61B 10/0283* (2013.01);
(Continued)

(58) Field of Classification Search
CPC .......... A61B 10/0096; A61B 10/0266; A61B 10/0275; A61B 10/0283; A61B 2010/0208; A61B 2010/0225
See application file for complete search history.

(56) References Cited

U.S. PATENT DOCUMENTS 2,853,071 A   9/1958  Saffir
3,007,471 A   11/1961  McClure, Jr.
(Continued)

FOREIGN PATENT DOCUMENTS

AU   2007242954   7/2008
AU   2013200957   3/2013
(Continued)

OTHER PUBLICATIONS

EnCor MRI Specifications and Breast Biopsy System, SenoRx (2005) p. 102.
(Continued)

*Primary Examiner* — Patrick Fernandes
(74) *Attorney, Agent, or Firm* — Frost Brown Todd LLC

(57) ABSTRACT

A biopsy system includes various features. A tissue sample holder kit of the system comprises a rotatable member with chambers configured to receive tissue receiving features of a tissue sample tray. A biopsy device of the system includes user input features and user feedback features disposed on a body. A user interface of the system includes a graphical representation of a tissues ample holder. A biopsy site marker applier of the system includes markings associated with different biopsy device configurations. The biopsy system may undergo a multi-step initialization process. In
(Continued)

operation, the biopsy system may execute pneumatic control algorithms including the use of vacuum, saline, and atmospheric air.

16 Claims, 67 Drawing Sheets

Related U.S. Application Data continuation-in-part of application No. 13/483,235, filed on May 30, 2012, now abandoned, and a continuation-in-part of application No. 13/099,497, filed on May 3, 2011, now abandoned, and a continuation-in-part of application No. 12/337,911, filed on Dec. 18, 2008, now Pat. No. 8,702,623, and a continuation-in-part of application No. 11/942,807, filed on Nov. 20, 2007, now Pat. No. 9,345,457.

(60) Provisional application No. 61/727,889, filed on Nov. 19, 2012, provisional application No. 61/682,418, filed on Aug. 13, 2012, provisional application No. 60/869,736, filed on Dec. 13, 2006, provisional application No. 60/874,792, filed on Dec. 13, 2006, provisional application No. 61/771,212, filed on Mar. 1, 2013.

(52) U.S. Cl.
CPC ...... *A61B 90/98* (2016.02); *A61B 2010/0225* (2013.01); *A61B 2017/00482* (2013.01)

(56) References Cited

U.S. PATENT DOCUMENTS

| | | | |
|---|---|---|---|
| 3,630,192 A | 12/1971 | Jamshidi | |
| 3,719,086 A | 3/1973 | Bannister et al. | |
| 3,732,858 A | 5/1973 | Banko | |
| 3,734,099 A | 5/1973 | Bender et al. | |
| 3,889,657 A | 6/1975 | Baumgarten | |
| 3,897,216 A | 7/1975 | Jones | |
| 3,945,375 A | 3/1976 | Banko | |
| 3,994,297 A | 11/1976 | Kopf | |
| 3,996,935 A | 12/1976 | Banko | |
| 4,038,988 A | 8/1977 | Perisse | |
| 4,051,852 A | 10/1977 | Villari | |
| 4,083,706 A | 4/1978 | Wiley | |
| 4,203,444 A | 5/1980 | Bonnell et al. | |
| 4,257,425 A | 3/1981 | Ryan | |
| 4,316,465 A | 2/1982 | Dotson, Jr. | |
| 4,320,761 A | 3/1982 | Haddad | |
| 4,368,734 A | 1/1983 | Banko | |
| 4,393,879 A | 7/1983 | Milgrom | |
| 4,454,931 A | 6/1984 | Leiner et al. | |
| 4,517,977 A | 5/1985 | Frost | |
| 4,554,473 A | 11/1985 | Muller | |
| 4,600,014 A | 7/1986 | Beraha | |
| 4,650,460 A * | 3/1987 | Roizenblatt ......... | A61F 9/00763 604/22 |
| 4,767,601 A | 8/1988 | Kuerzinger et al. | |
| 4,782,833 A | 11/1988 | Einhorn et al. | |
| 4,783,317 A | 11/1988 | Kuerzinger et al. | |
| 4,919,146 A | 4/1990 | Rhinehart et al. | |
| RE33,258 E | 7/1990 | Onik et al. | |
| 4,940,061 A | 7/1990 | Terwilliger et al. | |
| 4,989,614 A | 2/1991 | Dejter, Jr. et al. | |
| 4,995,877 A | 2/1991 | Ams et al. | |
| 5,047,008 A | 9/1991 | de Juan, Jr. et al. | |
| 5,074,756 A | 12/1991 | Davis | |
| 5,108,381 A | 4/1992 | Kolozsi | |
| 5,112,299 A | 5/1992 | Pascaloff | |
| 5,120,003 A | 6/1992 | Sacconi | |
| 5,133,359 A | 7/1992 | Kedem | |
| 5,167,927 A | 12/1992 | Karlson | |
| 5,188,118 A | 2/1993 | Terwilliger | |
| 5,197,484 A | 3/1993 | Kornberg et al. | |
| 5,213,110 A | 5/1993 | Kedem et al. | |
| 5,217,478 A | 6/1993 | Rexroth | |
| 5,217,479 A | 6/1993 | Shuler | |
| 5,226,909 A | 7/1993 | Evans et al. | |
| 5,228,055 A | 7/1993 | Uchida et al. | |
| 5,231,110 A | 7/1993 | Seele et al. | |
| 5,234,000 A | 8/1993 | Hakky et al. | |
| 5,249,121 A | 9/1993 | Baum et al. | |
| 5,249,583 A | 10/1993 | Mallaby | |
| 5,275,609 A | 1/1994 | Pingleton et al. | |
| 5,290,303 A | 3/1994 | Pingleton et al. | |
| 5,295,980 A | 3/1994 | Ersek | |
| 5,312,425 A | 5/1994 | Evans et al. | |
| 5,320,110 A | 6/1994 | Wang | |
| 5,320,635 A | 6/1994 | Smith | |
| 5,341,816 A | 8/1994 | Allen | |
| 5,353,804 A | 10/1994 | Kornberg et al. | |
| 5,403,276 A | 4/1995 | Schechter et al. | |
| 5,406,959 A | 4/1995 | Mann | |
| 5,415,169 A | 5/1995 | Siczek et al. | |
| 5,423,844 A | 6/1995 | Miller | |
| 5,424,625 A | 6/1995 | Haner | |
| 5,431,645 A | 7/1995 | Smith et al. | |
| 5,432,065 A | 7/1995 | Fuller | |
| 5,439,457 A | 8/1995 | Yoon | |
| 5,455,766 A | 10/1995 | Scheller et al. | |
| 5,505,210 A | 4/1996 | Clement | |
| 5,520,635 A | 5/1996 | Gelbfish | |
| 5,526,822 A | 6/1996 | Burbank et al. | |
| 5,532,168 A | 7/1996 | Marantz | |
| 5,543,695 A | 8/1996 | Culp et al. | |
| 5,580,347 A | 12/1996 | Reimels | |
| 5,601,585 A | 2/1997 | Banik et al. | |
| 5,624,418 A | 4/1997 | Shepard | |
| 5,628,446 A | 5/1997 | Geiste et al. | |
| 5,643,304 A | 7/1997 | Schechter et al. | |
| 5,645,209 A | 7/1997 | Green et al. | |
| 5,649,547 A | 7/1997 | Ritchart et al. | |
| 5,669,923 A | 9/1997 | Gordon | |
| 5,685,840 A | 11/1997 | Schechter et al. | |
| 5,689,159 A | 11/1997 | Culp et al. | |
| 5,769,086 A | 6/1998 | Ritchart et al. | |
| 5,775,333 A | 7/1998 | Burbank et al. | |
| 5,780,715 A | 7/1998 | Imblum | |
| 5,791,908 A | 8/1998 | Gillio | |
| 5,804,936 A | 9/1998 | Brodsky et al. | |
| 5,823,998 A | 10/1998 | Yamagata | |
| 5,848,978 A | 12/1998 | Cecchi | |
| 5,871,454 A | 2/1999 | Majlessi | |
| 5,873,967 A | 2/1999 | Clark et al. | |
| 5,876,329 A | 3/1999 | Harhen | |
| 5,910,139 A | 6/1999 | Cochran et al. | |
| 5,913,857 A | 6/1999 | Ritchart et al. | |
| 5,928,164 A | 7/1999 | Burbank et al. | |
| 5,944,673 A | 8/1999 | Gregoire et al. | |
| 5,964,716 A | 10/1999 | Gregoire et al. | |
| 5,976,164 A | 11/1999 | Bencini et al. | |
| 5,980,469 A | 11/1999 | Burbank et al. | |
| 6,007,497 A | 12/1999 | Huitema | |
| 6,010,476 A | 1/2000 | Saadat | |
| 6,013,956 A | 1/2000 | Anderson, Jr. | |
| 6,017,316 A | 1/2000 | Ritchart et al. | |
| 6,019,733 A | 2/2000 | Farascioni | |
| 6,042,593 A | 3/2000 | Storz et al. | |
| 6,050,955 A | 4/2000 | Bryan et al. | |
| 6,061,446 A | 5/2000 | Lester et al. | |
| 6,077,230 A | 6/2000 | Gregoire et al. | |
| 6,080,113 A | 6/2000 | Heneveld et al. | |
| 6,083,177 A | 7/2000 | Kobren et al. | |
| 6,086,544 A | 7/2000 | Hibner et al. | |
| 6,096,042 A | 8/2000 | Herbert | |
| 6,106,512 A | 8/2000 | Cochran et al. | |
| 6,120,462 A * | 9/2000 | Hibner ............... | A61B 10/0275 600/566 |
| 6,120,733 A | 9/2000 | Goodman et al. | |
| 6,142,946 A | 11/2000 | Hwang et al. | |

(56) References Cited

U.S. PATENT DOCUMENTS

| | | |
|---|---|---|
| 6,142,955 A | 11/2000 | Farascioni et al. |
| 6,142,956 A | 11/2000 | Kortenbach et al. |
| 6,162,187 A | 12/2000 | Buzzard et al. |
| 6,213,957 B1 | 4/2001 | Milliman et al. |
| 6,228,055 B1 | 5/2001 | Foerster et al. |
| 6,231,522 B1 | 5/2001 | Voegele et al. |
| 6,245,084 B1 | 6/2001 | Mark et al. |
| 6,273,862 B1 | 8/2001 | Privitera et al. |
| 6,346,107 B1 | 2/2002 | Cucin |
| 6,371,904 B1 | 4/2002 | Sirimanne et al. |
| 6,402,701 B1 | 6/2002 | Kaplan et al. |
| 6,406,970 B1 | 6/2002 | Phifer |
| 6,428,486 B2 | 8/2002 | Ritchart et al. |
| 6,428,487 B1 | 8/2002 | Burdorff et al. |
| 6,432,065 B1 | 8/2002 | Burdorff et al. |
| 6,436,054 B1 | 8/2002 | Viola et al. |
| 6,444,174 B1 | 9/2002 | Lascombes et al. |
| 6,485,436 B1 | 11/2002 | Truckai et al. |
| 6,488,636 B2 | 12/2002 | Bryan et al. |
| 6,527,731 B2 | 3/2003 | Weiss et al. |
| 6,544,194 B1 | 4/2003 | Kortenbach et al. |
| 6,551,253 B2 | 4/2003 | Worm et al. |
| 6,585,664 B2 | 7/2003 | Burdorff et al. |
| 6,592,530 B1 | 7/2003 | Farhadi |
| 6,602,203 B2 | 8/2003 | Stephens et al. |
| 6,602,227 B1 | 8/2003 | Cimino et al. |
| 6,620,111 B2 | 9/2003 | Stephens et al. |
| 6,626,849 B2 | 9/2003 | Huitema et al. |
| 6,638,235 B2 | 10/2003 | Miller et al. |
| 6,656,428 B1 | 12/2003 | Clark et al. |
| 6,659,338 B1 | 12/2003 | Dittmann et al. |
| 6,709,241 B2 | 3/2004 | Sabini et al. |
| 6,712,774 B2 | 3/2004 | Voegele et al. |
| 6,749,576 B2 | 6/2004 | Bauer |
| 6,752,768 B2 | 6/2004 | Burdorff et al. |
| 6,758,824 B1 | 7/2004 | Miller et al. |
| 6,849,080 B2 | 2/2005 | Lee et al. |
| 6,852,108 B2 | 2/2005 | Barry et al. |
| 6,887,209 B2 | 5/2005 | Kadziauskas et al. |
| 6,904,305 B2 | 6/2005 | Tsekos |
| 6,923,809 B2 | 8/2005 | Eggers et al. |
| 6,972,199 B2 | 12/2005 | Lebouitz et al. |
| 6,986,748 B2 | 1/2006 | McAlister et al. |
| 6,993,375 B2 | 1/2006 | Burbank et al. |
| 6,996,433 B2 | 2/2006 | Burbank et al. |
| 7,001,341 B2 | 2/2006 | Gellman et al. |
| 7,025,098 B2 | 4/2006 | Osborne |
| 7,025,732 B2 | 4/2006 | Thompson et al. |
| 7,044,957 B2 | 5/2006 | Foerster et al. |
| 7,047,063 B2 | 5/2006 | Burbank et al. |
| 7,053,586 B2 | 5/2006 | Jones |
| 7,108,660 B2 | 9/2006 | Stephens et al. |
| 7,153,274 B2 | 12/2006 | Stephens et al. |
| 7,156,815 B2 | 1/2007 | Leigh et al. |
| 7,185,681 B2 | 3/2007 | Romano |
| 7,189,206 B2 | 3/2007 | Quick et al. |
| 7,204,811 B2 | 4/2007 | Kortenbach et al. |
| 7,226,424 B2 | 6/2007 | Ritchart et al. |
| 7,229,417 B2 | 6/2007 | Foerster et al. |
| 7,229,419 B2 | 6/2007 | Hancock |
| 7,229,439 B2 | 6/2007 | Burbank et al. |
| 7,252,641 B2 | 8/2007 | Thompson et al. |
| 7,276,032 B2 | 10/2007 | Hibner |
| 7,278,991 B2 | 10/2007 | Morris et al. |
| 7,335,216 B2 | 2/2008 | Bender et al. |
| 7,372,510 B2 | 5/2008 | Abileah |
| 7,419,472 B2 | 9/2008 | Hibner et al. |
| 7,438,692 B2 | 10/2008 | Tsonton et al. |
| 7,442,171 B2 | 10/2008 | Stephens et al. |
| 7,445,739 B2 | 11/2008 | Tsonton et al. |
| 7,465,279 B2 | 12/2008 | Beckman et al. |
| 7,470,237 B2 | 12/2008 | Beckman et al. |
| 7,488,295 B2 | 2/2009 | Burbank et al. |
| 7,497,833 B2 | 3/2009 | Miller |
| 7,507,210 B2 | 3/2009 | Hibner et al. |
| 7,510,534 B2 | 3/2009 | Burdorff et al. |
| 7,517,322 B2 | 4/2009 | Weikel, Jr. et al. |
| 7,556,622 B2 | 7/2009 | Mark et al. |
| 7,575,556 B2 | 8/2009 | Speeg et al. |
| 7,641,668 B2 | 1/2010 | Perry et al. |
| 7,645,240 B2 | 1/2010 | Thompson et al. |
| 7,648,466 B2 | 1/2010 | Stephens et al. |
| 7,662,109 B2 | 2/2010 | Hibner |
| 7,693,567 B2 | 4/2010 | Tsonton et al. |
| 7,736,382 B2 | 6/2010 | Webb et al. |
| 7,740,594 B2 | 6/2010 | Hibner |
| 7,740,596 B2 | 6/2010 | Hibner |
| 7,740,597 B2 | 6/2010 | Cicenas et al. |
| 7,749,172 B2 | 7/2010 | Schwindt |
| 7,753,857 B2 | 7/2010 | Hibner |
| 7,758,515 B2 | 7/2010 | Hibner |
| 7,758,601 B2 | 7/2010 | Heywang-Koebrunner et al. |
| 7,769,426 B2 | 8/2010 | Hibner et al. |
| 7,794,409 B2 | 9/2010 | Damarati |
| 7,806,834 B2 | 10/2010 | Beckman et al. |
| 7,806,835 B2 | 10/2010 | Hibner et al. |
| 7,819,819 B2 | 10/2010 | Quick et al. |
| 7,826,883 B2 | 11/2010 | Hibner et al. |
| 7,828,745 B2 | 11/2010 | McAlister et al. |
| 7,828,748 B2 | 11/2010 | Hibner |
| 7,837,632 B2 | 11/2010 | Stephens et al. |
| 7,846,107 B2 | 12/2010 | Hoffman et al. |
| 7,846,109 B2 | 12/2010 | Parihar et al. |
| 7,854,706 B2 | 12/2010 | Hibner |
| 7,854,707 B2 | 12/2010 | Hibner et al. |
| 7,858,038 B2 | 12/2010 | Andreyko et al. |
| 7,867,173 B2 | 1/2011 | Hibner et al. |
| 7,871,384 B2 | 1/2011 | Thompson et al. |
| 7,893,817 B2 | 2/2011 | Kim |
| 7,896,817 B2 | 3/2011 | Garrison |
| 7,914,464 B2 | 3/2011 | Burdorff et al. |
| 7,918,803 B2 | 4/2011 | Ritchart et al. |
| 7,918,804 B2 | 4/2011 | Monson et al. |
| 7,938,786 B2 | 5/2011 | Ritchie et al. |
| 7,985,239 B2 | 7/2011 | Suzuki |
| 8,002,713 B2 | 8/2011 | Heske et al. |
| 8,016,772 B2 | 9/2011 | Heske et al. |
| 8,016,844 B2 | 9/2011 | Privitera et al. |
| 8,038,627 B2 | 10/2011 | Hibner |
| 8,057,402 B2 | 11/2011 | Hibner et al. |
| 8,083,687 B2 | 12/2011 | Parihar |
| 8,105,849 B2 | 1/2012 | McDevitt et al. |
| 8,109,885 B2 | 2/2012 | Heske et al. |
| 8,109,886 B2 | 2/2012 | Miller et al. |
| 8,118,755 B2 | 2/2012 | Hibner et al. |
| 8,172,773 B2 | 5/2012 | Heske et al. |
| 8,177,728 B2 | 5/2012 | Hibner et al. |
| 8,177,729 B2 | 5/2012 | Hibner et al. |
| 8,206,315 B2 | 6/2012 | Mark et al. |
| 8,206,316 B2 | 6/2012 | Hibner et al. |
| 8,226,677 B2 | 7/2012 | Kauker et al. |
| 8,235,913 B2 | 8/2012 | Hibner et al. |
| 8,241,226 B2 | 8/2012 | Hibner et al. |
| 8,251,916 B2 | 8/2012 | Speeg et al. |
| 8,262,586 B2 | 9/2012 | Almazan et al. |
| 8,277,394 B2 | 10/2012 | Hibner et al. |
| 8,282,573 B2 | 10/2012 | Shabaz et al. |
| 8,328,732 B2 | 12/2012 | Parihar et al. |
| 8,371,443 B2 | 2/2013 | Nock et al. |
| 8,376,957 B2 | 2/2013 | Hibner et al. |
| 8,414,605 B2 | 4/2013 | Gordon et al. |
| 8,454,531 B2 | 6/2013 | Speeg et al. |
| 8,460,206 B2 | 6/2013 | Parihar et al. |
| 8,480,595 B2 | 7/2013 | Speeg et al. |
| 8,485,987 B2 | 7/2013 | Videbaek et al. |
| 8,532,747 B2 | 9/2013 | Nock et al. |
| 8,532,748 B2 | 9/2013 | Leimbach et al. |
| 8,622,924 B2 | 1/2014 | Speeg et al. |
| 8,622,927 B2 | 1/2014 | Parihar et al. |
| 8,672,860 B2 | 3/2014 | Moore et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,858,465 B2 | 10/2014 | Fiebig |

(56) References Cited

U.S. PATENT DOCUMENTS

| | | |
|---|---|---|
| 8,932,233 B2 | 1/2015 | Haberstich et al. |
| 8,938,285 B2 | 1/2015 | Fiebig et al. |
| 9,095,326 B2 | 8/2015 | Ritchie et al. |
| 9,326,755 B2 | 5/2016 | Fiebig et al. |
| 9,345,457 B2 | 5/2016 | Speeg et al. |
| 2001/0014776 A1 | 8/2001 | Oriol et al. |
| 2001/0047183 A1 | 11/2001 | Privitera et al. |
| 2002/0120212 A1 | 8/2002 | Ritchart et al. |
| 2002/0193656 A1 | 12/2002 | Ravins et al. |
| 2003/0125639 A1 | 7/2003 | Fisher et al. |
| 2003/0199753 A1 | 10/2003 | Hibner et al. |
| 2004/0009100 A1 | 1/2004 | Simons et al. |
| 2005/0004559 A1 | 1/2005 | Quick et al. |
| 2005/0049521 A1 | 3/2005 | Miller et al. |
| 2005/0075581 A1 | 4/2005 | Schwindt |
| 2005/0082518 A1 | 4/2005 | Kunitz |
| 2005/0215922 A1 | 9/2005 | Tsonton et al. |
| 2005/0256445 A1 | 11/2005 | Cucin |
| 2006/0000296 A1* | 1/2006 | Salter .................. B01L 9/06 73/863.01 |
| 2006/0041230 A1 | 2/2006 | Davis |
| 2006/0074344 A1 | 4/2006 | Hibner |
| 2006/0074345 A1 | 4/2006 | Hibner et al. |
| 2006/0085759 A1 | 4/2006 | Knapheide |
| 2006/0258955 A1* | 11/2006 | Hoffman ............... A61B 10/06 600/564 |
| 2006/0282012 A1 | 12/2006 | McAlister et al. |
| 2007/0010738 A1 | 1/2007 | Mark et al. |
| 2007/0055173 A1 | 3/2007 | DeLonzor et al. |
| 2007/0112751 A1 | 5/2007 | Pyun |
| 2007/0167736 A1 | 7/2007 | Dietz et al. |
| 2007/0191732 A1 | 8/2007 | Voegele |
| 2007/0213632 A1 | 9/2007 | Okazaki et al. |
| 2007/0239067 A1 | 10/2007 | Hibner et al. |
| 2007/0270714 A1 | 11/2007 | Cushner et al. |
| 2008/0004545 A1 | 1/2008 | Garrison |
| 2008/0082021 A1 | 4/2008 | Ichikawa et al. |
| 2008/0146962 A1 | 6/2008 | Ritchie et al. |
| 2008/0214955 A1 | 9/2008 | Speeg et al. |
| 2008/0221479 A1 | 9/2008 | Ritchie et al. |
| 2009/0131821 A1 | 5/2009 | Speeg et al. |
| 2009/0192408 A1 | 7/2009 | Mack |
| 2009/0209854 A1 | 8/2009 | Parihar et al. |
| 2009/0216152 A1 | 8/2009 | Speeg et al. |
| 2010/0049084 A1 | 2/2010 | Nock et al. |
| 2010/0075664 A1 | 3/2010 | Maucksch |
| 2010/0081928 A1 | 4/2010 | Hyde et al. |
| 2010/0152610 A1 | 6/2010 | Parihar et al. |
| 2010/0160819 A1 | 6/2010 | Parihar et al. |
| 2010/0160824 A1 | 6/2010 | Parihar et al. |
| 2010/0160825 A1 | 6/2010 | Parihar et al. |
| 2011/0021948 A1 | 1/2011 | Lee et al. |
| 2011/0071391 A1 | 3/2011 | Speeg et al. |
| 2011/0071423 A1 | 3/2011 | Speeg et al. |
| 2011/0190660 A1 | 8/2011 | Levy |
| 2012/0059247 A1 | 3/2012 | Speeg et al. |
| 2012/0065542 A1 | 3/2012 | Hibner et al. |
| 2012/0109007 A1 | 5/2012 | Rhad et al. |
| 2012/0116246 A1 | 5/2012 | Hibner et al. |
| 2012/0265095 A1 | 10/2012 | Fiebig et al. |
| 2012/0283563 A1 | 11/2012 | Moore et al. |
| 2012/0310110 A1 | 12/2012 | Rhad et al. |
| 2013/0041256 A1 | 2/2013 | Fiebig et al. |
| 2013/0053724 A1 | 2/2013 | Fiebig et al. |
| 2013/0218047 A1 | 8/2013 | Fiebig et al. |
| 2013/0245494 A1 | 9/2013 | Speeg et al. |
| 2013/0324882 A1 | 12/2013 | Mescher et al. |
| 2014/0039343 A1 | 2/2014 | Mescher et al. |
| 2014/0207020 A1 | 7/2014 | Parihar et al. |

FOREIGN PATENT DOCUMENTS

| | | |
|---|---|---|
| AU | 2013200958 | 3/2013 |
| CN | 2397080 | 9/2000 |
| CN | 1700887 | 11/2005 |
| CN | 101068500 | 11/2007 |
| CN | 102018537 | 4/2011 |
| DE | 4212910 | 10/1993 |
| EP | 0178507 | 4/1986 |
| EP | 0262670 | 6/1988 |
| EP | 0378692 | 7/1990 |
| EP | 0890339 | 1/1999 |
| EP | 0995400 | 4/2000 |
| EP | 1074271 | 2/2001 |
| EP | 1040790 | 10/2002 |
| EP | 1520518 | 4/2005 |
| EP | 1642533 | 4/2006 |
| EP | 1642534 A2 | 4/2006 |
| EP | 1815815 | 8/2007 |
| EP | 1832234 | 9/2007 |
| EP | 1932481 | 6/2008 |
| EP | 1932482 | 6/2008 |
| EP | 2062537 | 5/2009 |
| EP | 2120724 A2 | 11/2009 |
| EP | 2412314 | 2/2012 |
| GB | 2018601 | 10/1979 |
| GB | 2191585 | 12/1987 |
| JP | 2000316867 | 11/2000 |
| JP | 200695313 | 4/2006 |
| JP | 2008-504915 A | 2/2008 |
| JP | 2008504915 | 2/2008 |
| JP | 2009532081 | 9/2009 |
| JP | 2010-512848 A | 4/2010 |
| JP | 5722380 B2 | 5/2015 |
| RU | 2021770 | 10/1994 |
| WO | WO 1990/008508 | 8/1990 |
| WO | WO 1993/014707 | 8/1993 |
| WO | WO 1995/025465 | 9/1995 |
| WO | WO 1997/024911 | 7/1997 |
| WO | WO 1998/006338 | 2/1998 |
| WO | WO 1998/025556 | 6/1998 |
| WO | WO 1998/033436 | 8/1998 |
| WO | WO 2000/030531 | 6/2000 |
| WO | WO 2003/077768 | 9/2003 |
| WO | WO 2004/016177 | 2/2004 |
| WO | WO 2004/052179 | 6/2004 |
| WO | WO 2004/052212 | 6/2004 |
| WO | WO 2004/075728 | 9/2004 |
| WO | WO 2006/005342 | 1/2006 |
| WO | WO 2006/005344 | 1/2006 |
| WO | WO 2006/038634 | 4/2006 |
| WO | WO 2006/058302 | 6/2006 |
| WO | WO 2006/090220 | 8/2006 |
| WO | WO 2006/124489 | 11/2006 |
| WO | WO 2007/019152 | 2/2007 |
| WO | WO 2007/019445 | 2/2007 |
| WO | WO 2007/021904 | 2/2007 |
| WO | WO 2007/112751 | 10/2007 |
| WO | WO 2008/076712 | 6/2008 |

OTHER PUBLICATIONS

Mammotome MR Biopsy System Operator's Manual, Ethicon Endo-Surgery, Inc., Cincinnati, Ohio (2006) pp. 1-86.

Defendants' Preliminary Invalidity Contentions, dated Apr. 25, 2008, *Ethicon Endo-Surgery, Inc. v. Hologic, Inc., et al.*; Case No. 1:07-cv-00834; US District Court, Southern District of Ohio, 9 pages.

Defendants' Supplemental Preliminary Invalidity Contentions, dated Jul. 25, 2008, *Ethicon Endo-Surgery, Inc. v. Hologic, Inc., et al.*; Case No. 1:07-cv-00834; US District Court, Southern District of Ohio, 58 pages.

Defendants' Third Supplemental Preliminary Invalidity Contentions, dated Dec. 1, 2008, *Ethicon Endo-Surgery, Inc. v. Hologic, Inc., et al.*; Case No. 1:07-cv-00834; US District Court, Southern District of Ohio, 78 pages.

Defendants' Final Invalidity Contentions, dated Sep. 11, 2009, *Ethicon Endo-Surgery, Inc. v. Hologic, Inc., et al.*; Case No. 1:07-cv-00834; US Distiict Court, Southern District of Ohio, 108 pages.

(56) References Cited

OTHER PUBLICATIONS

Defendants' Identification of Prior Art, dated Dec. 31, 2009, *Ethicon Endo-Surgery, Inc.* v. *Hologic, Inc., et al.*; Case No. 1:07-cv-00834; US District Court, Southern District of Ohio, 11 pages.
Transcript of Testimony by Dr. David Lipson on Feb. 12, 2010, at trial; *Ethicon Endo-Surgery, Inc.* v. *Hologic, Inc., et al.*; Case No. 1:07-cv-00834; US District Court, Southern District of Ohio, 161 pages.
Parker et al., "From the RSNA Refresher Courses: Performing a Breast Biopsy with a Directional, Vacuum-assisted Biopsy Instrument," *Radio Graphics 1997*; 17 (RSNA 1997) pp. 1233-1252.
Parker, et al., "Stereotactic Breast Biopsy with a Biopsy Gun," Radiology 1990; 176 (RSNA 1990) pp. 741-747.
Van Berkel, C., "55.1: 3D Touchless Display Interaction," SID 02 Digest, 2002, pp. 1410-1413.
Abstract for PCT Application No. 08253774, 1 page.
Abstract for PCT Application No. 08253776, 1 page.
Abstract for Chinese Patent No. 2397080, 2 pages.
Australian Patent Examination Report No. 1 dated Nov. 22, 2013 for Application No. AU 2012251064, 3pgs.
Australian Patent Examination Report No. 1 dated Jan. 24, 2014 for Application No. 2013200958, 5 pages.
Australian Patent Examination Report No. 1 dated Jan. 29, 2014 for Application No. AU 2013200957, 4pgs.
Australian Patent Examination Report No. 1 dated Jan. 31, 2014 for Application No. 2013201295, 3 pages.
Australian Patent Examination Report No. 1 dated Mar. 25, 2014 for Application No. 2013201864, 3 pages.
Australian Patent Examination Report No. 1 dated Jun. 24, 2014 for Application No. 2013202934, 5 pages.
Australian Patent Examination Report No. 1 dated Oct. 3, 2014 for Application No. 2009335989, 4 pages.
Australian Notice of Acceptance dated Oct. 17, 2014 for Application No. 2012251064, 3 pages.
Australian Notice of Acceptance dated Feb. 17, 2015 for Application No. 2013200957, 2 pages.
Australian Notice of Acceptance dated Feb. 27, 2015 for Application No. 2013200958.
Australian Notice of Acceptance dated May 28, 2015 for Application No. 2013201864, 2 pages.
Australian Notice of Acceptance dated Jul. 20, 2015 for Application No. 2013202934, 3 pages.
Australian Notice of Acceptance dated Jul. 29, 2015 for Application No. 2009335989, 2 pages.
Canadian Office Action dated Apr. 24, 2015 for Application No. 2,644,140, 4 pages.
Canadian Office Action dated Nov. 13, 2014 for Application No. 2,672,664, 6 pages.
Chinese Office Action dated Aug. 4, 2013 for Application No. 200980151310, 6 pages.
Chinese Office Action dated Sep. 30, 2013 for Application No. 200980151310, 9 pages.
Chinese Office Action dated Nov. 20, 2013 for Application No. 201210071979.2, 4 pages.
Chinese Office Action dated Dec. 19, 2013 for Application No. 201210367531.5, 5 pages.
Chinese Office Action dated Jan. 8, 2014 for Application No. 200980151310, 3 pages.
Chinese Office Action dated Feb. 28, 2014 for Application No. 201210470709.9, 33 pages.
Chinese Office Action dated Apr. 17, 2014 for Application No. 201210071979.2, 6 pages.
Chinese Office Action dated Sep. 9, 2014 for Application No. 20120367531.5, 10 pages.
Chinese Office Action dated Nov. 15, 2014for Application No. 201210071979.2, 5 pages.
Chinese Office Action dated Dec. 1, 2014 for Application No. 201210470709.9, 20 pages.
Chinese Office Action dated Jan. 19, 2015 for Application No. 201280021771.8, 12 pages.
Chinese Office Action dated Apr. 14, 2015 for Application No. 201210071979.2, 4 pages.
Chinese Office Action dated Jun. 17, 2015 for Application No. 201210470709.9, 20 pages.
Chinese Office Action dated Sep. 28, 2015 for Application No. 201410370712.2, 2 pages.
Chinese Office Action dated Mar. 24, 2016 for Application No. 201380049893.2, 8 pages.
Chinese Office Action dated Dec. 5, 2016 for Application No. 201380049893.2, 7 pages.
European Search Report dated Dec. 11, 2007 for Application No. 07253220, 3 pages.
European Search Report dated Feb. 18, 2009 for Application No. 08253776, 7 pages.
European Search Report dated Mar. 9, 2009 for Application No. 08253774, 6 pages.
European Search Report dated Mar. 9, 2009 for Application No. 08253775, 7 pages.
European Search Report dated Mar. 9, 2009 for Application No. 08253781, 7 pages.
European Search Report and Written Opinion dated Jan. 11, 2016 for Application No. 13829805.4.
European Communication dated Oct. 20, 2010 for Application No. EP 08 253 776.2, 9pgs.
European Communication dated Apr. 14, 2011 for Application No. EP 08 253 776.2, 1 pg.
European Communication dated Sep. 23, 2014 for Application No. 12779909.6, 6 pages.
European Communication dated Feb. 19, 2015 for Application No. 09775453.5, 5 pages.
International Preliminary Report on Patentability dated Feb. 5, 2008 for Application No. PCT/US2006/030022, 11 pages.
International Preliminary Report on Patentability dated Jun. 21, 2011 for Application No. PCT/US2009/067165, 8 pages.
International Preliminary Report on Patentability dated Nov. 5, 2013 for Application No. PCT/US2012/034169, 7 pages.
International Search Report and Written Opinion dated Aug. 19, 2013 for Application No. PCT/US2013/041784, 9 pages.
International Search Report and Written Opinion dated Nov. 19, 2013 for Application No. PCT/US2013/054486.
Japanese Office Action, Notification of Reasons for Refusal, dated Apr. 23, 2014 for Application No. 2011-542243, 4 pages.
Japanese Office Action dated Jun. 11, 2014 for Application No. JP 2013-090053, 7 pgs.
Japanese Office Action dated Sep. 9, 2014 for Application No. 2013-253905, 3 pages.
Japanese Office Action dated Sep. 12, 2014 for Application No. 2013-253905, 4 pages.
Japanese Office Action dated Sep. 24, 2014 for Application No. 2013-215367, 2 pages.
Japanese Office Action dated May 29, 2015 for Application No. 2013-215367, 2 pages.
Korean Notice of Preliminary Rejection dated Sep. 3, 2015 for Application No. 10-2011-7016301, 6 pages.
U.S. Appl. No. 13/795,931, filed Feb. 13, 2013.
U.S. Appl. No. 60/869,736, filed Dec. 13, 2006.
U.S. Appl. No. 60/874,792, filed Dec. 13, 2006.
U.S. Appl. No. 61/381,466, filed Sep. 10, 2010.
U.S. Appl. No. 61/566,793, filed Dec. 5, 2011.
U.S. Appl. No. 61/667,577, filed Jul. 3, 2012.
U.S. Appl. No. 61/682,418, filed Aug. 13, 2012.
U.S. Appl. No. 61/727,889, filed Nov. 19, 2012.
U.S. Appl. No. 61/771,212, filed Mar. 1, 2013.
European Communication dated Sep. 18, 2018 for Application No. 13829805.4, 160 pages.
Korean Office Action dated Dec. 7, 2018 for Application No. 10-2015-7006293, 2 pages.

\* cited by examiner

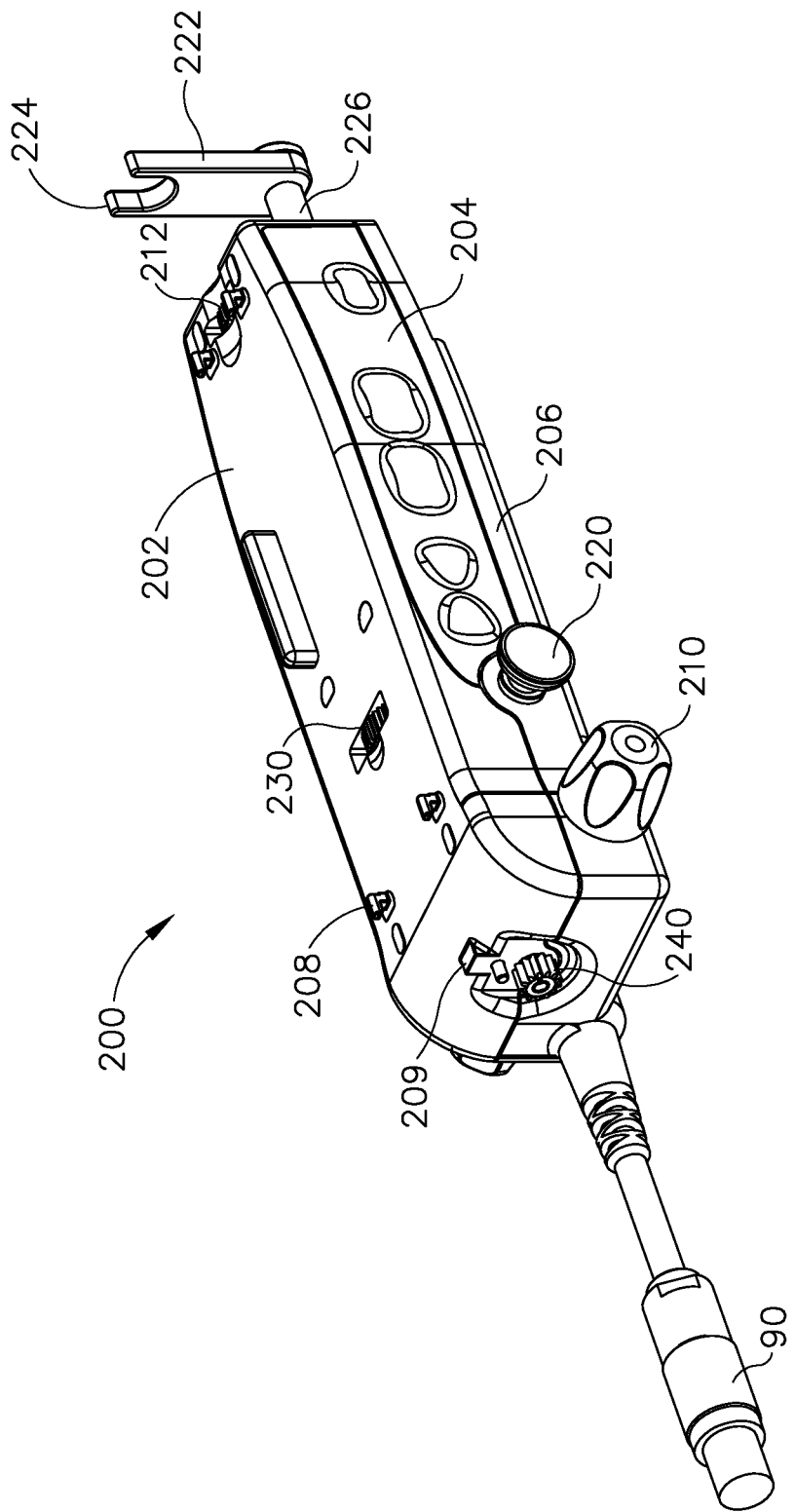

BIOPSY SYSTEM

PRIORITY

This application is a continuation of U.S. patent application Ser. No. 13/964,202, filed Aug. 12, 2013, published as U.S. patent publication number 2014/0039343 on Feb. 6, 2014, the disclosure of which is incorporated by reference herein.

U.S. Non-Provisional patent application Ser. No. 13/964,202 claims priority to U.S. Provisional Patent App. No. 61/682,418, entitled "Biopsy System with Graphical User Interface," filed Aug. 13, 2012, the disclosure of which is incorporated by reference herein.

U.S. Non-Provisional patent application Ser. No. 13/964,202 also claims priority to U.S. Provisional Patent App. No. 61/727,889, entitled "Biopsy System with Graphical User Interface," filed Nov. 19, 2012, the disclosure of which is incorporated by reference herein.

U.S. Non-Provisional patent application Ser. No. 13/964,202 also claims priority to U.S. Provisional Patent App. No. 61/771,212, entitled "Biopsy System with Graphical User Interface," filed Mar. 1, 2013, the disclosure of which is incorporated by reference herein.

U.S. Non-Provisional patent application Ser. No. 13/964,202 is also a continuation-in-part of U.S. patent application Ser. No. 11/942,807, entitled "Presentation of Biopsy Sample by Biopsy Device," filed Nov. 20, 2007, published as U.S. Pat. Pub. No. 2008/0214955 on Sep. 4, 2008, the disclosure of which is incorporated by reference herein. U.S. patent application Ser. No. 11/942,807 claims priority to U.S. Provisional Patent App. No. 60/874,792, entitled "Biopsy Sample Storage," filed Dec. 13, 2006, the disclosure of which is incorporated by reference herein. U.S. patent application Ser. No. 11/942,807 also claims priority to U.S. Provisional Patent App. No. 60/869,736, entitled "Biopsy System," filed Dec. 13, 2006, the disclosure of which is incorporated by reference herein.

U.S. Non-Provisional patent application Ser. No. 13/964,202 is also a continuation-in-part of U.S. patent application Ser. No. 12/337,911, entitled "Biopsy Device with Discrete Tissue Chambers," filed Dec. 18, 2008, published as U.S. Pat. Pub. No. 2010/0160824 on Jun. 24, 2010, the disclosure of which is incorporated by reference herein.

U.S. Non-Provisional patent application Ser. No. 13/964,202 is also a continuation-in-part of U.S. patent application Ser. No. 13/099,497, entitled "Biopsy Device with Manifold Alignment Feature and Tissue Sensor," filed May 3, 2011, published as U.S. Pat. Pub. No. 2012/0283563, the disclosure of which is incorporated by reference herein.

U.S. Non-Provisional patent application Ser. No. 13/964,202 is also a continuation-in-part of U.S. patent application Ser. No. 13/483,235, entitled "Control for Biopsy Device," filed May 30, 2012, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; and U.S. Pat. No. 8,118,755, entitled "Biopsy Sample Storage," issued Feb. 21, 2012. The disclosure of each of the above-cited U.S. patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006; U.S. Pat. Pub. No. 2008/0146962, entitled "Biopsy System with Vacuum Control Module," published Jun. 19, 2008; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008; U.S. Pat. Pub. No. 2009/0131821, entitled "Graphical User Interface For Biopsy System Control Module," published May 21, 2009; U.S. Pat. Pub. No. 2009/0131820, entitled "Icon-Based User Interface on Biopsy System Control Module," published May 21, 2009; U.S. Pat. Pub. No. 2010/0113973, entitled "Biopsy Device with Rotatable Tissue Sample Holder," published May 6, 2010; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0160824, entitled "Biopsy Device with Discrete Tissue Chambers," published Jun. 24, 2010; U.S. Pat. Pub. No. 2010/0317997, entitled "Tetherless Biopsy Device with Reusable Portion," published Dec. 16, 2010; U.S. Pat. Pub. No. 2012/0109007, entitled "Handheld Biopsy Device with Needle Firing," published May 3, 2012; U.S. Non-Provisional patent application Ser. No. 13/086,567, entitled "Biopsy Device with Motorized Needle Firing," filed Apr. 14, 2011; U.S. Non-Provisional patent application Ser. No. 13/150,950, entitled "Needle Assembly and Blade Assembly for Biopsy Device," filed Jun. 1, 2011; U.S. Non-Provisional patent application Ser. No. 13/205,189, entitled "Access Chamber and Markers for Biopsy Device," filed Aug. 8, 2011; U.S. Non-Provisional patent application Ser. No. 13/218,656, entitled "Biopsy Device Tissue Sample Holder with Bulk Chamber and Pathology Chamber," filed Aug. 26, 2011; U.S. Provisional Patent App. No. 61/566,793, entitled "Biopsy Device With Slide-In Probe," filed Dec. 5, 2011; and U.S. Non-Provisional patent application Ser. No. 13/483,235, entitled "Control for Biopsy Device," filed May 30, 2012. The disclosure of each of the above-cited U.S. Patent Application Publications, U.S. Non-Provisional patent applications, and U.S. Provisional Patent Applications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK™, MICROMARK®, and CORMARK™ brand devices from Devicor Medical Products, Inc. of Cincinnati, Ohio. Further exemplary devices and methods for marking a biopsy site are disclosed in U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pub. No. 2011/0071423, entitled "Flexible Biopsy Marker Delivery Device," published Mar. 24, 2011; U.S. Pub. No. 2011/0071424, entitled "Biopsy Marker Delivery Device," published Mar. 24, 2011; U.S. Pub. No. 2011/0071391, entitled "Biopsy Marker Delivery Device with Positioning Component," published Mar. 24, 2011; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; and U.S. Pat. No. 7,465,279, entitled "Marker Device and Method of Deploying a Cavity Marker Using a Surgical Biopsy Device," issued Dec. 16, 2008. The disclosure of each of the above-cited U.S. patents and U.S. Patent Application Publications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 24 depicts another perspective view of the holster of FIG. 23;

Figure 1:
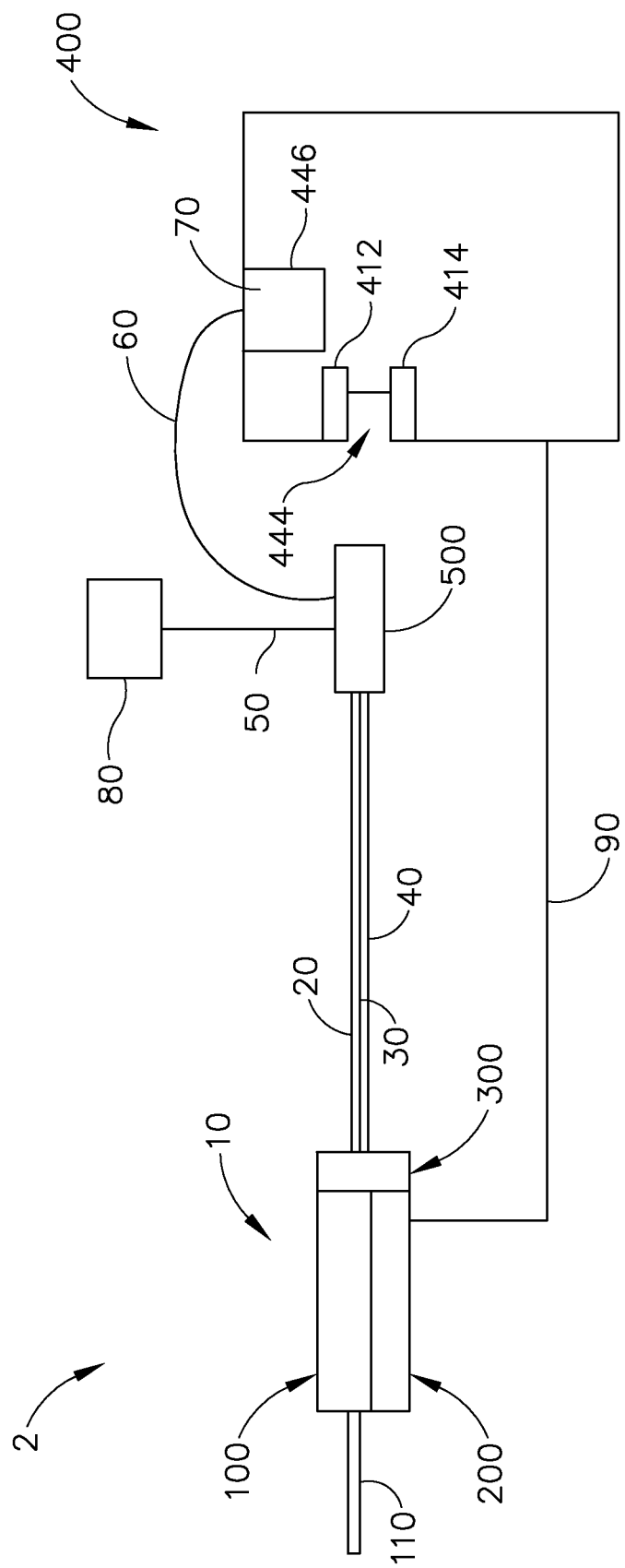
FIG. 1 depicts a schematic view of an exemplary biopsy system.
Figure 2:
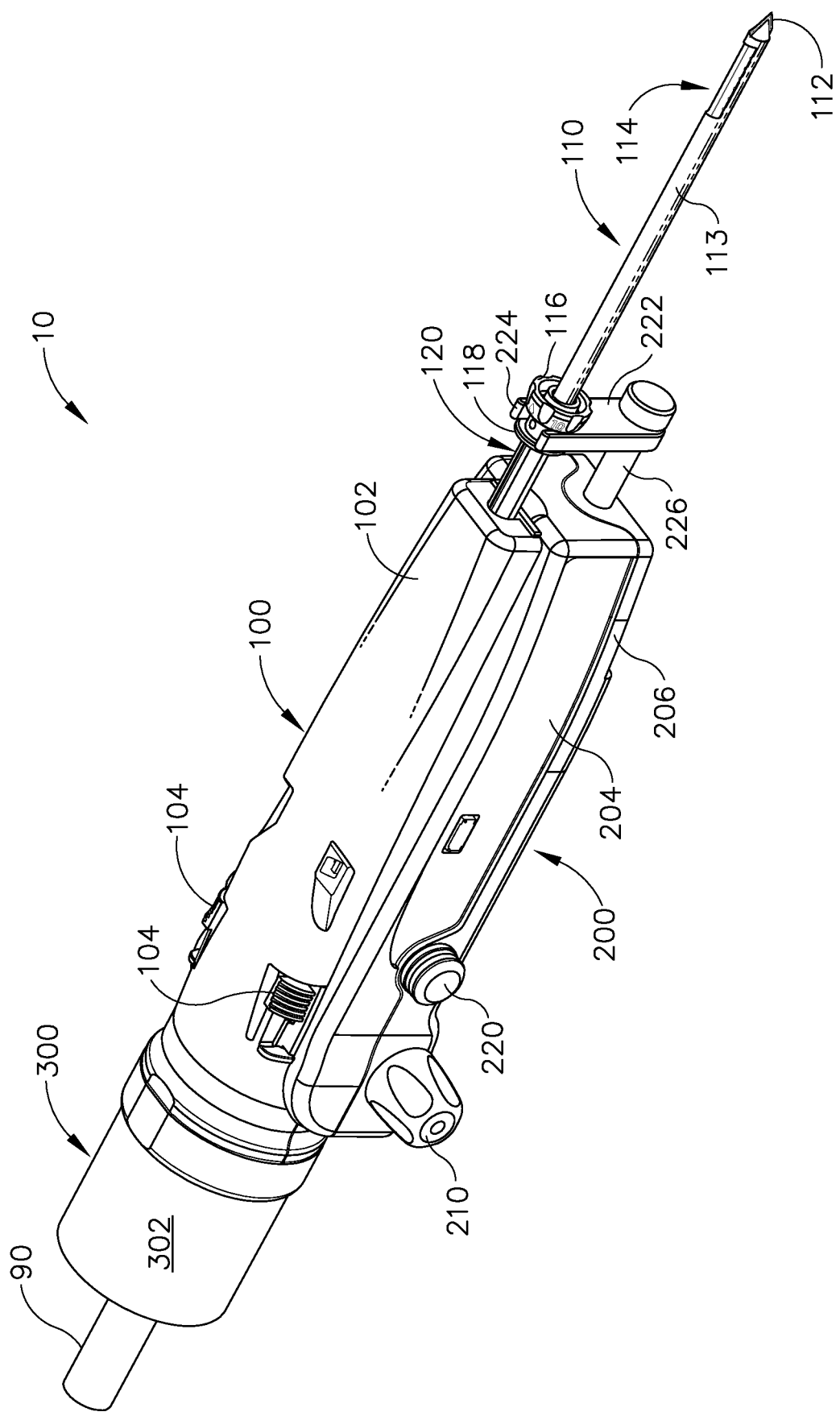
FIG. 2 depicts a perspective view of an exemplary biopsy device of the biopsy system of FIG. 1, including an exemplary probe coupled with an exemplary holster.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Biopsy System

FIG. 1 depicts an exemplary biopsy system (2) comprising a biopsy device (10) and a vacuum control module (400). Biopsy device (10) of this example comprises a probe (100) and a holster (200). A needle (110) extends distally from probe (100), and is inserted into a patient's tissue to obtain tissue samples as will be described in greater detail below. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (200). In the present example, holster (200) includes a set of prongs (208) that are received by the chassis (106) of probe (100) to releasably secure probe (100) to holster (200). In particular, probe (100) is first positioned on top of holster (200), just proximal to its final position relative to holster (200); then probe (100) is slid distally to fully engage prongs (208). Probe (100) also includes a set of resilient tabs (104) that may be pressed inwardly to disengage prongs (208), such that a user may simultaneously depress both tabs (104) then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

As will be described in greater detail below, vacuum control module (400) is coupled with probe (100) via a valve assembly (500), which is operable to selectively provide vacuum, saline, atmospheric air, and venting to probe (100). Vacuum control module (400) is coupled with holster (200) via a cable (90), which is operable to communicate electrical power to holster (200) and is further operable to communicate signals such as data and commands, etc., in a bi-directional fashion between holster (200) and vacuum control module (400). These components all cooperate to enable biopsy device (10) to acquire numerous tissue samples from a patient, such as from the patient's breast or other part of the patient's anatomy.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

II. Exemplary Probe

Figure 3:
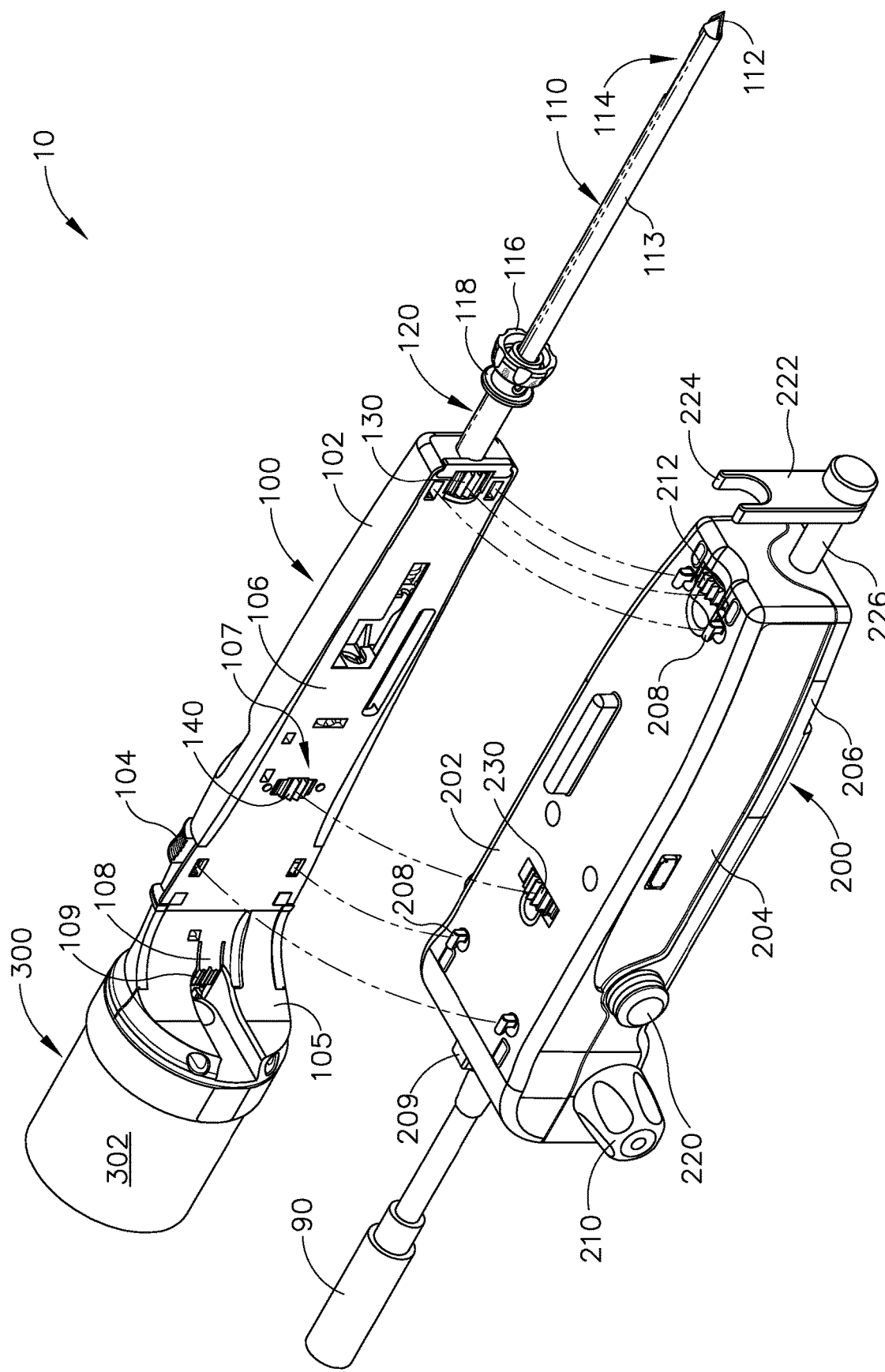
FIG. 3 depicts a perspective view of the biopsy device of FIG. 2, with the probe decoupled from the holster.

As shown in FIGS. 1-6, probe (100) of the present example includes a distally extending needle (110). Probe (100) also includes a chassis (106) and a top housing (102), which are fixedly secured together. As best seen in FIG. 3, a gear (140) is exposed through an opening (107) in chassis (106), and is operable to drive cutter actuation mechanism in probe (100). As also seen in FIG. 3, another gear (130) is exposed through chassis (106), and is operable to rotate needle (110) as will be described in greater detail below. Gear (140) of probe (100) meshes with exposed gear (230) of holster (200) when probe (100) and holster (200) are coupled together. Similarly, gear (130) of probe (100) meshes with exposed gear (212) of holster (200) when probe (100) and holster (200) are coupled together.

A. Exemplary Needle Assembly

Needle (110) of the present example comprises a cannula (113) having a piercing tip (112), a lateral aperture (114) located proximal to tip (112), and a hub member (120). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Non-Provisional patent application Ser. No. 13/150,950, entitled "Needle Assembly and Blade Assembly for Biopsy Device," filed Jun. 1, 2011, the disclosure of which is incorporated by reference herein. As another merely illustrative example, tip (112) may be configured in accordance with at least some of the teachings in U.S. Provisional Pat. App. No. 61/566,793, entitled "Biopsy Device with Slide-In Probe," filed Dec. 5, 2011, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (150) having a sharp distal edge (152) is located within needle (110). Cutter (150) is operable to rotate and translate relative to needle (110) and past lateral aperture (114) to sever a tissue sample from tissue protruding through lateral aperture (114). For instance, cutter (150) may be moved from an extended position to a retracted position, thereby "opening" lateral aperture (114) to allow tissue to protrude therethrough; then from the retracted position back to the extended position to sever the protruding tissue. As will be described in greater detail below, needle (110) may be rotated to orient lateral aperture (114) at any desired angular position about the longitudinal axis of needle (110). Such rotation of needle (110) is facilitated in the present example by hub member (120), which is described in greater detail below.

Figure 6:
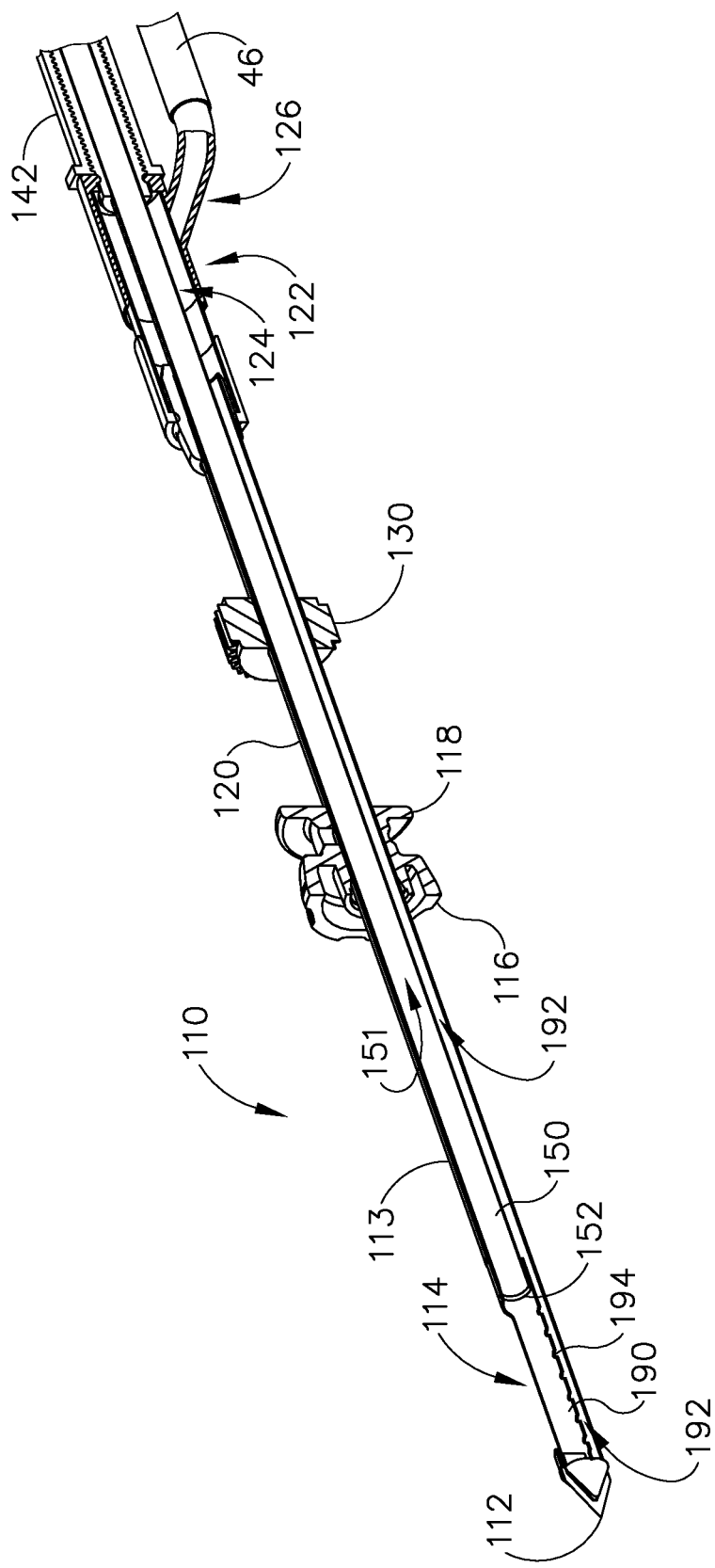
FIG. 6 depicts a cross-sectional view of a needle assembly of the probe of FIG. 4.

As best seen in FIG. 6, needle (110) also includes a longitudinal wall (190) extending proximally from the proximal portion of tip (112). While wall (190) does not extend along the full length of cannula (113) in this example, it should be understood that wall (190) may extend the full length of cannula (113) if desired. Wall (190) defines a distal portion of a second lumen (192) that is lateral to and parallel to cutter (150). Wall (190) proximally terminates at a longitudinal position that is just proximal to the location of distal cutting edge (152) of cutter (150) when cutter (150) is in a proximal-most position as shown in FIG. 6. The exterior of cutter (150) and the interior of cannula (113) together define the proximal portion of second lumen (192) in the length of needle (110) that is proximal to the proximal end of wall (190).

Wall (190) includes a plurality of openings (194) that provide fluid communication between second lumen (192) and the region within cannula (113) that is above wall (190) and below lateral aperture (114). This further provides fluid communication between second lumen (192) and the lumen (151) defined by the interior of cutter (150), as will be described in greater detail below. Openings (194) are arranged such that at least one opening (194) is located at a longitudinal position that is distal to the distal edge of lateral aperture (114). Thus, the lumen (151) of cutter (150) and second lumen (192) may remain in fluid communication even when cutter (150) is advanced to a position where the distal cutting edge of cutter (150) is located at a longitudinal position that is distal to the longitudinal position of the distal edge of lateral aperture (114). An example of such a configuration is disclosed in U.S. Pat. No. 7,918,803, entitled "Methods and Devices for Automated Biopsy and Collection of Soft Tissue," issued Apr. 5, 2011, the disclosure of which is incorporated by reference herein. Of course, as with any other component described herein, any other suitable configurations may be used.

A plurality of external openings (not shown) may also be formed in needle (110), and may be in fluid communication with second lumen (192). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings in needle (110) are merely optional.

Hub member (120) of the present example is overmolded about needle (110), such that hub member (120) and needle (110) rotate and translate unitarily with each other. By way of example only, needle (110) may be formed of metal, and hub member (120) may be formed of a plastic material that is overmolded about needle (110) to unitarily secure and form hub member (120) to needle (110). Hub member (120) and needle (110) may alternatively be formed of any other suitable material(s), and may be secured together in any other suitable fashion. Hub member (120) includes an annular flange (118) and a thumbwheel (116). Gear (130) is slidably and coaxially disposed on a proximal portion (150) of hub member (120) and is keyed to hub member (120), such that rotation of gear (130) will rotate hub member (120) and needle (110); yet hub member (120) and needle (110) may translate relative to gear (130). Gear (130) is rotatably driven by gear (212), as will be described in greater detail below. Alternatively, needle (110) may be rotated by rotating thumbwheel (116). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein. Examples of how needle (110) may be translated longitudinally relative to chassis (106) and top housing (102), particularly by a needle firing mechanism (224), will be described in greater detail below.

As shown in FIGS. 4-7, a manifold (122) is provided at the proximal end of needle (110). Manifold (122) defines a hollow interior (124) and includes a port (126) in fluid communication with hollow interior (124). As best seen in FIG. 6, hollow interior (124) is also in fluid communication with second lumen (192) of needle (110). Port (126) is coupled with tube (46), such that manifold (122) provides fluid communication between second lumen (192) and tube (46). Manifold (122) also seals against the exterior of needle (110) such that manifold (122) provides a fluid tight coupling between second lumen (192) and tube (46) even if needle (110) is translated and/or rotated relative to manifold (122), such as during firing of needle (110) or re-orientation of needle (110), respectively.

Figure 4:
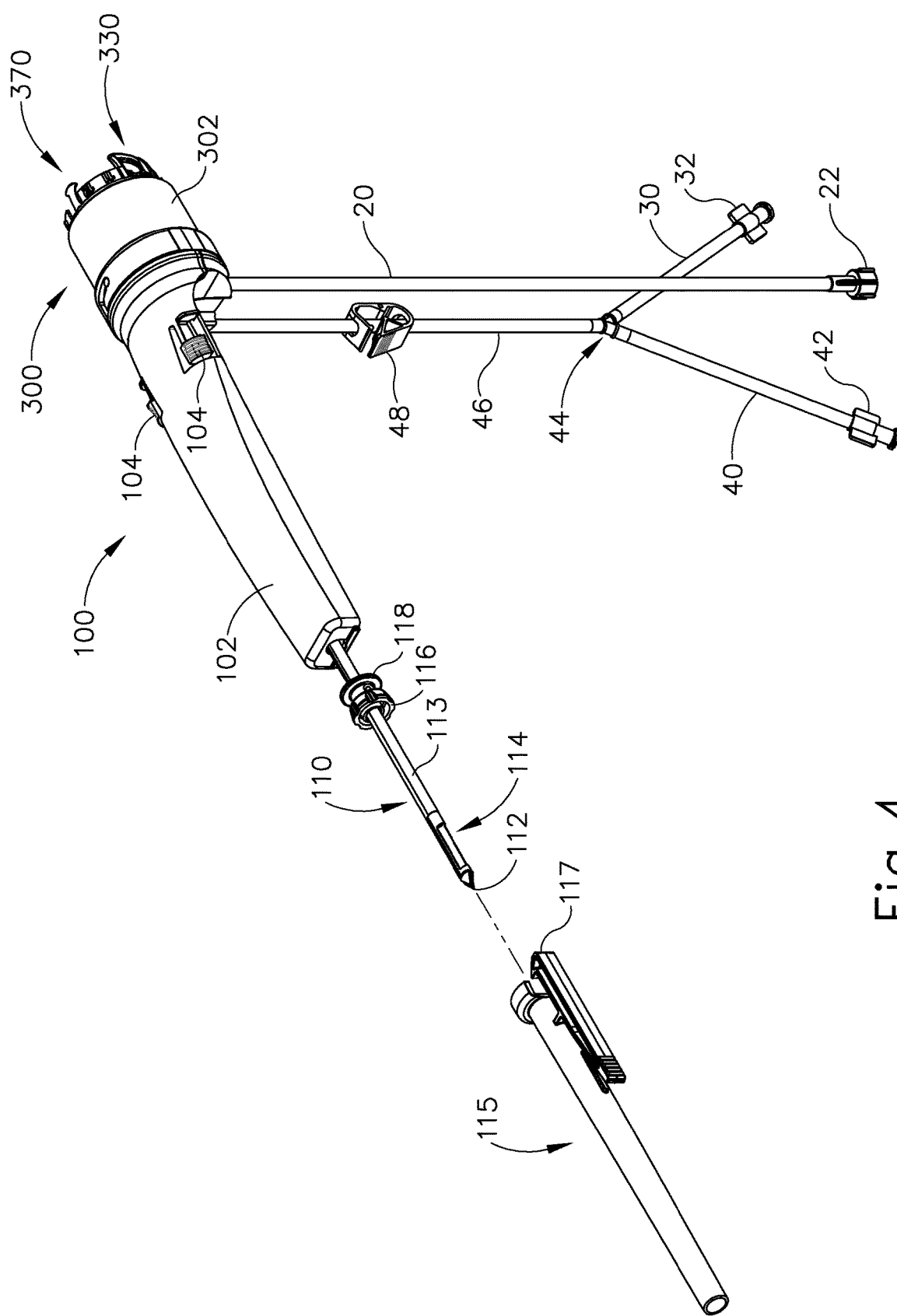
FIG. 4 depicts a perspective view of the probe of the biopsy device of FIG. 2.

As shown in FIG. 4, needle (110) may be provided with a removable cover (115). Cover (115) of this example includes a resiliently biased latch (117) that is configured to engage thumbwheel (116), to thereby removably secure cover (115) to needle (110). Cover (115) is configured to cover tip (112) when latch (117) is engaged with thumbwheel (116), such that cover (115) protects the user of biopsy device (10) from inadvertent contact with tip (112). Cover (115) may also include one or more wiper seals near the proximal end and/or distal end of cover (115), to seal against cannula (113). By way of example only, cover (115) may be configured in accordance with at least some of the teachings in U.S. Provisional Pat. App. No. 61/566,793, the disclosure of which is incorporated by reference herein. Various other suitable configurations for cover (115) will be apparent to those of ordinary skill in the art in view of the teachings herein. Of course, cover (115) may simply be omitted if desired. It should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pub. No. 2008/0214955, the disclosure of which is incorporated by reference herein, and/or in accordance with the teachings of any other reference cited herein.

B. Exemplary Cutter Assembly

Figure 5:
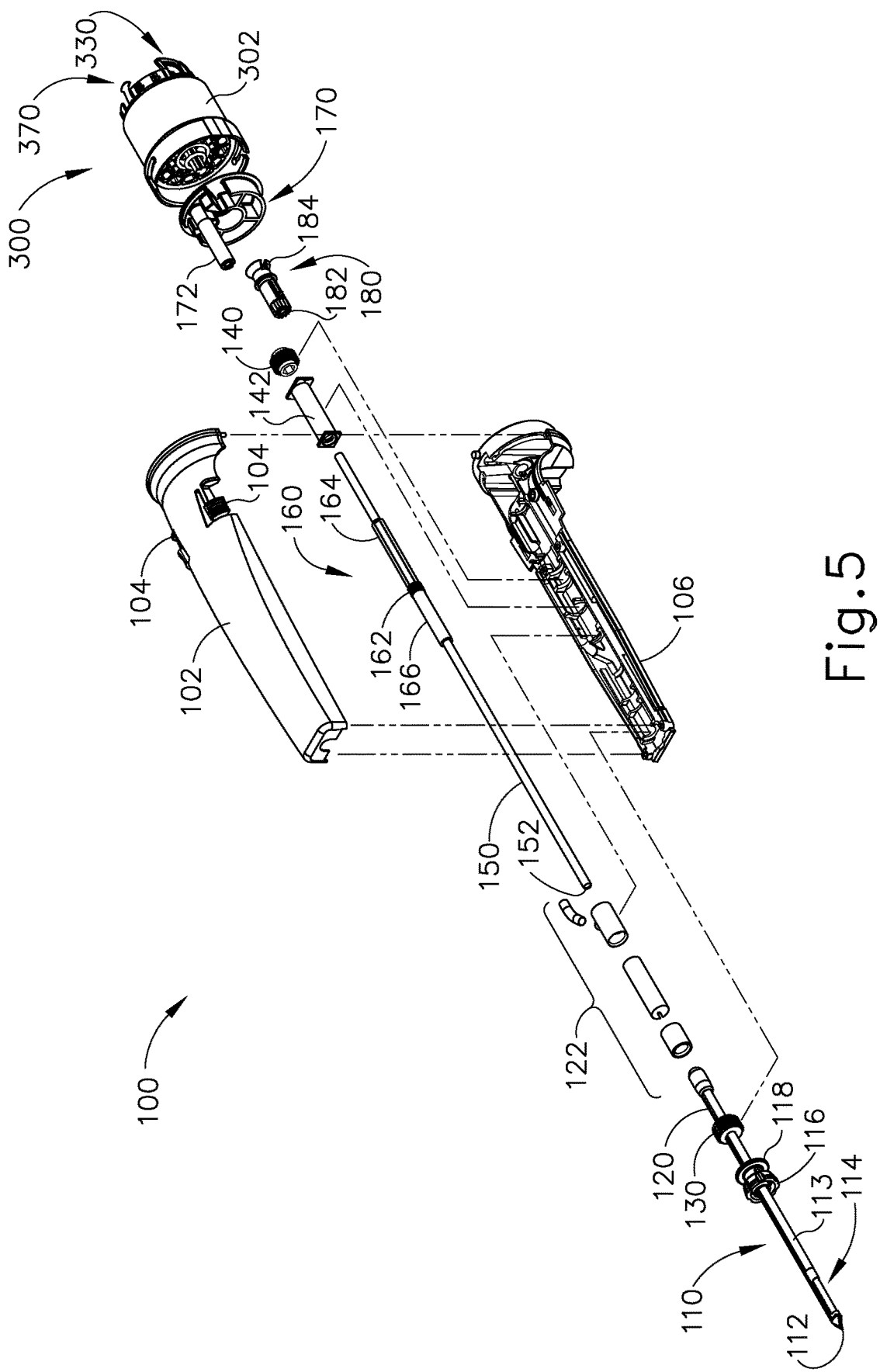
FIG. 5 depicts an exploded view of the probe of FIG. 4.
Figure 7:
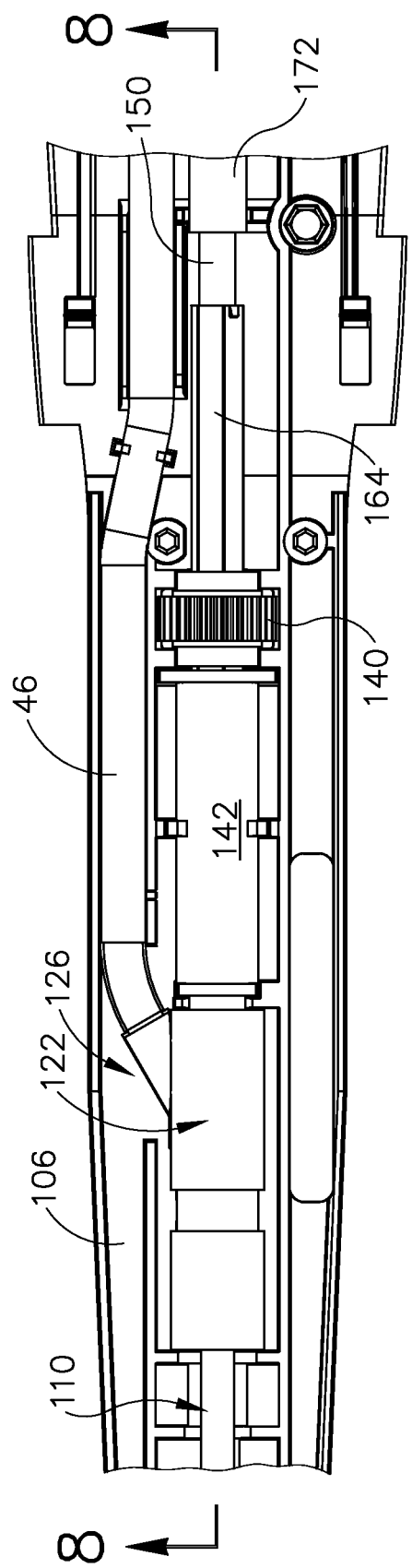
FIG. 7 depicts a partial top plan view of components of the probe of FIG. 4, with a top housing piece removed.
Figure 8:
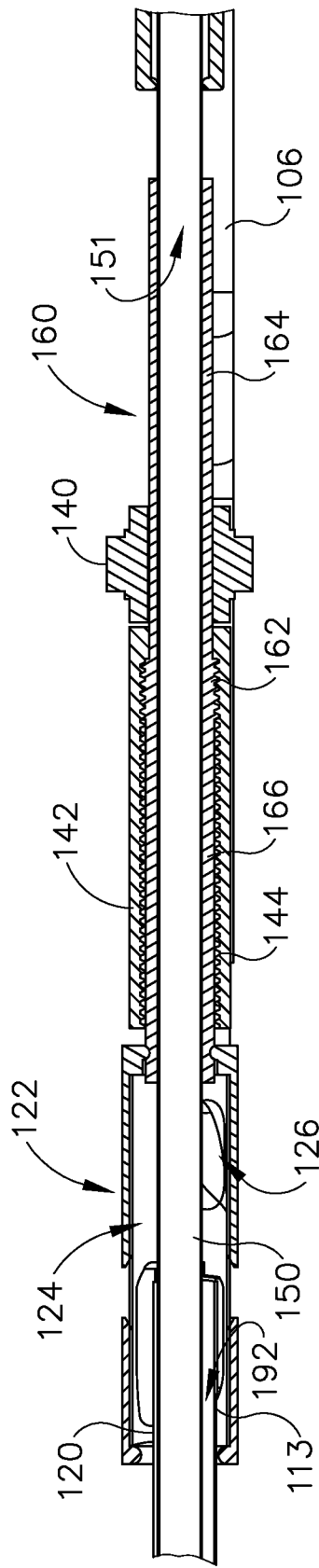
FIG. 8 depicts a side cross-sectional view of the components of FIG. 7, taken along line 8-8 of FIG. 7.

As noted above, cutter (150) is operable to simultaneously translate and rotate relative to needle (110) to sever a tissue sample from tissue protruding through lateral aperture (114). As best seen in FIGS. 5 and 7-8 cutter (150) includes an overmold (160) that is unitarily secured to cutter (150). Overmold (160) includes a generally smooth and cylindraceous distal portion (166), threading (162) in a mid-region of overmold (160), and a set of hexagonal flats (164) extending along a proximal portion of overmold (160). Distal portion (166) extends into manifold (122). Manifold (122) seals against distal portion (166) such that manifold (122) such that manifold (122) maintains the fluid tight coupling between second lumen (192) and tube (46) even when cutter (150) is translated and rotated relative to manifold (122).

A gear (140) is positioned on flats (164) and includes a set of internal flats (not shown) that complement flats (164). Thus, gear (140) rotates overmold (160) and cutter (150) when gear (140) is rotated. However, overmold (160) is slidable relative to gear (140), such that cutter (150) may translate relative to chassis (160) despite gear (140) being longitudinally fixed relative to chassis (160). As noted above and as will be described in greater detail below, gear (140) is rotated by gear (230). As best seen in FIGS. 7-8, a nut (142) is associated with threading (162) of overmold (160). In particular, nut (142) includes internal threading (144) that meshes with threading (162) of overmold (160). Nut (142) is fixedly secured relative to chassis (160). Thus, when gear (140) rotates cutter (150) and overmold (160), cutter (150) will simultaneously translate due to the meshing of threading (144, 162). In some versions, the foregoing cutter actuation components are further configured in accordance with at least some of the teachings of U.S. Pat. Pub. No. 2008/0214955, the disclosure of which is incorporated by reference herein. As yet another merely illustrative example, cutter (150) may be rotated and/or translated using pneumatic motors, etc. Still other suitable ways in which cutter (150) may be actuated will be apparent to those of ordinary skill in the art in view of the teachings herein.

C. Exemplary Tissue Sample Holder Assembly

Tissue sample holder (300) of the present example provides a plurality of discrete chambers that are configured to receive tissue samples that are severed by cutter (150) and communicated proximally through lumen (151) of cutter (150). In particular, and as will be described in greater detail below, tissue sample holder (300) includes tissue receiving trays (330) that are removably engaged with a manifold (310). Manifold (310) is removably engaged with a grasping feature (184) of a rotation member (180). Rotation member (180) is longitudinally fixed relative to chassis (106) yet is rotatable relative to chassis (106). Rotation member (180) includes an integral gear (182), which meshes with gear (240) of holster (200) when probe (100) and holster (200) are coupled together. Gears (182, 240) cooperate to rotate manifold (310) to index tissue chambers relative to lumen (151) of cutter (150) as will be described in greater detail below. A transparent cover (302) is positioned about manifold (310) and is removably secured to chassis (106). While bayonet features provide coupling between cover (302) and chassis (106), it should be understood that any suitable type of coupling may be used. Manifold (310) is freely rotatable within cover (302). However, manifold (310) is engaged with cover (302) such that manifold (310) will decouple relative to chassis (106) when cover (302) is removed from chassis (106). In other words, manifold (310) may be selectively coupled with and removed relative to chassis (106) by coupling and removing cover (302) from chassis (106).

1. Exemplary Manifold

Figure 12:
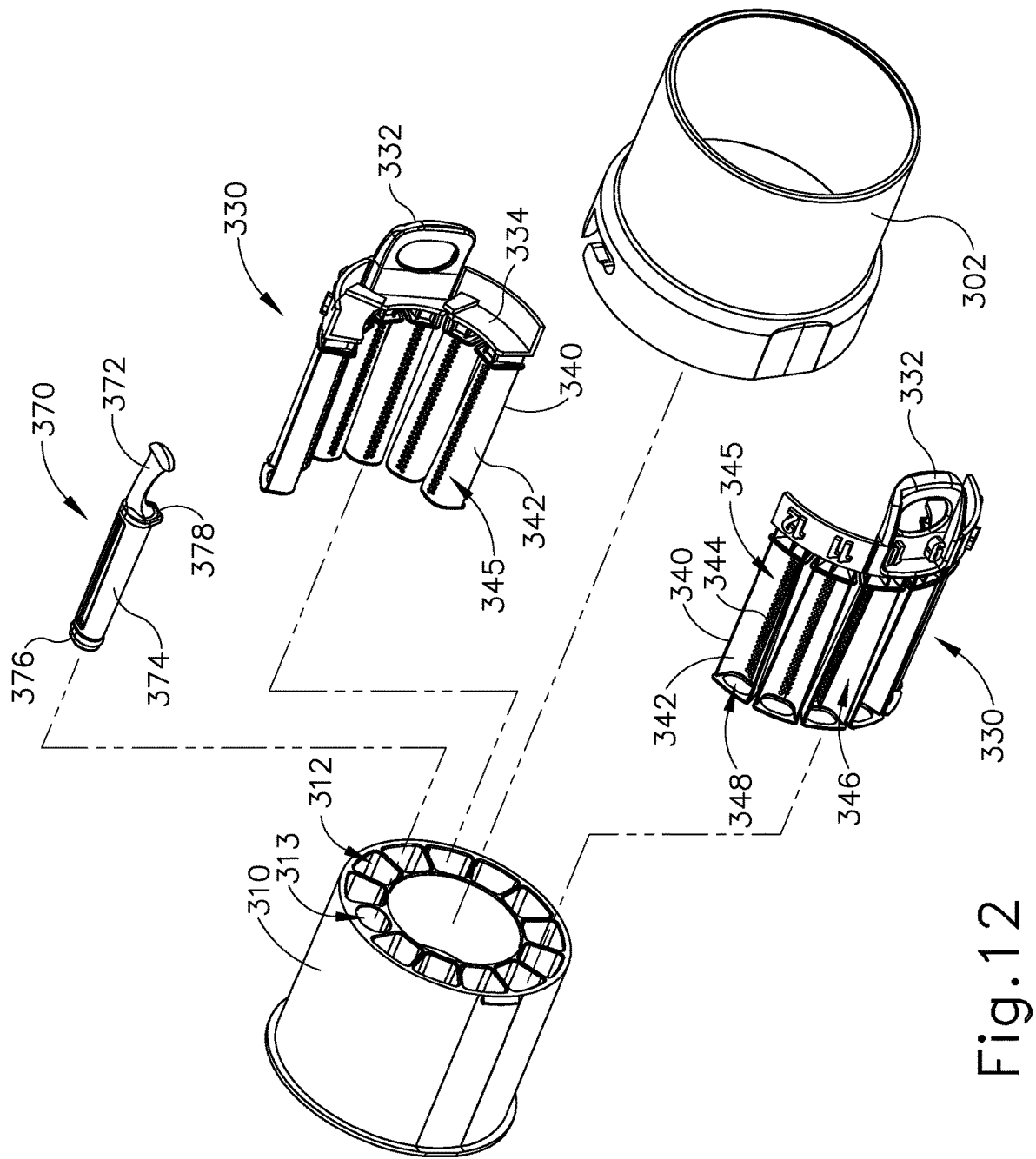
FIG. 12 depicts an exploded view of components of rotatable components of the tissue sample holder assembly of FIG. 9
Figure 13:
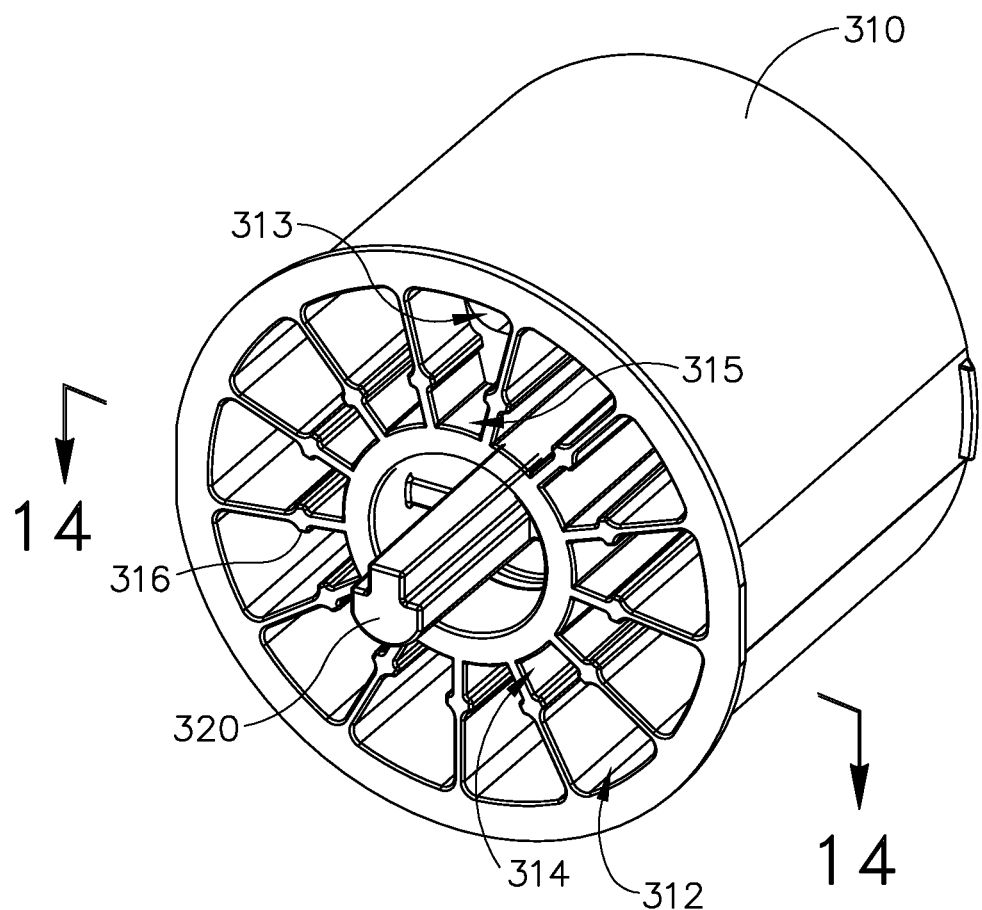
FIG. 13 depicts a perspective view of a rotatable manifold of the tissue sample holder assembly of FIG. 9.
Figure 14:
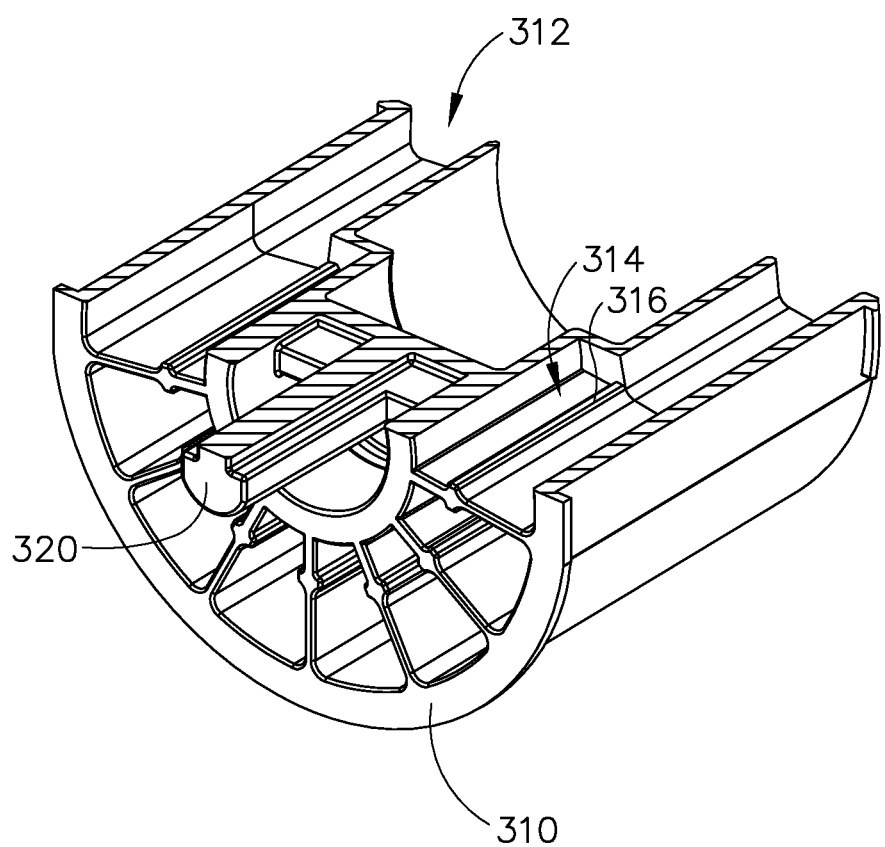
FIG. 14 depicts a cross-sectional view of the manifold of FIG. 13, taken along line 14-14 of FIG. 13.

As best seen in FIGS. 12-14, manifold (310) of the present example defines a plurality of chambers in the form of passages (312) that extend longitudinally through manifold (310) and that are angularly arrayed about the central axis of manifold (310). As best seen in FIG. 14, a lateral recess (314) is associated with a distal portion of each passage (312). Shelves (316) demarcate boundaries between each passage (312) and the associate lateral recess (314). As will be described in greater detail below, passages (312) receive trays (330) while recesses (314) provide pneumatic passages. An additional passage (313) and recess (315) are associated with a plug (370), as will also be described in greater detail below. Manifold (310) also includes a central shaft (320), which is configured to removably engage grasping feature (184). Central shaft (320) couples with grasping feature (184) upon coupling of cover (302) with chassis (106), as described above. Engagement between central shaft (320) and grasping feature (184) provides rotation of manifold (310) upon rotation of gear (182).

Figure 9:
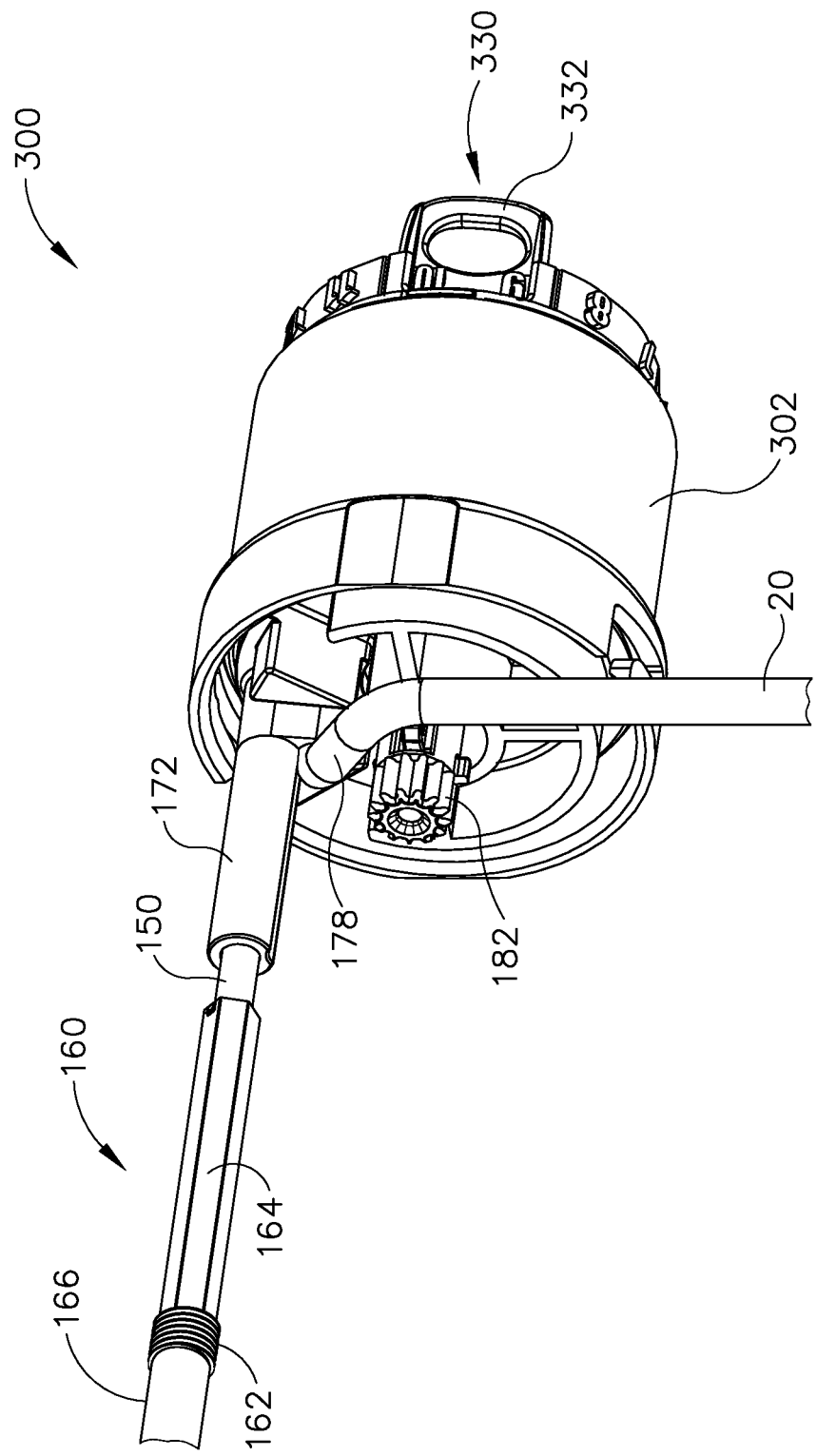
FIG. 9 depicts a perspective view of a tissue sample holder assembly of the probe of FIG. 4.
Figure 10:
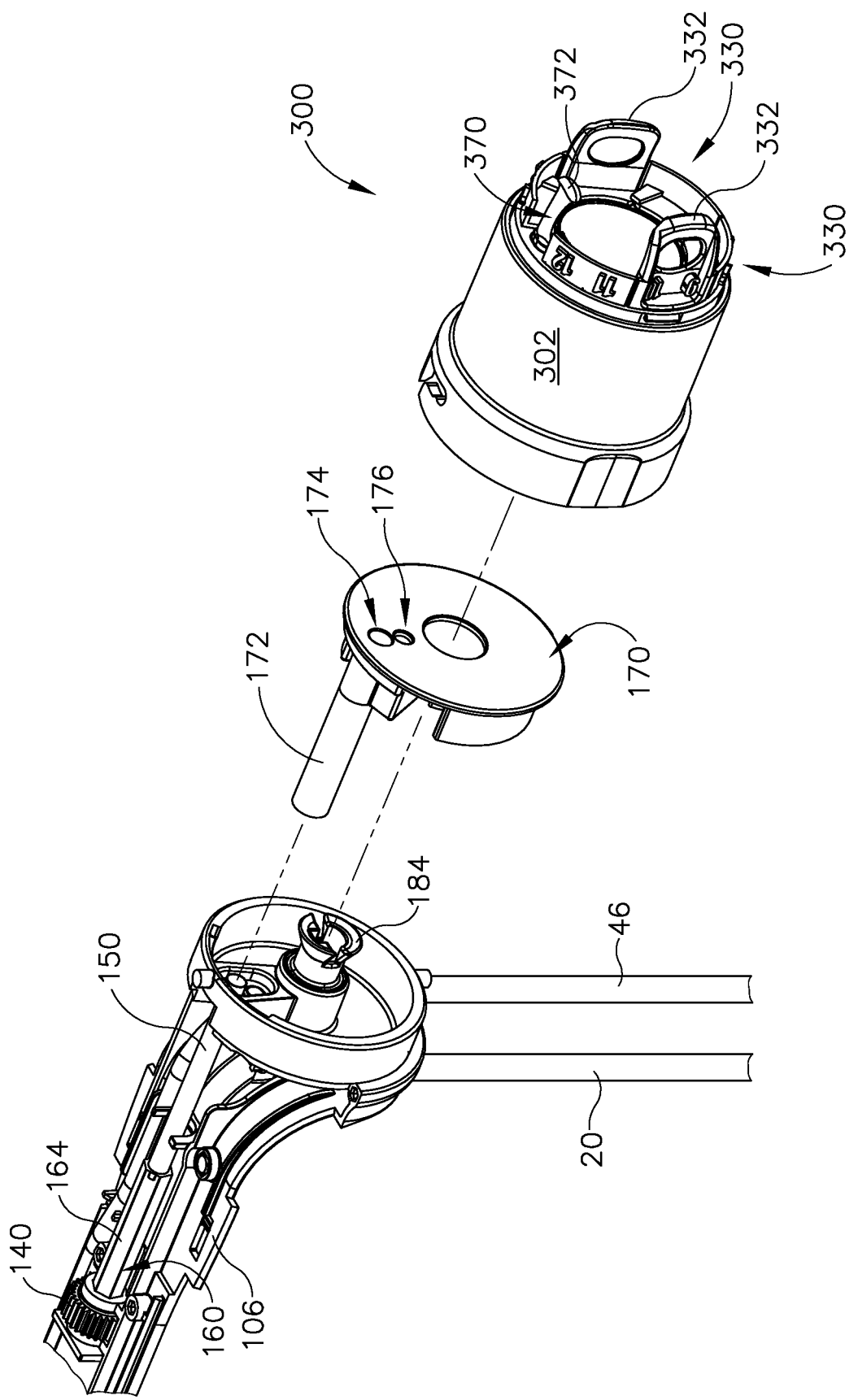
FIG. 10 depicts an exploded view of the tissue sample holder assembly of FIG. 9.
Figure 11:
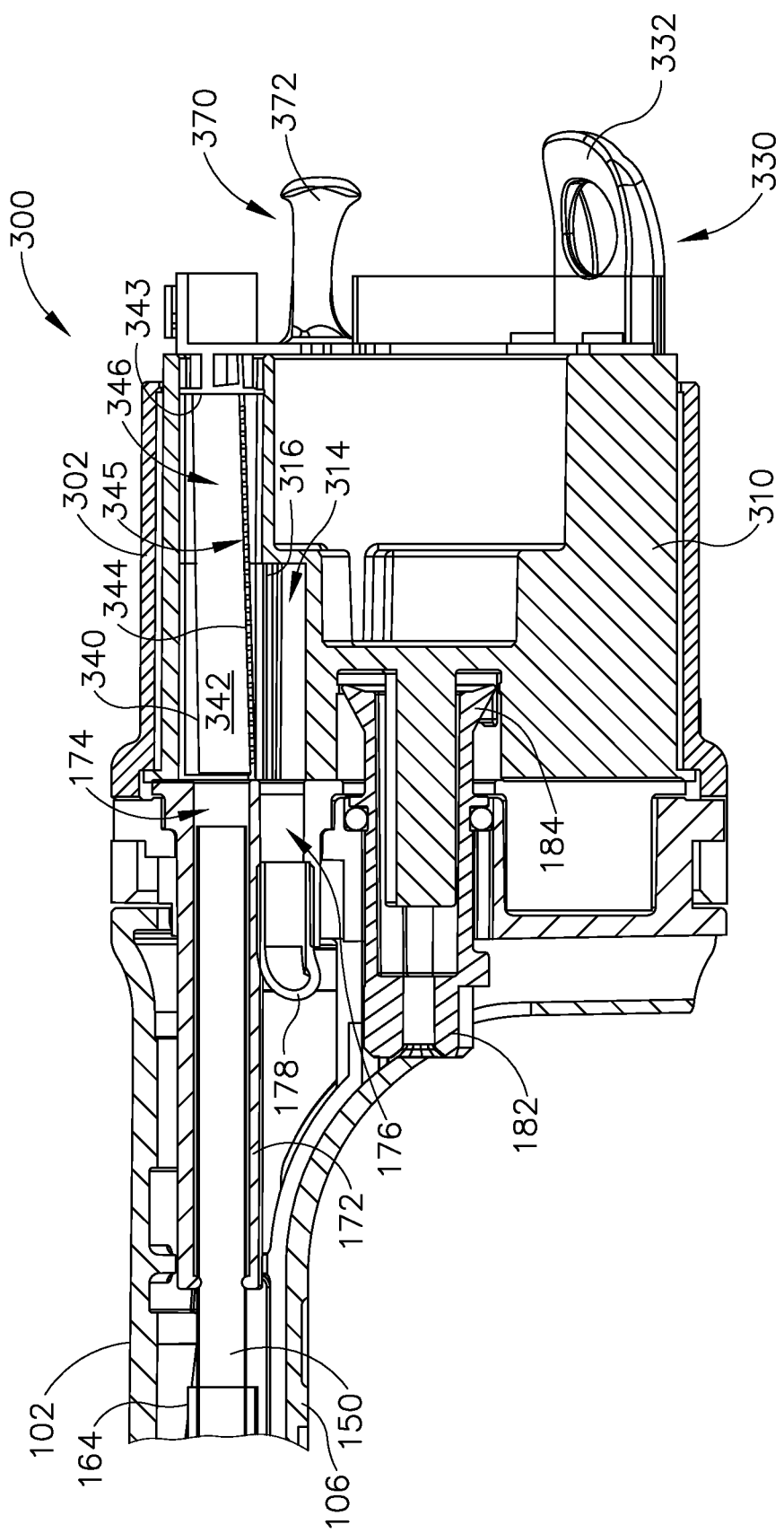
FIG. 11 depicts a side cross-sectional view of the tissue sample holder assembly of FIG. 9, with a tissue sample chamber aligned with the cutter.

As best seen in FIGS. 10-11, a sealing member (170) is provided at the proximal end of chassis (106) and interfaces with the distal face of manifold (310). In the present example, sealing member (170) comprises rubber, though it should be understood that any other suitable material(s) may be used. Sealing member (170) includes a longitudinally extending cutter seal (172), which receives cutter (150) and seals against the exterior of cutter (150). The proximal end of cutter (150) remains within cutter seal (172) throughout the full range of travel of cutter (150). Cutter seal (172) maintains a fluid tight seal against cutter (150) during this full range of motion, including during rotation and translation of cutter (150). An opening (174) is positioned at the proximal end of cutter seal (170). This opening (174) is configured to align with whichever passage (312, 313) is at the 12 o'clock position. Another opening (176) is positioned below opening (174). Opening (176) is configured to align with whichever recess (314, 315) is at the 12 o'clock position. As best seen in FIGS. 9 and 11, opening (176) is in fluid communication with a port (178), which is coupled with tube (20). Thus, sealing member (170) provides fluid communication between tube (20) and whichever recess (314, 315) is at the 12 o'clock position. As will be described in greater detail below, manifold (310) further provides fluid communication between such recess (314, 315) and the associated passage (312, 313) at the 12 o'clock position; and thereby further to lumen (151) of cutter (150). In other words, sealing member (170) and manifold (310) cooperate to provide fluid communication between tube (20) and lumen (151) of cutter (150) via whichever passage (312, 313) and recess (314, 315) are at the 12 o'clock position. It should be understood that sealing member (170) of the present example maintains a fluid tight seal against the distal face of manifold (310), even as manifold (310) is rotated relative to sealing member (170).

2. Exemplary Tissue Holder Trays

Figure 15:
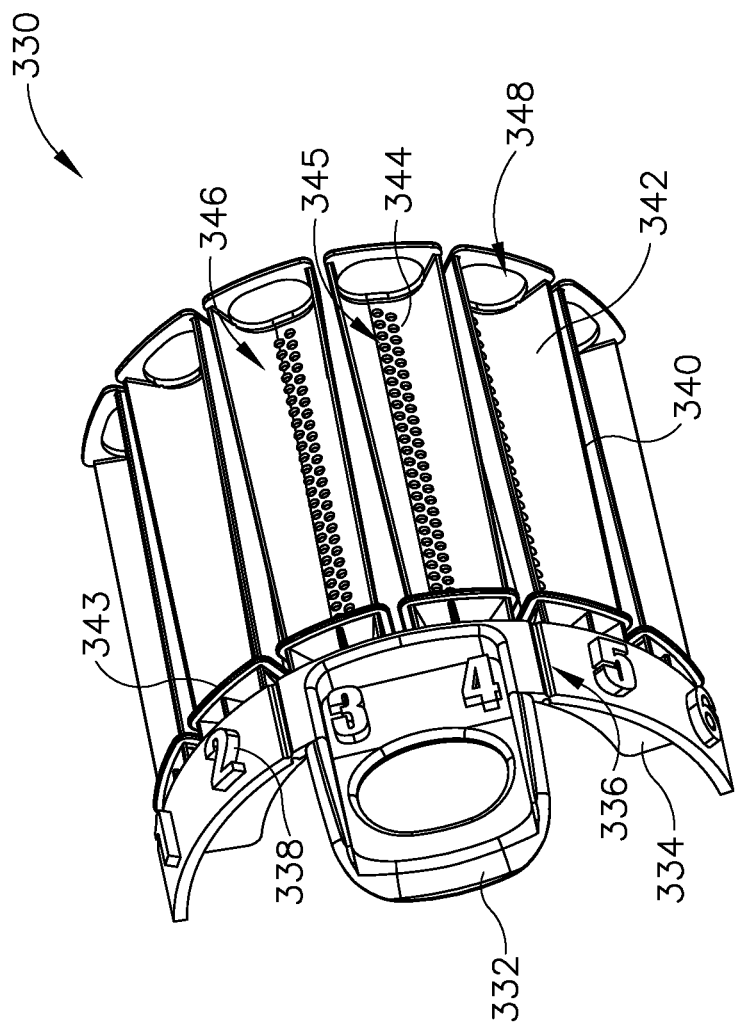
FIG. 15 depicts a perspective view of an tissue sample tray of the tissue sample holder assembly of FIG. 9.
Figure 16:
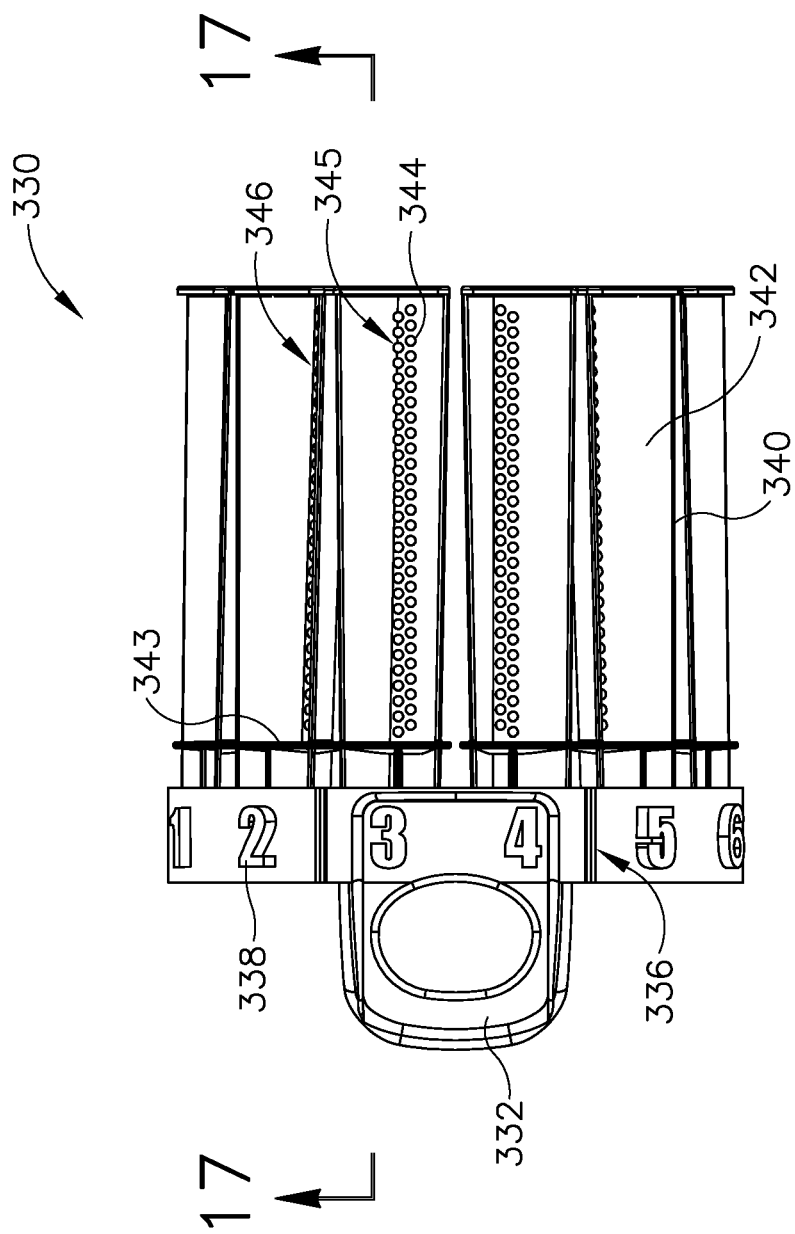
FIG. 16 depicts a top plan view of the tray of FIG. 15.
Figure 17:
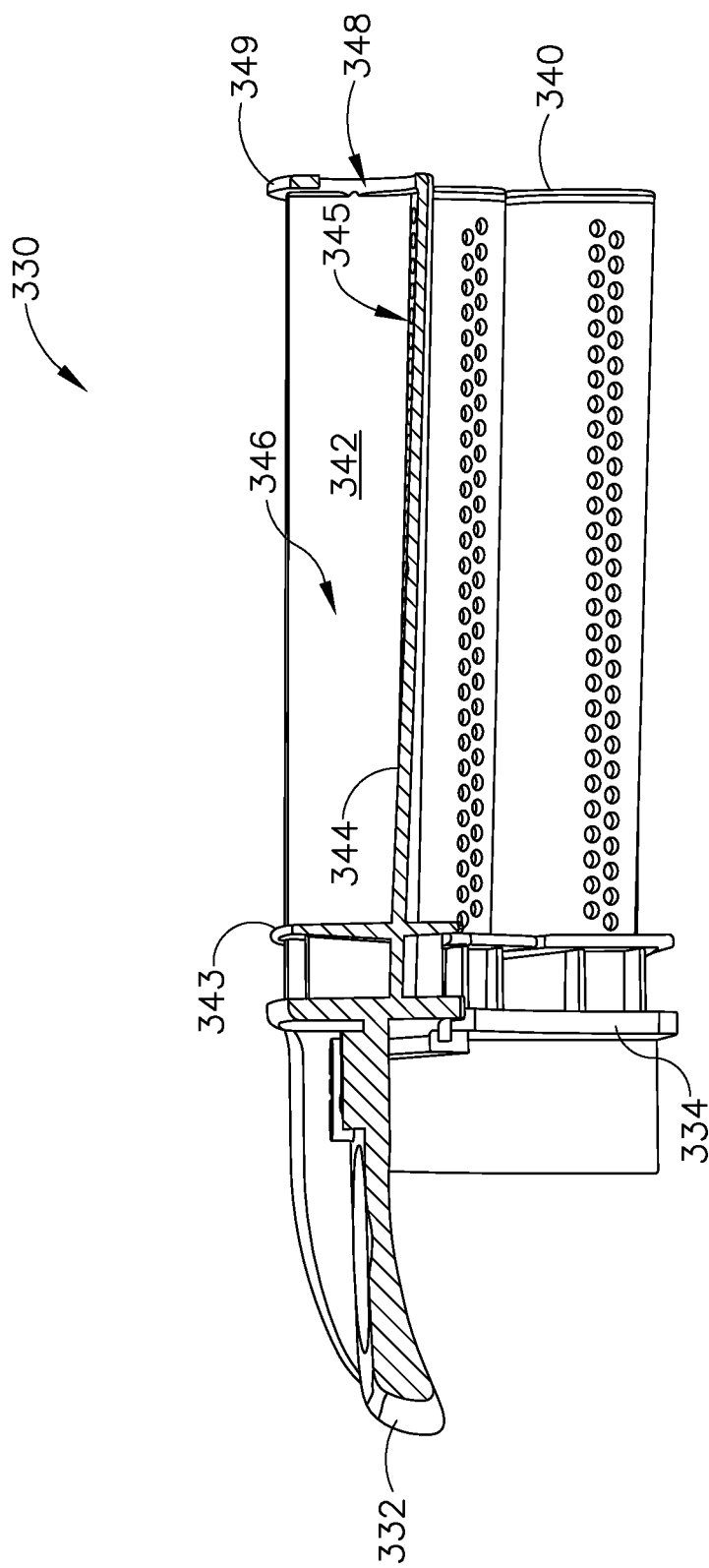
FIG. 17 depicts a cross-sectional view of the tray of FIG. 15, taken along line 17-17 of FIG. 16.

As noted above, tissue sample holder trays (330) are configured to removably engage manifold (310). As best seen in FIGS. 15-17, each tissue sample holder tray (330) of the present example includes a grip (332), a proximal wall (334), and a plurality of strips (340) extending distally from proximal wall (334). Strips (340) are sized and configured for insertion into associated passages (312) of manifold (310). Each strip (340) includes a pair of sidewalls (344) and a floor (342). Each pair of sidewalls (344) and floor (342) together define a corresponding tissue sample chamber (346). An opening (348) is provided at the distal end of each tissue sample chamber (346). Opening is sized and positioned to correspond with opening (174) of sealing member (170). Thus, the lumen (151) of cutter (150) is in fluid communication with the tissue sample chamber (346) of the strip (340) inserted in the passage (312) that is at the 12 o'clock position. As best seen in FIG. 11, strips (340) are configured such that the distal portion of each strip (340) receives support from a corresponding shelf (316) of manifold (310). Each floor (342) includes a plurality of openings (345) that provide fluid communication between tissue sample chamber (346) of strip (340) and lateral recess (314) of the passage (312) associated with strip (340). Thus, vacuum, atmospheric air, etc. that is communicated to opening (176) via tube (20) is further communicated to lumen (151) of cutter (150) via lateral recess (314), openings (345), and tissue sample chamber (346). During operation of biopsy device (10) as will be described in greater detail below, tissue samples severed by distal edge (152) of cutter (150) are communicated proximally through the lumen (151) of cutter (150) and are then deposited into the tissue sample chamber (346) that is aligned with lumen (151) of cutter (150). Manifold (310) is rotated to successively align tissue sample chambers (346) with lumen (151) of cutter (150), enabling several tissue samples to be separately deposited in different tissue sample chambers (346) during operation of biopsy device (10). Bodily fluids and saline, etc. that are pulled through lumen (151) will pass through tissue sample holder (300) and tube (20) and are eventually deposited in vacuum canister (70).

Each strip (340) also includes a pair of wiper seals (343, 349) that seal against the interior of passage (312) when strip (340) is fully inserted into passage (312). Wiper seals (343, 349) provide a fluid tight seal for tissue sample chambers (346) and further provide frictional resistance to removal of strips (340) from manifold (310). Grips (332) are configured to facilitate removal of strips (340) from manifold (310), such as during or after a biopsy procedure to retrieve or otherwise directly observe tissue samples deposited in tissue sample chambers (346). Trays (330) also include numerical indicia (338) associated with each tissue sample chamber (346). In addition, trays (330) include pinched regions (336) that facilitate flattening of trays (330). In particular, pinched regions (336) provide sufficient flexibility to enable trays (330) to form an arcuate configuration for insertion into manifold (310); while also enabling trays (330) to form a generally flat configuration such as after trays (330) are removed from manifold (310) for inspection of tissue samples in trays (330).

Figure 18:
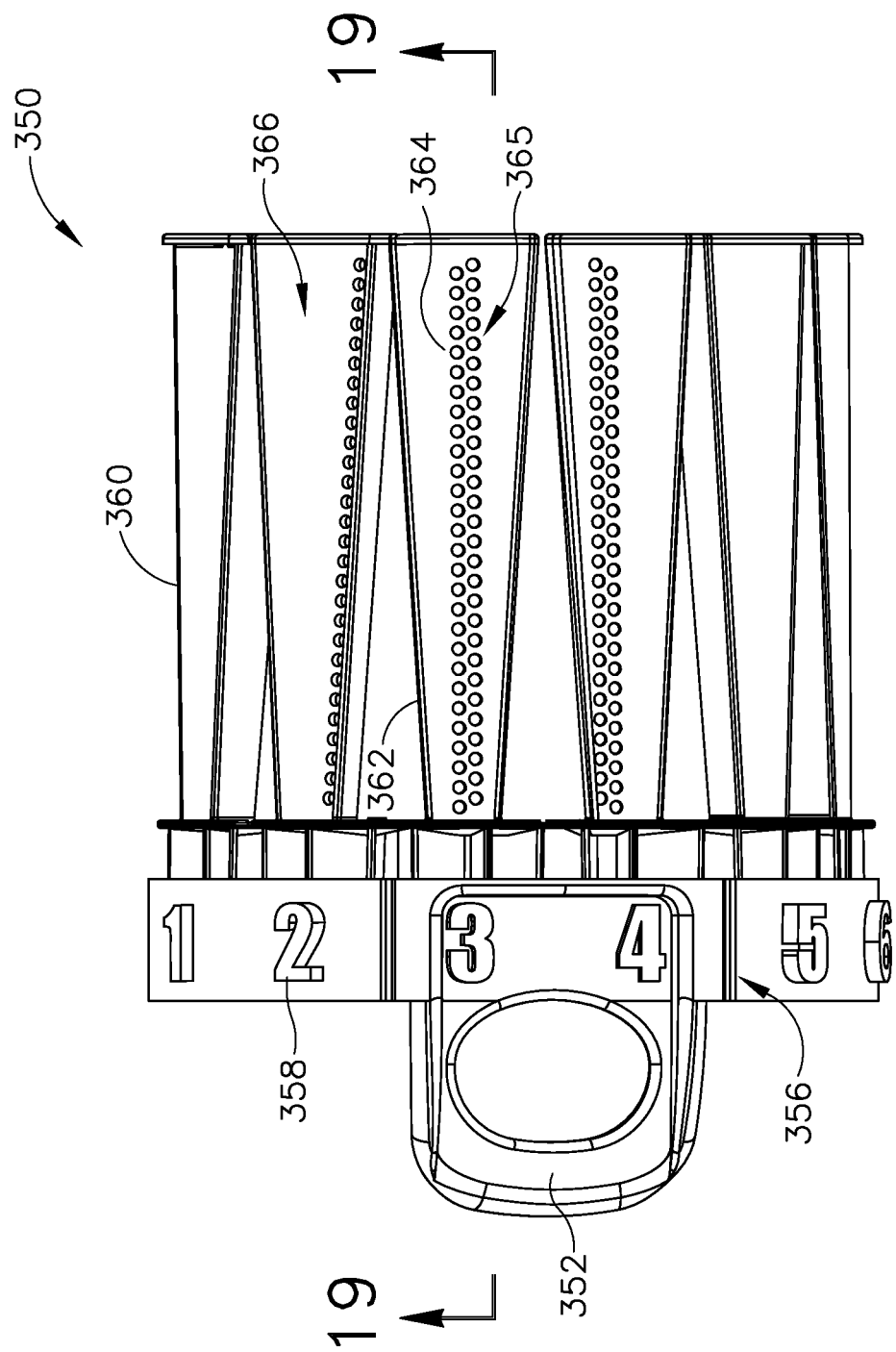
FIG. 18 depicts a top plan view of an exemplary alternative tissue sample tray.
Figure 19:
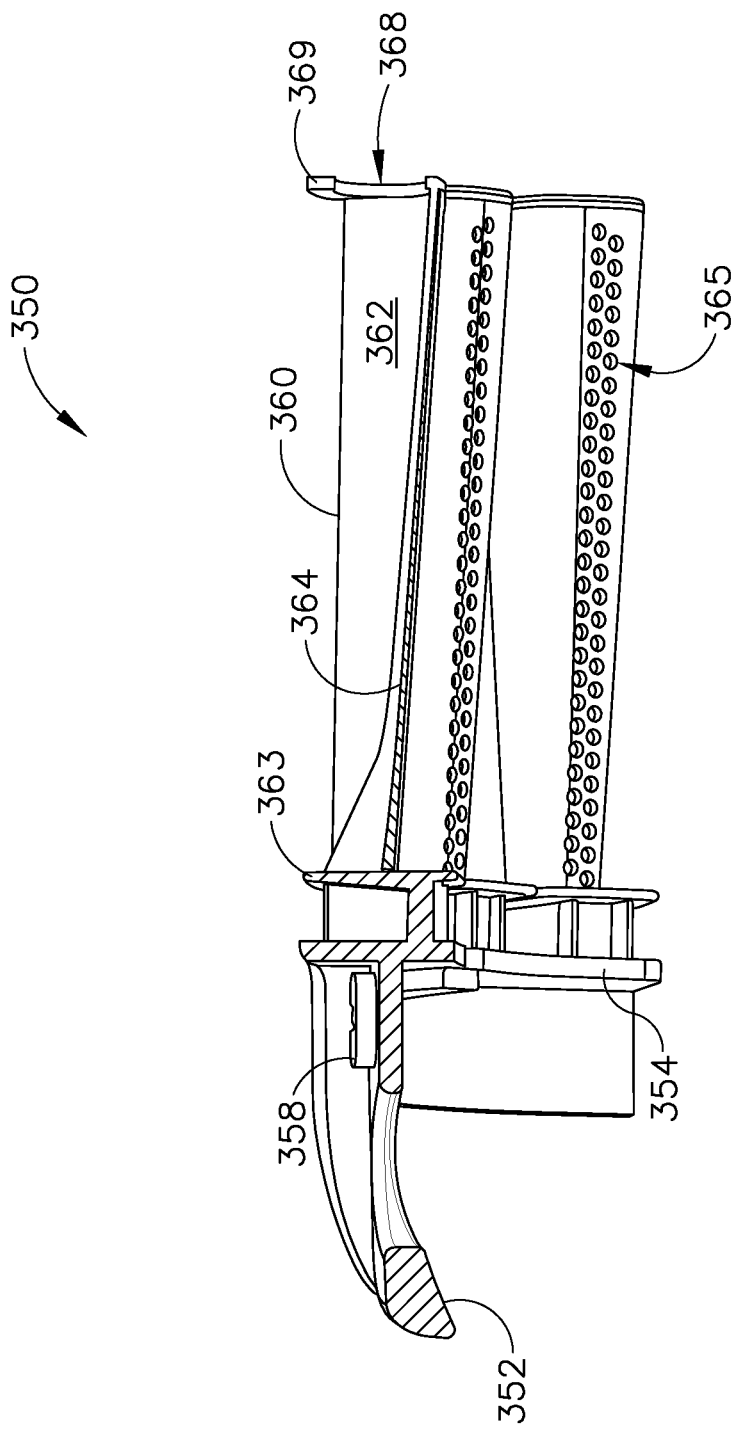
FIG. 19 depicts a cross-sectional view of the tray of FIG. 18, taken along line 19-19 of FIG. 18.

FIGS. 18-19 show an exemplary alternative tissue sample holder tray (350) that may removably engage manifold (310). Each tissue sample holder tray (350) of this example includes a grip (352), a proximal wall (354), and a plurality of strips (360) extending distally from proximal wall (354). Strips (360) are sized and configured for insertion into associated passages (312) of manifold (310). Each strip (360) includes a pair of sidewalls (364) and a floor (362). Each pair of sidewalls (364) and floor (362) together define a corresponding tissue sample chamber (366). An opening (368) is provided at the distal end of each tissue sample chamber (366). Each floor (362) includes a plurality of openings (365) that provide fluid communication between tissue sample chamber (366) of strip (360) and lateral recess (314) of the passage (312) associated with strip (360). Thus, vacuum, atmospheric air, etc. that is communicated to opening (176) via tube (20) is further communicated to lumen (151) of cutter (150) via lateral recess (314), openings (365), and tissue sample chamber (366).

Each strip (360) also includes a pair of wiper seals (363, 369) that seal against the interior of passage (312) when strip (360) is fully inserted into passage (312). Wiper seals (363, 369) provide a fluid tight seal for tissue sample chambers (366) and further provide frictional resistance to removal of strips (360) from manifold (310). Grips (352) are configured to facilitate removal of strips (3460) from manifold (310), such as during or after a biopsy procedure to retrieve or otherwise directly observe tissue samples deposited in tissue sample chambers (366). Trays (350) also include numerical indicia (358) associated with each tissue sample chamber (366). In addition, trays (350) include pinched regions (356) that facilitate flattening of trays (350). In particular, pinched regions (356) provide sufficient flexibility to enable trays (350) to form an arcuate configuration for insertion into manifold (310); while also enabling trays (350) to form a generally flat configuration such as after trays (350) are removed from manifold (310) for inspection of tissue samples in trays (350).

It should be understood from the foregoing that trays (330) are substantially similar to trays (350). However, significant differences include the configurations of floor (364) and sidewall (362) as compared to the configurations of floor (344) and sidewall (342). In particular, as best seen by comparing FIG. 18 to FIG. 16, sidewalls (362) form a relatively aggressive taper along the length of strips (360), as compared to strips (340). This taper provides width at the proximal end of chamber (366) that is significantly less than the width at the distal end of chamber (366). As best seen in FIG. 18, this taper is also augmented by floor (364), which angles upwardly along the length of strip (360). Angled floor (364) provides a height at the proximal end of chamber (366) that is significantly less than the height at the distal end of chamber (366). It should therefore be understood that the angled orientations of floor (364) and sidewalls (342) provide a cross-sectional area of chamber (366) that reduces along the length of chamber (366), with the cross-sectional area of chamber (366) being significantly smaller at the proximal end of chamber (366) as compared to the cross-sectional area at the distal end of chamber (366). By contrast, the cross-sectional area of chambers (346) in tray (330) is relatively more consistent along its length. While a slight taper is provided by walls (342) and floor (344), that taper is far less aggressive than the taper provided by walls (362) and floor (364).

In some versions, trays (330) are used with biopsy devices (10) having needles (110) with a relatively large diameter while trays (360) re used with biopsy devices (10) having needles (110) with a relatively small diameter. For instance, trays (330) may be configured for use with 8 gauge needles (110) while trays (350) are configured for use with 10 gauge needles (110). The relatively aggressive taper provided within chambers (366) may assist in keeping relatively thin severed tissue samples substantially straight when such relatively thin tissue samples are deposited in chambers. For instance, the aggressive taper in chambers (366) may assist in providing a more gradual deceleration of tissue samples as they are deposited in chambers (366), thereby reducing a tendency that such tissues samples might otherwise have to become smashed, curled up, or otherwise disfigured if they were to enter chambers (346) at a relatively higher speed due to the lack of such an aggressive taper.

It should be understood that manifold (310) and/or trays (330, 350) may be configured in numerous other ways. By way of example only, manifold (310) and/or trays (330, 350) may be configured in accordance with at least some of the teachings of U.S. Pat. Pub. No. 2008/0214955, the disclosure of which is incorporated by reference herein. As another merely illustrative example, manifold (310) and/or trays (330, 350) may be configured in accordance with at least some of the teachings of U.S. Pat. Pub. No. 2010/0160824, the disclosure of which is incorporated by reference herein. As another merely illustrative example, manifold (310) and/or trays (330, 350) may be configured in accordance with at least some of the teachings of U.S. Pat. Pub. No. 2013/0041256, the disclosure of which is incorporated by reference herein. It should also be understood that tissue sample holder (300) need not necessarily position chambers (346, 366) coaxially with lumen (151) of cutter (150). Tissue sample holder (300) may index chambers (346, 366) relative to cutter (150) in any other suitable fashion. For instance, chambers (346, 366) may extend along axes that are always offset from the axis of lumen (151), along axes that are oblique or perpendicular relative to the axis of lumen (151), or along other axes. Similarly, it should be understood that manifold (310) may rotate about an axis that is oblique or perpendicular relative to the axis of lumen (151). Still other suitable configurations will be apparent to those of ordinary skill in the art in view of the teachings herein.

3. Exemplary Accessory Chamber and Plug

Figure 20:
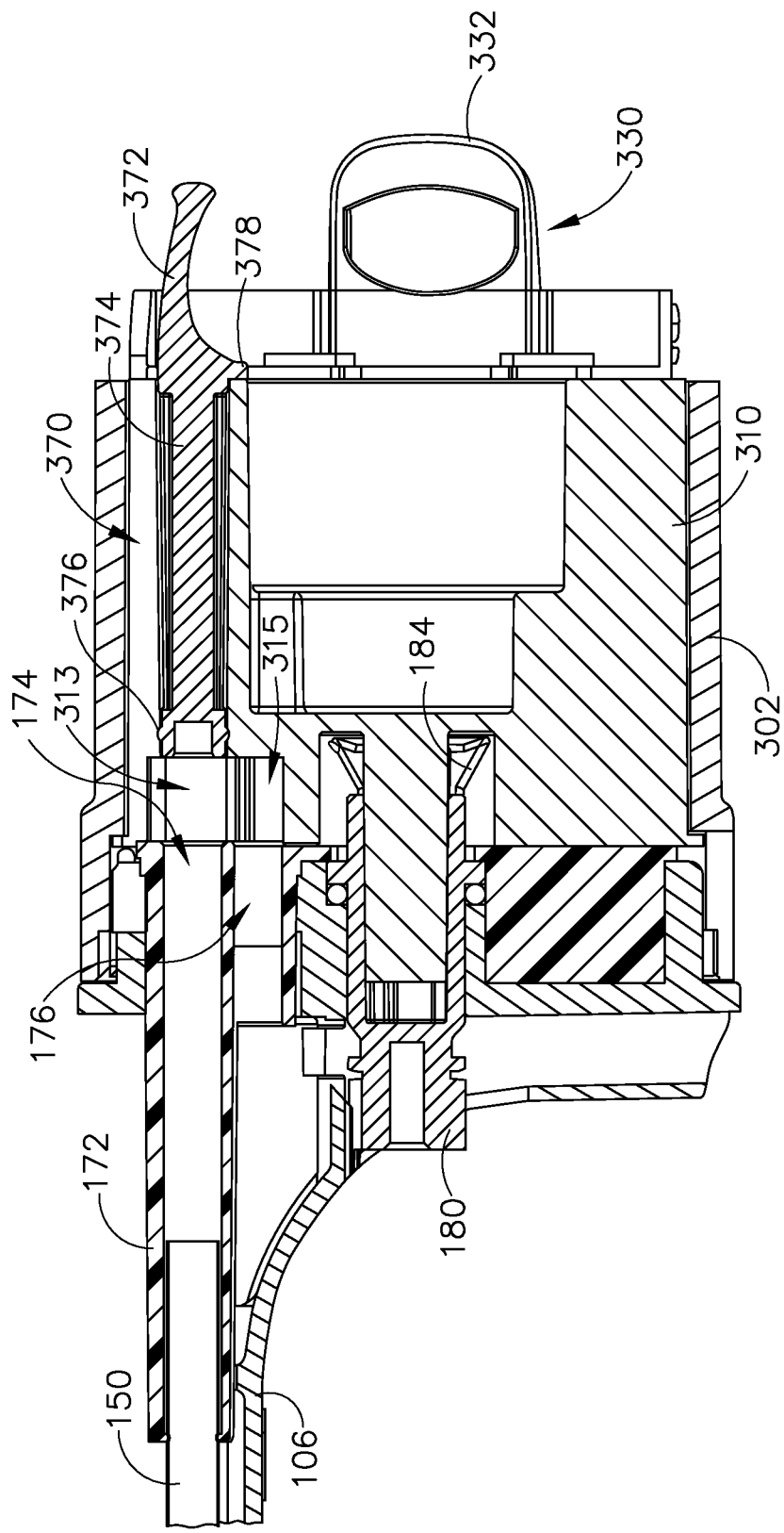
FIG. 20 depicts a side cross-sectional view of the tissue sample holder assembly of FIG. 9, with a plug aligned with the cutter.

As best seen in FIGS. 12 and 20 and as noted above, tissue sample holder (300) of the present example includes a plug (370) that is received in a dedicated passage (313) of manifold (310). Plug (370) includes a grip (372) and a longitudinally extending body (374). Body (374) extends through part of the length of passage (313), distally terminating at the longitudinal position corresponding with the proximal end of recess (315). Plug (370) includes a pair of seals (376, 378) that seal against the interior of passage (313) when plug (370) is fully inserted in passage (313). Seals (376, 378) thus keep passage (313) fluid tight when plug (370) is inserted in passage (313). Passage (313) is configured to receive the shaft of a biopsy site marker applier, as will be described in greater detail below. Passage (313) may also receive an instrument for delivering medicine, etc. to a biopsy site. By way of example only, passage (313) may receive an adapter configured to provide an interface between passage (313) and a conventional medicine deliver device. An example of such an adapter and other uses/configurations for a passage like passage (313) are described in U.S. Pat. Pub. No. 2008/0221480, the disclosure of which is incorporated by reference herein. Plug (370) and/or passage (313) may also be configured and operable in accordance with at least some of the teachings of U.S. Non-Provisional patent application Ser. No. 13/205,189, the disclosure of which is incorporated by reference herein. Still other suitable configurations will be apparent to those of ordinary skill in the art in view of the teachings herein. In some other versions, plug (370) and/or passage (313) are simply omitted.

4. Exemplary Parking Pawl

Figure 21:
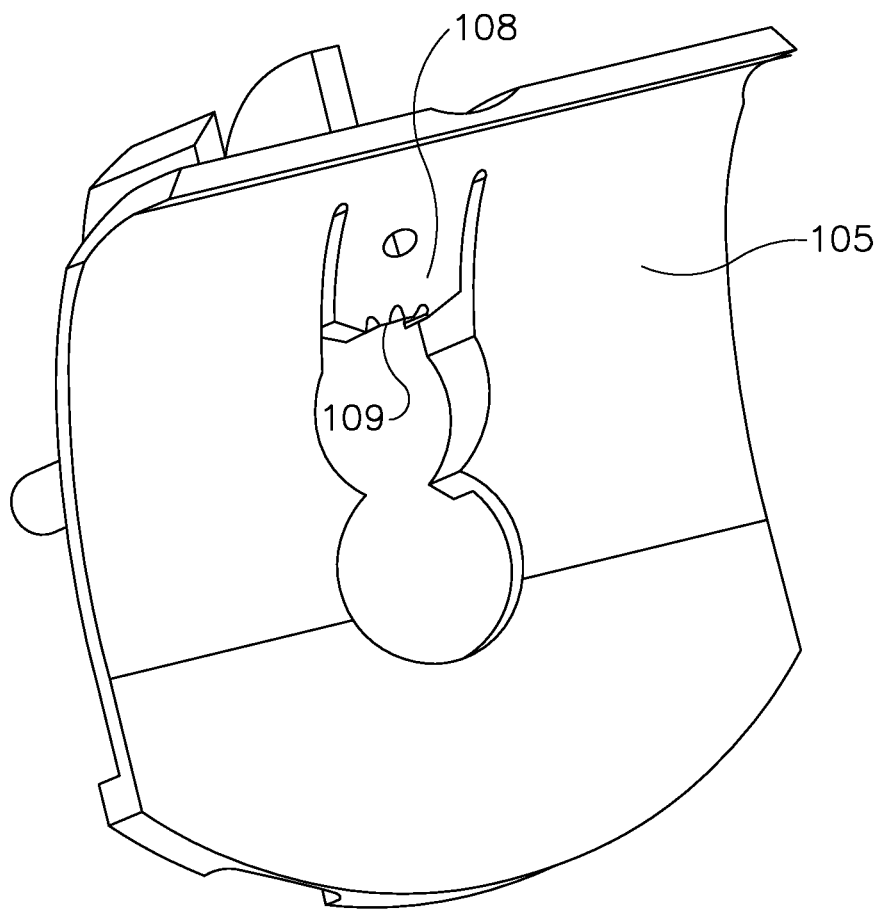
FIG. 21 depicts a perspective view of a component of the probe of FIG. 4 including a parking pawl.
Figure 23:
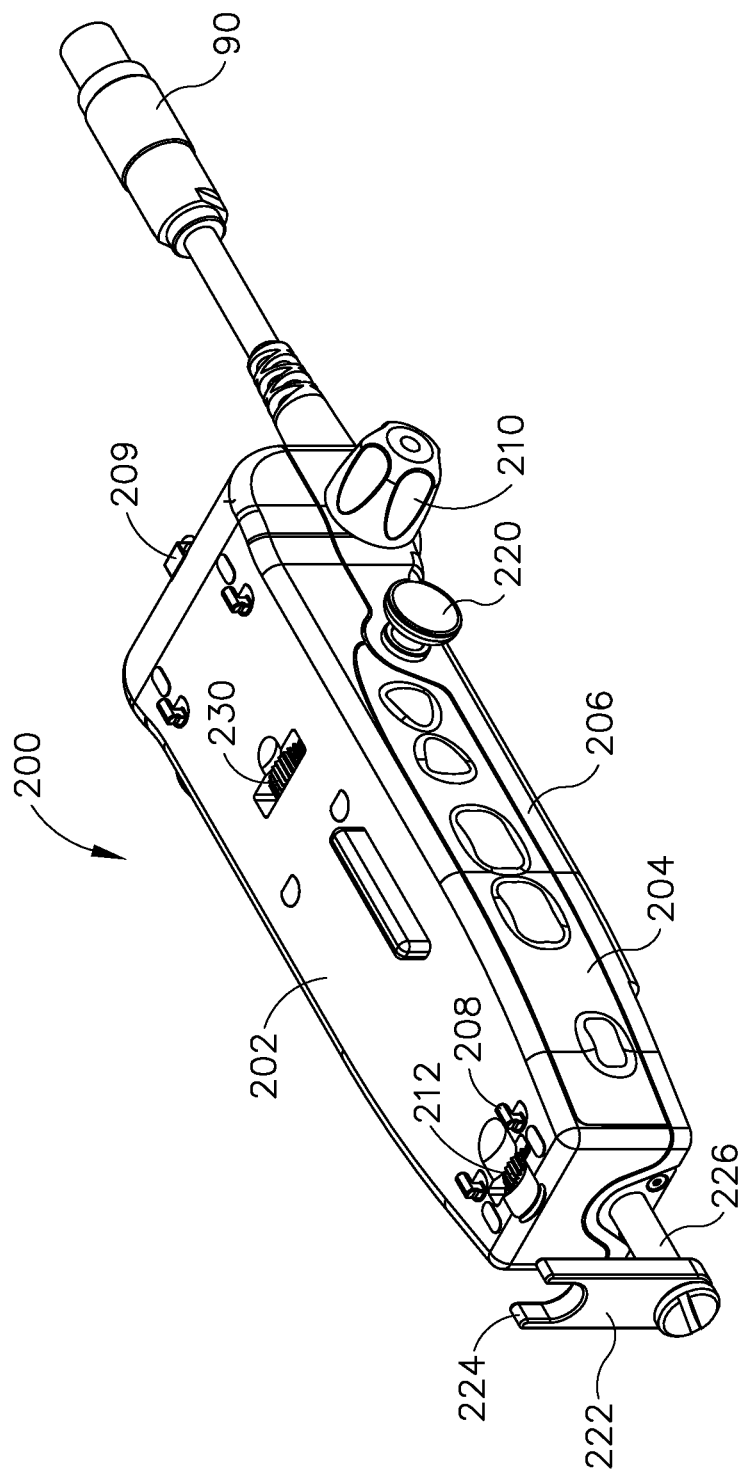
FIG. 23 depicts a perspective view of the holster of the biopsy device of FIG. 2.

As best seen in FIGS. 3 and 21, a rear plate (105) is provided at the proximal end of chassis (106). Rear plate (105) includes a pawl (108) having teeth (109) that are configured to engage the splines of gear (182) of tissue sample holder (300). Pawl (108) is resiliently biased to urge teeth (109) into engagement with the splines of gear (182). This engagement prevents gear (182) from rotating, thereby substantially securing the rotational position of manifold (310). As shown in FIGS. 3 and 23-24, holster (200) includes a cam (209) that is configured to disengage teeth (109) from the splines of gear (182) when probe (100) is coupled with holster (200). Manifold (310) is thus free to rotate under the influence of drive gear (240) when probe (100) is coupled with holster (200). Still other suitable ways in which the rotational position of manifold (310) may be selectively fixed will be apparent to those of ordinary skill in the art in view of the teachings herein.

III. Exemplary Holster

As shown in FIGS. 3 and 23-26, holster (200) of the present example includes a top housing cover (202), side panels (204), and a housing base (206), which are fixedly secured together. As noted above, gears (212, 230) are exposed through top housing cover (202), and mesh with gears (130, 140) of probe (100) when probe (100) and holster (200) are coupled together. In particular, gears (230, 140) drive the actuation assembly of cutter (150); while gears (212, 130) are employed to rotate needle (110). Gear (240) is located at the proximal end of holster (200) and meshes with gear (182) of probe (100) to rotate manifold (310). Holster (200) also includes a firing rod (226) and fork (222), which couple with needle (110) and fire needle (110) distally as will be described in greater detail below.

Figure 22A:
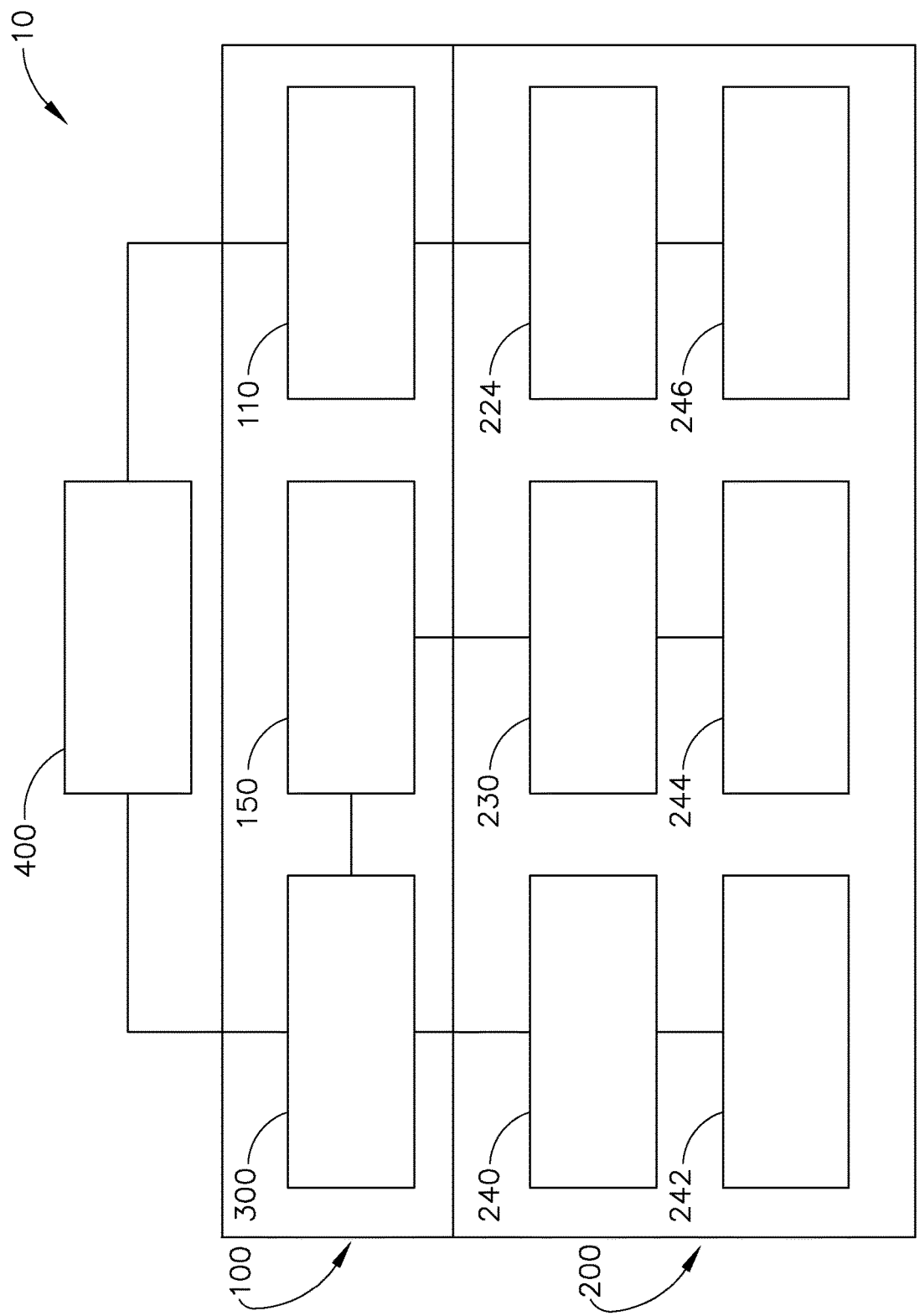
FIG. 22A depicts a basic block schematic view of exemplary components of the holster of the biopsy device of FIG. 2.

As shown in FIG. 22A, holster (200) further includes three motors (242, 244, 246). Motor (242) is operable to drive gear (240), to thereby drive gear (182), to thereby rotate manifold (310) of tissue sample holder (300). Holster (200) may also include an encoder (not shown) and/or some other type of feature that is operable to track movement and rotational positioning of the drive shaft that drives gears (240, 182). By way of example only, these features and/or other features associated with driving rotation of manifold (310) may be configured in accordance with at least some of the teachings of U.S. Pat. Pub. No. 2008/0214955, the disclosure of which is incorporated by reference herein. Motor (244) is operable to drive gear (230), to thereby drive gear (140), to thereby simultaneously rotate and translate cutter (150). By way of example only, these features and/or other features associated with driving rotation and translation of cutter (150) may be configured in accordance with at least some of the teachings of U.S. Pat. Pub. No. 2008/0214955, the disclosure of which is incorporated by reference herein. Motor (246) is operable to drive firing rod (226), to thereby arm and fire needle (110) as will be described in greater detail below. Gear (212) is driven manually by knobs (210) to rotate needle (110), as will also be described in greater detail below.

All motors (242, 244, 246) referred to herein are contained within holster (200) in the present example and receive power from vacuum control module (400) via cable (90). In addition, data may be communicated between vacuum control module (400) and holster (200) via cable (90). In some other versions, one or more motors (242, 244, 246) are powered by one or more batteries located within holster (200) and/or probe (100). It should therefore be understood that, as with other components described herein, cable (90) is merely optional. As yet another merely illustrative variation, motors (242, 244, 246) may be powered pneumatically, such that cable (90) may be substituted with a conduit communicating a pressurized fluid medium to holster (200). As still other merely illustrative variation, cable (90) may include one or more rotary drive cables that are driven by motors (242, 244, 246) that are located external to holster (200). It should also be understood that two or three of motors (242, 244, 246) may be combined as a single motor. Other suitable ways in which various motors (242, 244, 246) may be driven will be apparent to those of ordinary skill in the art in view of the teachings herein.

Figure 22B:
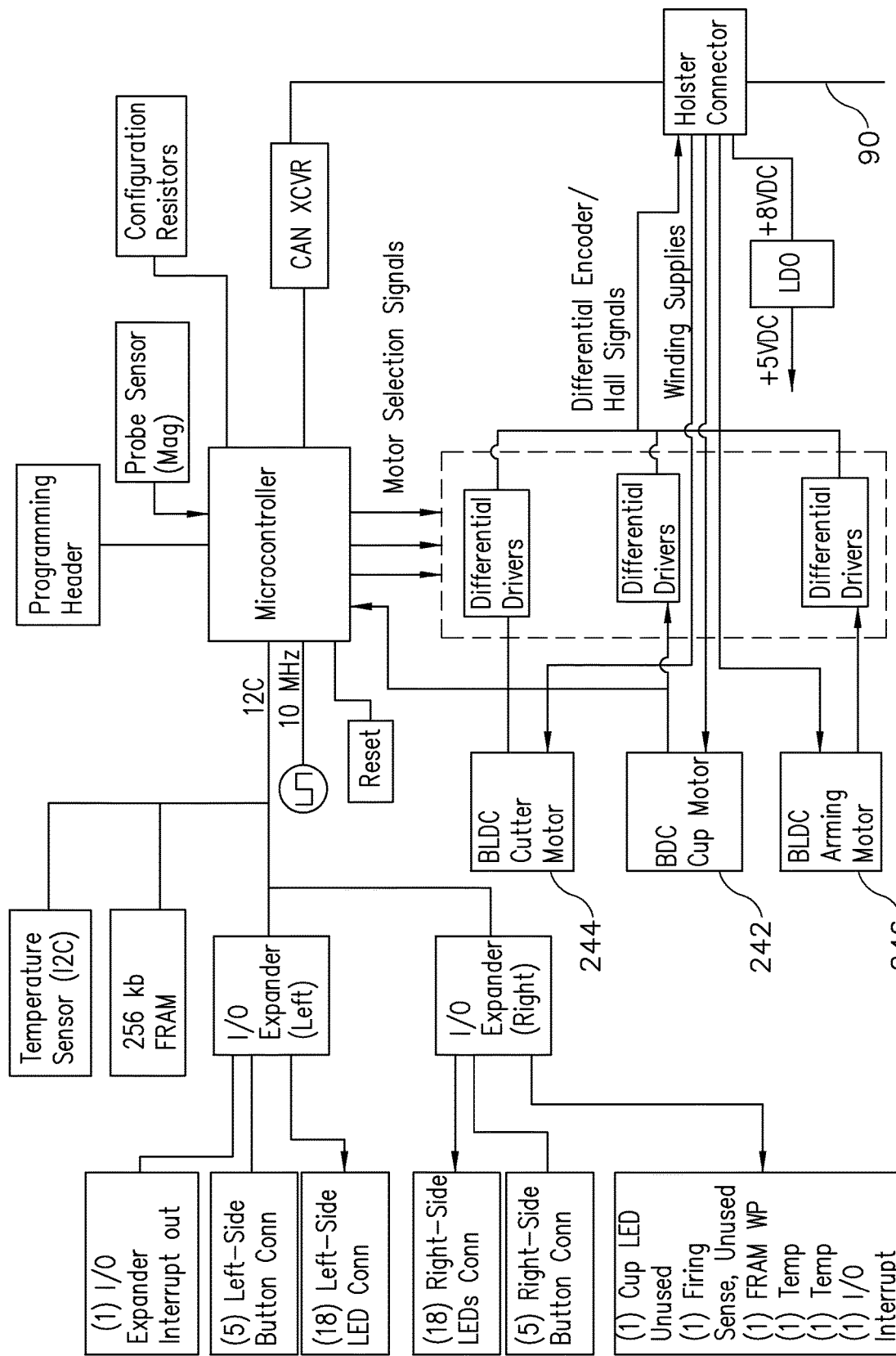
FIG. 22B depicts a detailed block schematic view of exemplary components of the holster of the biopsy device of FIG. 2.

FIG. 22B shows additional electrical and electromechanical components that are provided within holster (200) of the present example. In particular, FIG. 22B shows a microcontroller in communication with motors (242, 244, 246), buttons (254, 262, 266, 270, 272), user interface features (250, 256, 258, 260, 264, 268), a sensor operable to detect coupling of probe (100) with holster (200), a clock, a coupling with cable (90), and various other components. Various kinds of hardware that may be used for the microcontroller and/or for other components shown in FIG. 22B will be apparent to those of ordinary skill in the art in view of the teachings herein. The microcontroller may include control logic to carry out numerous aspects of the functionality described herein. For instance, the temperature sensor may detect the temperature within holster (200), and the microcontroller may track these temperatures and render holster (200) at least partially inoperable when the temperature exceeds a threshold. In the event that the temperature exceeds the threshold in the middle of a biopsy procedure (e.g., while cutter (150) is in motion), the microcontroller may at least permit completion of the biopsy procedure (e.g., by allowing cutter (150) to complete a cutting stroke) before rendering holster (200) at least partially inoperable. Various other suitable electrical/electromechanical components that may be incorporated into holster (200), as well as different arrangements and functionalities for such components, will be apparent to those of ordinary skill in the art in view of the teachings herein.

A. Exemplary Needle Rotation Assembly

As noted above, rotation of gear (212) provides rotation of needle (110) relative to probe (100). In the present example, gear (212) is rotated by rotating knob (210). In particular, knob (210) is coupled with gear (212) by a series of gears (not shown) and shafts (not shown), such that rotation of knob (210) rotates gear (212). A second knob (210) extends from the other side of holster (200). By way of example only, such a needle rotation mechanism may be constructed in accordance with the teachings of U.S. Pub. No. 2008/0214955, the disclosure of which is incorporated by reference herein. As another merely illustrative example, a needle rotation mechanism may be constructed in accordance with the teachings of U.S. Pub. No. 2010/0160819, the disclosure of which is incorporated by reference herein. In some other versions, needle (110) is rotated by a motor. In still other versions, needle (110) is simply rotated by rotating thumbwheel (116). Various other suitable ways in which rotation of needle (110) may be provided will be apparent to those of ordinary skill in the art in view of the teachings herein. It should also be understood that some versions may provide no rotation of needle (110).

B. Exemplary Needle Firing Assembly

Figure 25A:
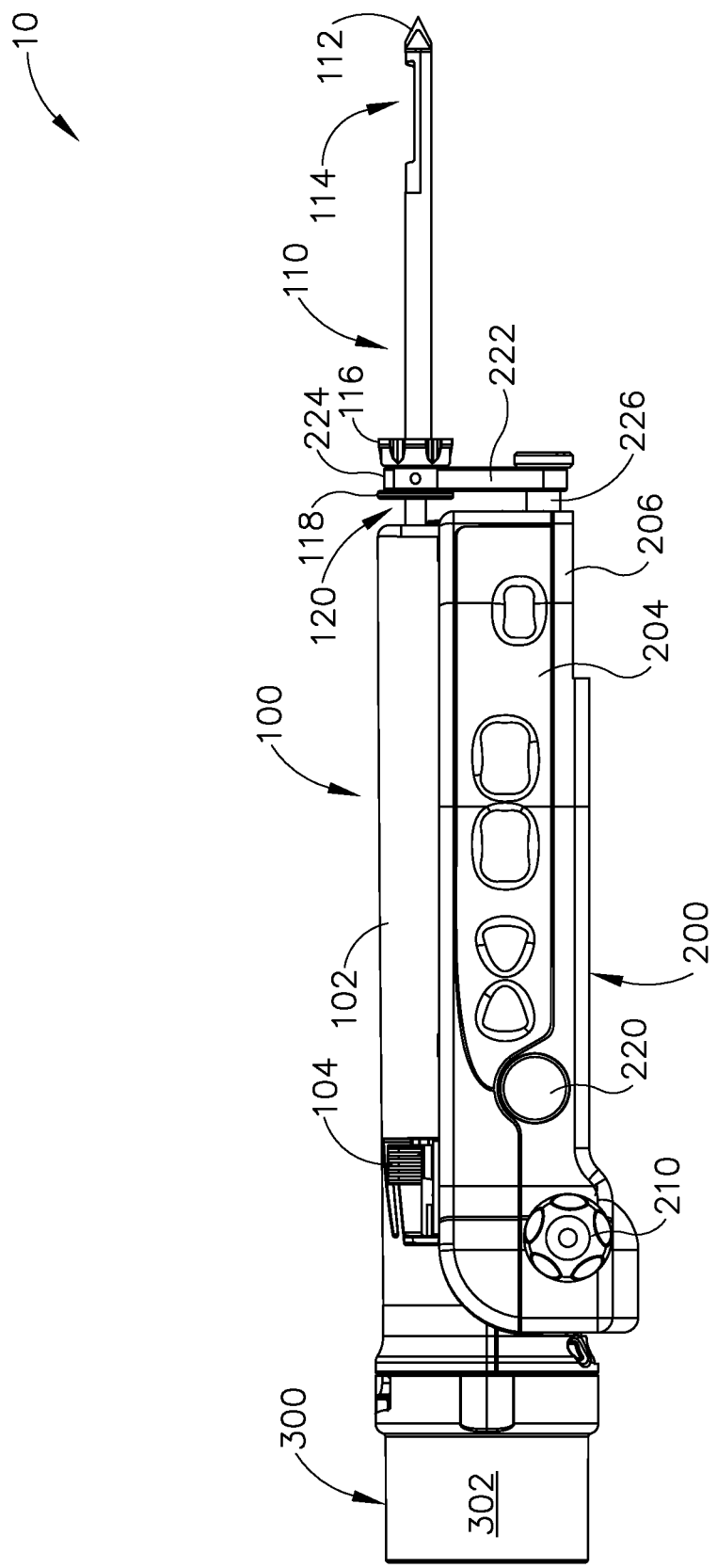
FIG. 25A depicts a side elevational view of the holster of FIG. 23 with the needle in a proximal position.
Figure 25B:
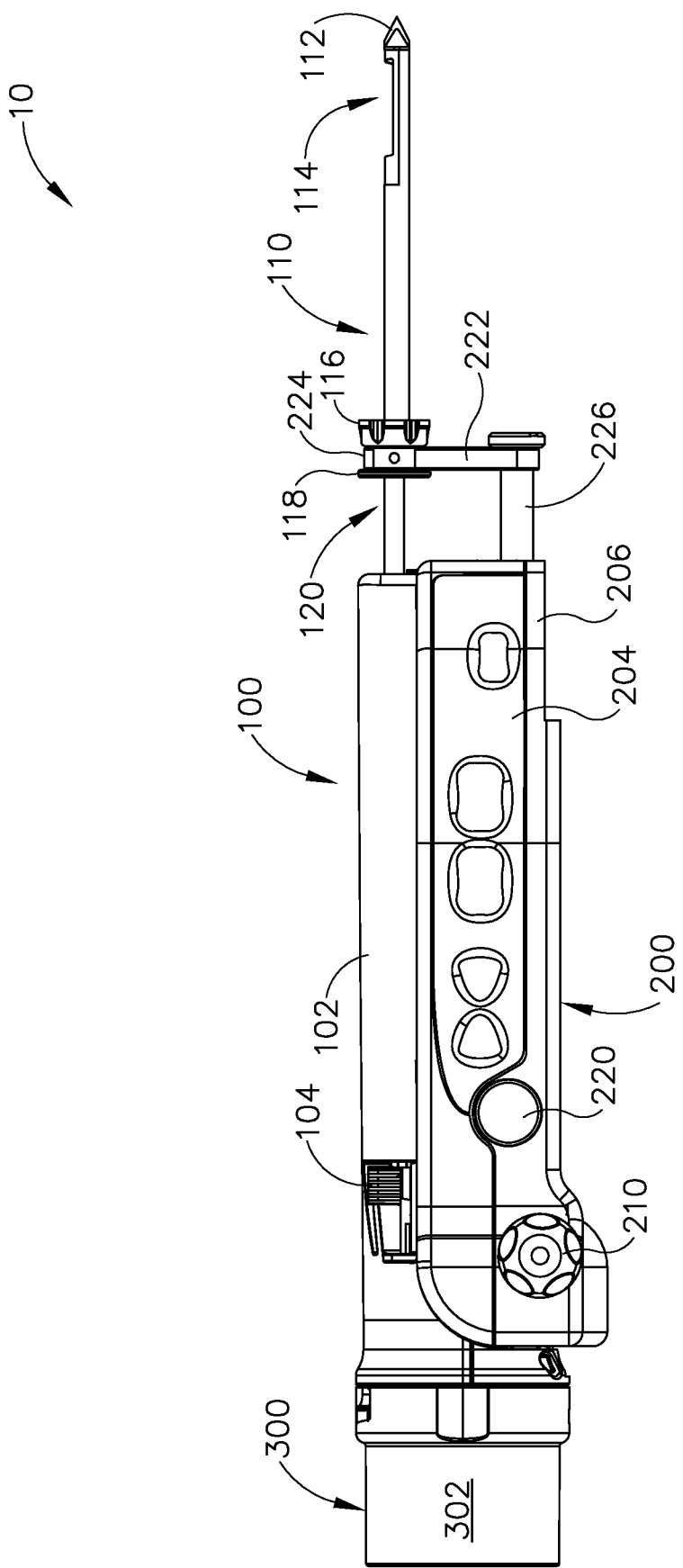
FIG. 25B depicts a side elevational view of the holster of FIG. 23 with the needle in a distal position.
Figure 26:
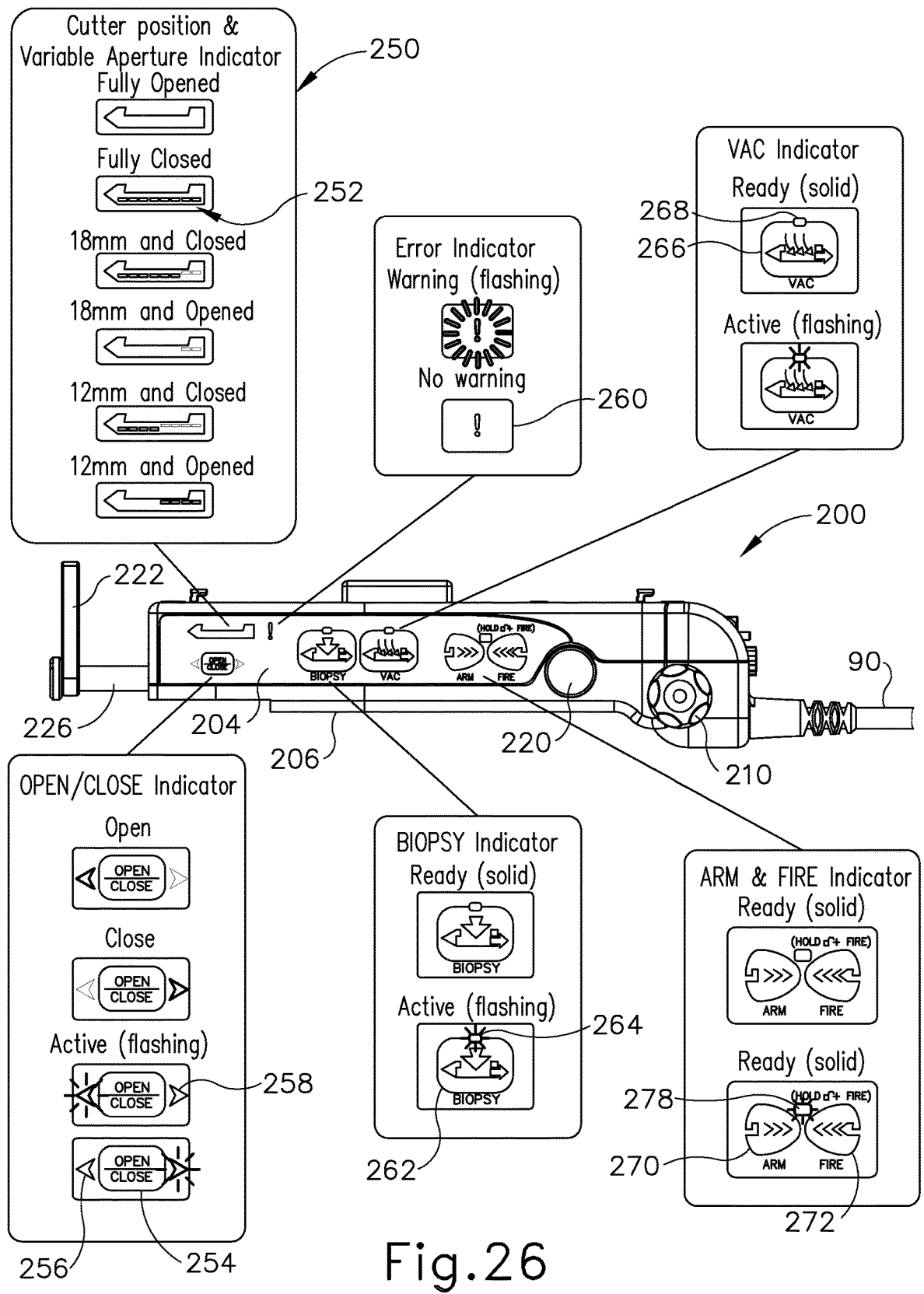
FIG. 26 depicts a side elevational view of the holster of FIG. 23, showing user interface features in various states.

Holster (200) of the present example further includes a needle firing mechanism, which is operable to fire needle (110) from a loaded position as shown in FIG. 25A to a fired position as shown in FIG. 25B. By way of example only, such firing may be useful in instances where biopsy device (10) is mounted to a stereotactic table fixture or other fixture, with tip (112) adjacent to a patient's breast, such that the needle firing mechanism may be activated to drive needle (110) into the patient's breast. The needle firing mechanism may be configured to drive needle (110) along any suitable range of motion, to drive tip (112) to any suitable distance relative to fixed components of probe (100).

The needle firing mechanism of the present example is armed by depressing an arming button (270); and is fired by simultaneously depressing a firing button (272) and a safety button (220). Arming button (270) and firing button (272) each comprise a thin film switch presented on side panel (204) of holster (200). In some versions, arming buttons (270) and firing buttons (272) are on both sides of holster (200) while in other versions arming button (270) and firing button (272) are either on just one side of holster (200) or are located elsewhere (e.g., remote user interface, at vacuum source (400) or elsewhere, etc.). Arming button (270) is operable to selectively activate motor (246) as will be described in greater detail below. Safety buttons (220) are also provided on both sides of holster (200) in the present example, and are mechanically movable transversely relative to side panels (204). In some versions, each safety button (220) includes a bellows that provides a fluid tight seal with side panel (204). Of course, either type of button (270, 272, 222) may have various other components, features, configurations, and operabilities.

In the present example, the needle firing mechanism is coupled with needle (110) via a firing rod (226) and a firing fork (222). Firing rod (226) and firing fork (222) are unitarily secured together. Firing fork (222) includes a pair of prongs (224) that receive hub member (120) of needle (110) therebetween. Prongs (224) are positioned between annular flange (118) and thumbwheel (116), such that needle (110) will translate unitarily with firing rod (226) and fork (222). Prongs (224) nevertheless removably receive hub member (120), such that fork (222) may be readily secured to hub member (120) when probe (100) is coupled with holster (200); and such that hub member (120) may be readily removed from fork (222) when probe (100) is decoupled from holster (200). Prongs (224) are also configured to permit hub member (120) to rotate between prongs (224), such as when knob (320) is rotated to change the angular orientation of lateral aperture (114) about the axis defined by needle (110). Other suitable components, configurations, and relationships will be apparent to those of ordinary skill in the art in view of the teachings herein.

The internal components of the needle firing mechanism of the present example are configured and arranged as described in U.S. Non-Provisional patent application Ser. No. 13/086,567, entitled "Biopsy Device with Motorized Needle Firing," filed Apr. 14, 2011, the disclosure of which is incorporated by reference herein. As described in that reference, a coil spring resiliently biases firing rod (226) distally. Upon activation of button (270), motor (246) drives a firing tube distally in order to compress the coil spring and in order to engage the firing rod (226). In some instances, the user must hold button (270) for at least certain period of time before motor (246) begins driving the firing tube distally. LED (278) and/or the sound of motor (246) may provide the user with feedback indicating that motor (246) is being activated. Once the firing tube compresses the coil spring and engages firing rod (226), motor (246) reverses direction to retract the firing tube, the coil spring, and the firing rod (226) proximally to an armed position. In some versions, button (270) must be activated a second time in order to reverse the direction of rotation by motor (246). In some other versions, a single activation of button (270) causes motor (246) to drive the firing tube distally and automatically reverse as soon as the firing tube reaches the distal position. By way of example only, an encoder, proximity sensor, motor load detection algorithm, and/or various other components/techniques may be used to provide automatic reversal of motor (246). An LED (278) at side panel (204) illuminates to indicate to the user that the needle firing mechanism has reached the armed configuration. In addition or in the alternative, an audio device in holster (200) and/or in vacuum control module (400) may provide an audible indication that the needle firing mechanism has reached the armed configuration. LED (278) may flash while needle firing mechanism is in the process of transitioning from a non-armed configuration to the armed configuration.

With the firing tube, the coil spring, and the firing rod (226) in the armed position as described above, the user must depress safety button (220) and simultaneously press firing button (272) in order to fire needle (110) from the armed position. In particular, a cross-bar associated with button (220) prevents the firing tube from retracting further proximally until button (220) is fully depressed. When button (220) is fully depressed, the cross-bar is moved to provide clearance for further proximal retraction of the firing tube. With this clearance provided, motor (246) will retract the firing tube further proximally when button (272) is depressed. When the firing tube is retracted further proximally in response to activation of button (272), the firing tube releases firing rod (226). With firing rod (226) released, the coil spring immediately and forcefully decompresses, rapidly pushing firing rod (226) and needle (110) distally. Components within holster (200) cooperate to arrest distal movement of firing rod (226) at the end of the firing stroke of needle (110).

In some versions, biopsy device (10) permits the user to "soft fire" needle (110) in addition to or in lieu of permitting the rapid firing of needle (110) as described above. For instance, in some such versions, motor (246) is first activated by pressing arming button (270) to move the firing tube, the coil spring, and firing rod (226) proximally to the armed position as described above. Motor (246) stops even if the user fails to release button (270) at this stage. If the user releases button (270) and then re-presses button (270) when the firing tube, the coil spring, and firing rod (226) are in the armed position, motor (246) reverses direction and slowly advances these components (and needle (110)) distally, without releasing firing rod (226) from the firing tube. In other words, the coil spring remains compressed during this "soft fire" distal movement of needle (110). It should be understood that such operation may allow the distal translation speed of fork (222) and needle (110) to be controlled selectively, and may also allow the distal motion of fork (222) and needle (110) to be interrupted, slowed or sped up, or otherwise controlled as fork (222) and needle (110) traverse a distal range of motion. Of course, such "soft fire" control may be provided through one or more other buttons and/or through any other suitable form of control. It should be understood that, in some versions, a "soft fire" firing of needle (110) may be less audible to the patient than firing of needle (110) by the coil spring. As yet another merely illustrative variation, a motor may be use to provide a rapid firing of needle (110), such that coil spring may be omitted altogether. Examples of such firing are described in U.S. Pub. No. 2009/0216152, entitled "Needle Tip for Biopsy Device," published Aug. 27, 2009, the disclosure of which is incorporated by reference herein. As another merely illustrative variation, needle (110) may be fired in accordance with at least some of the teachings of U.S. Pub. No. 2012/0265095, entitled "Biopsy Device with Motorized Needle Firing," published Oct. 18, 2012, the disclosure of which is incorporated by reference herein. Other suitable ways in which firing of needle (110) may be provided will be apparent to those of ordinary skill in the art in view of the teachings herein. Furthermore, it should be understood that some versions may simply lack firing of needle (110) altogether.

C. Exemplary User Interface

As noted above, holster (200) of the present example includes buttons (220, 270, 272) for firing of needle (110). Holster (200) also includes additional buttons (254, 262, 266) and other user interface features (250, 256, 258, 260, 264, 268). Buttons (254, 262, 266) are operable to initiate various functions within biopsy system (2) as will be described in greater detail below. It should be understood that, in some instances, after one button (254, 262, 266) has been pressed to initiate one function, another button (254, 262, 266) may be pressed to stop that function (without necessarily starting another function before that other button (254, 262, 266) is pressed again). The other user interface features (250, 256, 258, 260, 264, 268) provide visual feedback to the user regarding operational states of biopsy system (2). In particular, holster (200) includes a cutter position indicator (250). Cutter position indicator (250) includes a graphical representation of the distal end of needle (110), including tip (112) and lateral aperture (114). Cutter position indicator (250) also includes a row of LEDs (252) adjacent to the graphical representation of lateral aperture (114). LEDs (252) are configured to illuminate to correspond with the longitudinal position of distal edge (152) of cutter (150), in real time. For instance, when cutter (150) is in a distal-most position, the entire row of LEDs (252) may be illuminated in a first color. As cutter (150) is retracted, the LEDs (252) may become progressively non-illuminated along the row to indicate the proximal movement of cutter (150), in real time. As cutter (150) is again advanced, the LEDs (152) may progressively re-illuminate in the first color along the row to indicate the distal movement of cutter (150), in real time.

As described in greater detail below, biopsy system (2) permits the user to selectively vary the proximal-most position to which cutter (150) retracts, to thereby vary the effective size of aperture (114). LEDs (252) further provide illumination in a second color to indicate the selected proximal-most position. For instance, the four proximal-most LEDs (252) may be illuminated in the second color to indicate the user's selection of a 12 mm effective aperture (114) size. The two proximal-most LEDs (252) may be illuminated in the second color to indicate the user's selection of an 18 mm effective aperture (114) size. Cutter position indicator (250) may have no LEDs (252) illuminated in the second color when the user selects a full effective aperture (114) size. In such versions, any LEDs (252) that are illuminated in the second color may remain illuminated in the second color during proximal retraction and distal advancement of cutter (250). The LEDs (252) that are distal to the LEDs (252) of the second color may progressively illuminate/darken to indicate the position of cutter (150) as described above. Of course, a variety of other types of interface features may be used to indicate the position of cutter (150). Furthermore, it should be understood that cutter position indicator (250) may be omitted from holster (200) and/or be located elsewhere.

Holster (200) of the present example also includes an open/close button (254) with associated LED indicators (256, 258). Button (254) comprises a thin film switch that is operable to selectively advance and retract cutter (150) in a manual fashion. In some versions, a user may briefly press and release button (254) to either advance cutter (150) distally (if cutter (150) is already retracted) or retract cutter (150) proximally (if cutter (150) is already advanced), with cutter (150) continuing to move in the distal or proximal direction after the user releases button (254) until cutter (150) reaches the distal-most or proximal-most position. In some other versions, the user must continue depressing button (254) to either advance cutter (150) distally or retract cutter (150) proximally, with cutter (150) only moving in the distal or proximal direction while the user is depressing button (254). Cutter (150) will stop such movement as soon as the user releases button (254) and/or as soon as cutter (150) reaches the distal-most or proximal-most position. In some versions, when cutter (150) is already in a distal-most position and the user presses button (254) to retract cutter (150), motor (242) may automatically rotate manifold (310) to align passage (313) with lumen (151) to facilitate biopsy site marking as will be described in greater detail below.

Indicator (256) includes a representation of a distally directed arrow, with an LED that illuminates when cutter (150) is in a proximal position, to indicate that pressing button (254) will advance cutter (150) distally. Indicator (256) may flash when cutter (150) is being advanced distally in response to pressing of button (254). Indicator (258) includes a representation of a proximally directed arrow, with an LED that illuminates when cutter (150) is in a distal position, to indicate that pressing button (254) will retract cutter (150) proximally. Indicator (258) may flash when cutter (150) is being retracted proximally in response to pressing of button (254). Of course, button (254) and/or indicators (256, 258) may be modified, substituted, or supplemented in numerous ways; or may even be omitted altogether if desired.

Holster (200) of the present example also includes an error indicator (260). Error indicator (260) comprises a graphical representation of an explanation point with an LED that is configured to illuminate and/or flash when there is an error condition. By way of example only, the LED of error indicator (260) may flash in a certain pattern to indicate a certain kind of error, such that the flash patterns may be interpreted to identify the type of error and/or the type of corrective action needed. Of course, error indicator (260) may be modified, substituted, or supplemented in numerous ways; or may even be omitted altogether if desired. For instance, in addition or in the alternative to error indicator (260), an audio device in holster (200) and/or in vacuum control module (400) may provide an audible indication to identify an error condition and/or corrective action that is needed.

Holster (200) of the present example also includes a biopsy button (262) and associated LED indicator (264). Button (262) comprises a thin film switch that is operable to initiate a biopsy cycle. For instance, the user may simply press and release button (262) to initiate a biopsy cycle as will be described in greater detail below. This may cause cutter (150) to move through a full stroke of proximal retraction and distal advancement to capture a tissue sample, with cutter (150) ceasing movement until button (262) is again depressed to capture a second tissue sample and so on. In some versions, the user may also hold down button (262) to capture several tissue samples in a continuous fashion. In some such versions, cutter (150) will simply repeat the above described cutting strokes until the user releases button (262). The user may monitor movement of cutter (150) by viewing cutter position indicator (250), and may rotate knob (210) to re-orient needle (110) between each cutting stroke. Indicator (264) may include an LED that remains illuminated when system (2) is ready to take a biopsy sample. Indicator (264) may flash during a biopsy sample process to indicate that an active biopsy procedure is taking place. Of course, button (262) and/or indicator (264) may be modified, substituted, or supplemented in numerous ways; or may even be omitted altogether if desired. For instance, in addition or in the alternative to indicator (264), an audio device in holster (200) and/or in vacuum control module (400) may provide an audible indication that an active biopsy procedure is taking place.

Holster (200) of the present example also includes a vacuum button (266) and associated LED indicator (268). Button (266) comprises a thin film switch that is operable to provide vacuum through lumen (151) of cutter (150) and/or through second lumen (192) of needle (110). Button (266) of the present example is operable to provide different responses based on how the user activates button (266). If the user presses and quickly releases button (266), biopsy system (2) will initiate a probe clearing sequence (1300) as described in greater detail below with reference to FIG. 41. If the user presses and holds button (266) down, cutter (150) will partially retract and vacuum will be communicated to lumen (151) and/or lumen (192). By way of example only, this additional vacuum may be provided in order to draw additional bodily fluids from the biopsy site. Indicator (268) may include an LED that remains illuminated when system (2) is ready to provide this additional vacuum. Indicator (268) may flash during application of this additional vacuum to indicate that additional vacuum is being provided to the biopsy site. Indicator (268) may also flash when the probe clearing sequence (1300) is being executed. Of course, button (266) and/or indicator (268) may be modified, substituted, or supplemented in numerous ways; or may even be omitted altogether if desired. For instance, in addition or in the alternative to indicator (268), an audio device in holster (200) and/or in vacuum control module (400) may provide an audible indication that an additional vacuum and/or probe clearing sequence is being provided/executed.

Still other suitable types of user interface features that may be incorporated into holster (200) will be apparent to those of ordinary skill in the art in view of the teachings herein. It should also be understood that the above-described user interface features are incorporated into both side panels (204) of holster (200) in the present example. In some versions, the user must select which side panel's (204) buttons will be active; and the other side panel's (204) buttons are rendered inactive after the user makes their selection. For instance, the LEDs on both side panels (204) may flash when the user is to assign active status to one of the side panels (204). The user may activate a selected side panel (204) by depressing one of the buttons (254, 262, 266, 270, 272) on the selected side panel. In response to such selection, at least one of the LEDs on the selected side panel (204) may remain steadily illuminated while the LEDs on the other side panel (204) may go dark. In addition, the buttons (254, 262, 266, 270, 272) on the selected side panel may be operable while the buttons (254, 262, 266, 270, 272) on the selected side panel on the other side panel may be rendered inoperable.

In order to change the active status of the selected side panel (204) (e.g., to select the other side panel (204) for activation), the user may depress buttons (254, 262, 266, 270, 272) on both side panels (204) and hold such buttons (254, 262, 266, 270, 272) depressed for a certain time period until the LEDs start to flash. The flashing of the LEDs indicates that holster (200) is ready to accept a new assignment of activation for panels (204). The user may then select the desired active side panel (204) by pressing one of the buttons (254, 262, 266, 270, 272) on the selected side panel (204) and holding such button (254, 262, 266, 270, 272) until the LEDs stop flashing (e.g., for two seconds). In some other versions, the user may just depress at least one button (254, 262, 266, 270, 272) on the inactive side panel (204) for a certain time period either to assign active status to that side panel (204) or to reset holster (200) to accept a new assignment of activation for panels (204). In some other versions, one or more of the above-described user interface features (and/or other user interface features) are incorporated into only one side panel (204) of holster (200). It should also be understood that the above-described functionality and selective activation of buttons (254, 262, 266, 270, 272) may be provided in accordance with at least some of the teachings of, the disclosure of which is incorporated by reference herein U.S. Pat. Pub. No. 2011/0046513, entitled "Multi-Button Biopsy Device," published Feb. 24, 2011; and/or at least some of the teachings of U.S. Provisional Pat. App. No. 61/667,577, entitled "Multi-Button Biopsy Device," filed Jul. 3, 2012, the disclosure of which is incorporated by reference herein.

IV. Exemplary Control Module

In the present example, vacuum control module (400) provides power and control functionality to biopsy device (10); and also provides regulated pneumatics to biopsy device (10). In particular, vacuum control module (400) provides power and control functionality to biopsy device (10) via cable (90); and regulated pneumatics to biopsy device (10) via tubes (20, 30, 40). The pneumatics are regulated through a tube set interface (500), which will be described in greater detail below.

Figure 27A:
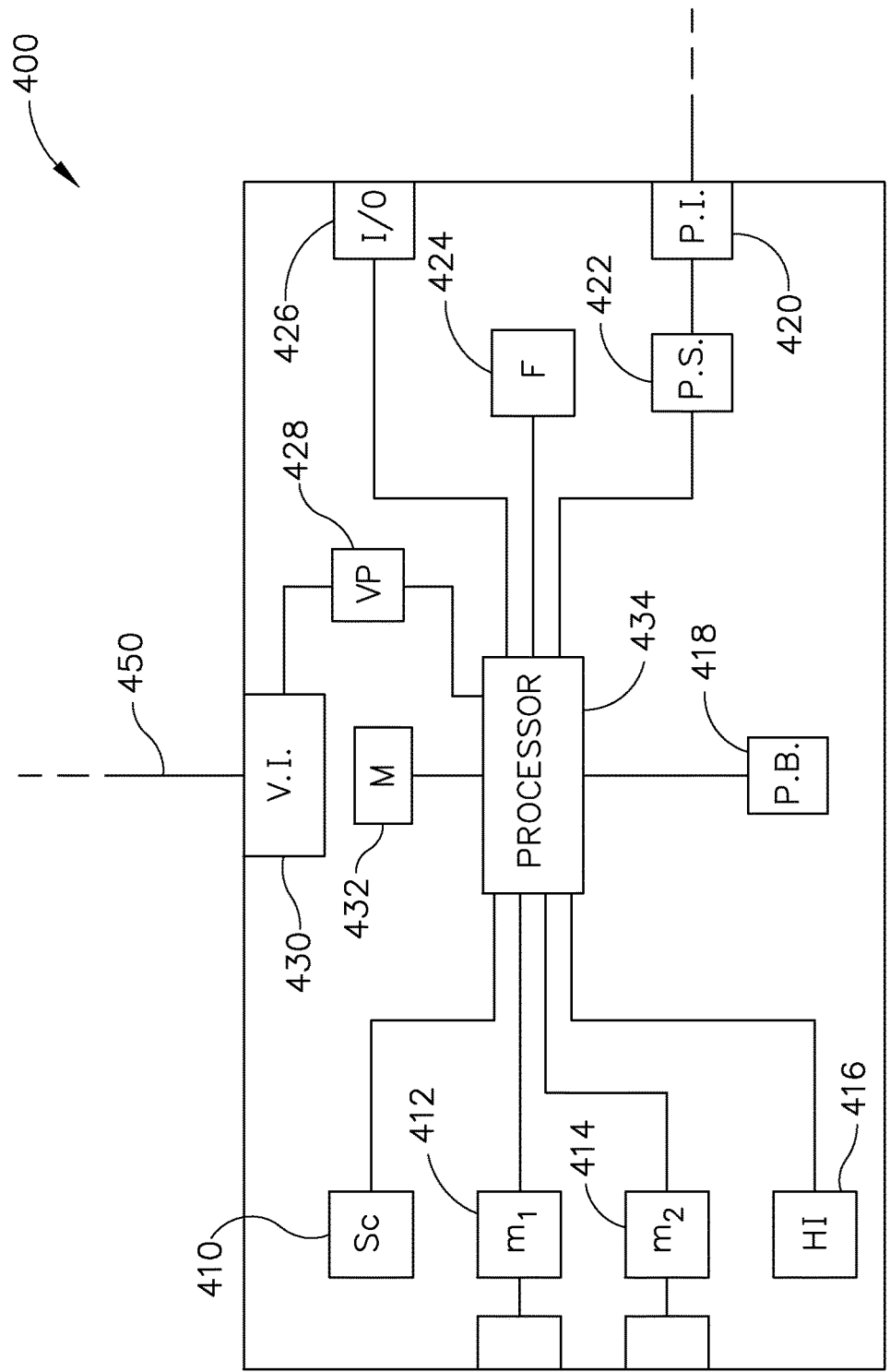
FIG. 27A depicts a basic block schematic view of exemplary components of the vacuum control module of the biopsy system of FIG. 1.
Figure 27B:
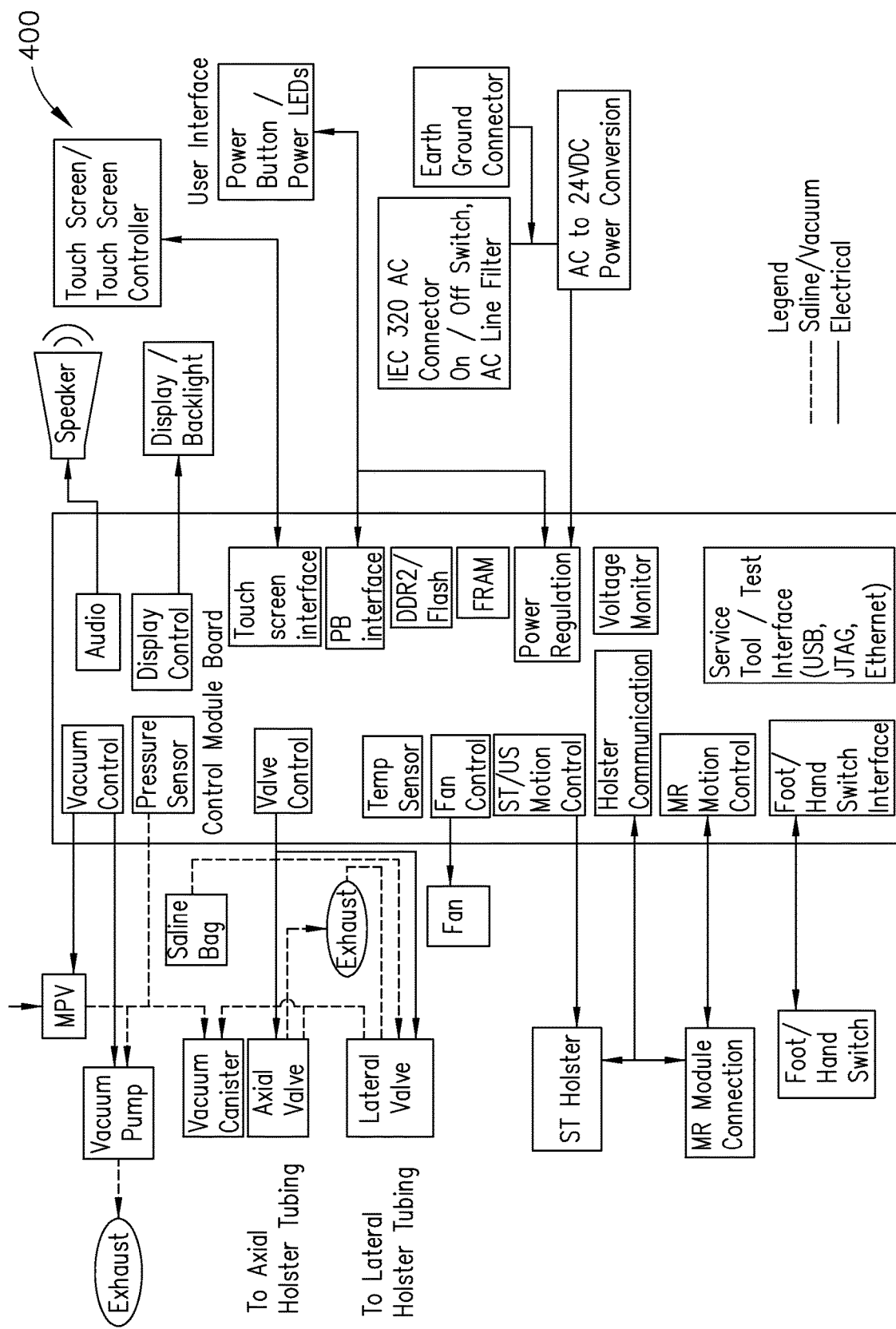
FIG. 27B depicts a detailed block schematic view of exemplary components of the vacuum control module of the biopsy system of FIG. 1.
Figure 28A:
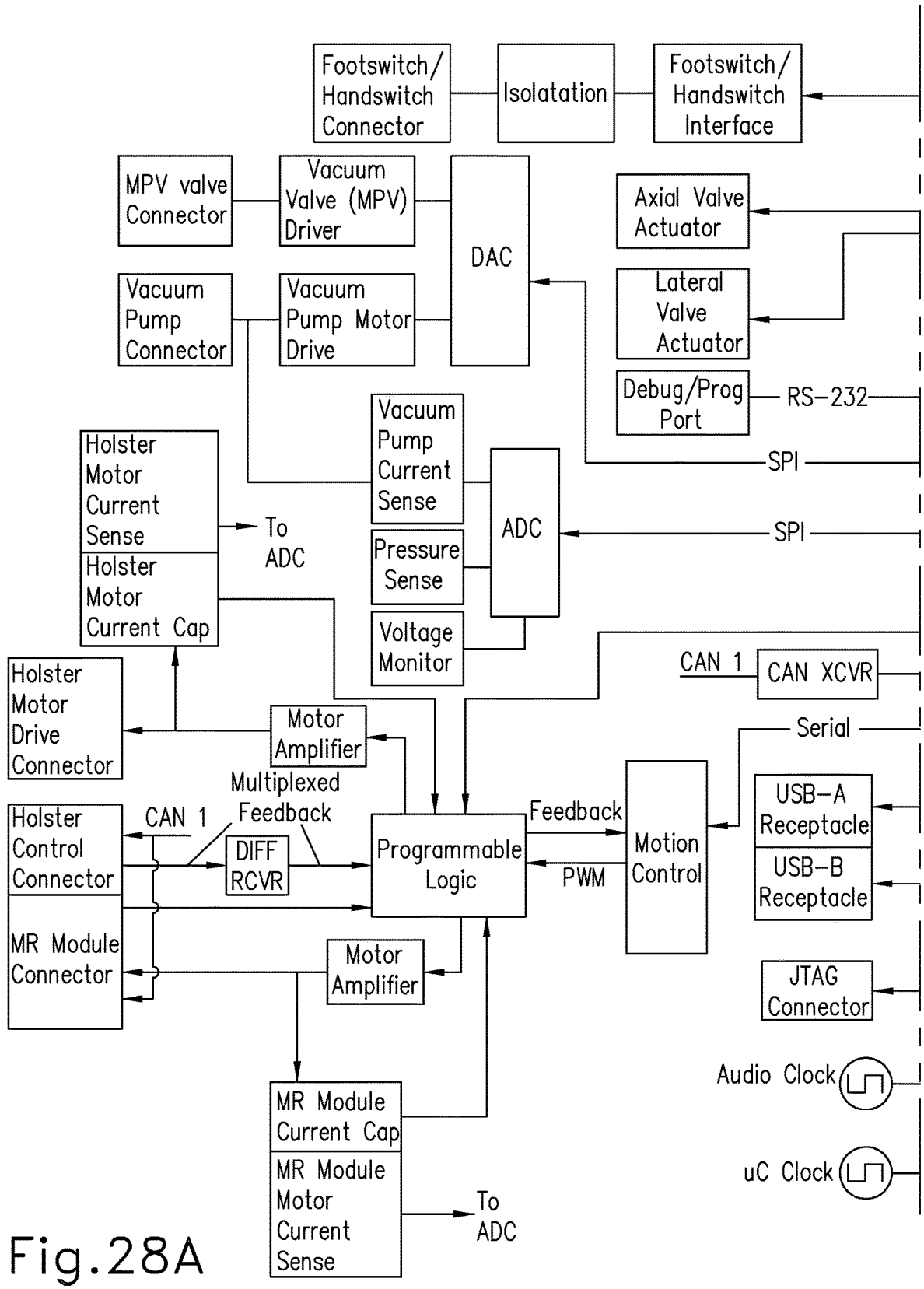
FIGS. 28A-28B together depict a block schematic view of an exemplary controller architecture for the vacuum control module of FIG. 27.
Figure 28B:
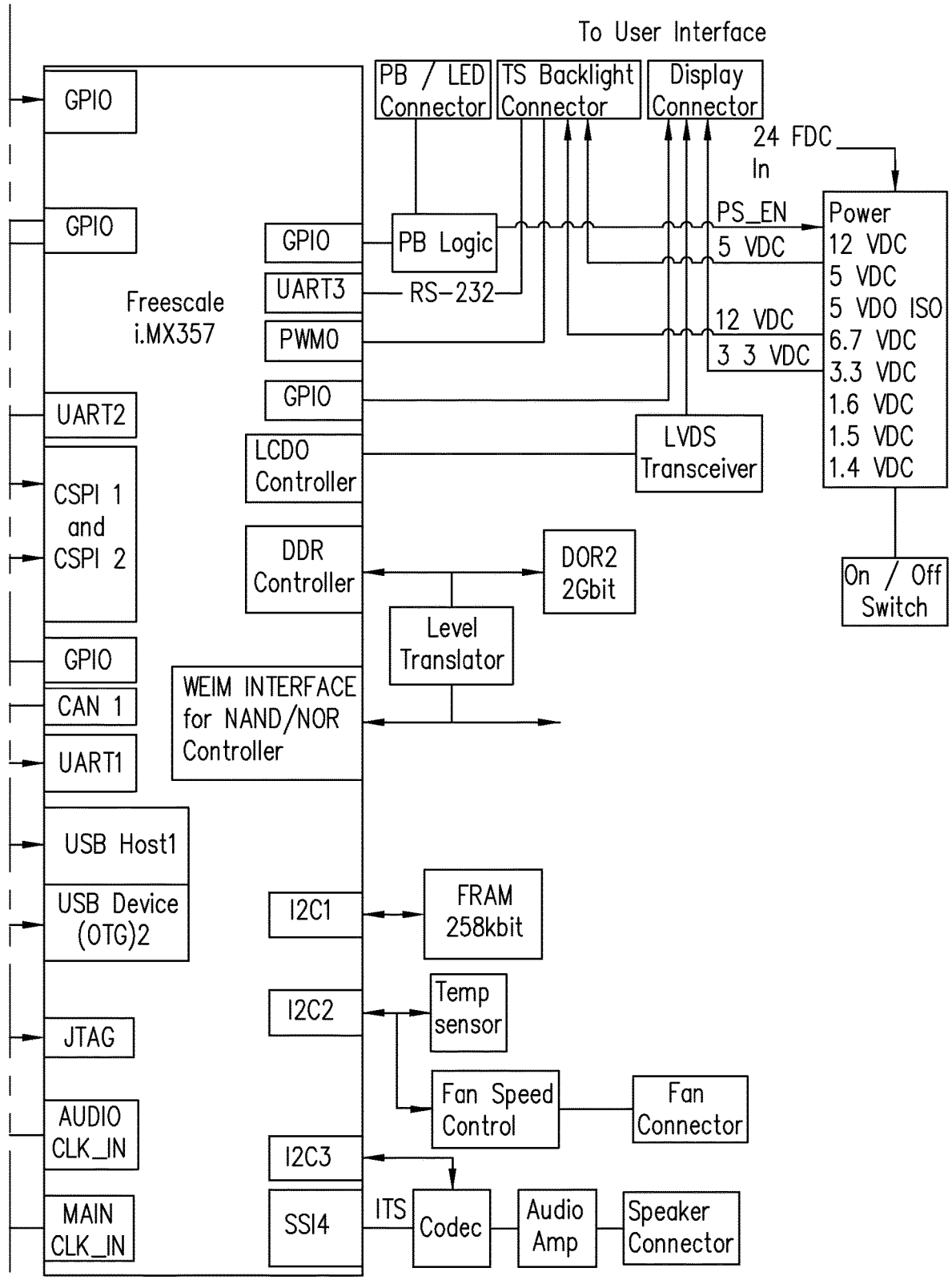

FIGS. 27A-27C show merely exemplary components that may be incorporated into vacuum control module (400). In particular, as shown in FIG. 27A, vacuum control module (27A) of the present example includes a touchscreen (410), a first motor (412), a second motor (414), a holster cable socket (416), a power button (418), a power input (420), a power switch (422), a fan (424), a remote control input (426), a vacuum pump (428), a vacuum interface (430), a memory (432), and a processor (434). Touchscreen (410), motors (412, 414), holster cable socket (416), power button (418), power switch (422), fan (424), remote control input (426), vacuum pump (428), and memory (432) are all in communication with processor (434). Memory (432) stores control algorithms that are executed by processor (434). Processor (434) is also operable to store data on memory (432). In the present example, memory (432) comprises a non-volatile memory. Memory (432) and processor (434) may be formed using conventional components. FIGS. 27B and 28 show additional components and features that may be in communication with processor (434). For instance, FIGS. 27B and 28 show a micro proportional valve (MPV) that is used to regulate vacuum level from vacuum pump (428). In versions having an MPV, the MPV may be controlled by processer (434) via a hardware interface as will be apparent to those of ordinary skill in the art in view of the teachings herein.

Touchscreen (410) serves as a primary interface with the user of system (2), providing information to the user and accepting input from the user. Touchscreen (410) may include conventional touchscreen technology, and may display screens to the user as described in greater detail below.

Motors (412, 414) are operable to drive spool valves in tube set interface (500) as will be described in greater detail below, to thereby execute pneumatic control algorithms through closed loop position control in order to achieve multiple valve states. Motors (412, 414) comprise conventional stepper motors in the present example, though it should be understood that any other suitable type of motor may be used. In other words, motors (412, 414) need not necessarily comprise stepper motors, and may in fact comprise one or more different kinds of motors other than stepper motors.

Socket (416) is operable to receive a plug at the end of cable (90), to thereby provide power to holster (200) and communicate data/commands between holster (200) and vacuum control module (400) in a bi-directional fashion. While a single cable (90) and socket (416) is used in the present example, it should be understood that more than one cable (90) and socket (416) may be used. In addition, while socket (416) and the plug at the end of cable (90) have a proprietary configuration in the present example, these components may alternatively have a conventional configuration.

Power input (420) is configured to receive power from a conventional wall outlet (e.g., 120V at 60 Hz) via a cord. It should also be understood that power input (420) may be configured to receive power from a range of sources including those providing power at 120V-240V and 50 Hz-60 Hz, to function in many global settings without the need for user reconfiguration and without the need for the system itself to be reconfigured to accommodate such varying power sources. In some other versions, vacuum control module (400) includes an integral power source such as one or more batteries. Power switch (422) is operable to selectively complete a circuit between power input (420) and processor (434) as well as other components of system (2), such that power switch (422) serves as a primary power switch. Power button (418) acts as a secondary power switch, and essentially transitions vacuum control module (400) between a standby mode and an active mode. In some versions, power button (418) is simply omitted. It should also be understood that power button (418) may be incorporated into holster (200) if desired.

Fan (424) of the present example comprises a conventional fan that is operable to draw heat away from the above-described components of vacuum control module (400). In some versions, fan (424) runs continuously when vacuum control module is in an active mode. In some other versions, fan (424) only runs when a sensed temperature within vacuum control module (400) exceeds a threshold. As yet another merely illustrative variation, fan (424) may be configured to initially run at a relatively low flow rate by default; then run at a higher flow rate when a sensed temperature within vacuum control module (400) exceeds a threshold.

Remote control input (426) of the present example comprises a socket that is operable to receive a plug (950, 970) from a remote hand control (940) or a foot switch (960), examples of which will be described in greater detail below.

Vacuum pump (428) of the present example comprises a conventional vacuum pump that is operable to create a vacuum. "Vacuum" as used herein should not be read as being limited to a particular level, but should be read broadly enough to encompass at least some level of suction. Vacuum pump (428) is in fluid communication with vacuum interface (430), such that vacuum pump (428) is operable to communicate vacuum through vacuum interface (430). In the present example, vacuum interface (430) comprises a conventional flexible tube (450) that is operable to couple with a conventional vacuum canister (e.g., a Bemis® 800 cc vacuum canister, by Bemis Manufacturing Company of Sheboygan Falls, Wis.). As will be described in greater detail below, the vacuum canister is further in communication with biopsy device (10) via tube set interface (500).

Figure 29:
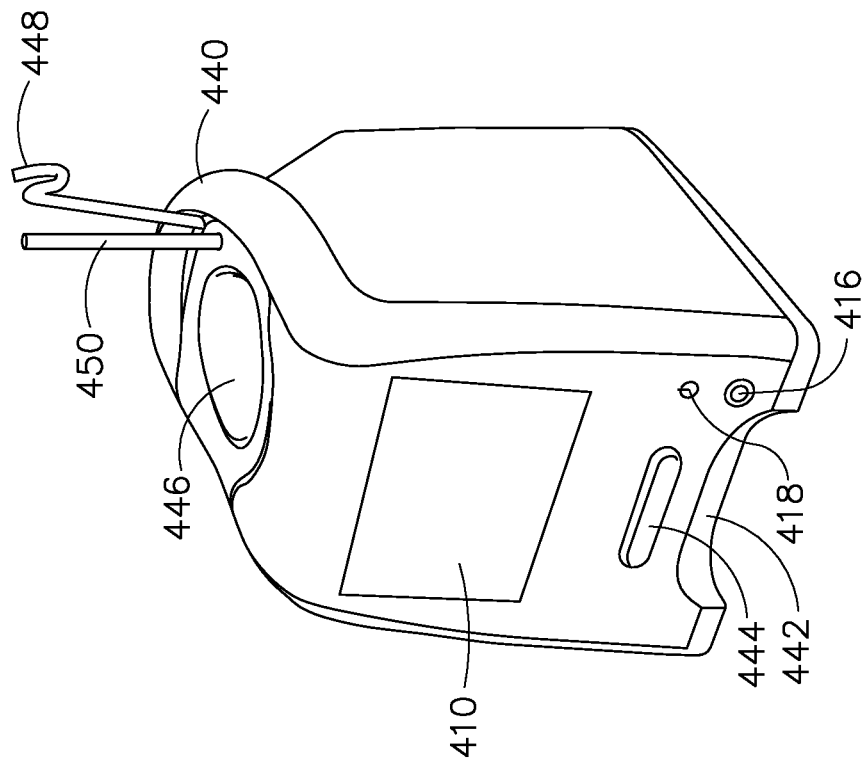
FIG. 29 depicts a perspective view of an exemplary form taken by the vacuum control module of FIG. 27.
Figure 30:
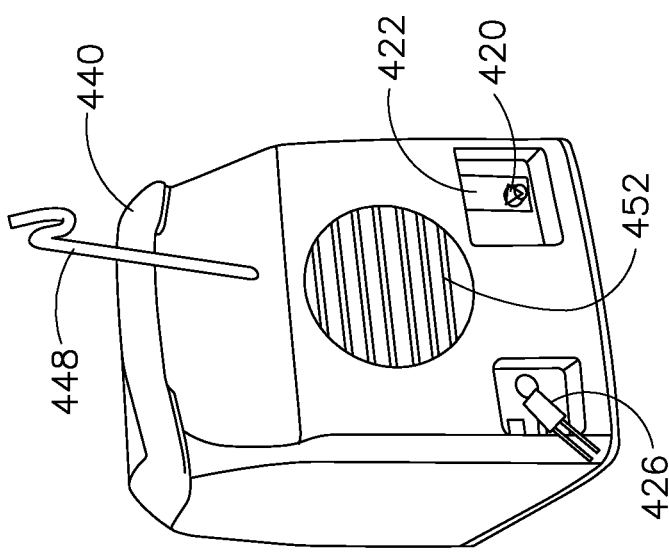
FIG. 30 depicts another perspective view of the vacuum control module of FIG. 29.

FIG. 29 shows an exemplary form that vacuum control module (400) may take. In particular, FIG. 29 shows vacuum control module (400) as including a rear hand grip (440), a front hand grip (442), a tube set interface socket (444), a vacuum canister receptacle (446), a saline pole (448), and an exhaust vent (452). Hand grips (440, 442) facilitate lifting and carrying of vacuum control module (400) by a single person with two hands. Tube set interface socket (440) is configured to couple with tube set interface (500) as will be described in greater detail below. Tube set interface socket (444) includes a pair of exposed spindles that are rotatably driven by motors (412, 414). Vacuum canister receptacle (446) is configured to receive and hold a conventional vacuum canister. Flexible tube (450) is sized and positioned to couple with the vacuum canister that is inserted in vacuum canister receptacle (446). Saline pole (448) includes a hook that is configured to hold a conventional bag of saline. Exhaust vent (452) is configured to provide a vent for heated air forced by fan (424). As also shown, touchscreen (410), holster cable socket (416), and power button (418) are at the front of vacuum control module (400) in this example; while power input (420), power switch (422), and remote control input (426) are at the back of vacuum control module (400) in this example. Of course, vacuum control module (400) may have a variety of alternative components, features, and configurations; and may alternatively take a variety of other forms as will be apparent to those of ordinary skill in the art in view of the teachings herein.

While not shown, it should be understood that vacuum control module (400) may also include a peripheral input/output, may comprise one or more input/output ports of various kinds. By way of example only, such a peripheral input/output may comprise a USB port, an Ethernet port, a wireless adapter, and/or any other suitable type(s) of ports, including combinations thereof. Such a peripheral input/output may be operable to transmit firmware updates and/or additional control algorithms, etc., to processor (434) and memory (432). In addition or in the alternative, a peripheral input/output may be operable to transmit data from vacuum control module (400) to another device, another piece of capital equipment, a hospital database, a remote database, etc. Such transmitted data may relate to operation of system (2) and/or such data may relate to the particular patient. Various suitable ways in which a peripheral input/output may be provided and used will be apparent to those of ordinary skill in the art in view of the teachings herein.

A. Exemplary Tube Set Interface

Figure 31:
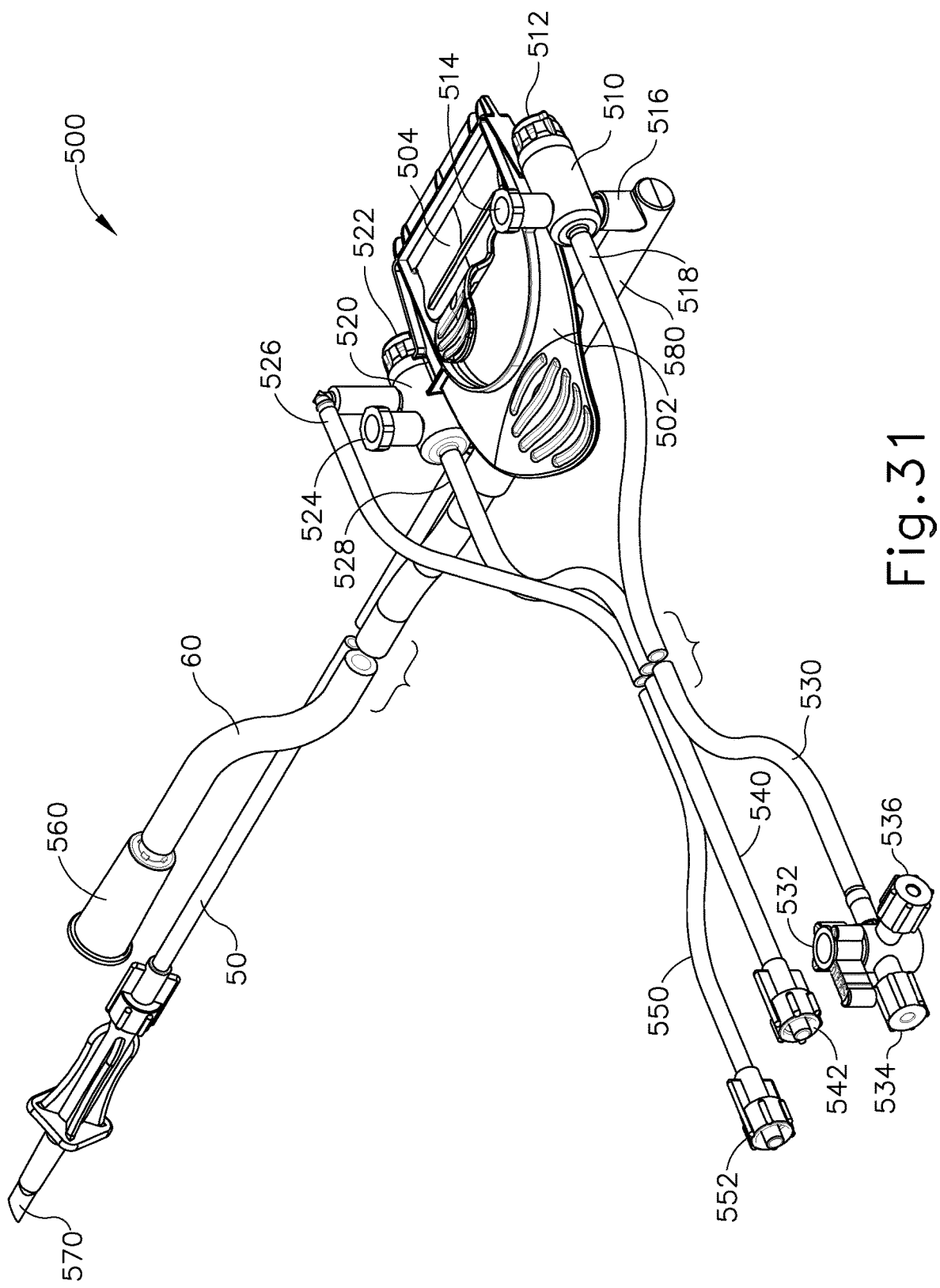
FIG. 31 depicts a perspective view of an exemplary valve assembly and tube set of the biopsy system of FIG. 1.
Figure 32:
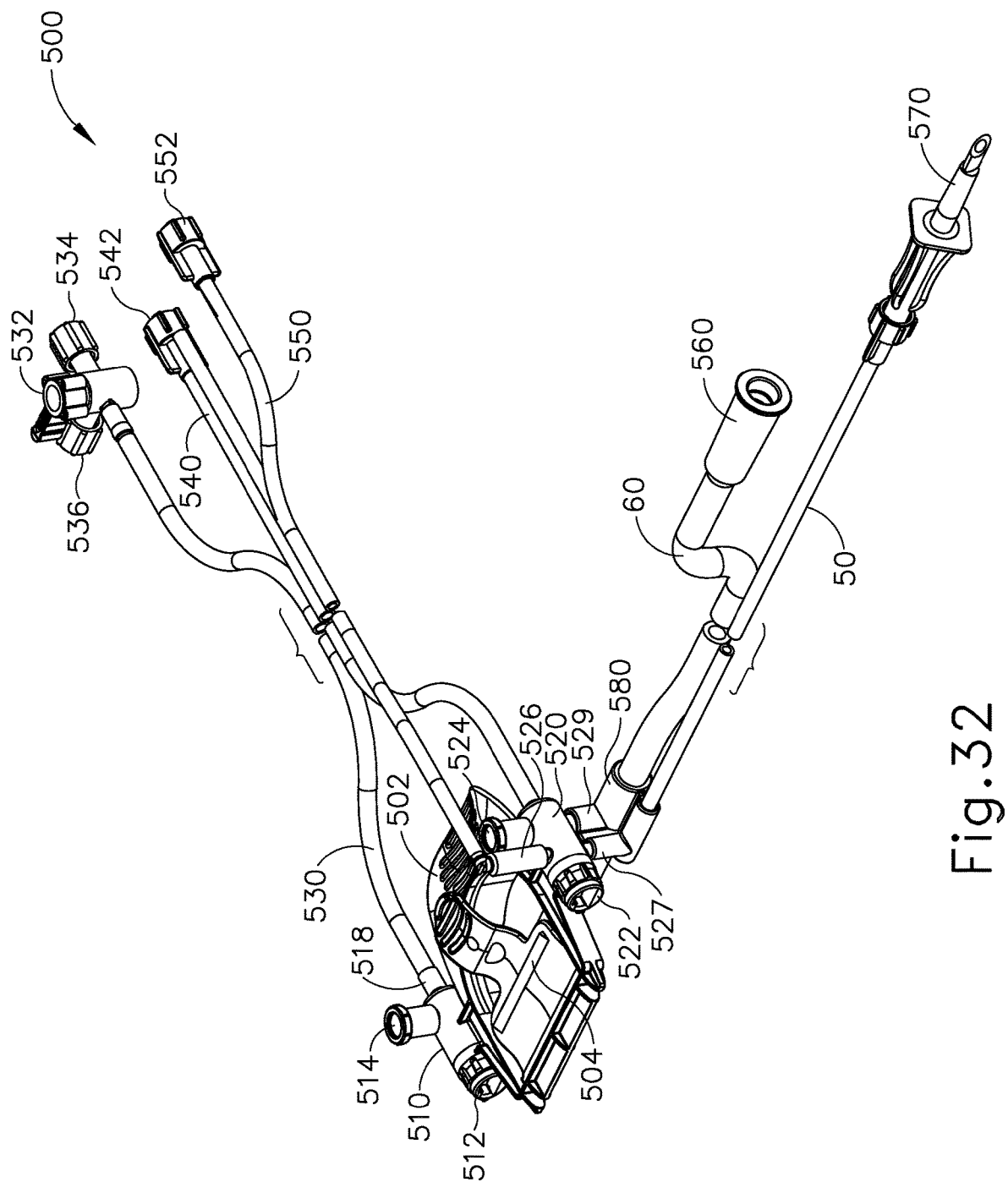
FIG. 32 depicts another perspective view of the valve assembly and tube set of FIG. 31.

FIGS. 31-32 show tube set interface (500) of the present example. In particular, tube set interface (500) includes a frame (502) that has a resilient locking tab (504). Locking tab (504) is configured to releasably couple frame (502) with tube set interface socket (444). Tube set interface (500) further includes a first integral valve body (510) and a second integral valve body (520). First integral valve body (510) includes a rotary actuator (512) that is operable to rotate a spool valve within valve body (510) to change pneumatic states through valve body (510). Rotary actuator (512) is configured to engage the spindle that is driven by first motor (412) when frame (502) is coupled with tube set interface socket (444). Similarly, second integral valve body (520) includes a rotary actuator (522) that is operable to rotate a spool valve within valve body (520) to change pneumatic states through valve body (520). Rotary actuator (522) is configured to engage the spindle that is driven by second motor (414) when frame (502) is coupled with tube set interface socket (444).

Valve body (510) also includes a first port (514), second port (516), and third port (518). First port (514) is in communication with atmospheric air, and includes a filter. Second port (516) is coupled with a vacuum manifold (580). Third port (518) is in communication with a tube (530). Tube (530) includes a stopcock (532) that is operable to selectively place a leur fitting (534) in communication with either tube (530) or leur fitting (536). Luer fitting (534) is configured to couple with tube (20), such that tube (530) may ultimately communicate with lumen (151) of cutter (150). Luer fitting (536) is configured to serve as an injection port, enabling administration of medicine etc., through lumen (151) of cutter (150). For instance, while needle (110) is inserted in a patient's breast, the user may at least partially retract cutter (150), couple a source of medicine with leur fitting (536), switch stopcock (536) to couple luer fitting (536) with leur fitting (534), then administer the medicine through these components to reach the patient's breast via lateral aperture (114). When this is being done, it may be desirable to secure clip (48) to tube (46), shown in FIG. 4, to reduce leakage of the injected medicine back through tube (46). It should be understood that stopcock (532) may be switched to effectively seal off leur fitting (536) during the actual biopsy procedure of tissue sampling. The spool valve within valve body (510) is operable to selectively couple third port (518) with either first port (514), second port (516), or neither (i.e., thereby effectively sealing third port (518)), based on the rotational position of the spool valve, in accordance with the control algorithms described below.

Valve body (520) includes a first port (524), second port (526), third port (528), fourth port (527), and fifth port (529). First port (524) is in communication with atmospheric air, and includes a filter. Second port (526) is coupled with a tube (550), which is further coupled with a leur fitting (552). Second port (526) and tube (550) are configured to communicate saline based on the operational position of the spool valve within valve body (520). Third port (528) is coupled with a tube (540), which is further coupled with a leur fitting (542). Third port (528) and tube (540) are configured to communicate vacuum based on the operational position of the spool valve within valve body (520). Fourth port (527) is in communication with tube (50), which is further in communication with saline port (570). Saline port (570) is configured to couple with a saline bag (80) as shown in FIG. 1. Fifth port (529) is in communication with vacuum manifold (580), which is in communication with tube (60). Tube (60) is in communication with a port (560), which is configured to couple with vacuum canister (70). The spool valve within valve body (520) is operable to selectively couple second and third ports (526, 528) with either first port (524), fourth port (527), fifth port (529), or none of the above (i.e., thereby effectively sealing second port (526) and/or third port (528)), based on the rotational position of the spool valve, in accordance with the control algorithms described below.

Luer fitting (552) is configured to couple with leur fitting (32), which is coupled with tube (30). As shown in FIG. 4, tube (30) is coupled with Y-connector (44), which is further coupled with tube (46). As described above, tube (46) is coupled with manifold (122). Thus, tubes (30, 550) are ultimately in fluid communication with second lumen (192) of needle (110). Leur fitting (552) is configured to couple with leur fitting (42), which is coupled with tube (40). Tube (40) is also coupled with Y-connector (44). Thus, tubes (40, 540) are also ultimately in fluid communication with second lumen (192) of needle (110).

By way of example only, tube set interface (500) may be constructed in accordance with at least some of the teachings of U.S. patent application Ser. No. 13/765,931, entitled "Biopsy Device Valve Assembly," filed Feb. 13, 2013, the disclosure of which is incorporated by reference herein. Other suitable configurations for tube set interface (500) will be apparent to those of ordinary skill in the art in view of the teachings herein. It should also be understood that at least some of the valving functionality of tube set interface (500) may be incorporated into biopsy device (10) and/or into vacuum control module (400). For instance, the valving functionality may instead be provided by a combination of solenoids and a vacuum canister lid in a system of pinch valves as described in U.S. Pat. Pub. No. 2008/0214955, the disclosure of which is incorporated by reference herein.

B. Exemplary Graphical User Interface

As noted above, vacuum control module (400) includes a touchscreen (410) that serves as a primary graphical user interface feature for vacuum control module (400). Examples of interactive screens that may be displayed through touchscreen (410) will be described in greater detail below, while further examples will be apparent to those of ordinary skill in the art in view of the teachings herein. It should also be understood that vacuum control module (400) may further include various other kinds of user interface features, including but not limited to various kinds of buttons, dials, knobs, sliders, a microphone, a speaker, etc.

1. Exemplary Setup Screens

FIGS. 33A-33D show exemplary screens (600, 620, 640, 660) that may be displayed on touchscreen (410) during setup of biopsy system (2). In particular, screen (600) shown in FIG. 33A includes a graphical representation (602) of holster (200) and a graphical representation (604) of vacuum control module (400), with a textual instruction (606) to attach holster (200) to vacuum control module (400). Screen (600) also includes a volume adjustment button (608), a brightness adjustment button (610), and an accessory attachment indication field (612). If the user taps volume adjustment button (608), a sub-screen will pop up enabling the user to select a volume level for audio feedback emitted by vacuum control module (400). If the user taps brightness adjustment button (610), a sub-screen will pop up enabling the user to select a brightness level for touchscreen (410). Accessory attachment indication field (612) provides a visual indication of an accessory attached to vacuum control module (400). In the view depicted in FIG. 33A, a graphical representation (614) of a footswitch is shown in accessory attachment indication field (612), indicating that a footswitch is coupled with remote control input (426). An exemplary footswitch (960) and other exemplary accessories will be described in greater detail below.

Figure 33A:
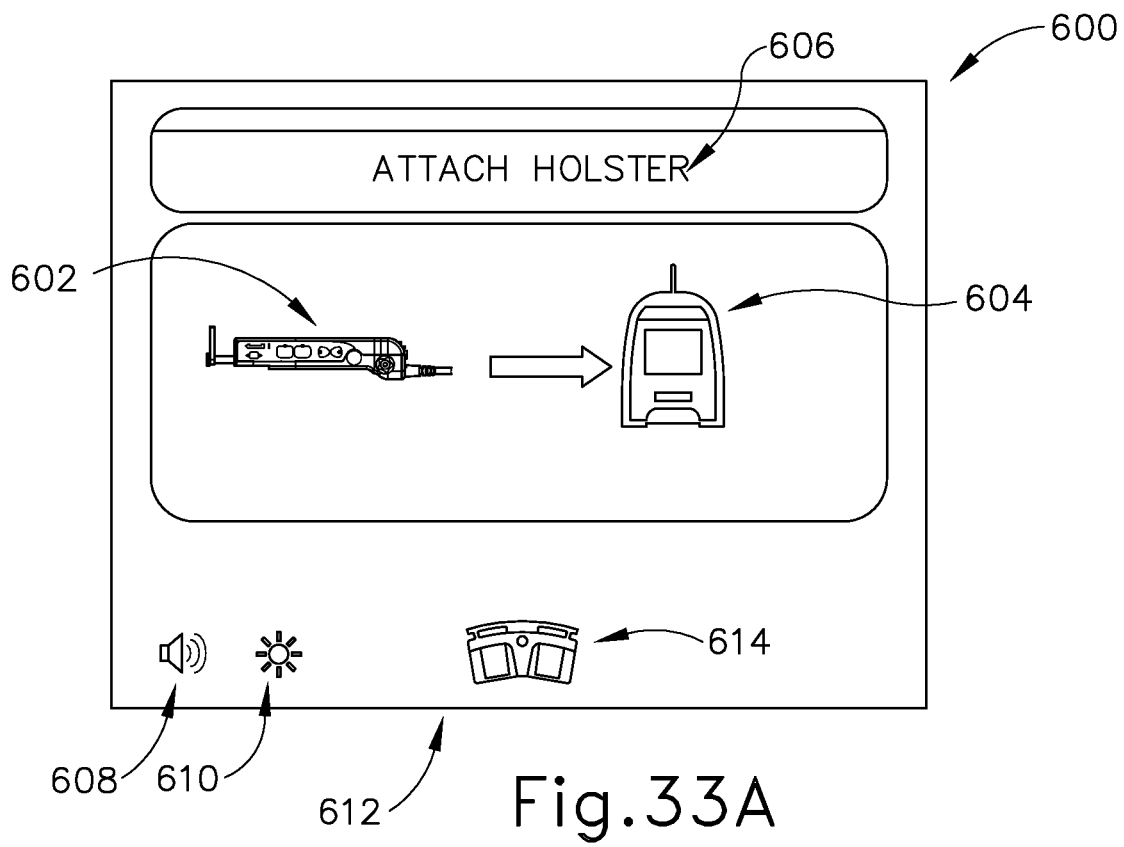
FIG. 33A depicts an exemplary first user interface screen for display on the vacuum control module of FIG. 27.
Figure 33B:
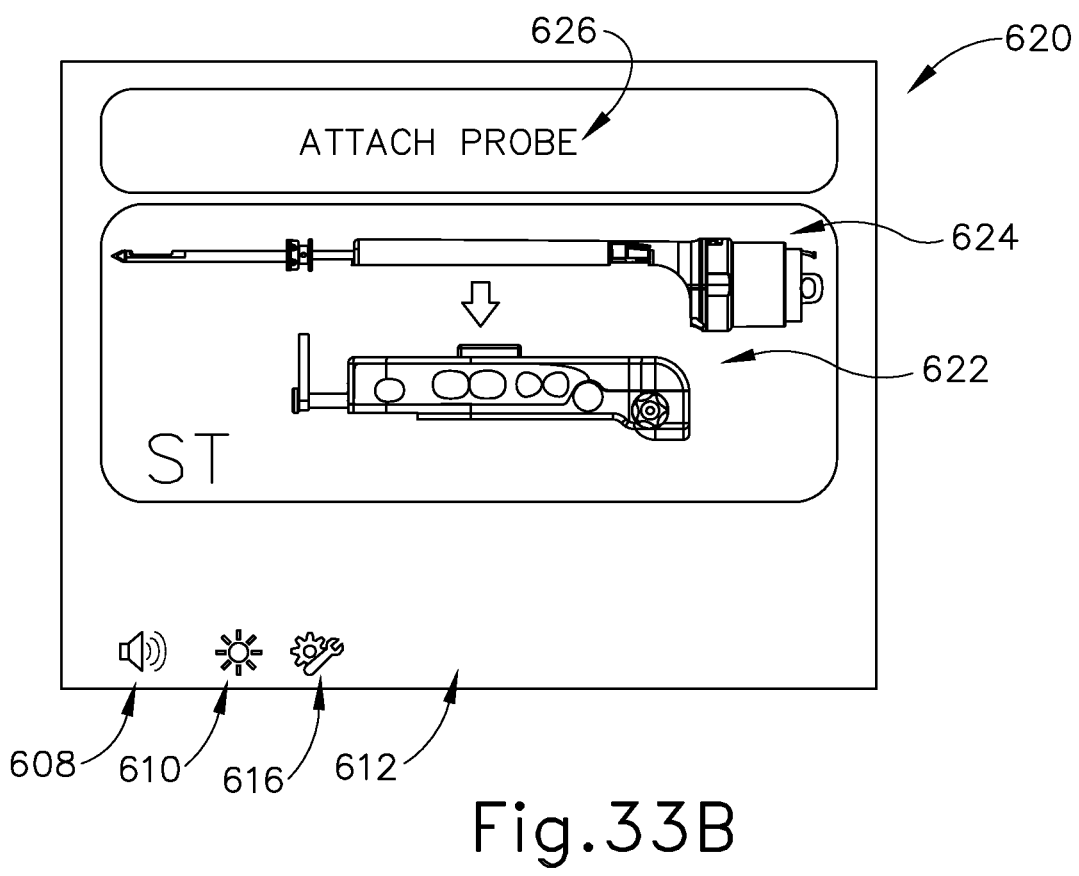
FIG. 33B depicts an exemplary second user interface screen for display on the vacuum control module of FIG. 27.

As soon as the user plugs cable (90) into holster cable socket (416), touchscreen (410) automatically transitions to screen (620) shown in FIG. 33B. It should therefore be understood that vacuum control module (400) includes circuitry configured to sense when cable (90) is plugged into holster cable socket (416). Various forms that such circuitry may take will be apparent to those of ordinary skill in the art in view of the teachings herein. Screen (620) includes a graphical representation (622) of holster (200) and a graphical representation (624) of probe (100), with a textual instruction (626) to attach probe (100) to holster (200). Screen (600) also includes volume adjustment button (608), brightness adjustment button (610), accessory attachment indication field (612), and a settings adjustment button (616). Accessory attachment indication field (612) is empty in this example, indicating that neither a footswitch nor any other accessory is coupled with control input (426). If the user taps settings adjustment button (616), a sub-screen will pop up enabling the user to adjust various settings for vacuum control module (400) (e.g., language, etc.).

Figure 33C:
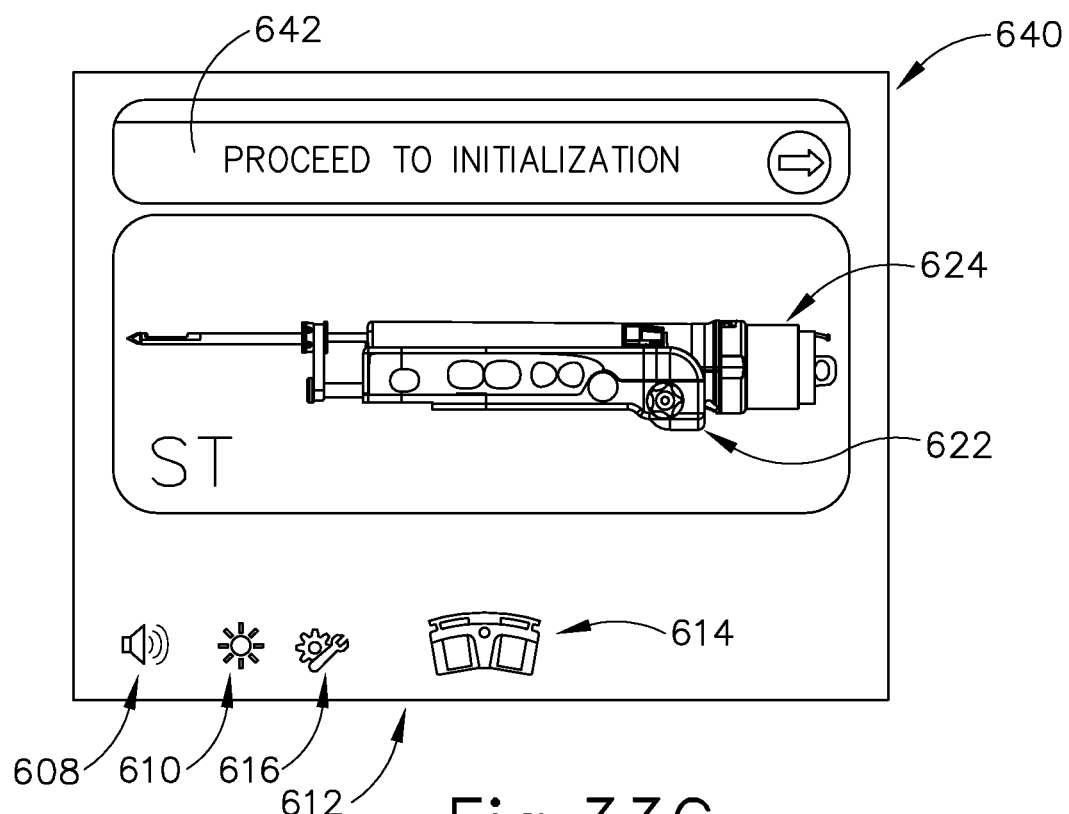
FIG. 33C depicts an exemplary third user interface screen for display on the vacuum control module of FIG. 27.

Once the user attaches probe (100) to holster (200), touchscreen (410) automatically transitions to screen (640). As noted above, a magnet in probe (100) and corresponding sensor in holster (200) are operable to provide sensing of attachment between probe (100) and holster (200), and such sensing is communicated to vacuum control module (400) via cable (90). In some instances, probe (100) may already be coupled with holster (200) before cable (90) is coupled with holster cable socket (416). In some such instances, vacuum control module (400) senses this and simply skips screen (620), transitioning directly from screen (600) to screen (640). As shown in FIG. 33C, screen (640) includes graphical representation (624) of probe (100) coupled with graphical representation of holster (200), as well as a textual invitation (642) to proceed to initialization. When the user taps on textual invitation (642), biopsy system (2) runs through an initialization algorithm as will be described in greater detail below.

Figure 33D:
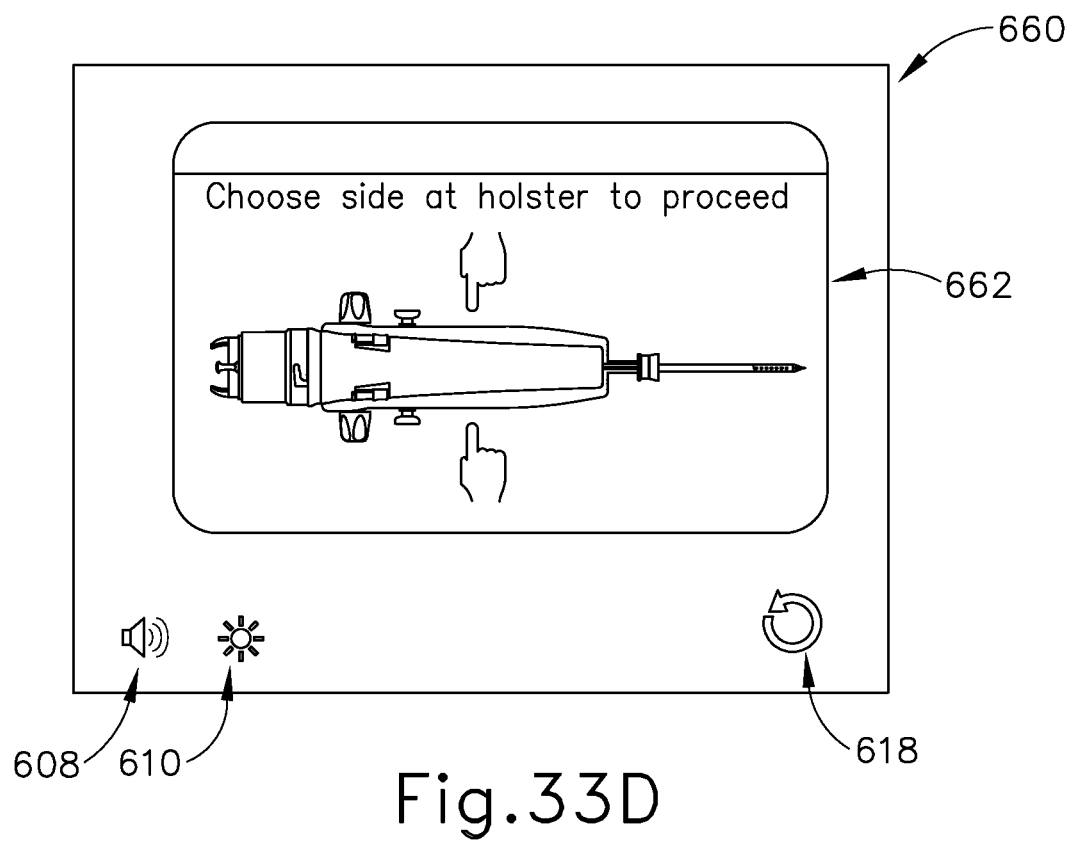
FIG. 33D depicts an exemplary fourth user interface screen for display on the vacuum control module of FIG. 27.

When that initialization process is complete, touchscreen (410) automatically transitions to screen (660). As shown in FIG. 33D, screen (660) includes an instruction (662) to choose a particular side of holster (200) for activation. At this stage the user must choose which side panel (204) will have active buttons (254, 262, 266, 270, 272) as described above. For instance, the user may press one or more of buttons (254, 262, 266, 270, 272) on the preferred side panel (204) to select the preferred side panel (204). Until the user makes this selection, the LEDs on both side panels (204) may flash as described above. As also shown in FIG. 33D, screen (660) includes a standby button (618) that is operable to toggle biopsy system (2) between an active mode and a standby mode. It should be understood that other screens may also include standby button (618); or that standby button (618) may simply be omitted.

Figure 33E:
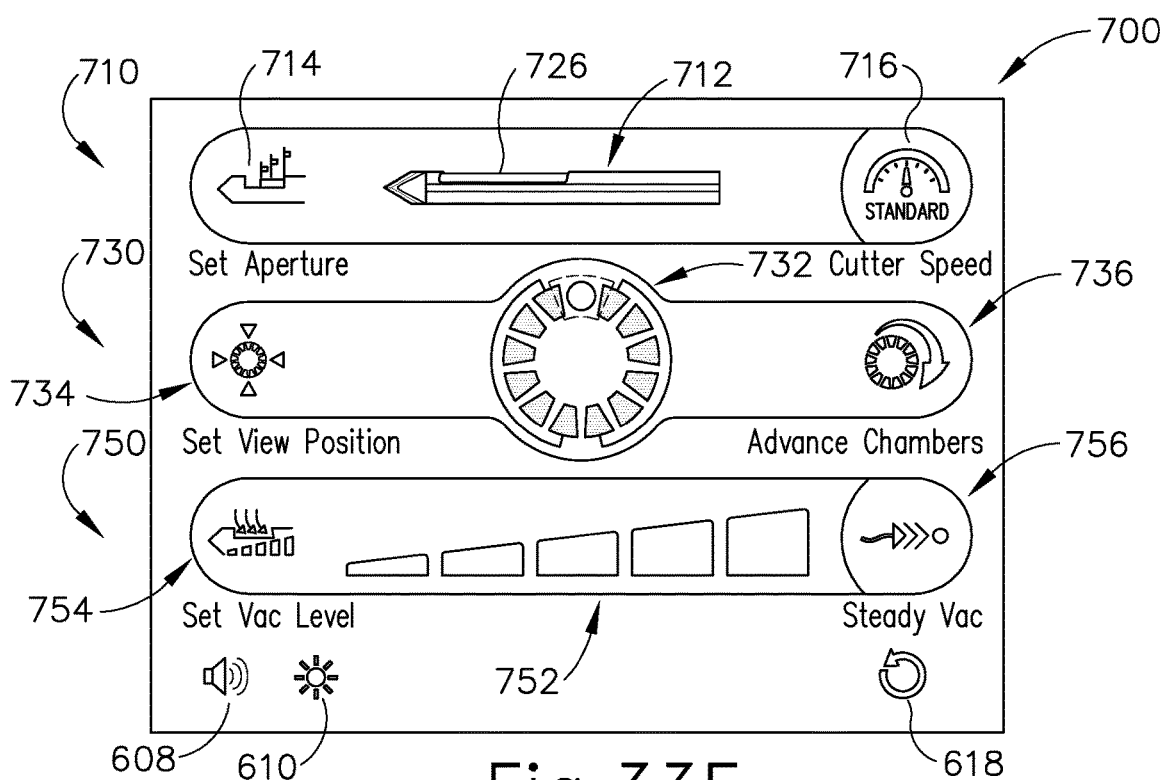
FIG. 33E depicts an exemplary fifth user interface screen for display on the vacuum control module of FIG. 27.

After the user has selected a particular side panel (204) for activation, touchscreen (410) automatically transitions to screen (700). As shown in FIG. 33E, screen (700) includes a cutter control region (710), a tissue sample holder control region (730), and a vacuum control region (750). Regions (710, 730, 750) extend horizontally and are vertically stacked relative to each other, though it should be understood that regions (710, 730, 750) may be provided in numerous other ways as will be apparent to those of ordinary skill in the art in view of the teachings herein. Exemplary features and operabilities of regions (710, 730, 750) will be described in greater detail below, with reference to FIGS. 33E-33I. In some instances where a biopsy procedure is interrupted, touchscreen (410) may transition to screen (840), shown in FIG. 33J. By way of example only, screen (840) may be displayed when a user taps standby button (618). This screen (840) is substantially similar to screen (640) shown in FIG. 33C, except that this screen (840) includes an invitation (642) to return to the biopsy procedure. When a user taps invitation (642), touchscreen (410) may revert back to screen (700) shown in FIG. 33E.

2. Exemplary Cutter Interface Features

As shown in FIG. 33E, cutter control region (710) of screen (700) includes a graphical representation (712) of the distal end of needle (110), a graphical representation (726) of cutter (150), a "set aperture" button (714), a cutter speed adjustment button (716). When a user taps cutter speed adjustment button (716), a submenu pops up enabling the user to select from available speeds for advancement of cutter (150). For instance, the submenu may enable selection from slow, standard, and fast speeds. By way of example only, motor (244) may rotate at approximately 20000 RPM during advancement of cutter (150) when slow speed is selected and at approximately 12000 RPM during retraction of cutter when slow speed is selected. Motor (244) may rotate at approximately 20000 RPM during advancement of cutter (150) when standard speed is selected and at approximately 20000 RPM during retraction of cutter when standard speed is selected. Motor (244) may rotate at approximately 25000 RPM during advancement of cutter (150) when fast speed is selected and at approximately 25000 RPM during retraction of cutter when fast speed is selected. Of course, any other suitable speeds may be used. The user may select one of these speeds based on the nature of the tissue being biopsied and/or based on other considerations.

In one merely illustrative alternative version, when the user taps on cutter speed adjustment button (716) a submenu pops up enabling the user to select from various biopsy modes, some of which may provide different cutter speeds, different saline usage, and/or other variations. For instance, in some versions, the biopsy modes include a "low saline" biopsy mode, a "standard" speed biopsy mode, and a "high" speed biopsy mode. By way of example only, motor (244) may rotate at approximately 20000 RPM during advancement of cutter (150) when "low saline" biopsy mode or "standard" speed biopsy mode is selected; and at approximately 20000 RPM during retraction of cutter (150) when "low saline" biopsy mode or "standard" speed biopsy mode is selected. Motor (244) may rotate at approximately 25000 RPM during advancement of cutter (150) when "high" speed biopsy mode is selected and at approximately 25000 RPM during retraction of cutter when "high" speed biopsy mode is selected. Of course, any other suitable speeds may be used. The user may select one of these speeds based on the nature of the tissue being biopsied and/or based on other considerations. For instance, the "low saline" biopsy mode may be selected for alternative tissue types; the "standard" speed biopsy mode for standard tissue types; and the "high" speed biopsy mode for providing relatively high cutter speeds to obtain more tissue samples in a shorter time period than would otherwise be obtained in the other modes.

Of course, as with other features of vacuum control module (400) described herein, cutter speed adjustment button (716) may be omitted if desired. For instance, some versions may provide advancement of cutter (150) in only one speed.

Figure 33F:
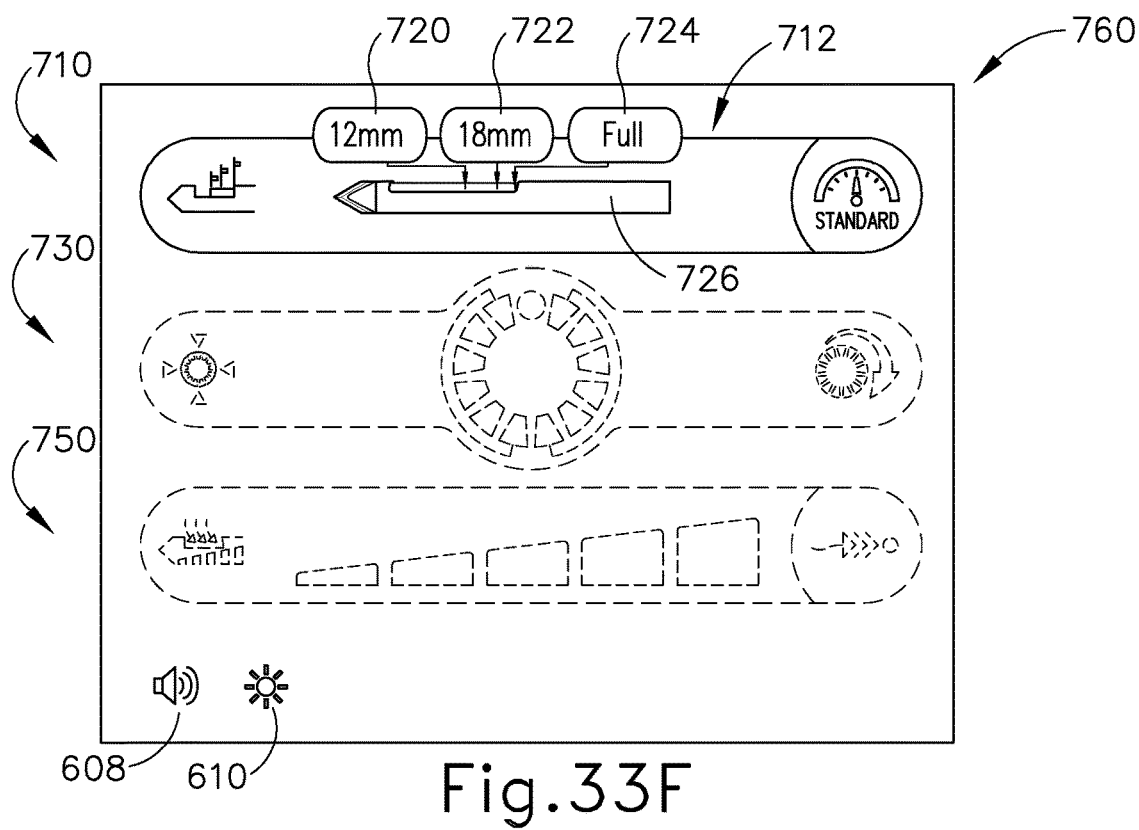
FIG. 33F depicts an exemplary sixth user interface screen for display on the vacuum control module of FIG. 27.

When the user taps on "set aperture" button (714), touchscreen (410) transitions to the screen (760) shown in FIG. 33F. Screen (760) is generally similar to screen (700), except that regions (730, 750) are dark, buttons (714, 716) are dark, and additional buttons (720, 722, 724) appear over graphical representation (712) of the distal end of needle (110). Buttons (720, 722, 724) enable the user to set the proximal-most position for distal edge (152) of cutter (150) during operation of biopsy device (100). In particular, button (720) establishes a proximal-most position for distal edge (152) of cutter (150) during operation of biopsy device (100) whereby lateral aperture (114) is only opened 12 mm by cutter (150) before cutter (150) advances distally. Button (722) establishes a proximal-most position for distal edge (152) of cutter (150) during operation of biopsy device (100) whereby lateral aperture (114) is only opened 18 mm by cutter (150) before cutter (150) advances distally. Button (724) establishes a proximal-most position for distal edge (152) of cutter (150) during operation of biopsy device (100) whereby lateral aperture (114) is fully opened by cutter (150) before cutter (150) advances distally. Of course, these increments are mere examples, and any other suitable increments may be used. In the present example, biopsy system (2) will default to a fully opened aperture (114) setting in the event that the user does not select a different aperture size through screen (760).

When a user taps a particular button (720, 722, 724), screen (760) provides feedback by positioning the graphical representation (726) of cutter (150) such that the distal end of graphical representation (726) corresponds with the position just selected by the user. This positioning of graphical representation (726) may persist until the positioning is later changed by the user. For instance, FIG. 33I shows graphical representation (726) in the 18 mm position during use of biopsy device (100).

By way of example only, system (2) may provide the above-described "variable aperture" functionality in accordance with at least some of the teachings of U.S. Pat. No. 7,517,322, entitled "Biopsy Device with Variable Side Aperture," issued Apr. 14, 2009, the disclosure of which is incorporated by reference herein; and/or in accordance with at least some of the teachings of U.S. Pat. Pub. No. 2008/0214955, the disclosure of which is incorporated by reference herein. In some versions, the graphical representation (726) of cutter (150) as described above is provided in a first color; while a second graphical representation of cutter (150) is provided in a second color. This second graphical representation may show the actual position of cutter in real time. Thus, the graphical representations (712, 726) may operate in a substantially similar manner as cutter position indicator (250) on holster (200).

It should be understood that the foregoing features relating to control of cutter (150) through touchscreen (410) are merely illustrative examples; and that they may be modified, substituted, supplemented, or omitted as desired. Various other features that may be used to provide control of cutter (150) through touchscreen (410) will be apparent to those of ordinary skill in the art in view of the teachings herein.

3. Exemplary Tissue Sample Holder Interface Features

As shown in FIG. 33E, tissue sample holder control region (730) of screen (700) includes a graphical representation (732) of tissue sample holder (300), a "set view position" button (734), and an "advance chambers" button (736). "Set view position" button (734) enables a user to select which side of tissue sample holder (300) will be designated for presentation of tissue samples each time a tissue sample is acquired. In particular, the user may select from four positions for tissue sample presentation—the 12 o'clock position, the 3 o'clock position, the 6 o'clock position, and the 9 o'clock position. These positions correspond to the angular positions about the central axis of tissue sample holder (300). Of course, any other suitable position options may be provided. The user may select a position to provide the user with the best visibility of severed tissue samples, based on considerations such as the user's physical location in relation to biopsy device (10), the location of adjacent equipment, etc. It should be understood that one of the above-listed positions (or some other position), such as the 12 o'clock position, may be automatically selected by default, in the event that the user does not affirmatively select a presentation position through set view position" button (734). Further details of tissue sample presentation are described in greater detail below. Additional details relating to examples of tissue sample presentation are described in U.S. Pat. Pub. No. 2008/0214955, the disclosure of which is incorporated by reference herein.

Figure 33G:
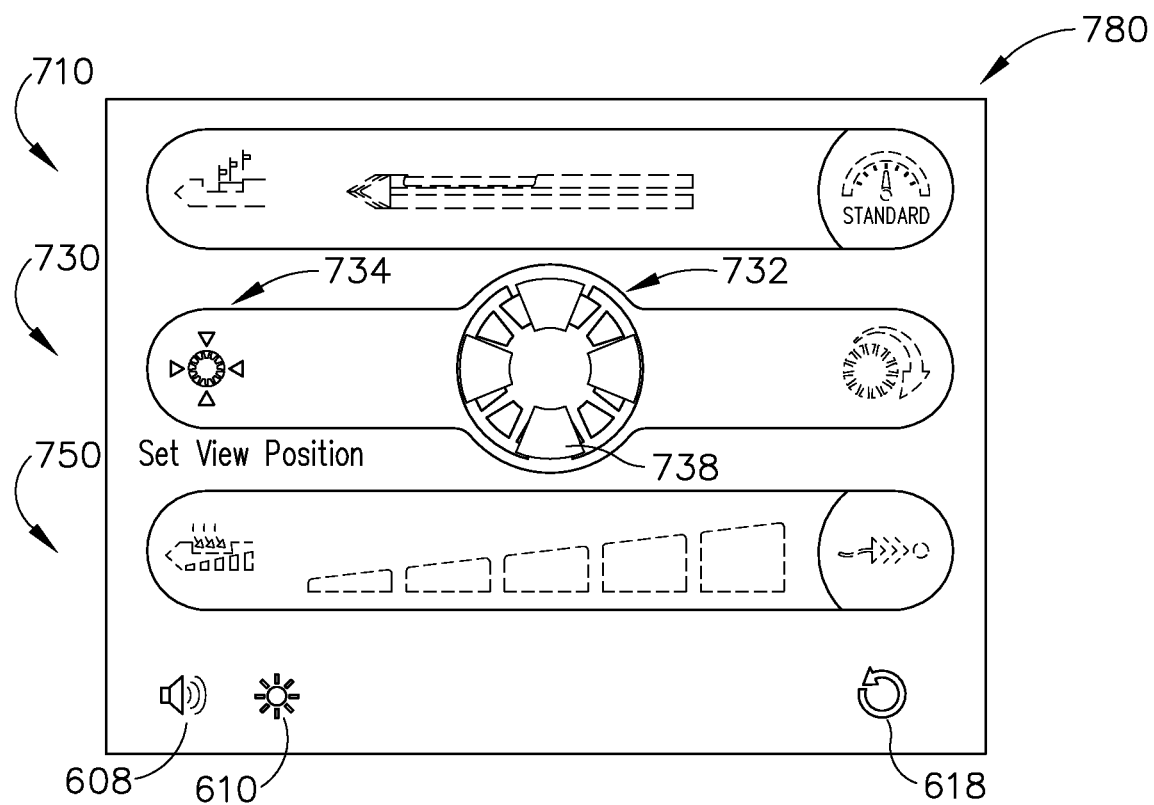
FIG. 33G depicts an exemplary seventh user interface screen for display on the vacuum control module of FIG. 27.
Figure 33H:
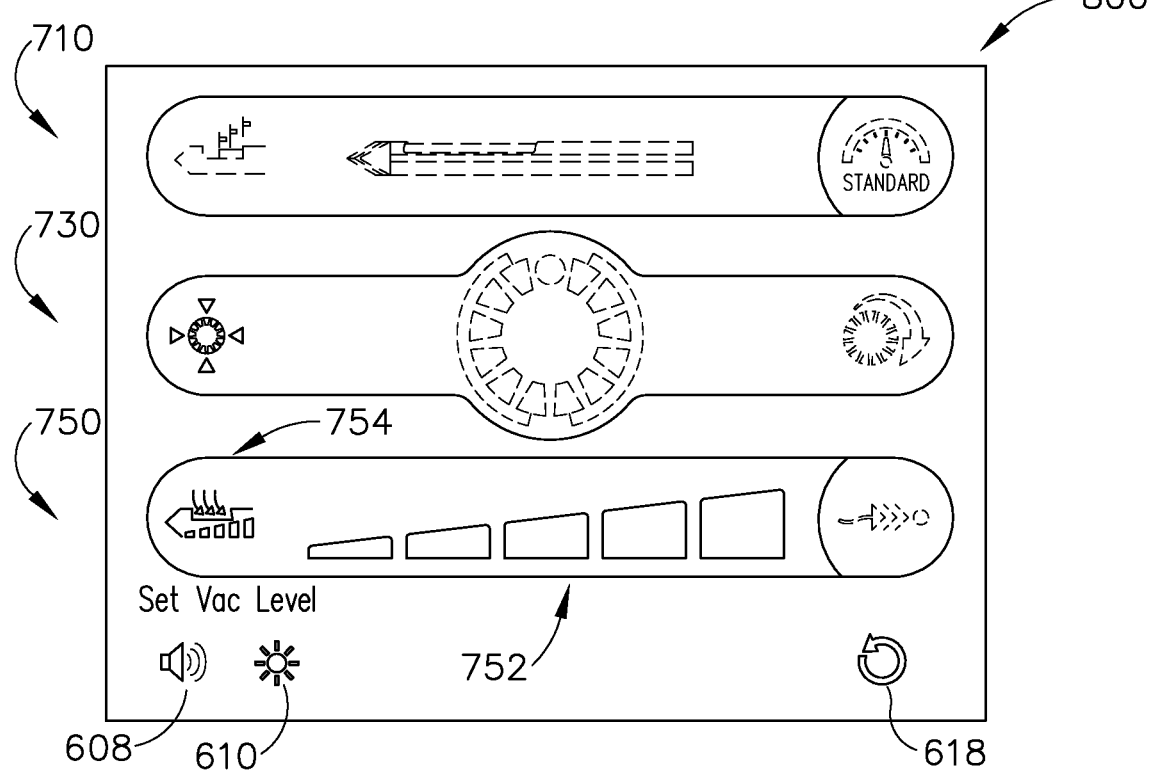
FIG. 33H depicts an exemplary eighth user interface screen for display on the vacuum control module of FIG. 27.
Figure 33I:
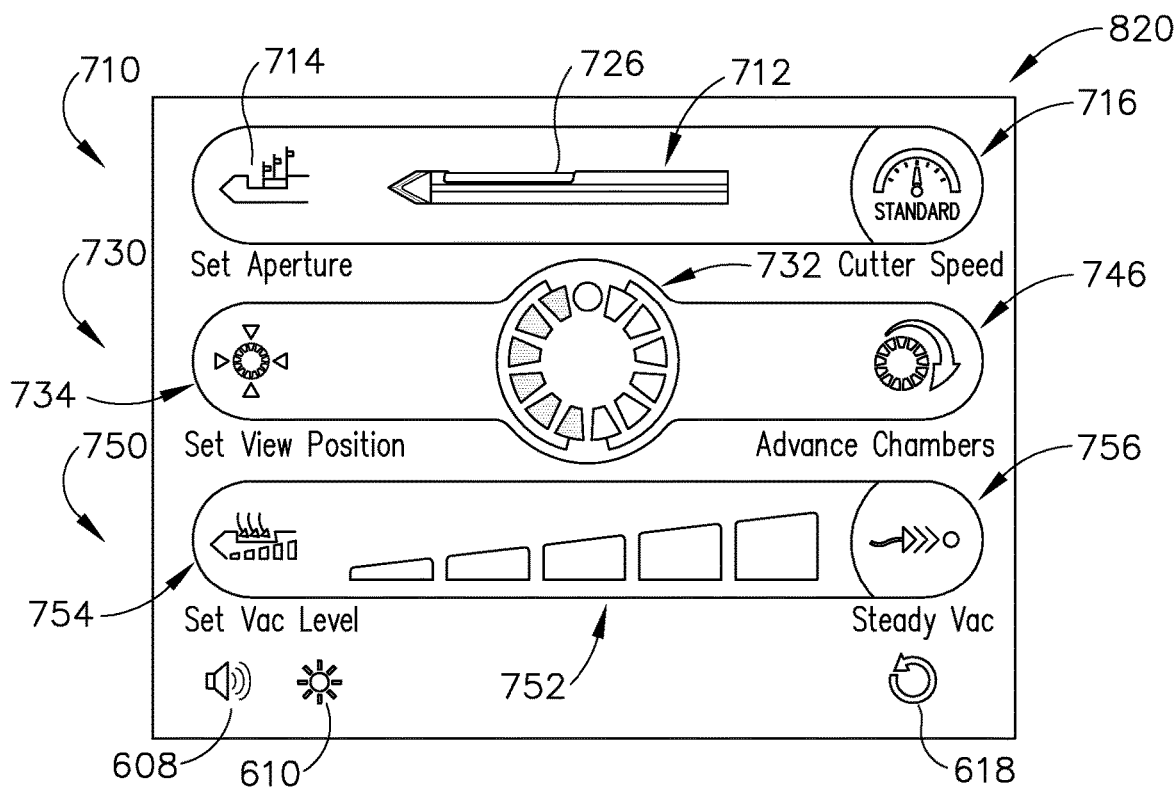
FIG. 33I depicts an exemplary ninth user interface screen for display on the vacuum control module of FIG. 27.
Figure 33J:
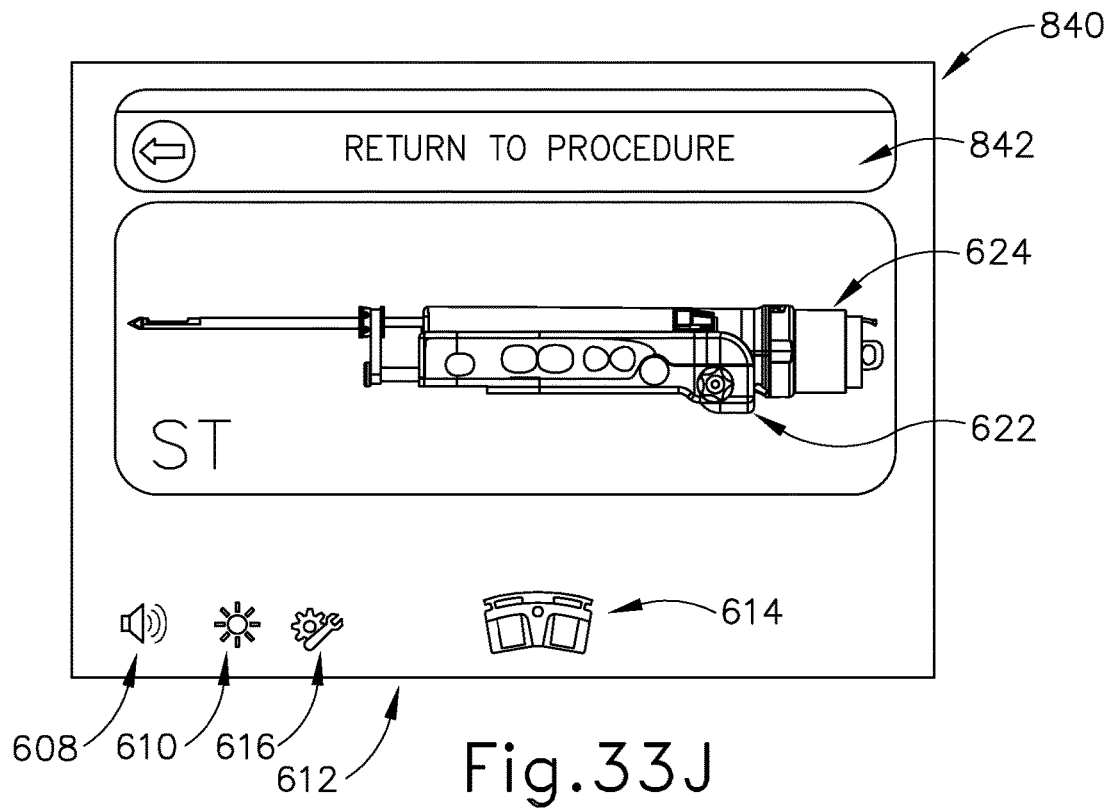
FIG. 33J depicts an exemplary tenth user interface screen for display on the vacuum control module of FIG. 27.

When a user taps on "set view position" button (734), touchscreen (410) transitions to the screen (780) shown in FIG. 33G. Screen (780) is generally similar to screen (700), except that regions (710, 750) are dark, button (736) is dark, and four highlights (738) appear over graphical representation (732) of tissue sample holder (300). These highlights (738) correspond to the 12 o'clock position, the 3 o'clock position, the 6 o'clock position, and the 9 o'clock position. With highlights (738) illuminated, the user may tap one of the highlights (738) to select whichever angular position is preferred for presentation of biopsy samples.

During operation of biopsy device (10), tissue sample holder control region (730) of screen (820) as shown in FIG. 33I indicates the successive filling of each chamber (346) in the graphical representation (732) of tissue sample holder (300). In particular, FIG. 33I shows the first six chambers (346) as being full, by illuminating those first six chambers in graphical representation (732) in a color that is different from the color used to illuminate the rest of the chambers in graphical representation (732). Thus, as each tissue sample is acquired, the chambers in graphical representation (732) successively change colors to indicate the filling of tissue sample holder (300). In instances where the "advance chambers" button (736) is used to skip one or more chambers (346), those skipped chambers may be illuminated in yet a different color in graphical representation (732). In other words, graphical representation (732) may show available chambers in one color, occupied chambers in another color, and skipped chambers in yet another color.

As noted above, in some instances the user may wish to skip chambers (346) in tissue sample holder (300) (e.g., such that the first tissue sample is deposited in the chamber (346) at the 5 o'clock position, etc.). To that end, the user may tap "advance chambers" button (736) to rotate manifold (310) in increments corresponding to one chamber (346) at a time. In other words, each time the user taps "advance chambers" button (736), manifold (310) is incrementally rotated to align the next chamber (346) with lumen (151) of cutter (150). In some versions, tapping "advance chambers" button (736) will automatically rotate manifold (310) to align the seventh chamber (346) with lumen (151) of cutter (150), regardless of which chamber (346) was previously aligned with lumen (151) of cutter (150). For instance, this may be desirable in instances where a user has removed a first tray (330) (providing the first six chambers (346)) from manifold (310) in the middle of a biopsy procedure where less than six tissue samples have been acquired; and the user wishes to continue the biopsy procedure beginning with the seventh chamber (346) (which would be the first chamber (346) of the second tray (330)).

There may also be occasions during a biopsy procedure where the user wishes to remove tissue sample holder (300) from probe (100) and couple a new tissue sample holder (300) with probe (100) (e.g., while needle (110) is still inserted in the patient's breast). When a user does this, the user may tap "reset chambers" button (740) as shown in FIG. 33I. When the user taps "reset chambers" button (740), vacuum control module (400) resets graphical representation (732) of tissue sample holder (300) to show all chambers (346) being empty.

It should be understood that the foregoing features relating to control of tissue sample holder (300) through touchscreen (410) are merely illustrative examples; and that they may be modified, substituted, supplemented, or omitted as desired. Various other features that may be used to provide control of tissues sample holder (300) through touchscreen (410) will be apparent to those of ordinary skill in the art in view of the teachings herein.

Figure 34A:
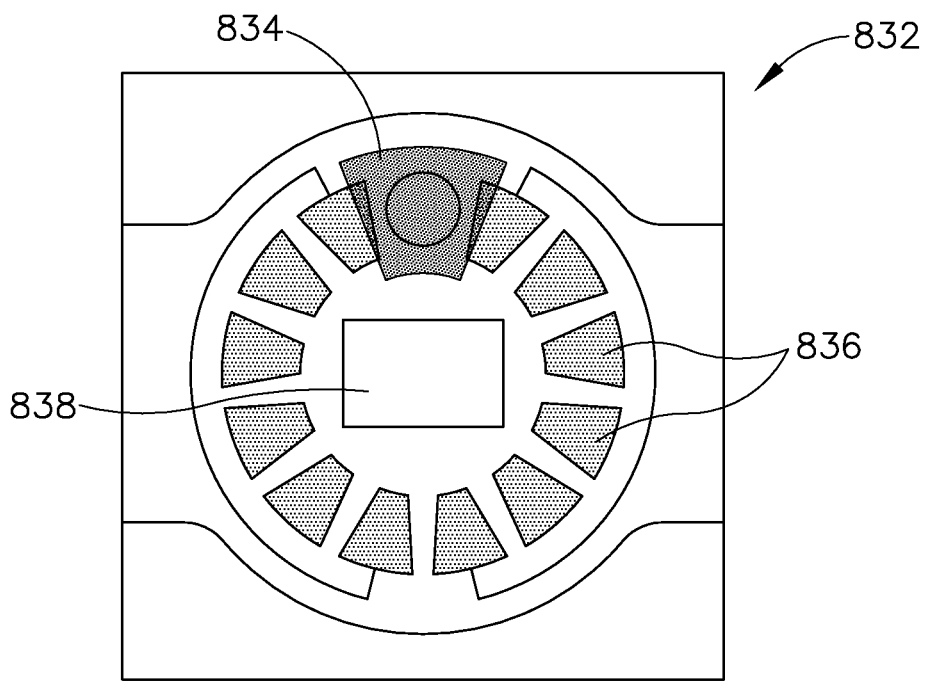
FIG. 34A depicts an exemplary graphical representation for a tissue sample holder control region for display on the user interface screen of FIG. 33A in an initial state.
Figure 34B:
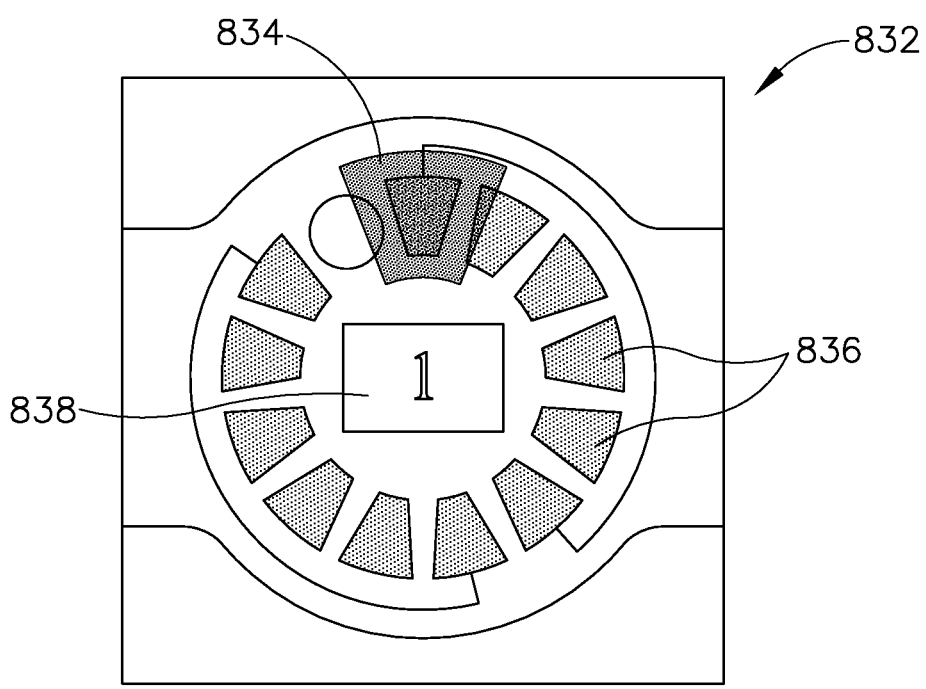
FIG. 34B depicts the graphical representation of FIG. 34A in a second state.

For example, FIGS. 34A-34H show another exemplary graphical representation (832) that may be readily incorporated for use with tissue sample holder control region (730) of screen (700). Graphical representation (832) is similar to graphical representation (732) except that graphical representation (832) comprises a counter (838) in the central portion of graphical representation (832) to store the total number of biopsy samples attempted. For instance, FIG. 34A shows graphical representation (832) in an initial state before a biopsy sample has been attempted. In the initial state, counter (838) is blank to represent that a sample has not been attempted by biopsy device (10). Chamber indicators (836) are lit with a first color (e.g. gray) to visually indicate that chambers (346) of tissue sample holder (300) are empty. FIG. 34B shows graphical representation (832) while one biopsy sample is being collected, e.g. after the user has pressed biopsy button (262). Counter (838) displays a "1" to indicate the attempt of the first biopsy sample. Counter (838) may be displayed in a first color to indicate that the first biopsy sample is currently being attempted. Chamber indicators (836) rotate on screen (700) as manifold (310) of tissue sample holder (300) rotates to provide a visual indication of the rotational position of manifold (310). In the present example, chamber indicators (836) have rotated counterclockwise by a single chamber (346). During the collection of a tissue sample, chamber indicator (836) corresponding to the selected chamber (346) of tissue sample holder (300) that is receiving the tissue sample is positioned under highlighted portion (834) of graphical representation (832). Highlighted portion (834) represents the angular position of cutter lumen (151) in relation to chambers (346) of manifold (310).

Figure 34C:
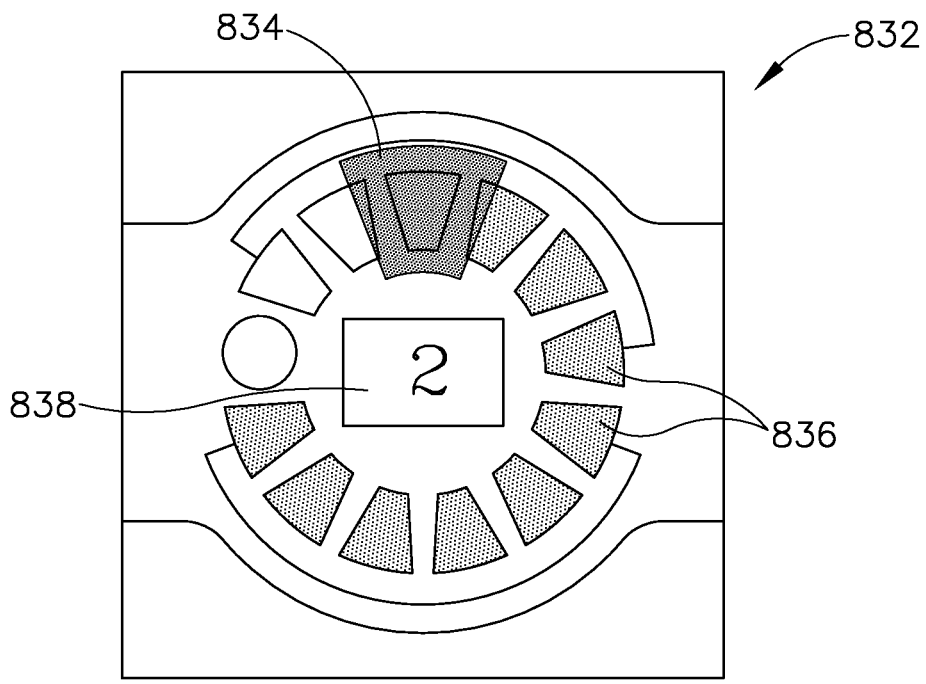
FIG. 34C depicts the graphical representation of FIG. 34A in a third state.

Once a sample has been taken by device (10), chamber indicators (836) and counter (838) may change to a second color to indicate that the sample has been collected. FIG. 34C shows graphical representation (832) after two tissue samples have been collected. Two chambers of chamber indicators (836) have changed to a second color (e.g. purple) to indicate that the corresponding chambers (346) contain samples. Chamber indicators (836) have also rotated such that the third chamber indicator (836) is positioned under highlighted portion (834) to indicate that the next empty chamber (346) is positioned to receive the next tissue sample attempted. Counter (838) displays a "2" to show that two tissue samples have been attempted by device (10). Counter (838) has also changed to a second color to indicate that the second tissue sample has been attempted. Alternatively, screen (700) may change the brightness of chamber indicators (836) and counter (838) to indicate whether a tissue sample has been attempted.

Figure 34D:
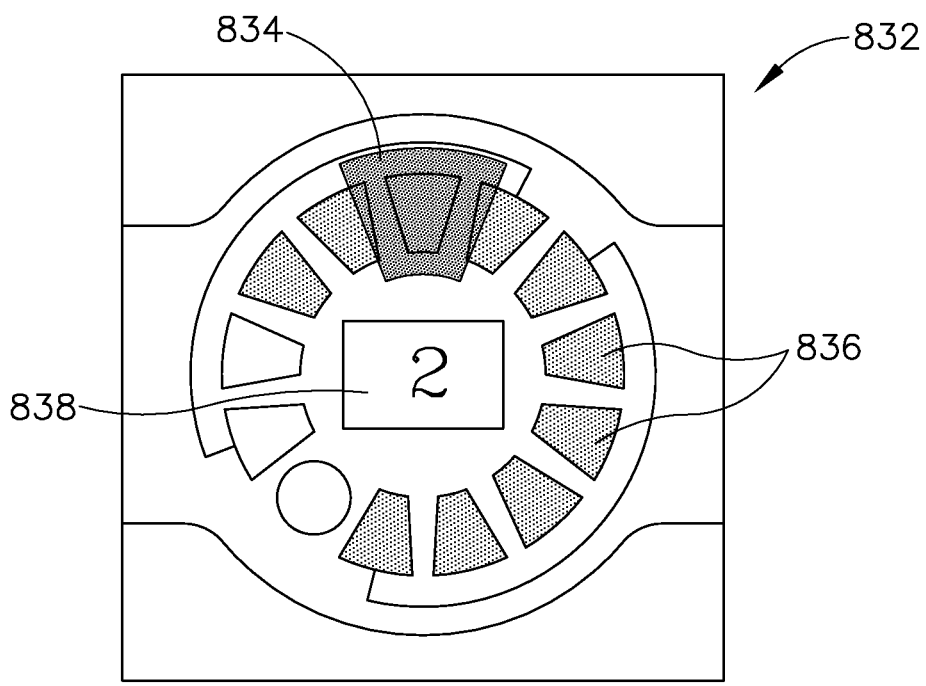
FIG. 34D depicts the graphical representation of FIG. 34A in a fourth state.
Figure 34E:
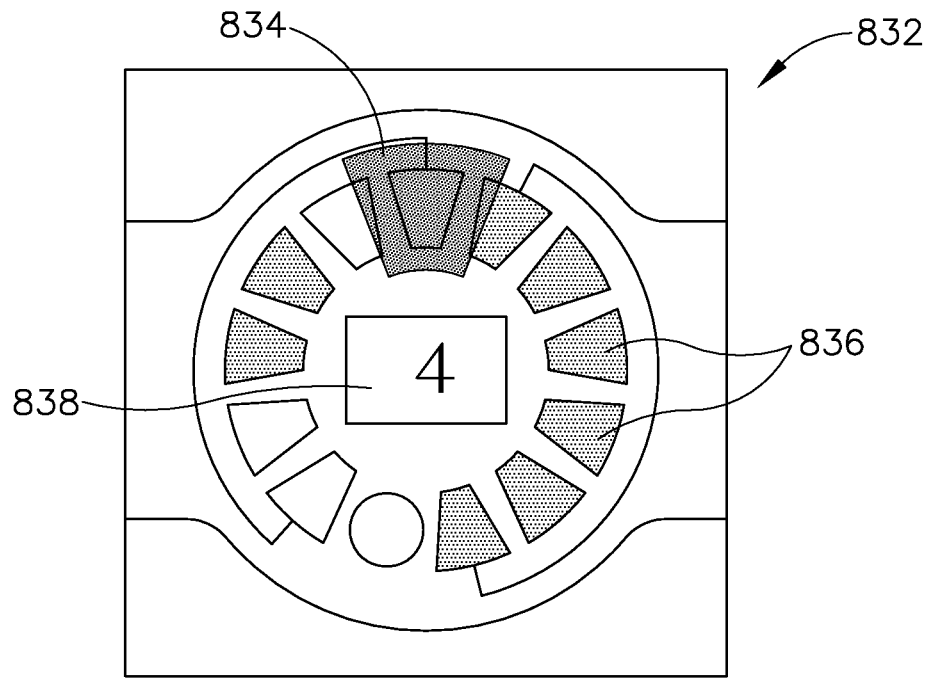
FIG. 34E depicts the graphical representation of FIG. 34A in a fifth state.
Figure 34F:
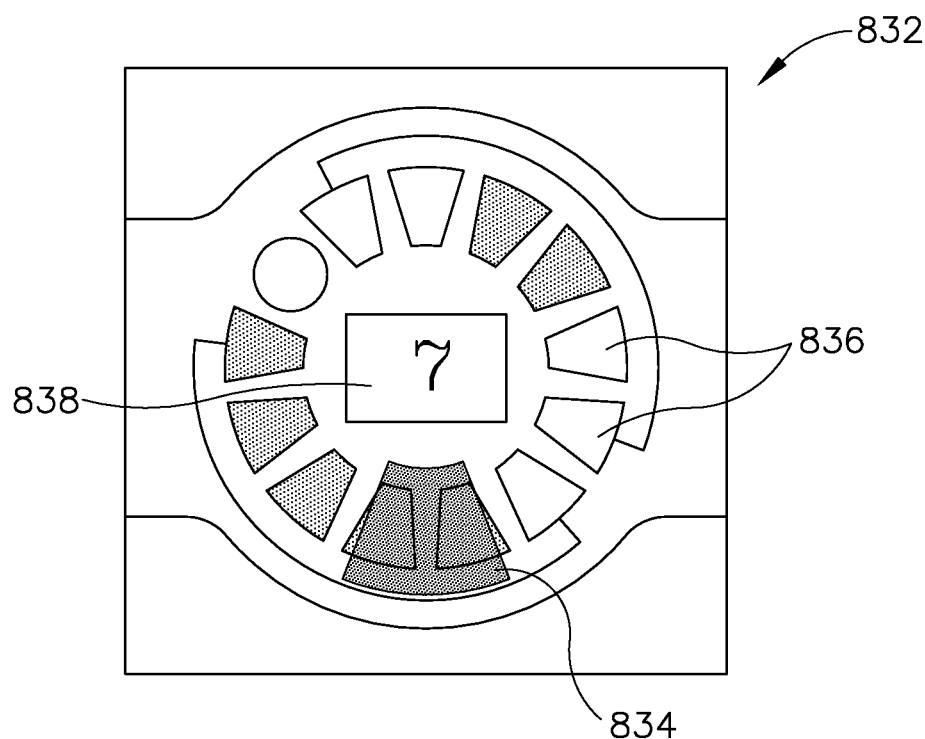
FIG. 34F depicts the graphical representation of FIG. 34A in a sixth state.

In some instances, chambers (346) of tissue sample holder (300) are advanced without receiving a tissue sample by pressing "advance chambers" button (736). FIG. 34D shows that tissue sample holder (300) has been advanced by two chambers (346) without collecting a tissue sample. Chamber indicators (836) have rotated by two chamber indicators (836) such that the fifth chamber indicator (836) is positioned under highlighted portion (834). The third and fourth chamber indicators (836) remain in the first color to indicate that the corresponding chambers (346) of tissue sample holder (300) have not received a tissue sample. Counter (838) also remains displaying a "2" in the second color to show that two tissue samples have been attempted by device (10). Biopsy device (10) may then continue to collect additional tissue samples. FIG. 34E shows graphical representation (832) while a second additional tissue sample is being attempted. Chamber indicators (836) have been rotated such that the sixth chamber indicator (836) is positioned under highlighted portion (834). The fifth chamber indicator (836) has changed to the second color to indicate that a sample has been collected in the corresponding chamber (346). Counter (838) displays a "4" in the first color to indicate that the fourth total tissue sample is currently being attempted by device (10). Additional tissue samples may be attempted. FIG. 34F shows graphical representation (832) while a seventh tissue sample is being attempted. Chamber indicators (836) have rotated to align the ninth chamber indicator (836) under highlighted portion (834) and chamber indicators (836) corresponding to chambers (346) containing tissue samples have changed to the second color. Highlighted portion (834) repositioned to the bottom of graphical representation (832) to show that device (10) has been rotated to the corresponding position. Counter (838) displays a "7" in the first color to show that the seventh tissue sample is currently being attempted by device (10).

Figure 34G:
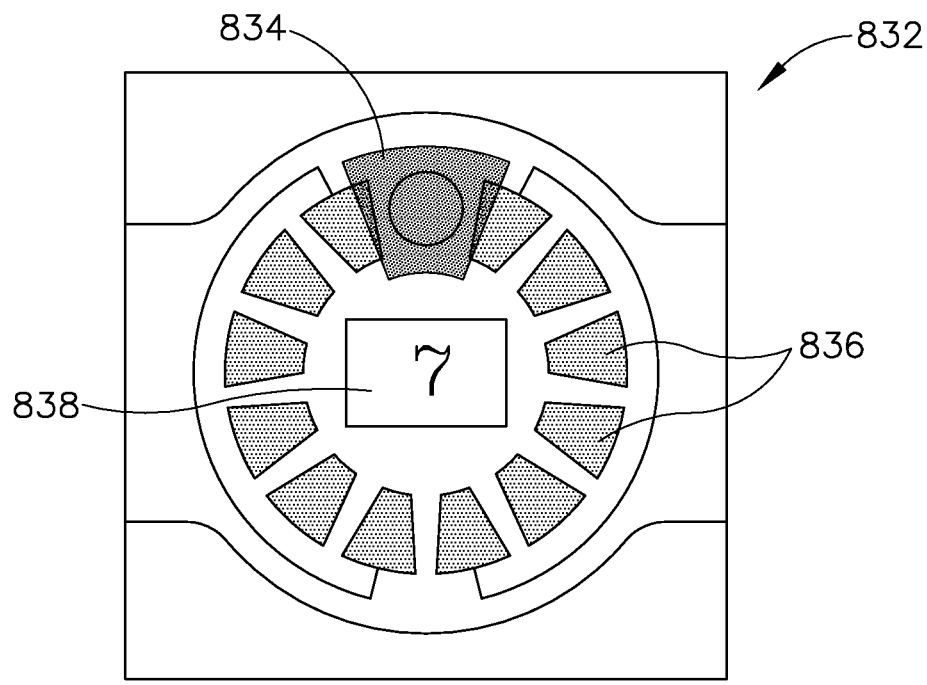
FIG. 34G depicts the graphical representation of FIG. 34A in a seventh state.
Figure 34H:
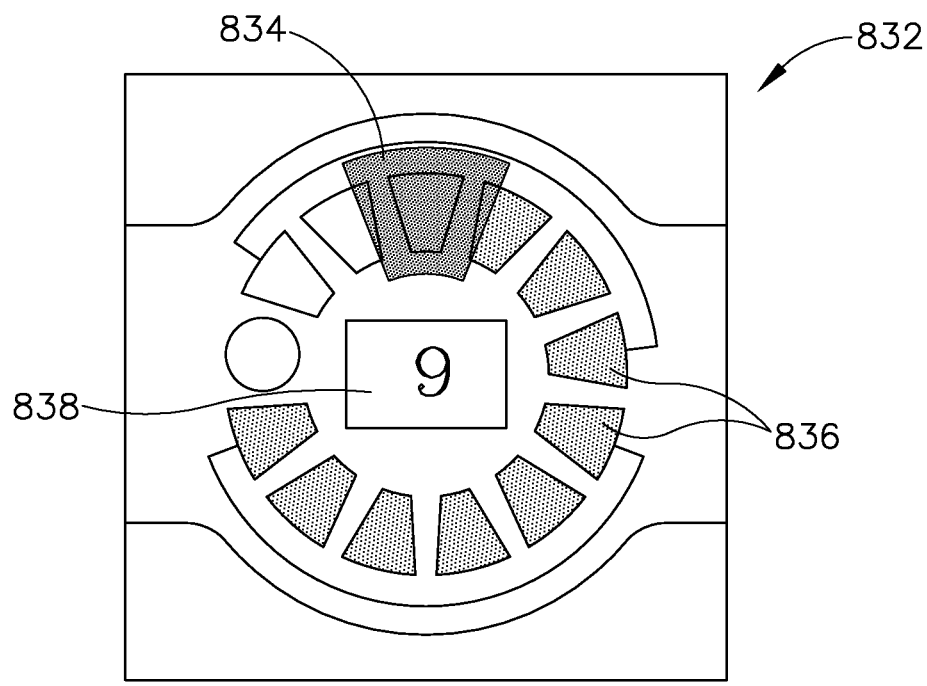
FIG. 34H depicts the graphical representation of FIG. 34A in an eighth state.

In some instances, manifold (340) of tissue sample holder (300) is emptied and/or replaced with a new manifold (340). In the present example, manifold (340) has been replaced after the seventh tissue sample was collected by device (10), as shown in FIG. 34G. A user may tap "reset chambers" button (740) to reset chamber indicators (836) to the initial position such that chamber indicators (836) are displayed in the first color to show that the corresponding chambers (346) are empty. Counter (838) continues to display a "7" in the second color to show that a total of seven tissue samples have been attempted by device (10). Two additional tissue samples were then attempted by device (10), as shown in FIG. 34H. Chamber indicators (836) rotated to correspond to the rotation of manifold (340). The first and second chamber indicators (836) changed to the second color to show that the corresponding chambers (346) contain tissue samples. The next available chamber (346) is then aligned to receive to the next tissue sample, as shown by the third chamber indicator (836) positioned under highlighted portion (834). Counter (838) displays a "9" in the second color to show that a total of nine tissue samples have been attempted by device (10).

Counter (838) may be reset to restart the count of tissue samples. For instance, chamber indicators (836) are first manually reset to the initial position by pressing "reset chambers" button (740), as shown in FIG. 34A, to clear the "full" chamber indicators (836) on graphical representation (832). The user then touches the center portion of graphical representation (832) on counter (838) to clear counter (838), as shown in FIG. 34A. The user may tap graphical representation (832), or the user may press graphical representation (832) for a predetermined amount of time to clear counter (838). After counter (838) is cleared, counter (838) is reset to display a "1" for the next biopsy sample attempted. Alternatively, counter (838) may automatically reset when probe (100) is removed from holster (200) and probe (100) is recoupled and/or replaced. Other suitable methods of resetting counter (838) will be apparent to one with ordinary skill in the art in view of the teachings herein.

4. Exemplary Vacuum Interface Features

As shown in FIG. 33E, vacuum control region (750) of screen (700) includes a set of bars (752) that gradually increase in height from left to right, a "set vac level" button (754), and a "steady vac" button (756). When a user taps "set vac level" button (754), touchscreen (410) transitions to the screen (800) shown in FIG. 33H. Screen (800) is generally similar to screen (700), except that regions (710, 730) are dark and button (756) is dark. Button (754) enables the user to select an amount of vacuum provided by vacuum pump (428). In particular, each time the user taps button (754), the vacuum level will increase incrementally, which will be reflected through successive illumination of bars (752) with each tap of button (754). If the user taps button (754) when the far-right bar (752) is illuminated, bars (752) will reset back to the far-left bar, and the vacuum level will transition back from the highest level to the lowest level. The user may thus repeatedly press button (754) to cycle through the various vacuum levels until the desired vacuum level is selected. As shown in FIG. 33I, screen (820) persistently displays the selected vacuum level through bars (752) during use of biopsy device (10).

The user may tap "steady vac" button (756) to initiate a "steady vac" cycle. An example of such a cycle will be described in greater detail below. The user may subsequently tap button (756) again to stop the "steady vac" cycle. In addition or in the alternative, the "steady vac" cycle may automatically cease when the user activates biopsy button (262) or provides some other user input.

It should be understood that the foregoing features relating to control of vacuum through touchscreen (410) are merely illustrative examples; and that they may be modified, substituted, supplemented, or omitted as desired. Various other features that may be used to provide control of vacuum through touchscreen (410) will be apparent to those of ordinary skill in the art in view of the teachings herein. Similarly, various other features of system (2) that may be controlled through touchscreen (410), and ways in which such features may be controlled through touchscreen (410), will be apparent to those of ordinary skill in the art in view of the teachings herein.

C. Exemplary Control Module Accessories

FIGS. 34-37 depict examples of accessories that may be provided for use with vacuum control module (400). It should be understood that these accessories are not required for operation of vacuum control module (400). It should also be understood that additional types of accessories may be used with vacuum control module (400). Other suitable types of accessories, as well as variations of the below described accessories, will be apparent to those of ordinary skill in the art in view of the teachings herein.

Figures 35A, 35B:
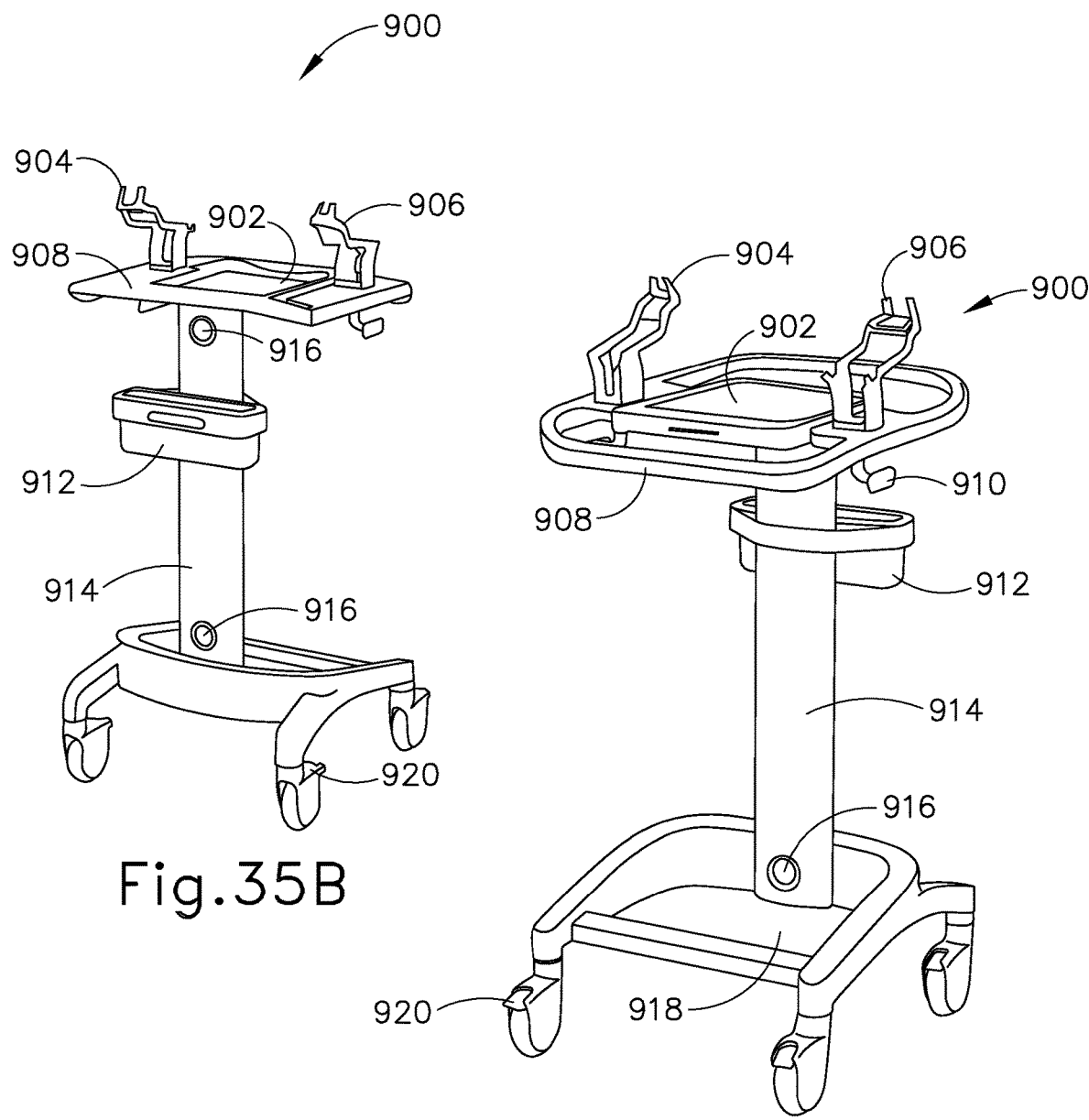
FIG. 35A depicts a perspective view of an exemplary cart that may be used to support the vacuum control module of FIG. 27.
FIG. 35B depicts another perspective view of the cart of FIG. 35A.

FIGS. 34-35 show an exemplary cart (900) that may be used with vacuum control module (400). Cart (900) of this example includes a platform (902), a probe dock (904), a holster dock (906), and handles (908). Platform (902) is configured to receive vacuum control module (400). In some versions, one or more locking features are provided to further secure vacuum control module (400) to platform (902). Probe dock (904) is configured to removably hold probe (100); while holster dock (906) is configured to removably hold holster (200). A bracket (910) is positioned underneath platform (902) and is configured to hold a coiled length of cable (90). Platform (902) is positioned atop a column (914), which includes a storage bin (912) and cable pass-throughs (906) that enable cables to be fed into the hollow interior of column (914). A base shelf (918) is positioned at the bottom of column (914). Wheels (920) provide mobility for cart (900) and include locking features to selectively secure the position of cart (900). Still other suitable features and functionalities that may be provided through cart (900) will be apparent to those of ordinary skill in the art in view of the teachings herein.

Figure 36:
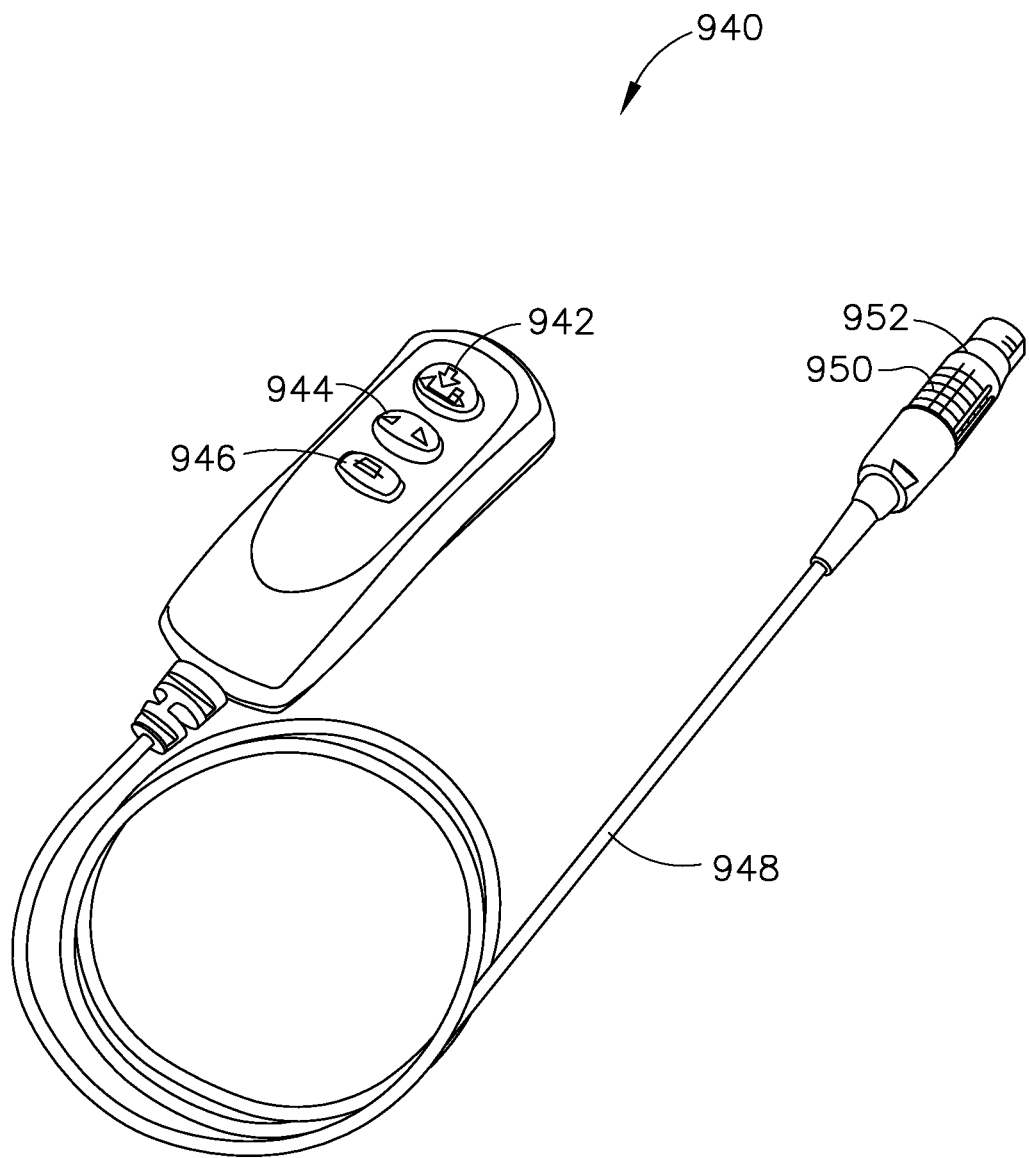
FIG. 36 depicts a perspective view of an exemplary remote control that may be coupled with the vacuum control module of FIG. 27.

FIG. 36 shows an exemplary remote hand control (940) that may be used with vacuum control module (400). Remote hand control (940) of this example includes a biopsy button (942), a vacuum button (944), and an open/close button (946). Biopsy button (942) is the functional equivalent of biopsy button (262) described above. Vacuum button (944) is the functional equivalent of vacuum button (266) described above. Open/close button (946) is the functional equivalent of open/close button (254) described above. Remote hand control (940) of the present example also includes a cable (948) with a plug (950) that is operable to couple with remote control input (426) of vacuum control module (400). Plug (950) also includes an indicator (952) to facilitate proper rotational alignment of plug (950) with remote control input (426). In some other versions, remote hand control (940) communicates with vacuum control module (400) wirelessly (e.g., using the Bluetooth protocol, etc.). In the present example, vacuum control module (400) emits an audible tone when plug (950) is inserted into remote control input (426) and displays a graphical representation of remote hand control (940) in accessory attachment indication field (912) of touchscreen (410). In some versions, buttons (254, 262, 266) on holster (200) are inoperable when plug (950) is inserted in remote control input (426), while buttons (270, 272) remain operable. In some other versions, buttons (254, 262, 266) also remain operable despite plug (950) being inserted in remote control input (426). It should also be understood that cutter position indicator (250) and error indicator (260) may also remain operable regardless of whether plug (950) is inserted in remote control input (426). Still other suitable features and functionalities that may be provided through remote hand control (940) will be apparent to those of ordinary skill in the art in view of the teachings herein.

Figure 37:
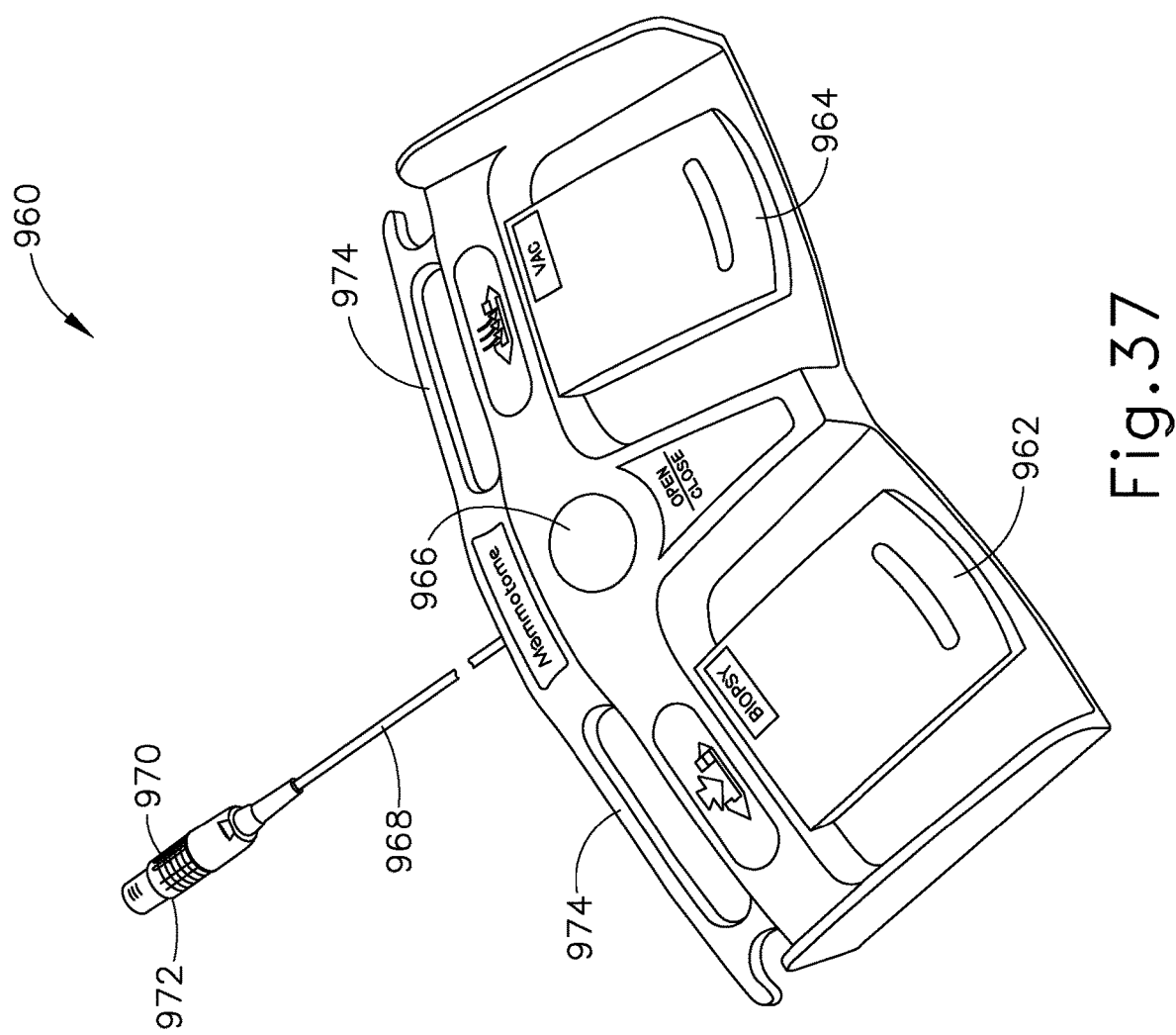
FIG. 37 depicts a perspective view of an exemplary footswitch that may be coupled with the vacuum control module of FIG. 27.

FIG. 37 shows an exemplary remote footswitch (960) that may be used with vacuum control module (400). Remote footswitch (960) of this example includes a biopsy pedal (962), a vacuum pedal (964), and an open/close button (946). Biopsy pedal (962) is the functional equivalent of biopsy button (262) described above. Vacuum pedal (964) is the functional equivalent of vacuum button (266) described above. Open/close button (966) is the functional equivalent of open/close button (254) described above. Remote footswitch (960) of the present example also includes a cable (968) with a plug (970) that is operable to couple with remote control input (426) of vacuum control module (400). Plug (970) also includes an indicator (972) to facilitate proper rotational alignment of plug (970) with remote control input (426). In some other versions, remote footswitch (960) communicates with vacuum control module (400) wirelessly (e.g., using the Bluetooth protocol, etc.). In the present example, vacuum control module (400) emits an audible tone when plug (970) is inserted into remote control input (426) and displays a graphical representation (614) of remote footswitch (960) in accessory attachment indication field (912) of touchscreen (410), as described above. In some versions, buttons (254, 262, 266) on holster (200) are inoperable when plug (970) is inserted in remote control input (426), while buttons (270, 272) remain operable. In some other versions, buttons (254, 262, 266) also remain operable despite plug (970) being inserted in remote control input (426). It should also be understood that cutter position indicator (250) and error indicator (260) may also remain operable regardless of whether plug (970) is inserted in remote control input (426). Remote footswitch (960) of the present example also includes integral handles (974) to facilitate carrying of remote footswitch (960). Still other suitable features and functionalities that may be provided through remote footswitch (960) will be apparent to those of ordinary skill in the art in view of the teachings herein.

V. Exemplary Control Algorithms

Biopsy system (2) may be operable to run through a variety of different control algorithms. Such control algorithms may be stored on memory (432) in vacuum control module (400) and/or elsewhere. In addition, such control algorithms may be executed at least partially through processor (434). Several exemplary control algorithms will be described in greater detail below, while additional control algorithms will be apparent to those of ordinary skill in the art in view of the teachings herein. Similarly, various hardware and techniques that may be used to store and execute control algorithms in biopsy system (2) will be apparent to those of ordinary skill in the art in view of the teachings herein.

A. Exemplary Initialization Sequence

Figure 38A:
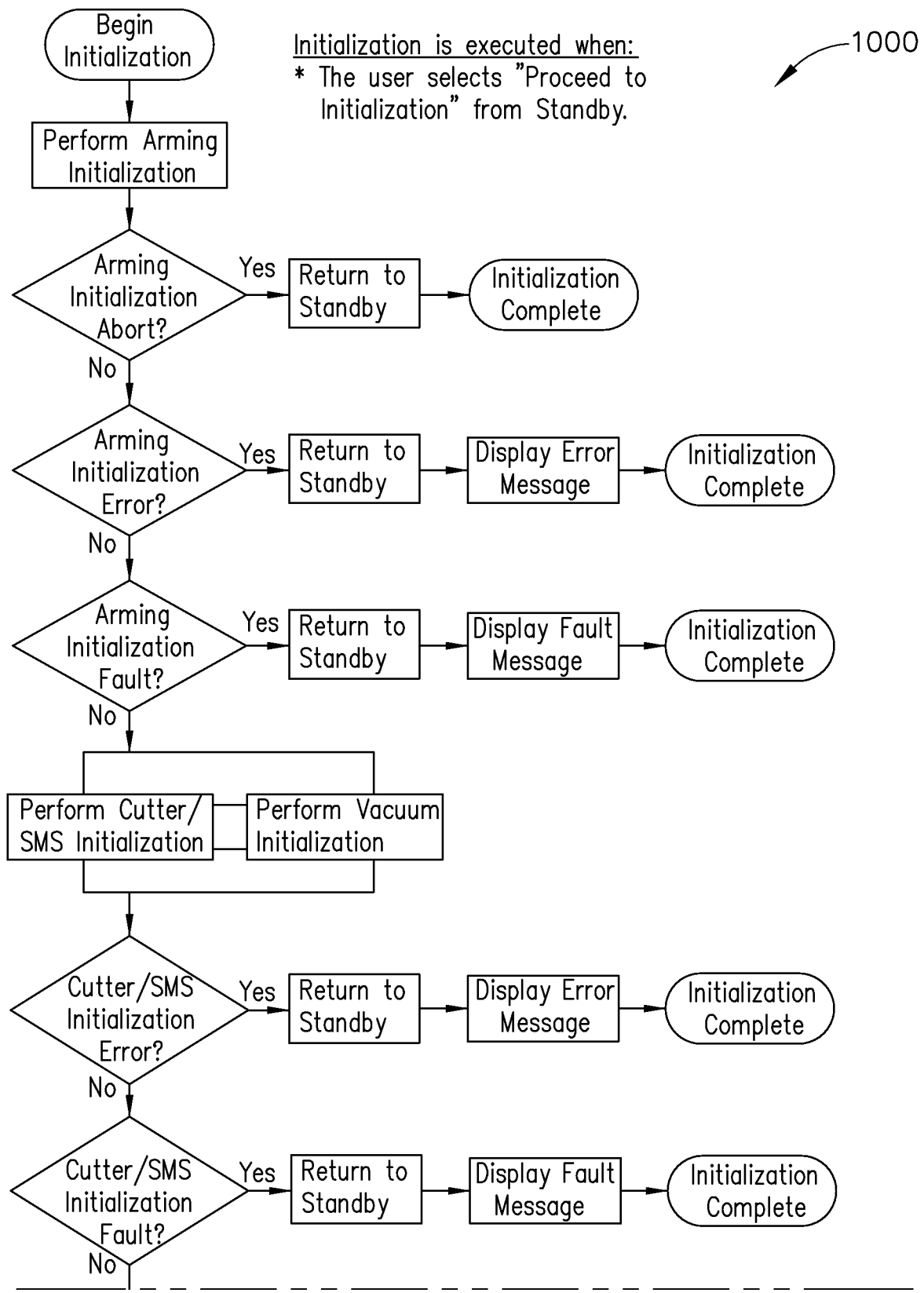
FIGS. 38A-38B together depict a flow chart showing general steps carried out during an exemplary initialization sequence carried out in the biopsy system of FIG. 1.
Figure 38B:
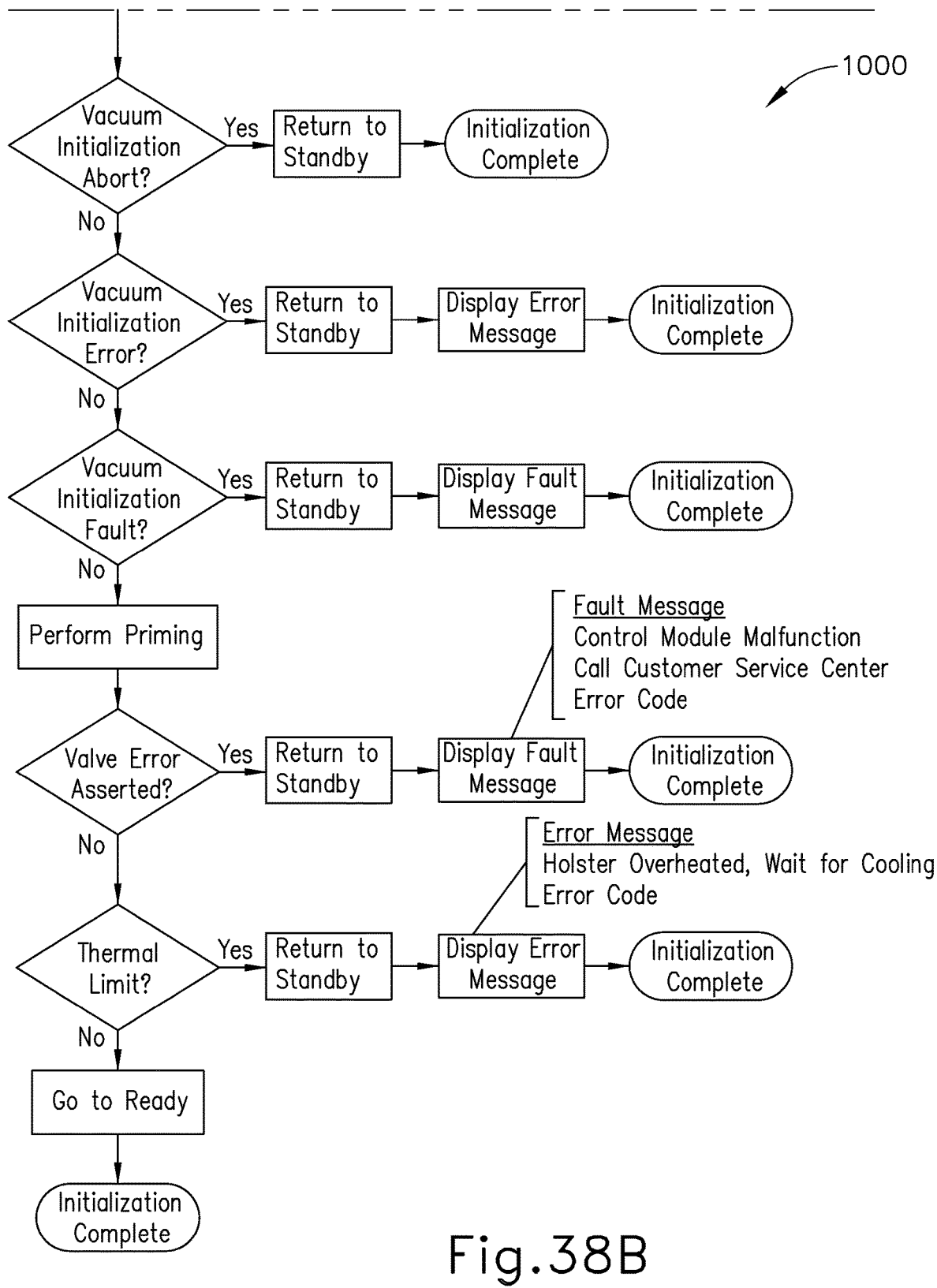

FIGS. 38A-38B together show an exemplary initialization sequence (1000) that may be carried out by biopsy system (2) before a biopsy procedure. FIGS. 39A-44 depict various sub-sequences, which are performed as part of initialization sequence (1000), in greater detail. By way of example only, the initialization sequence (1000) may be carried out as soon as the user taps the textual invitation (642) in the screen (640) shown in FIG. 40 after probe (100) has been coupled with holster (200) and cable (90) has been coupled with holster cable socket (416). In the present example, the initialization sequence (1000) starts out with an arming initialization sequence, which is shown in greater detail in FIGS. 39A-39B and which is described in greater detail below. The initialization sequence (1000) then moves on to perform a combined cutter and tissue sample management system initialization sequence, in parallel with a vacuum initialization sequence. The cutter and tissue sample management system initialization sequence are shown in greater detail in FIGS. 40-42B and are described in greater detail below. The vacuum initialization sequence is shown in greater detail in FIGS. 43A-43B and is described in greater detail below. The initialization sequence (1000) then moves on to perform a priming sequence, which is shown in greater detail in FIG. 44 and is described in greater detail below. Next, the initialization sequence (1000) checks for valve errors, then checks whether the temperature of holster (200) is above a threshold, and is then complete. It should be understood that the initialization steps and sequences as described herein may be modified, substituted, supplemented, and/or omitted in numerous ways. Furthermore, the sequences may be re-ordered in any suitable arrangement, including running different sequences serially or in parallel, etc.

Figure 39A:
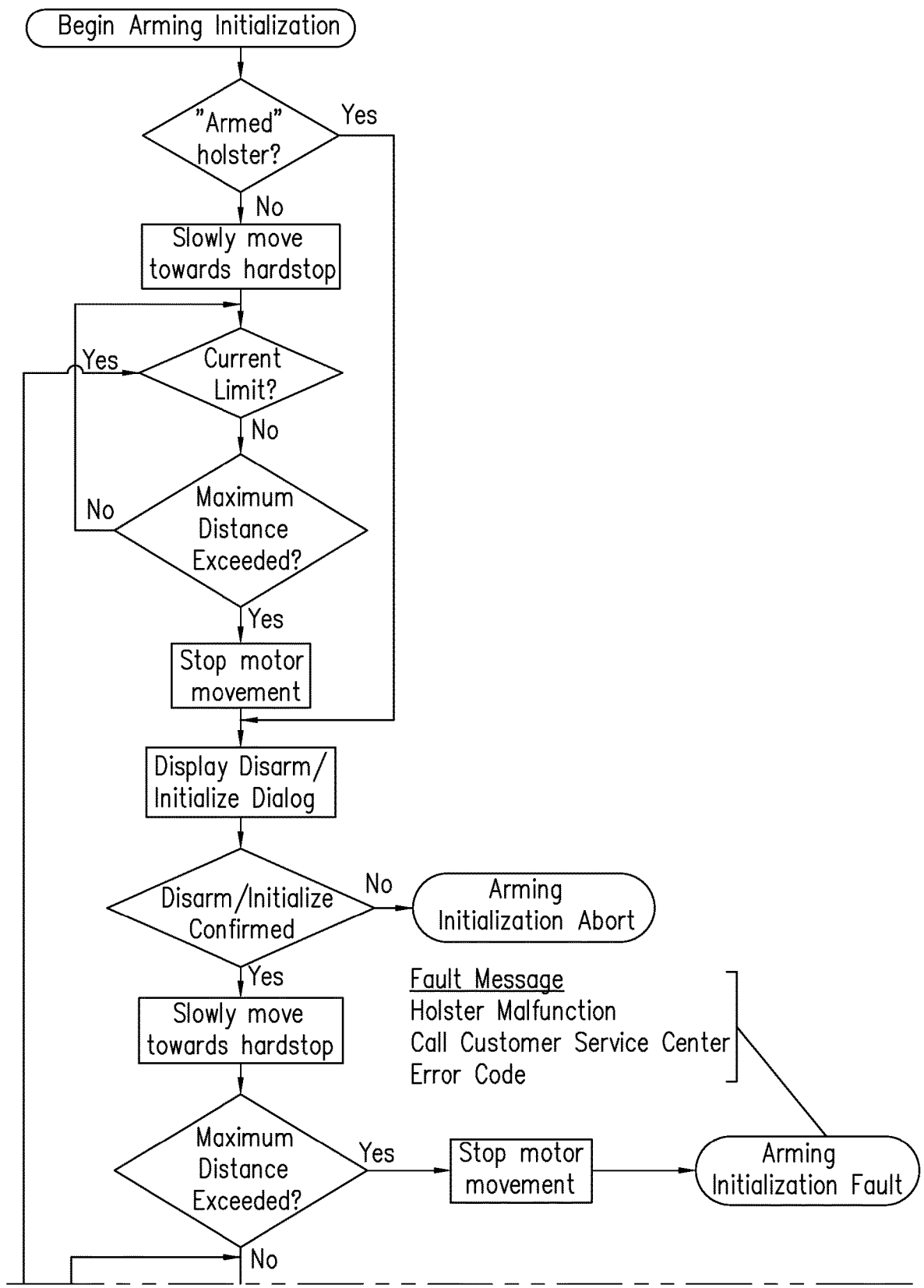
FIGS. 39A-39B together depict a flow chart showing steps carried out during an exemplary arming initialization sequence, which is carried out as part of the sequence depicted in FIGS. 38A-38B.
Figure 39B:
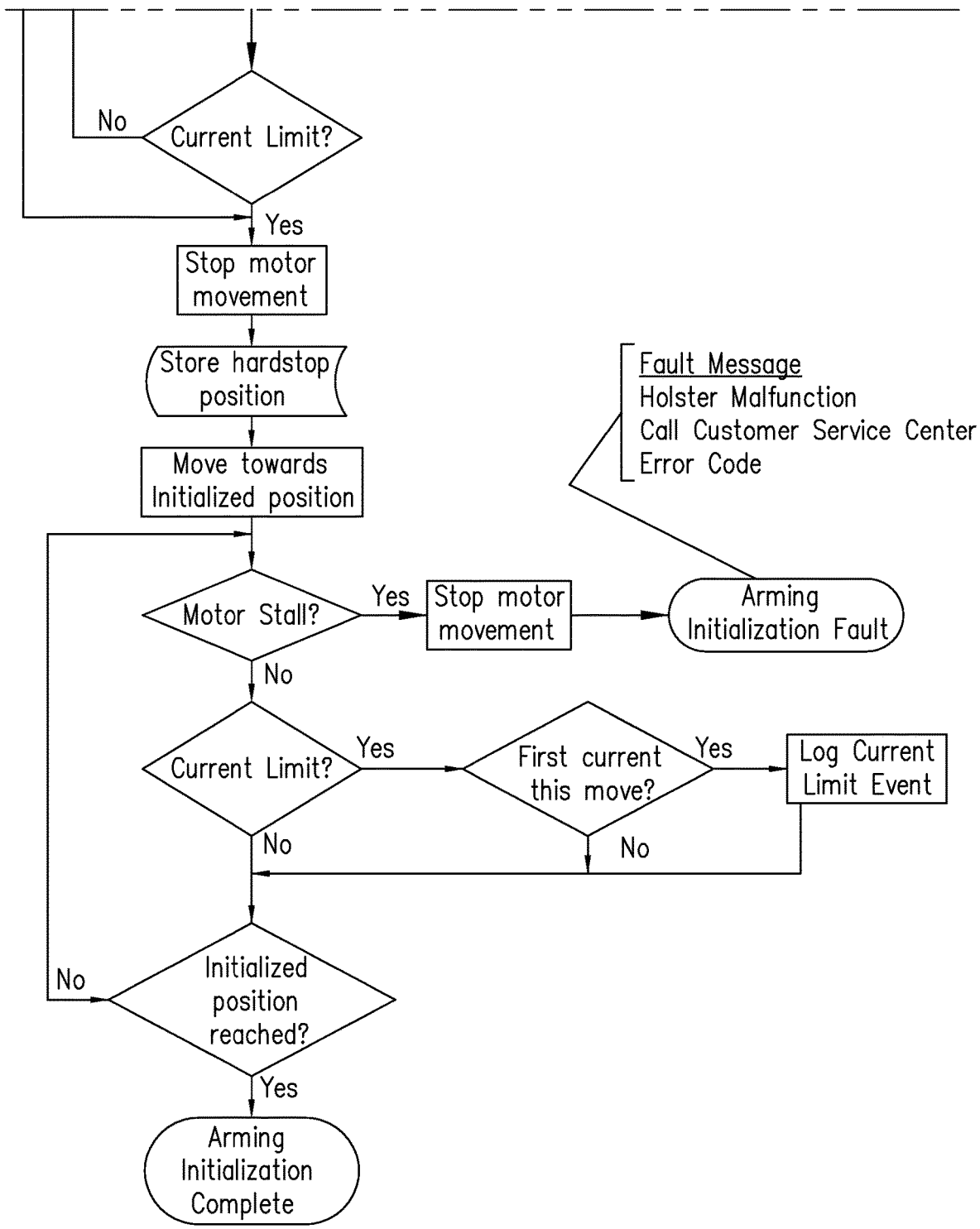

FIGS. 39A-39B together show an exemplary arming initialization sequence in greater detail. This sequence is performed to initialize the components of needle firing mechanism (224). In particular, the process first determines whether needle firing mechanism (224) is in an armed state (e.g., with needle (110) in a proximal position as shown in FIG. 25A). If needle firing mechanism (224) is in an armed state, needle firing mechanism (224) will be disarmed. Otherwise, motor (246) is activated to translate firing rod (226) proximally until it reaches a hard stop. During this time, processor (434) tracks the motor current to determine whether that current exceeds a predetermined threshold. If the motor current exceeds a threshold, motor (246) is stopped. Otherwise, processor (434) further tracks the positioning of firing rod (226) and determines whether firing rod (226) reaches a predetermined maximum distance before reaching the hard stop. If the maximum distance is not yet exceeded, motor (246) continues to translate firing rod (226) until the hard stop is reached or until firing rod (226) reaches the predetermined maximum distance. Upon reaching the maximum distance or hard stop, motor (246) is stopped and needle firing mechanism (224) transitions to a disarming mode. In particular, the direction of rotation of motor (246) is reversed to translate firing rod (226) distally. Again, processor (434) tracks the motor current to determine whether that current exceeds a predetermined threshold. If the motor current exceeds a threshold, the motor is stopped. Otherwise, processor (434) further tracks the positioning of firing rod (226) and determines whether firing rod (226) reaches a predetermined maximum distance before reaching a hard stop. If the maximum distance is not yet exceeded, motor (246) continues to translate firing rod (226) until the hard stop is reached or until firing rod (226) reaches the predetermined maximum distance. Upon reaching the maximum distance or hard stop, motor (246) is stopped. It should be understood that the hard stops may be detected in the above sequences by the motor current exceeding a limit.

After completing the above sequences, processor (434) may then store the hard stop position(s) in memory (432). Processor (434) then activates motor (246) to move needle (110) toward an initialized position. During this movement, processor (434) monitors for stalling of motor (246). If motor (246) stalls, motor (246) is stopped and an error message is generated. Processor (434) also monitors the motor current to determine whether that current exceeds a predetermined threshold. When the current threshold is exceeded, processor (434) determines whether it is the first occurrence of exceeding the threshold during movement toward the initialized position. If it is the first time, the event is logged and processor (434) then determines whether the initialized position has been reached. If it is not the first time there is no logging and processor (434) moves on to determining whether the initialized position has been reached. The foregoing steps are looped until needle (110) reaches the initialized position, at which time the sequence is complete. Of course, the foregoing steps are merely illustrative, and the foregoing sequence may be modified in numerous ways as will be apparent to those of ordinary skill in the art in view of the teachings herein.

Figure 40:
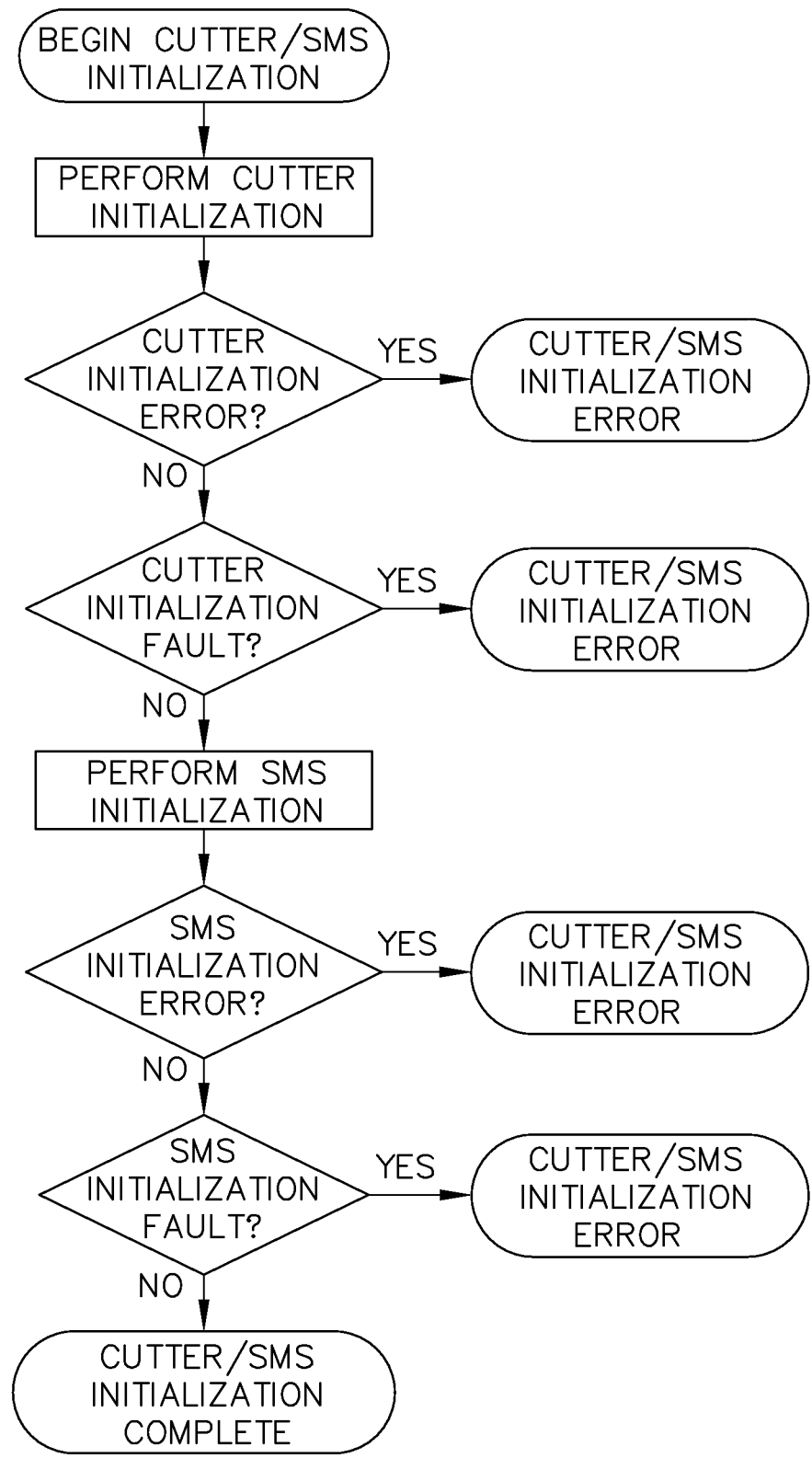
FIG. 40 depicts a flow chart showing general steps carried out during a combined cutter and tissue sample management system initialization sequence, which is carried out as part of the sequence depicted in FIGS. 38A-38B.
Figure 41A:
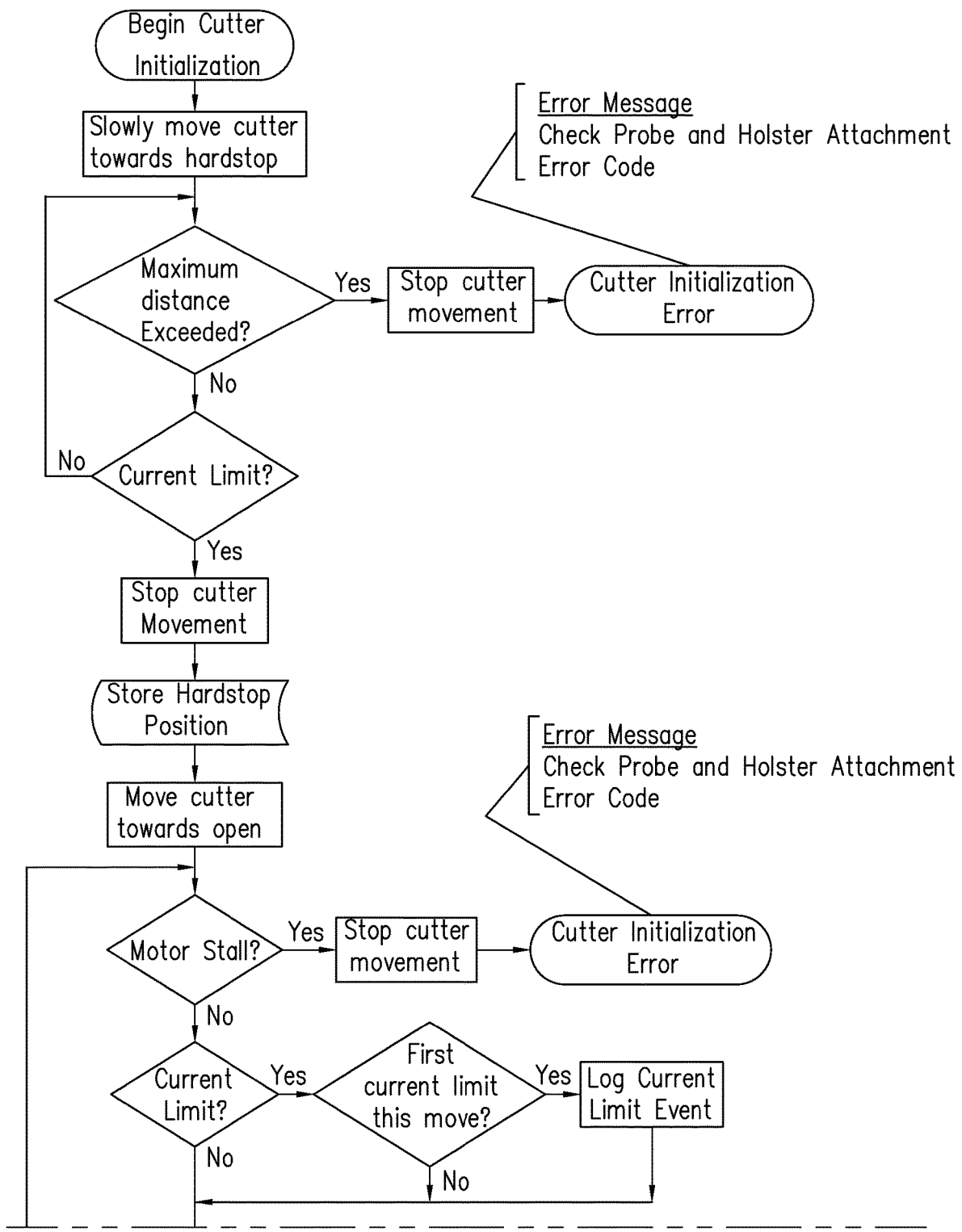
FIGS. 41A-41B together depict a flow chart showing steps carried out during an exemplary cutter initialization sequence, which is carried out as part of the sequence of FIG. 40, which is further carried out as part of the sequence depicted in FIGS. 38A-38B.
Figure 41B:
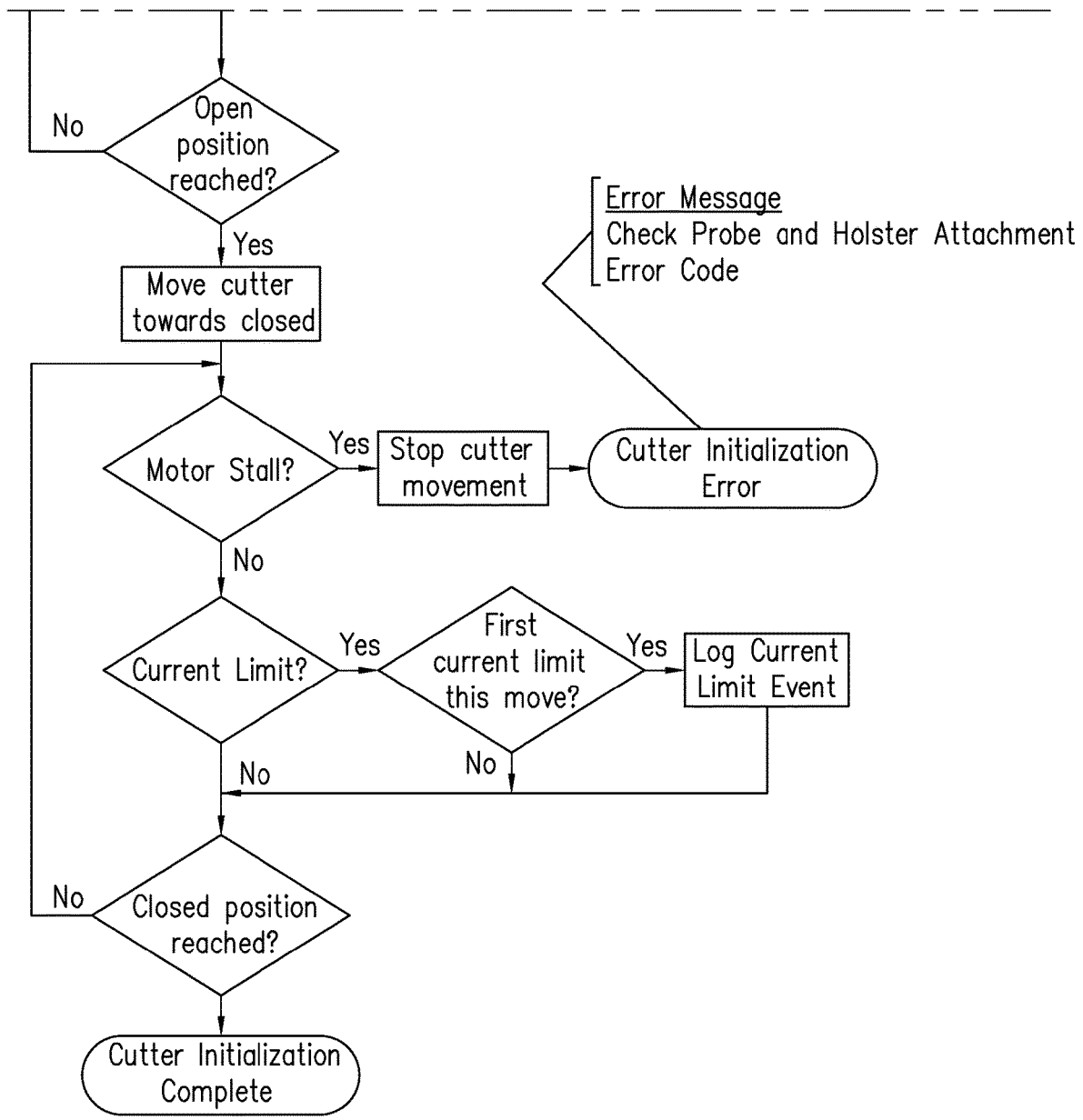

FIG. 40 shows an exemplary combined cutter and tissue sample management system initialization sequence in greater detail. As shown in FIG. 40, the sequence begins with a cutter actuation assembly initialization sequence, which first checks for errors in the cutter actuation assembly and then faults in the cutter actuation assembly. Next, the sequence checks for errors in the tissue sample management system and then faults in the tissue sample management system. As shown in FIGS. 41A-41B, the cutter actuation assembly initialization sequence begins with processor (434) activating motor (244) to translate cutter (150) distally toward a hard stop. During this time, processor (434) tracks the motor current to determine whether that current exceeds a predetermined threshold. If the motor current exceeds a threshold, motor (244) is stopped. Otherwise, processor (434) further tracks the positioning of cutter (150) and determines whether cutter (150) reaches a predetermined maximum distance before reaching the hard stop. If the maximum distance is not yet exceeded, motor (246) continues to translate cutter (150) until the hard stop is reached or until cutter (150) reaches the predetermined maximum distance. Upon reaching the maximum distance or hard stop, motor (244) is stopped, and the hard stop position is stored.

Then, processor (434) activates motor (244) to translate cutter (150) proximally to effectively open lateral aperture (114). During this movement, processor (434) monitors for stalling of motor (244). If motor (244) stalls, motor (244) is stopped and an error message is generated. Processor (434) also monitors the motor current to determine whether that current exceeds a predetermined threshold. When the current threshold is exceeded, processor (434) determines whether it is the first occurrence of exceeding the threshold during movement of cutter (150) toward the open position. If it is the first time, the event is logged and processor (434) then determines whether the open position has been reached. If it is not the first time there is no logging and processor (434) moves on to determining whether the open position has been reached. The foregoing steps are looped until cutter (150) reaches the open position, at which time the direction of rotation of motor (244) is reversed to translate cutter (150) distally to effectively close lateral aperture (114). During this movement, processor (434) monitors for stalling of motor (244). If motor (244) stalls, motor (244) is stopped and an error message is generated. Processor (434) also monitors the motor current to determine whether that current exceeds a predetermined threshold. When the current threshold is exceeded, processor (434) determines whether it is the first occurrence of exceeding the threshold during movement of cutter (150) toward the closed position. If it is the first time, the event is logged and processor (434) then determines whether the closed position has been reached. If it is not the first time there is no logging and processor (434) moves on to determining whether the closed position has been reached. The foregoing steps are looped until cutter (150) reaches the closed position, at which time the sequence is complete. Of course, the foregoing steps are merely illustrative, and the foregoing sequence may be modified in numerous ways as will be apparent to those of ordinary skill in the art in view of the teachings herein.

Figure 42A:
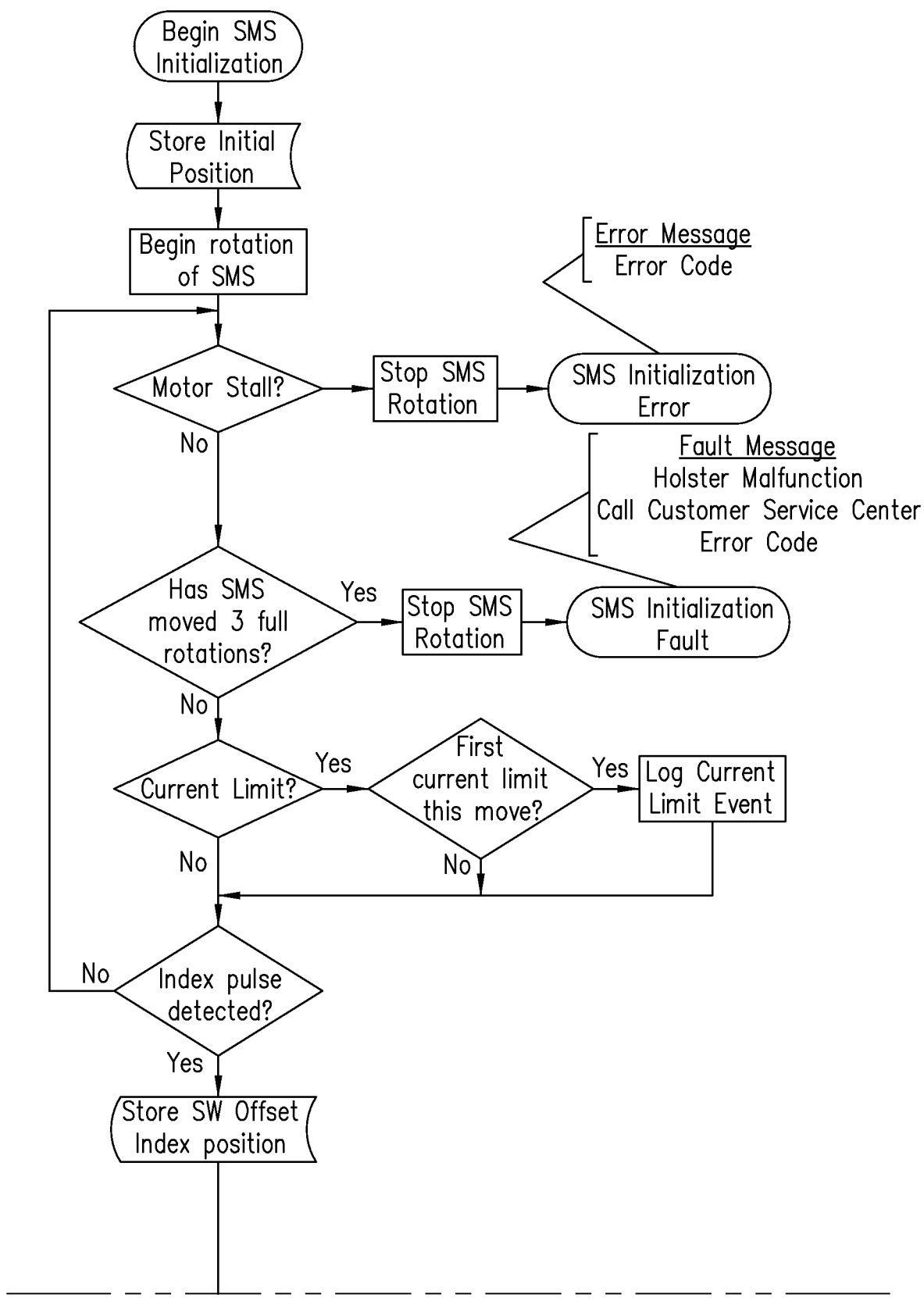
FIGS. 42A-42B together depict a flow chart showing steps carried out during an exemplary tissue sample management system initialization sequence, which is carried out as part of the sequence of FIG. 40, which is further carried out as part of the sequence depicted in FIGS. 38A-38B.
Figure 42B:
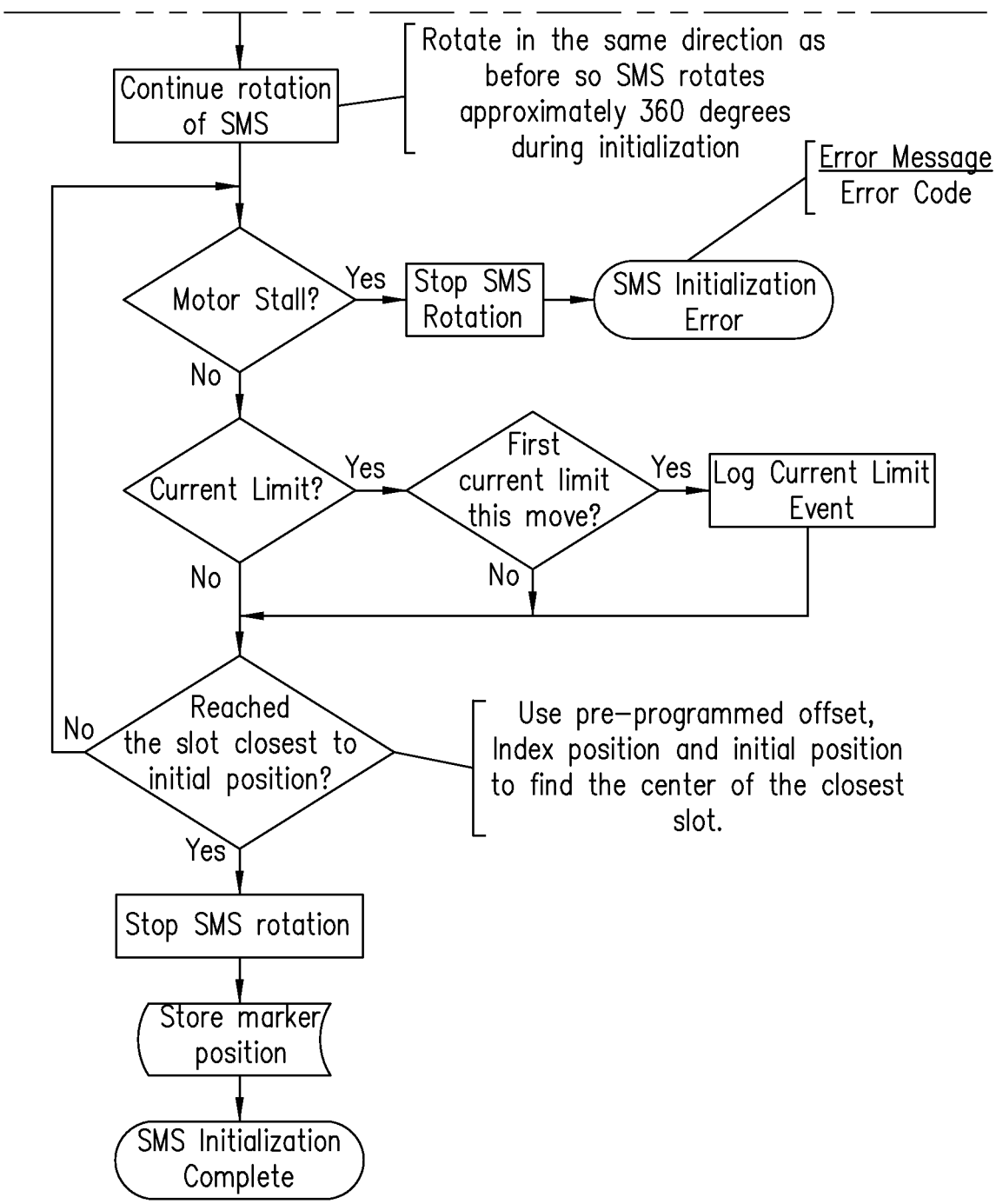

FIGS. 42A-42B together show an exemplary tissue sample management system initialization sequence in greater detail. As shown in FIGS. 42A-42B, the sequence begins with storing the initial rotational position of manifold (310). Then, motor (242) is activated to rotate manifold (310). During this movement, processor (434) monitors for stalling of motor (242). If motor (242) stalls, motor (242) is stopped and an error message is generated. Otherwise, motor (242) continues rotating and processor (434) counts the number of rotations of manifold (310). If processor (434) counts three full rotations of manifold (310), motor (242) is stopped and an error message is generated. Otherwise, motor (242) continues rotating and processor (434) monitors the motor current to determine whether that current exceeds a predetermined threshold. When the current threshold is exceeded, processor (434) determines whether it is the first occurrence of exceeding the threshold during this initial rotation of manifold (310). If it is the first time, the event is logged and processor (434) then determines whether an index pulse has been detected (e.g., from an encoder coupled with manifold (310), etc.). If it is not the first time there is no logging and processor (434) moves on to determining whether the index pulse has been detected. The foregoing steps are looped until the index pulse is detected. After the index pulse is detected, processor (434) compares the position of manifold (310) to the initial position stored at the beginning of the sequence, to determine an offset index position.

This offset determined above enables processor (434) to find the center of a passage (312) that is closest to the proper initial position, thereby enabling processor (434) to best align that passage (312) with cutter (150). To that end, motor (242) continues rotating manifold (310) until manifold (310) reaches the position where the above-noted passage (312) is aligned with cutter (150). During this rotation, processor (434) monitors for stalling of motor (242). If motor (242) stalls, motor (242) is stopped and an error message is generated. Processor (434) also monitors the motor current to determine whether that current exceeds a predetermined threshold. When the current threshold is exceeded, processor (434) determines whether it is the first occurrence of exceeding the threshold during movement of manifold (310) toward the corrected initial position. If it is the first time, the event is logged and processor (434) then determines whether the corrected initial position has been reached. If it is not the first time there is no logging and processor (434) moves on to determining whether the corrected initial position has been reached. The foregoing steps are looped until manifold (310) reaches the corrected position, at which time the sequence is complete. Of course, the foregoing steps are merely illustrative, and the foregoing sequence may be modified in numerous ways as will be apparent to those of ordinary skill in the art in view of the teachings herein.

Figure 43A:
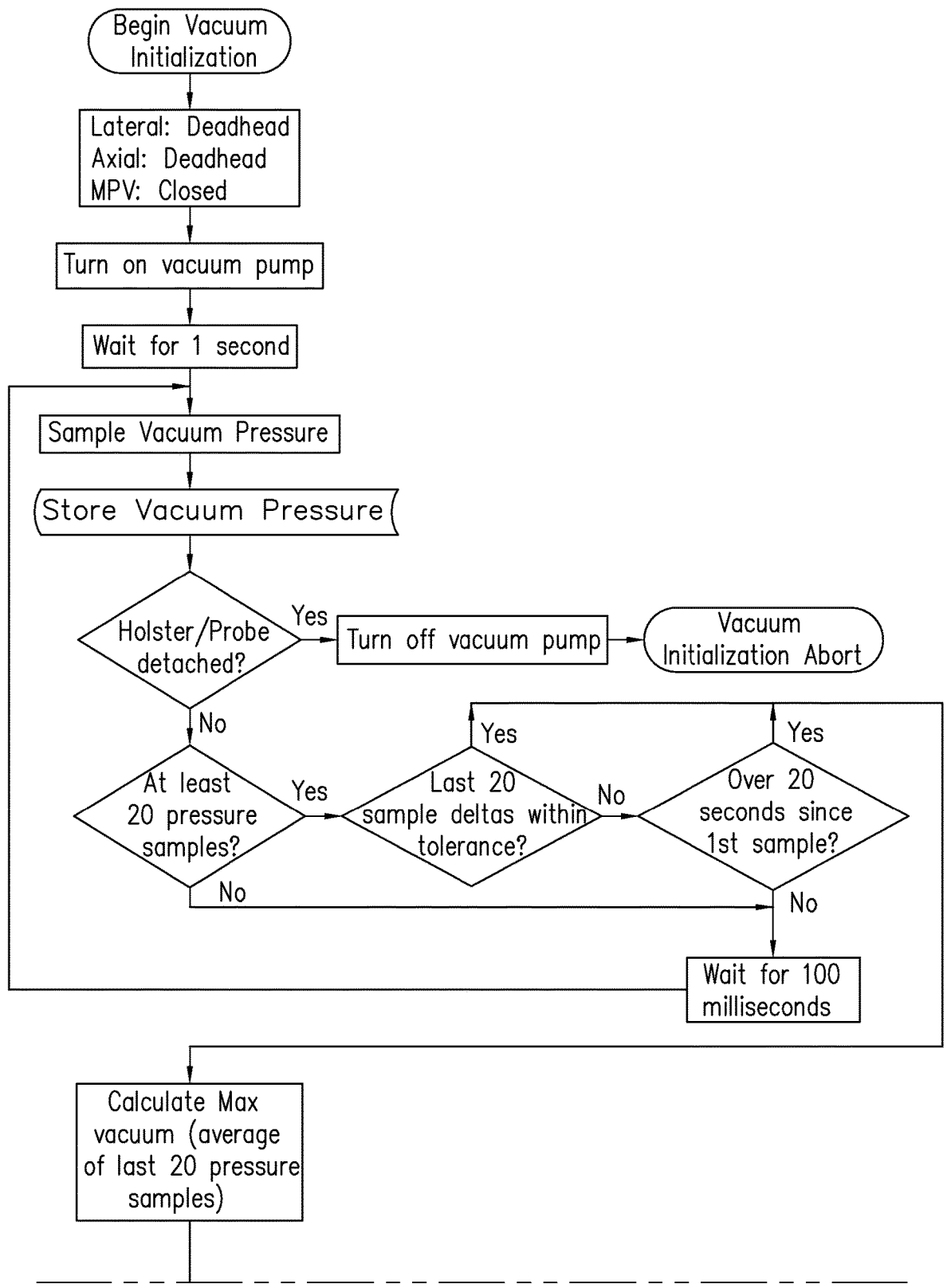
FIGS. 43A-43B together depict a flow chart showing steps carried out during an exemplary vacuum initialization sequence, which is carried out as part of the sequence depicted in FIGS. 38A-38B.
Figure 43B:
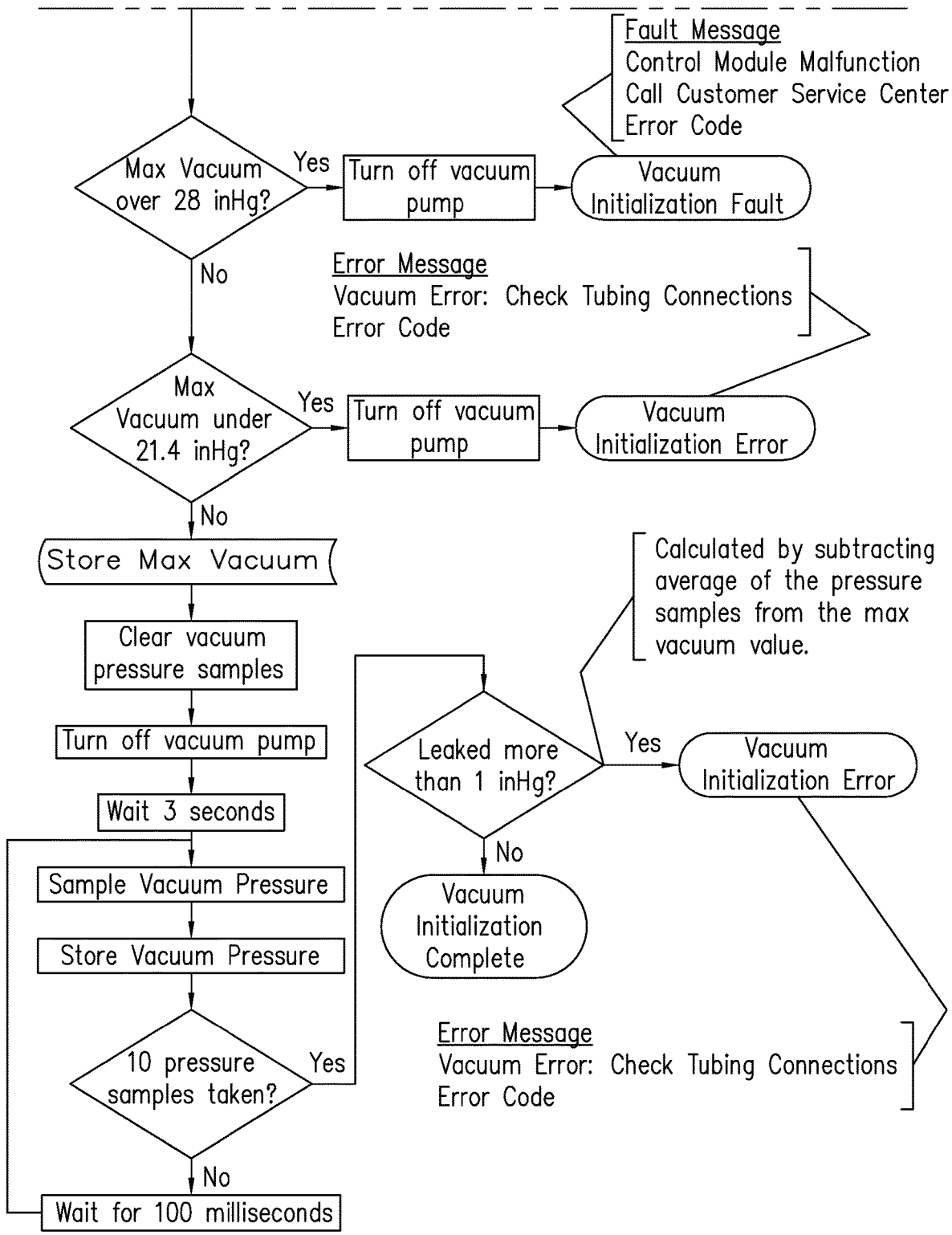

FIGS. 43A-43B together show an exemplary vacuum initialization sequence in greater detail. This sequence is performed to initialize vacuum pump (428) and associated pneumatic components. In particular, the sequence starts by activating vacuum pump (428) with actuators (512, 522) being positioned to seal tubes (20, 46). After one second of vacuum pump (428) being activated, processor (434) checks the vacuum pressure level and stores it in memory (432). Processor (434) also checks to determine whether biopsy device (10) is coupled with vacuum control module (400). If biopsy device (10) is not coupled with vacuum control module (400), processor (434) terminates the sequence. If biopsy device (10) is coupled with vacuum control module (400), processor (434) continues checking the vacuum pressure level every 100 milliseconds until twenty pressure samples have been taken. Once twenty pressure samples have been taken, processor (434) determines whether the last twenty pressure changes are within tolerance. If they are, the process proceeds to calculation of a maximum vacuum as described below. If the last twenty pressure changes are not within tolerance, processor (434) determines whether over twenty seconds have passed since the first vacuum level sample was taken. If over twenty seconds have passed, the proceeds to calculation of a maximum vacuum as described below. If twenty seconds have not passed, processor (434) continues taking vacuum pressure samples.

As noted above, the sequence eventually reaches a stage where processor (434) calculates the maximum vacuum, represented by the average of the last twenty pressure samples. Processor (434) then determines whether this maximum vacuum value is within a predefined range. In the present example, that range is between 21.3 inHg and 28 inHg, though it should be understood that any other suitable range may be used. If the maximum vacuum value is outside the range, vacuum pump (428) is deactivated and a fault message is provided. If the maximum vacuum value is inside the range, the maximum vacuum value is stored and the collected pressure sample values are cleared. Processor (434) then deactivates vacuum pump (428), waits three seconds, then checks the vacuum pressure and stores the value. Processor (434) repeats this sampling every 100 milliseconds until ten pressure sample values are taken. Processor (434) then determines whether more than 1 inHg of pressure has leaked. This determination is made by subtracting the average of the ten pressure sample values from the maximum vacuum value described above. If processor (434) determines that more than 1 inHg of pressure has leaked, an error message is generated. Otherwise, the sequence is complete. Of course, the foregoing steps are merely illustrative, and the foregoing sequence may be modified in numerous ways as will be apparent to those of ordinary skill in the art in view of the teachings herein.

Figure 44:
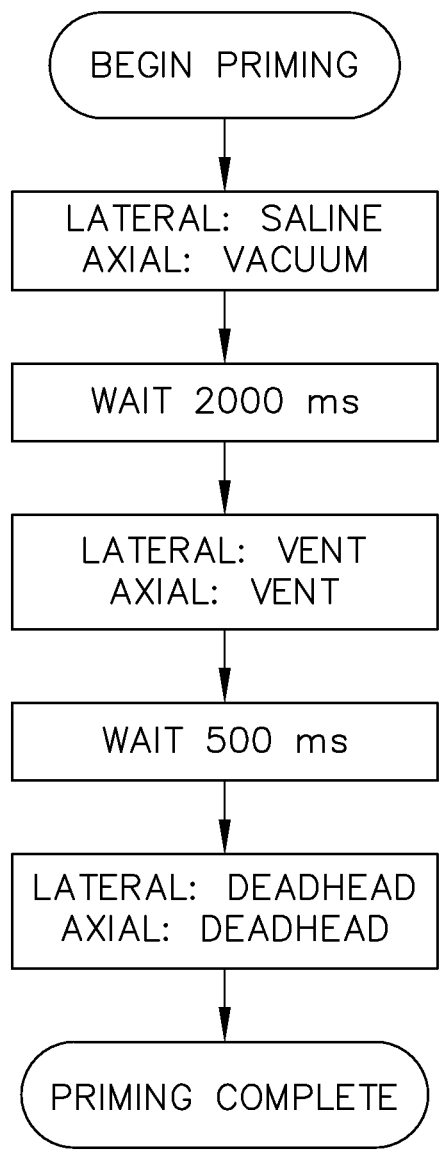
FIG. 44 depicts a flow chart showing steps carried out during an exemplary saline priming sequence, which is carried out as part of the sequence depicted in FIGS. 38A-38B.

FIG. 44 shows an exemplary saline priming sequence in greater detail. This sequence is performed to initialize tube (46). In particular, the sequence starts with actuators (512, 522) being positioned to provide saline to tube (46) while providing vacuum to tube (20). Vacuum pump (428) is activated. This state is maintained for 2000 milliseconds. Processor (434) then activates motors (412, 414) to rotate actuators (512, 522) to provide atmospheric air to tubes (20, 46). This state is maintained for 500 milliseconds. Processor (434) then activates motors (412, 414) to rotate actuators (512, 522) to seal tubes (20, 46). This completes the priming sequence. Of course, the foregoing steps are merely illustrative, and the foregoing sequence may be modified in numerous ways as will be apparent to those of ordinary skill in the art in view of the teachings herein.

Various other suitable initialization sequences that may be performed by biopsy system (2) will be apparent to those of ordinary skill in the art in view of the teachings herein. In some other versions, biopsy system (2) simply does not perform an initialization sequence.

B. Exemplary Sampling Sequence

Figure 45:
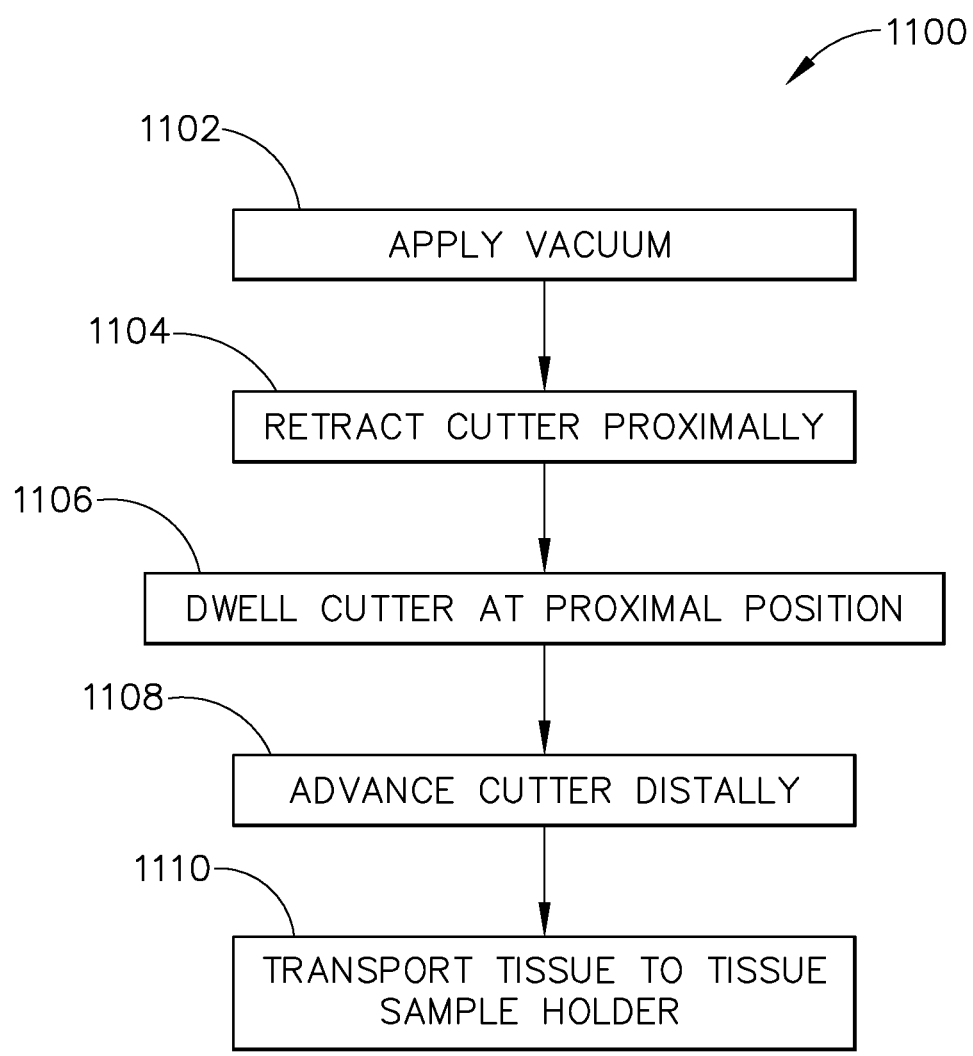
FIG. 45 depicts a flow chart showing steps carried out during an exemplary tissue sampling sequence.

FIG. 45 depicts general steps that may be carried out in an exemplary sampling sequence (1100), such as in response to a user activating biopsy button (262) after needle (110) has been inserted into the patient's breast. In particular, vacuum control module (400) first communicates a vacuum to probe (100), as shown in block (1102). Then, holster (200) drives cutter (150) to retract proximally, thereby at least partially opening lateral aperture (114), as shown in block (1104). Cutter (150) then dwells at the proximal position, as shown in block (1106), facilitating prolapse of tissue into lateral aperture (114). Holster (200) then drives cutter (150) to advance distally, thereby severing a tissue sample from the tissue prolapsed into lateral aperture (114), as shown in block (1108). A pressure differential within lumen (151) of cutter (150) then provides proximal transport of the severed tissue sample through lumen (151) into the indexed chamber (346) of tissue sample holder (300), as shown in block (1110). Sampling sequence (1100) may be repeated numerous times to acquire a plurality of tissue samples, with manifold (310) rotating between each iteration of sampling sequence (1100) to successively index empty chambers (346) relative to lumen (151) of cutter (150) to separately receive the tissue samples acquired in each sampling sequence (1100).

Of course, sampling sequence (1100) may include numerous sub-steps within the above-listed steps and/or may include other steps in addition to or in lieu of those listed above. By way of example only, some variations may include a slight reciprocation of cutter (150) once cutter (150) reaches the distal-most position. This slight reciprocation may include just slightly retracting cutter (150) before again advancing cutter (150), without significantly opening lateral aperture (114). An example of such reciprocation at the end of a cutting stroke is described in U.S. Pat. Pub. No. 2008/0214955, the disclosure of which is incorporated by reference herein.

Figure 46:
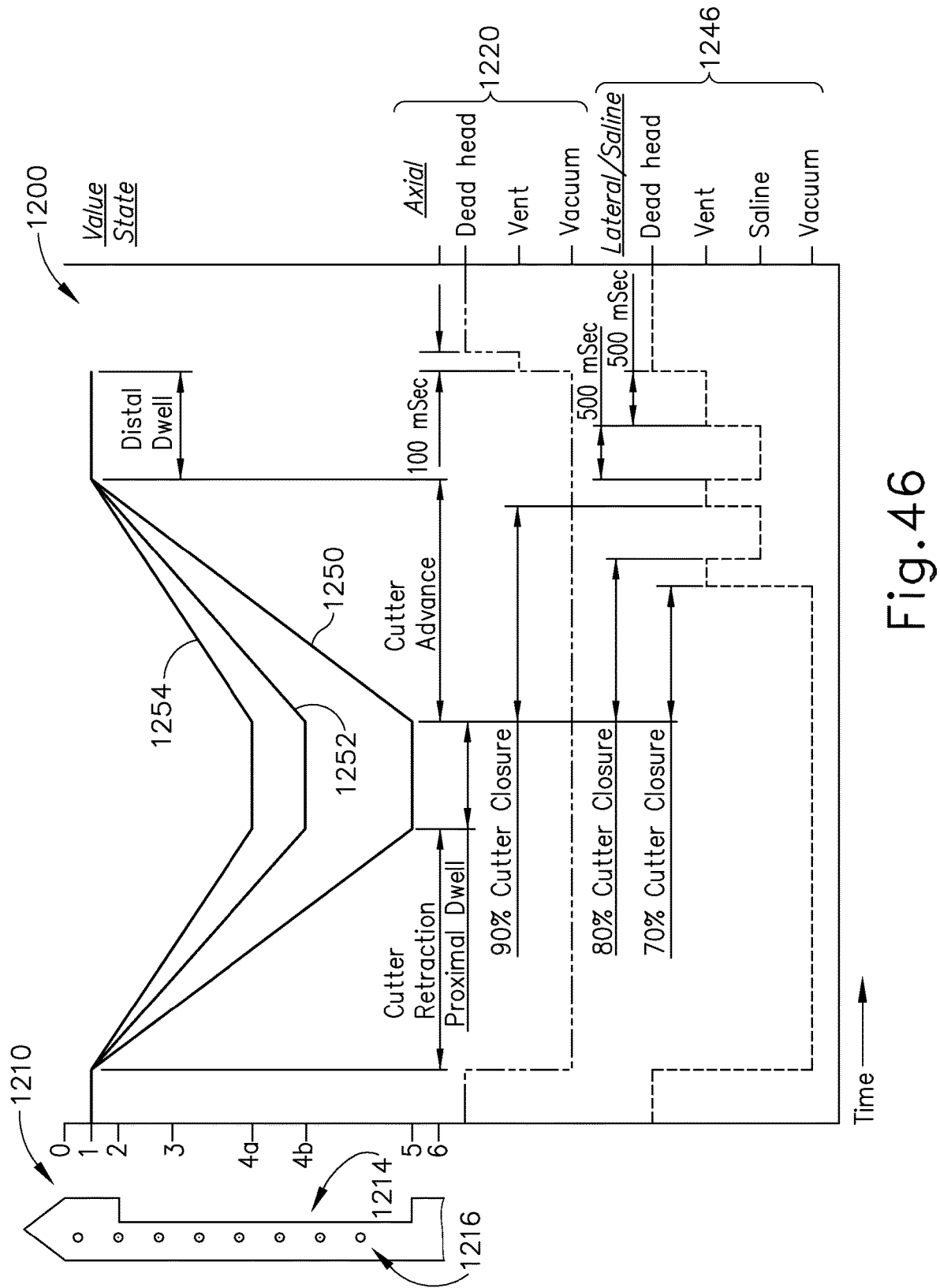
FIG. 46 depicts a graph showing various exemplary pneumatic states within the biopsy system of FIG. 1 during the tissue sampling sequence of FIG. 45.

FIG. 46 depicts an exemplary pneumatic algorithm (1200) that may be carried out during the sampling sequence (1100) depicted in FIG. 45. In particular, FIG. 46 shows movements of cutter (150) in relation to needle (110), which is represented by graphical representation (1210) including a graphical representation (1214) of lateral aperture (114) and graphical representations (1216) of openings (194) in wall (190). Movements of cutter (150) are shown in three different lines (1250, 1252, 1254). Line (1250) represents travel of cutter (150) when a full range of travel is selected for cutter (150). Line (1252) represents travel of cutter (150) when a medium range of travel (e.g., 18 mm effective aperture size) is selected for cutter (150). Line (1254) represents travel of cutter (150) when a short range of travel (e.g., 12 mm effective aperture size) is selected for cutter (150). Region (1220) represents pneumatic states of tube (20) during the sampling sequence (1100), thereby indicating the pneumatic states of lumen (151) in cutter (150). Region (1246) represents pneumatic states of tube (46) during the sampling sequence (1100), thereby indicating the pneumatic states of second lumen (192) of needle (110). The term "dead head" in FIG. 46 is intended to mean that the corresponding tube (20, 46) is sealed relative to atmosphere, and that neither vacuum nor saline is being provided to tube (20, 46) during that stage.

As shown in FIG. 46, vacuum is communicated to both lumens (151, 192) during proximal retraction of cutter (150). This vacuum continues in both lumens (151, 192) as cutter (150) dwells at a proximal position with aperture (114) at least partially open. At this stage, the vacuum communicated to lumens (151, 192) assists in drawing tissue into aperture (114). The duration for which cutter (150) dwells at the proximal position may vary based on the cutter speed selected through cutter speed adjustment button (716). For instance, cutter (150) may dwell at the proximal position for approximately 1000 ms when a slow cutter speed has been selected through cutter speed adjustment button (716). Cutter (150) may dwell at the proximal position for approximately 500 ms when a standard cutter speed has been selected through cutter speed adjustment button (716). In some other versions, cutter (150) may dwell at the proximal position for approximately 500 ms when "low saline" biopsy mode or "standard" speed biopsy mode is selected. Cutter (150) may dwell at the proximal position for approximately 0 ms (i.e., no dwell period at all) when a fast cutter speed or "high" speed biopsy mode has been selected through cutter speed adjustment button (716). Other suitable dwell durations will be apparent to those of ordinary skill in the art in view of the teachings herein. Furthermore, some versions may provide the same dwell time regardless of whether a different cutter speed or biopsy mode is selected.

It should also be understood that vacuum may be communicated to both lumens (151, 192) during proximal retraction of cutter (150). In some versions, this vacuum continues in both lumens (151, 192) as cutter (150) retracts to its proximal position with aperture (114) at least partially open. At this stage, the vacuum communicated to lumens (151, 192) assists in drawing tissue into aperture (114). The duration for which vacuum continues as cutter (150) retracts to the proximal position may vary based on the cutter speed or biopsy mode selected through cutter speed adjustment button (716). For instance, vacuum for lumens (151, 192) may start as cutter (150) is approximately 35% of the proximal position when fast cutter speed or "high" speed biopsy mode has been selected through cutter speed adjustment button (716). The vacuum on trigger points can be independent for lumens (151, 192). For instance, vacuum for cutter lumen (151) may start as cutter (150) is approximately 35% of the proximal position and vacuum for second lumen (192) may start as cutter (150) is approximately 75% of the proximal position when a cutter speed or biopsy mode has been selected through cutter speed adjustment button (716). Dwell time may also be added to additional functions of the device, for instance dwell time may be added if cutter (150) was fully proximal and the user decided to attempt to biopsy. If the user activates the open cutter function while in the patient or fires the device into the patient, cutter (150) will be fully proximal at this point, and if the user attempts a biopsy this would bypass the system parameters. Dwell time can be added to maintain common vacuum on time while accessing a biopsy function after another function. For instance, cutter (150) may dwell at the proximal position for approximately 500 ms when a fast cutter speed or "high" speed biopsy mode has been selected through cutter speed adjustment button (716). The time and vacuum control can be independent from lumens (151, 192). Other suitable vacuum trigger points with cutter (150) positions will be apparent to those of ordinary skill in the art in view of the teachings herein.

The vacuum further continues in both lumens (151, 192) as cutter (150) begins to advance distally to begin severing a tissue sample from the tissue protruding into aperture (114). Once cutter (150) closes off aperture (114) by approximately 70%, motor (414) in vacuum control module (400) actuates rotary actuator (522) to transition tube (46) from vacuum to atmospheric air from first port (524), such that second lumen (192) is vented to atmosphere. Vacuum control module (400) continues to provide vacuum to lumen (151) at this stage. In this example, "70%" means 70% of the effective size of aperture (114) when cutter (150) was at the proximal-most position during that particular cutting stroke. Thus, the 70% position is different for each line (1150, 1152, 1154) since the proximal-most position is different for each line (1150, 1152, 1154). The same principle will apply to the other percentage values referred to in this example.

When cutter (150) reaches a position where it closes off aperture (114) by approximately 80%, motor (414) actuates rotary actuator (522) to transition tube (46) from atmospheric air to saline from saline bag (80), such that saline is provided to second lumen (192). Vacuum control module (400) continues to provide vacuum to lumen (151) at this stage. When cutter (150) reaches a position where it closes off aperture (114) by approximately 90%, motor (414) actuates rotary actuator (522) to transition tube (46) from saline back to atmospheric air from first port (524), such that second lumen (192) is again vented to atmosphere. Vacuum control module (400) continues to provide vacuum to lumen (151) at this stage. When cutter (150) reaches a position where it closes off aperture (114) completely, motor (414) actuates rotary actuator (522) to transition tube (46) from atmospheric air back to saline from saline bag (80), such that saline is again provided to second lumen (192). Vacuum control module (400) continues to provide vacuum to lumen (151) at this stage.

It should be understood that, as cutter (150) advances, the vacuum communicated to lumens (151, 192) assists in drawing tissue into aperture (114), and lumens (151, 192) will receive a sequence of vacuum, vent or saline to aid in transporting tissue proximally through cutter lumen (151). The duration for which these events occur may vary based on the cutter speed or biopsy mode selected through cutter speed adjustment button (716). As noted above, the state of second lumen (192) may change throughout advancement of cutter (150), with vacuum at approximately 0 to 70% cutter closed, venting to atmosphere at approximately 70-80% cutter closed, saline at approximately 80-90% cutter closed and venting to atmosphere at approximately 90-100% cutter closed. In addition or in the alternative, saline may be communicated to second lumen (192) for approximately 0 ms, then atmospheric air to second lumen (192) for approximately 1500 ms while cutter lumen (151) receives vacuum for approximately 1500 ms when a "low saline" biopsy mode speed has been selected through cutter speed adjustment button (716). Saline may be communicated to second lumen (192) for approximately 500 ms, then atmospheric air to second lumen (192) for approximately 1000 ms while cutter lumen (151) receives vacuum for approximately 1500 ms when "standard" speed biopsy mode or "high" speed biopsy mode has been selected through cutter speed adjustment button (716). Additionally the valve staging events could repeat for a second time or more, or the valve staging events could be altered for the second time or more. Other suitable states for post cut valve staging will be apparent to those of ordinary skill in the art in view of the teachings herein. It should be understood that cutter lumen (151) may maintain a vacuum state throughout the advancement of cutter (150). Other suitable states or trigger points with cutter (150) positions will be apparent to those of ordinary skill in the art in view of the teachings herein.

As cutter (150) advances fully, the MPV that is used to regulate vacuum level from vacuum pump (428) will close off providing full vacuum to the system. After the system completes the biopsy function, the MPV will reset to maintain vacuum at the level set by the user or default to the level at power up. The MPV can be controlled to open and close for different vacuum levels and times. Other suitable vacuum control points with cutter (150) positions will be apparent to those of ordinary skill in the art in view of the teachings herein.

Once cutter (150) has closed off aperture (114) completely as described above, distal edge (152) of cutter (150) has fully severed a tissue sample from tissue that was protruding through aperture (114). This severed tissue sample is captured in lumen (151) of cutter (150), and is initially positioned at the distal end of lumen (151). After having reached the distal position where it closes off aperture (114) completely, cutter (150) dwells at this distal position. Second lumen (192) receives saline as described above for the first approximately 500 ms of this dwell time. Vacuum control module (400) continues to provide vacuum to lumen (151) during this first 500 ms. After passage of this first 500 ms, motor (414) actuates rotary actuator (522) to transition tube (46) from saline back to atmospheric air from first port (524), such that second lumen (192) is again vented to atmosphere. This venting occurs for a second period of approximately 500 ms. Vacuum control module (400) continues to provide vacuum to lumen (151) during this second 500 ms. During this full second (first and second 500 ms periods combined), the combination of venting and saline impinges against the distal face of the severed tissue sample that is captured within lumen (151) of cutter (150). The vacuum that is provided to lumen (151) via tube (20) pulls on the proximal face of the severed tissue sample that is captured within lumen (151). Thus, the severed tissue sample experiences a pressure differential within lumen (151) for this full second after cutter (150) closes off aperture (114) completely. This pressure differential causes the severed tissue sample to travel proximally through lumen (151) and into whichever tissue chamber (346) is indexed to lumen (151). Of course, in practice the tissue sample may actually reach chamber (346) before the full second expires.

After the full second expires after cutter (150) closes off aperture (114) completely as described above, motor (414) in vacuum control module (400) actuates rotary actuator (522) to transition tube (46) from atmospheric air to a "dead head," such that second lumen (192) is sealed relative to atmospheric air, is sealed relative to saline bag (80), and receives no vacuum. Simultaneously, motor (412) in vacuum control module (400) actuates rotary actuator (512) to transition tube (20) from vacuum to atmospheric air from first port (514), such that lumen (151) of cutter (150) (and the interior of tissue sample holder (300), etc.) is vented to atmosphere. This venting occurs for approximately 100 ms. Upon expiration of that 100 ms, motor (412) in vacuum control module (400) actuates rotary actuator (512) to transition tube (20) from atmospheric air to a "dead head," such that lumen (151), etc., is sealed relative to atmospheric air and receives no vacuum. Second lumen (192) also remains "dead-headed" during this period. Both lumens (151, 192) remain in this state until the next biopsy sampling cycle begins.

At the end of the biopsy function, the valve states will vent prior to deadheading the system to assist in reducing pressure in the system for the user to apply meds, apply a marker or remove the sample management assembly. The duration for which these events occur may vary based on the vacuum capability of the pump and volume of the system. For instance, vent may activate for approximately 500 ms for both lumens (151, 192) prior to deadheading the system. Other suitable vent time durations will be apparent to those of ordinary skill in the art in view of the teachings herein. The foregoing sampling sequence (1100) and pneumatic algorithm (1200) are merely illustrative examples. Again, numerous other variations will be apparent to those of ordinary skill in the art in view of the teachings herein.

C. Exemplary Probe Clearing Sequence

Figure 47:
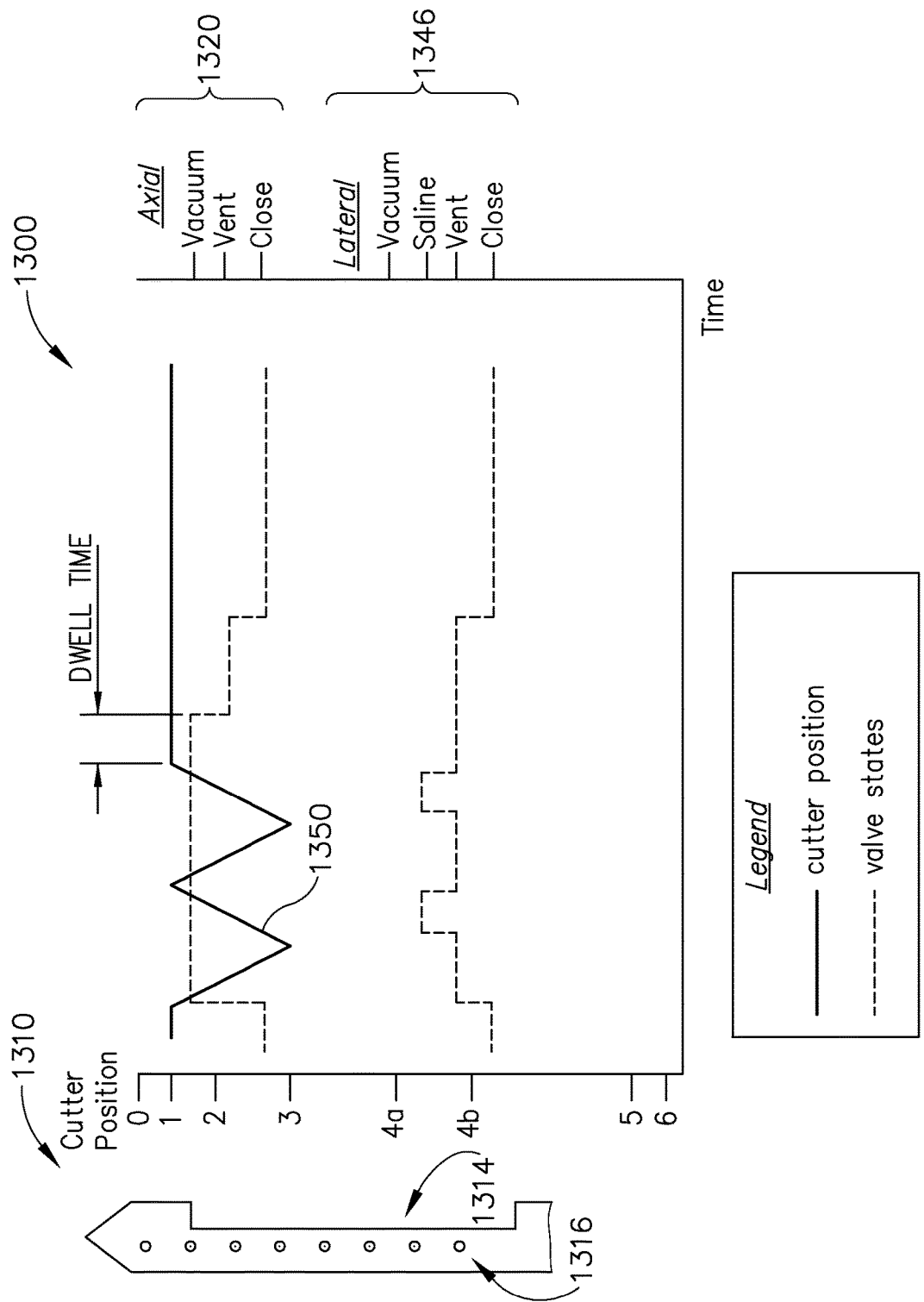
FIG. 47 depicts a graph showing various exemplary pneumatic states within the biopsy system of FIG. 1 during an exemplary probe clearing cycle.

FIG. 47 shows an exemplary pneumatic algorithm (1300) that may be carried out during a probe clearing sequence at any suitable stage. By way of example only, probe clearing algorithm (1300) may be executed when tissue gets jammed in lumen (151) of cutter (150) (a.k.a. a "dry tap"). Probe clearing algorithm (1300) may be initiated in response to a user pressing and quickly releasing vacuum button (266) on holster (200) as described above. In addition or in the alternative, probe clearing algorithm (1300) may be automatically initiated when a dry tap is detected. For instance, a vacuum sensor may detect an excessive vacuum buildup in tissue sample holder (300) or elsewhere, with the vacuum level exceeding a threshold value associated with a dry tap. This detection may automatically trigger a probe clearing algorithm (1300). Other suitable ways in which a probe clearing algorithm (1300) may be manually and/or automatically triggered will be apparent to those of ordinary skill in the art in view of the teachings herein.

FIG. 47 specifically shows movements of cutter (150) in relation to needle (110), which is represented by a graphical representation (1310) including a graphical representation (1314) of lateral aperture (114) and graphical representations (1316) of openings (194) in wall (190). Line (1350) represents travel of cutter (150). Region (1320) represents pneumatic states of tube (20) during the sampling sequence (1100), thereby indicating the pneumatic states of lumen (151) in cutter (150). Region (1346) represents pneumatic states of tube (46) during the sampling sequence (1100), thereby indicating the pneumatic states of second lumen (192) of needle (110). The term "close" in FIG. 41 is similar to the term "dead head" referenced above and in FIG. 46, and is intended to mean that the corresponding tube (20, 46) is sealed relative to atmosphere, and that neither vacuum nor saline is being provided to tube (20, 46) during that stage.

As shown in FIG. 47, vacuum is communicated to lumen (151) and lumen (192) is vented to atmosphere during proximal retraction of cutter (150). Cutter (150) eventually reaches a partially retracted position then reverses direction and advances distally. Lumen (151) receives vacuum during both this proximal retraction of cutter (150) and during the distal advancement of cutter (150). Lumen (192) is vented to atmosphere during the proximal retraction of cutter (150) and shortly after cutter (150) reverses to distal advancement. However, shortly after cutter (150) begins advancing distally, lumen (192) transitions from atmosphere to saline. In some other versions, lumen (192) transitions from atmosphere to saline at approximately the same time that cutter (150) reverses the direction of translation. In still some other versions, lumen (192) transitions from atmosphere to saline shortly before cutter (150) reverses the direction of translation.

When cutter (150) reaches the distal position, cutter (150) again reverse direction and retracts proximally. Lumen (151) continues to receive vacuum. Lumen (192) transitions from saline back to atmosphere shortly before cutter (150) reaches the distal position. In some other versions, lumen (192) switches from saline to atmosphere at substantially the same time that cutter (150) reverses from distal advancement to proximal retraction. In still some other versions, lumen (192) switches from saline to venting just slightly after the time that cutter (150) reverses from distal advancement to proximal retraction.

Once cutter (150) again reaches the partially retracted position, cutter (150) again reverses direction and advances distally. Lumen (151) continues to receive vacuum. Lumen (192) transitions back from atmosphere to saline shortly after cutter (150) reverses from proximal retraction to distal advancement for the second time. In some other versions, lumen (192) switches from atmosphere to saline at substantially the same time that cutter (150) reverses from proximal retraction to distal advancement for the second time. In still some other versions, lumen (192) switches from venting to saline just slightly before the time that cutter (150) reverses from proximal retraction to distal advancement for the second time.

Once cutter (150) again reaches the distal position, cutter (150) remains at the distal position. Lumen (151) continues to receive vacuum for a certain period of time. Lumen (192) transitions back from saline to atmosphere shortly before cutter (150) reaches the distal position for the second time. In some other versions, lumen (192) switches from saline to atmosphere at substantially the same time that cutter (150) reaches the distal position for the second time. In still some other versions, lumen (192) switches from venting to saline just slightly after the time that cutter (150) reaches the distal position for the second time.

While cutter (150) remains at the distal position, lumen (151) eventually transitions from vacuum to venting. Lumens (151, 192) then both continue to vent to atmosphere for a period of time, until both lumens (151, 192) are both eventually simultaneously sealed. Cutter (150) continues to remain at the distal position until commanded to move by a subsequent user input.

In the foregoing example, cutter (150) is reciprocated only twice during clear probe algorithm (1300). It should be understood that any other suitable number of reciprocations may be used, including one, single reciprocation or more than two reciprocations. It should also be understood that manifold (122) is stationary during clear probe algorithm (1300). Furthermore, in some versions the longitudinal position at which cutter (150) reverses from proximal retraction to distal advancement may be selected to avoid cutting tissue samples during clear probe algorithm (1300). Still other suitable ways in which a clear probe algorithm may be provided will be apparent to those of ordinary skill in the art in view of the teachings herein.

D. Exemplary Idling Vacuum

In some instances it may be desirable to provide continuous suction at a biopsy site. For instance, after obtaining a few biopsy samples, a user may wish to extract tray (330) from manifold (310) to inspect tissue samples therein. The user may wish to leave needle (110) inserted in the patient's breast during this time, particularly if the user intends to obtain more biopsy samples. Biopsy device (10) thus remains substantially idle during this time. It may be desirable to provide some sort of pneumatic flow within biopsy device (10) during this idle time. By way of example only, it may be desirable to provide suction at the biopsy site in instances where the biopsy site is bleeding significantly, such that the suction will draw away the blood. In addition or in the alternative, maintaining a pneumatic flow through biopsy device (10) may reduce the likelihood of blood and/or other bodily fluids coagulating on certain internal components of probe (100); and/or may reduce the likelihood of a hematoma forming at the biopsy site.

In the present example, vacuum control module (400) is operable to provide suction at the biopsy site during the above-described idle time. In the present example, this idling vacuum sequence is initiated in response to the user tapping the "steady vac" button (756) on touchscreen (410). In addition or in the alternative, the idling vacuum sequence may be automatically initiated when biopsy system (2) receives no user input for a certain period of time. At the beginning of the idling vacuum sequence, cutter (150) is retracted proximally just enough to slightly open aperture (114) but not enough to sever an appreciable tissue sample when cutter (150) is later advanced distally. In some versions, cutter (150) is retracted to a position where aperture (114) is effectively opened approximately 52%, though of course any other suitable degree of opening may be used. With cutter (150) slightly retracted, a continuous low level vacuum is provided to lumen (151) via tube (20). Simultaneously, second lumen (192) is vented to atmosphere via tube (46). Alternatively, second lumen (192) may receive saline from bag (80) via tube (46). As yet another merely illustrative example, motor (414) may drive rotary actuator (522) to alternate between providing atmospheric air and saline to tube (46) and second lumen (192) while vacuum is provided to lumen (151). Other suitable sequences for second lumen (192) will be apparent to those of ordinary skill in the art in view of the teachings herein. It should also be understood that lumen (151) may receive a pulsed vacuum and/or some other pneumatic communication during the idling vacuum sequence.

Continuing with the present example, lumen (151) may receive continuous vacuum indefinitely and second lumen (192) may receive atmospheric air indefinitely during the idling vacuum sequence. The sequence may end when the user taps "steady vac" button (756) again. In addition or in the alternative, the idling vacuum sequence may automatically cease when the user activates biopsy button (262) or provides some other user input; and/or after a predetermined time period has elapsed. At the end of the idling vacuum sequence, cutter (150) is advanced distally to close aperture (114).

E. Exemplary Intra-Procedure Presentation of Tissue Samples

Figure 48:
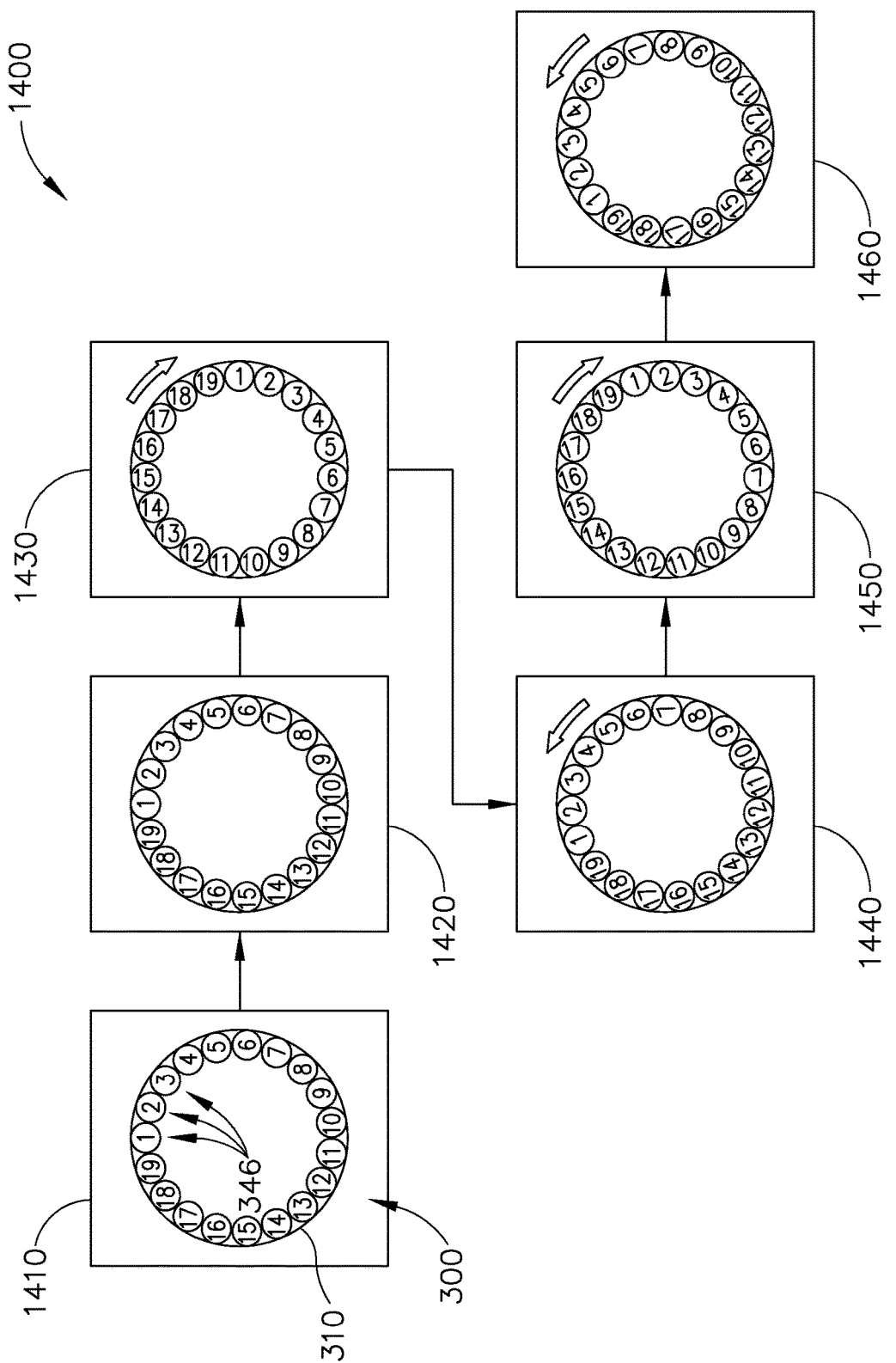
FIG. 48 depicts a flow chart showing steps carried out during an exemplary tissue sample presentation sequence.

As noted above, biopsy system is operable to present severed tissue samples to the user during a biopsy procedure. An example of this tissue sample presentation process (1400) is shown in FIG. 48. In the example depicted in FIG. 48, tissue sample holder (300) is shown as having nineteen chambers (346). It should be understood that tissue sample holder (300) may have any suitable number of chambers (346) (e.g., twelve, thirteen, etc.), and that tissue sample presentation process (1400) may be carried out with a tissue sample holder (300) having any suitable number of chambers (346).

As shown in block (1410), a first tissue sample chamber (346) labeled as "1" is in the 12 o'clock position, aligned with lumen (151) of cutter (150), at the beginning of a biopsy sampling process. As shown in block (1420), a severed tissue sample chamber is communicated proximally through lumen (151) of cutter (150) and into the first tissue sample chamber (346) as described above. As shown in block (1430), motor (240) then rotates manifold (310) to position the first tissue sample chamber (346) at the 3 o'clock position, to thereby present the severed tissue sample to the user for viewing through the transparent manifold (310) and transparent cover (302). In the present example, biopsy system (10) automatically transitions from block (1420) to block (1430) immediately after completion of a cutting stroke by cutter (150). In some other versions, biopsy system (10) waits a predetermined time period before transitioning from block (1420) to block (1430). As yet another merely illustrative variation, biopsy system (10) may require a separate user input in order to transition from block (1420) to block (1430).

As noted above, the "set view position" button (734) in touchscreen (410) enables the user to select from four positions for tissue sample presentation—the 12 o'clock position, the 3 o'clock position, the 6 o'clock position, and the 9 o'clock position. In the example shown in FIG. 48, the user had selected the 3 o'clock position, though a tissue sample presentation process (1400) like the one shown in FIG. 48 may be just as readily carried out when the user has selected a different position for tissue sample presentation.

Continuing with the present example, manifold (310) dwells for a predetermined time period in the presentation position shown in block (1430). By way of example only, that predetermined time period may be approximately 2 seconds or some other time period. In addition or in the alternative, manifold (310) may dwell in the tissue presentation position until the user provides an input (e.g., by activating the biopsy button (262) again, etc.). Once the predetermined time period has elapsed (or some user input has been provided), motor (242) rotates manifold (310) to position a second tissue sample chamber (346) (labeled as "2" in FIG. 48) at the 12 o'clock position, to thereby align the second chamber (346) with lumen (151) of cutter (150) as shown in block (1440). After a second tissue sample is communicated to this second chamber (346), motor (242) rotates manifold (310) to position the second chamber (346) to the 3 o'clock presentation position, as shown in block (1450). Manifold (310) may again dwell at this position for the predetermined time period before rotating back in the other direction to position a third tissue sample chamber (346) (labeled as "3" in FIG. 48) at the 12 o'clock position, to thereby align the third chamber (346) with lumen (151) of cutter (150) as shown in block (1460). The foregoing process may be repeated each time a biopsy sample is captured.

It should be understood that tissue sample presentation process (1400) may be modified in any way desired, or even be omitted altogether. By way of example only, tissue sample presentation process (1400) may be modified in accordance with at least some of the teachings of U.S. Pat. Pub. No. 2008/0214955, the disclosure of which is incorporated by reference herein.

VI. Exemplary Biopsy Site Marker Applier

Figure 49:
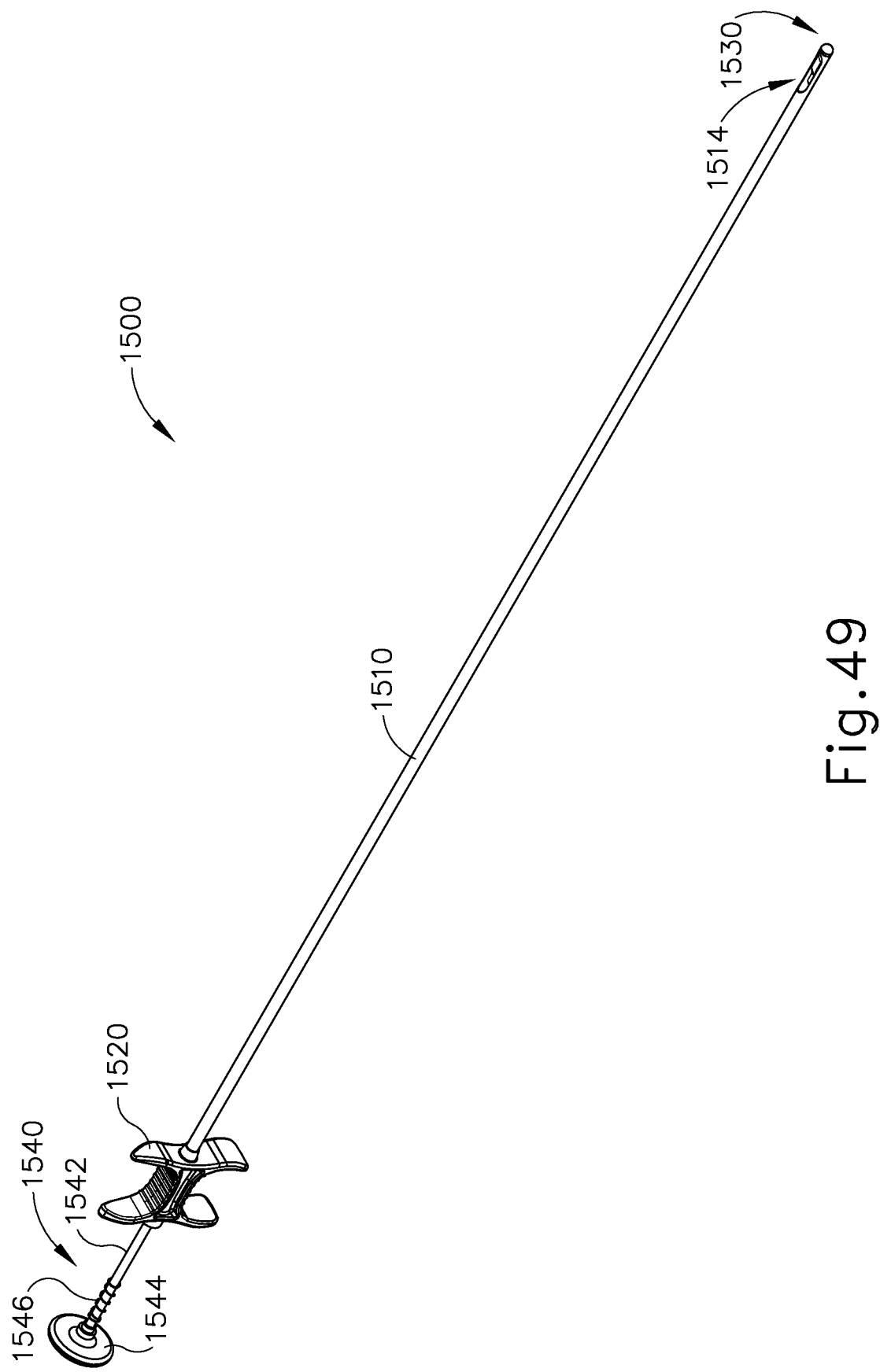
FIG. 49 depicts a perspective view of an exemplary biopsy site marker applier.
Figure 50:
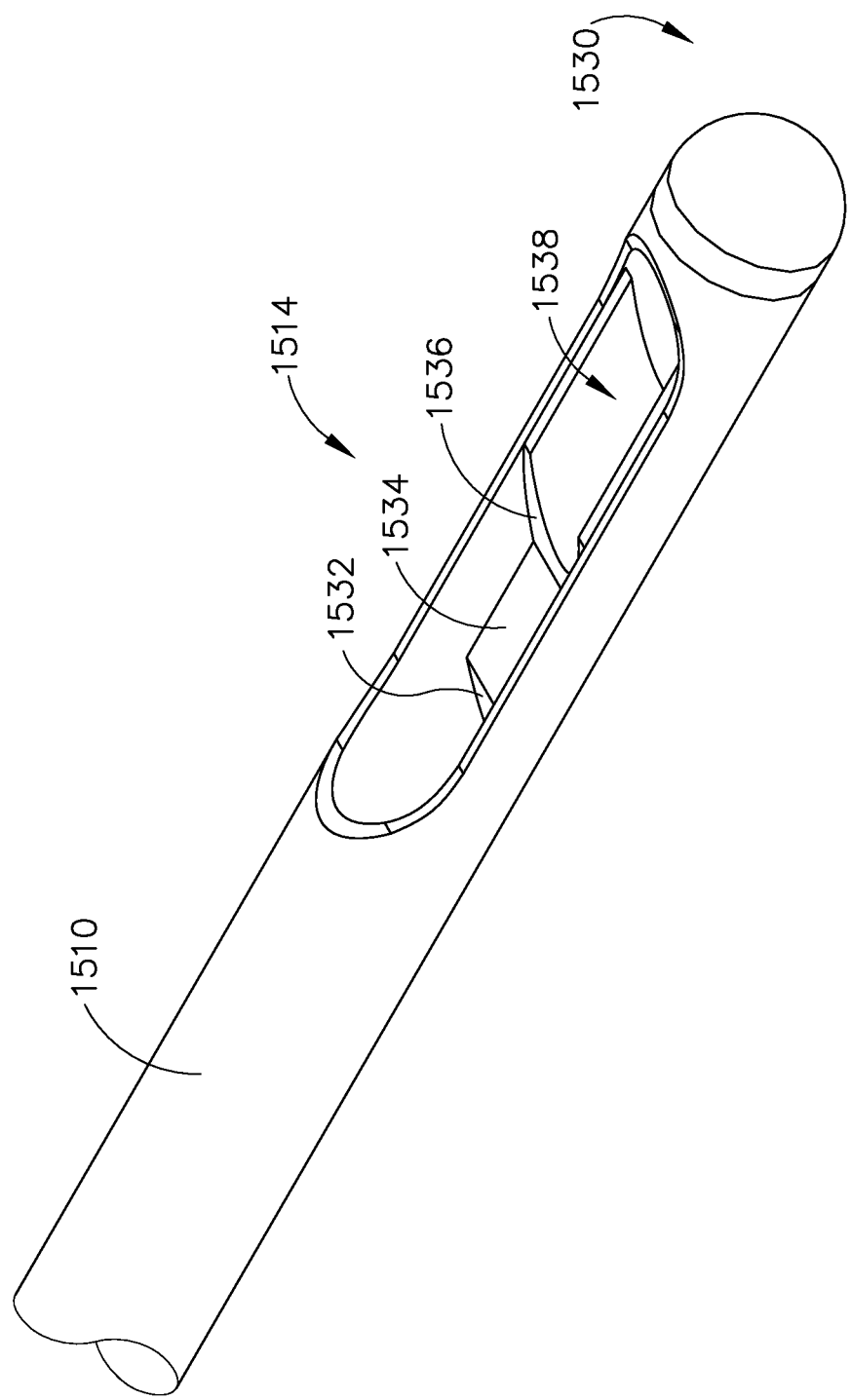
FIG. 50 depicts a perspective view of the distal end of the marker applier of FIG. 49.
Figure 51:
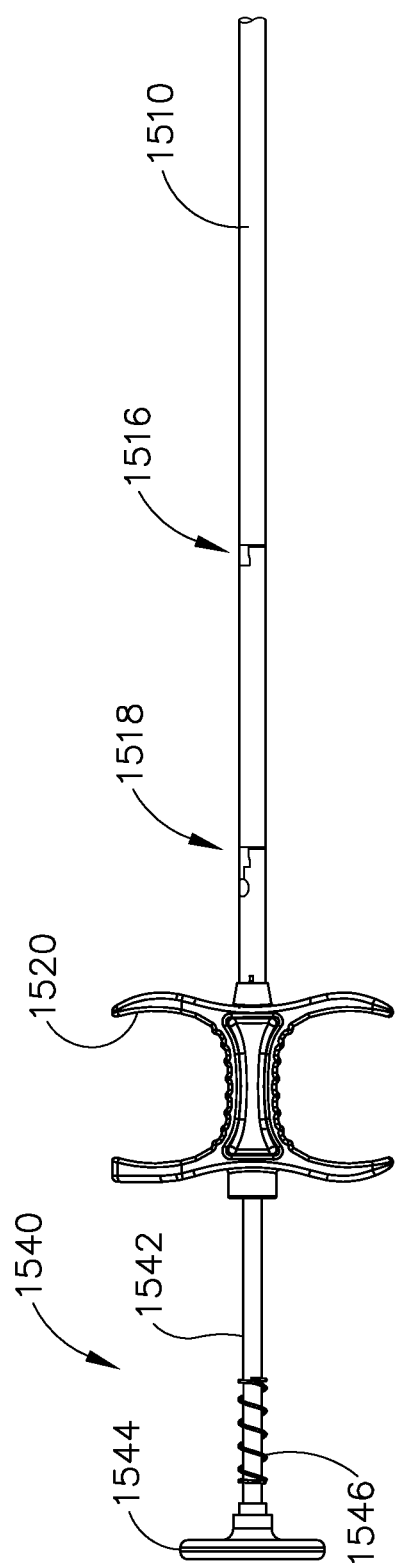
FIG. 51 depicts a side elevational view of the proximal end of the marker applier of FIG. 49, showing insertion depth indicia.

FIGS. 49-51 depict an exemplary marker applier (1500) that may be used with biopsy device (10). Marker applier (1500) may be configured and/or operable in accordance with at least some of the teachings of the various relevant references cited herein. Marker applier (1500) of the present example includes a cannula (1510) with a grip (1520) at the proximal end of cannula (1510) and a tip (1530) at the distal end of cannula (1510). A lateral aperture (1514) is positioned proximal to tip (1530). A plunger (1540) is positioned within the lumen of cannula (1510) and includes a push-rod (1542), a thumb actuator (1544) at the proximal end of push-rod (1542), and a coil spring (1546) coaxially disposed about push-rod (1542). Coil spring (1546) is configured to bear against grip (1520) as plunger (1540) is advanced distally; and thereby bias plunger (1540) proximally.

Cannula (1510) is configured to receive a marker body (not shown) and deposit the marker body at a biopsy site as will be described in greater detail below. Tip (1530) of the present example comprises features that are configured to both prevent the marker body from inadvertently falling out of lateral aperture (1514) yet also guide the marker body out through lateral aperture (1514) when the user wishes to deploy the marker body at the biopsy site. In particular, and as best seen in FIG. 50, tip (1530) includes a proximal ramp (1532), a longitudinally extending flat (1534), and a distal ramp (1536), all of which are positioned adjacent to lateral aperture (1514). Proximal ramp (1532) and flat (1534) are configured to assist in retaining the marker body within cannula (1510) (e.g., with the marker body being positioned proximal to ramp (1532)) by providing an interference. These components thus function like (and may be configured like) the similar components described in U.S. Pub. No. 2010/0049084, the disclosure of which is incorporated by reference herein. When a user pushes distally on thumb actuator (1544) relative to grip (1520), the distal end of push-rod (1542) urges the marker body over ramp (1532) and flat (1534). As the user continues to push distally on thumb actuator (1544) relative to grip (1520), the marker body eventually encounters ramp (1536), which deflects the marker body outwardly and through lateral aperture (1514). The marker body is thereby deployed from cannula (1510).

In use, cannula (1510) may be inserted through lumen (151) of cutter (150) as described in greater detail below, to position lateral aperture (1514) directly under lateral aperture (114) of needle (110) after at least one tissue sample has been acquired from the patient's breast and while needle (110) is still inserted in the breast. With cutter (150) retracted to open aperture (114) (e.g., by pressing button (254) as described above), the user may push distally on thumb actuator (1544) relative to grip (1520), to thereby expel the marker body from cannula (1510) for deployment at the biopsy site. The marker body may itself be later visible (or may carry something that is later visible) under some sort of imaging modality (e.g., X-ray, ultrasound, MRI, PEM, BSGI, etc.), enabling a physician to later relocate the biopsy site. Once the marker body is deployed at the biopsy site, the user may withdraw marker applier (1500) from lumen (151) of cutter (150). In some instances, the user may continue holding thumb actuator (1544) in a distal position while withdrawing marker applier (1500) from lumen (151). With thumb actuator (1544) in such a distal position, the distal end of push-rod (1542) may be positioned within recess (1538) of tip (1530). This may avoid the distal end of push-rod (1542) being scraped by cutting edge (152) of cutter (150) as marker applier (1500) is withdrawn from lumen (151). Of course, recess (1538) is merely optional and the distal end of push-rod (1542) will not necessarily be scraped by cutting edge (152) of cutter (150) as marker applier (1500) is withdrawn from lumen (151) if recess (1538) is omitted.

Marker applier (1500) may be inserted into lumen (151) of cutter (150) in at least two different ways. In one example, where tissue sample holder (300) remains coupled with probe (100), the user may rotate manifold (310) until passage (313) is aligned with lumen (151). This may be done by repeatedly tapping (or holding down on) "advance chambers" button (736) until passage (313) is aligned with lumen (151). In some versions, touchscreen (410) includes a separate button (not shown) that is dedicated to aligning passage (313) with lumen (151) with a single tap of the dedicated button, regardless of the rotational position of manifold (310) before the dedicated button is tapped. Alternatively, processor (434) may command motor (242) to automatically rotate manifold (310) to align passage (313) with lumen (151) in response to the user pressing button (254) as described above. In any of these cases, once passage (313) is aligned with lumen (151), the user may grasp grip (372) and pull plug (370) from passage (313). The user may then insert tip (1530) and cannula (1510) into passage (313), and advance marker applier (1500) distally until lateral aperture (1514) reaches the longitudinal position associated with lateral aperture (114) as described below. In another example, the user may first remove tissue sample holder (300) from probe, then insert tip (1530) and cannula (1510) into opening (174) of cutter seal (170), and advance marker applier (1500) distally until lateral aperture (1514) reaches the longitudinal position associated with lateral aperture (114) as described below.

It should be understood from the foregoing that a certain proximal length of marker applier (1500) will be exposed relative to probe (100) when cannula (1510) is inserted to a depth where lateral aperture (1514) reaches the longitudinal position associated with lateral aperture (114). It should also be understood that the amount of exposed proximal length will be different depending on whether tissue sample holder (300) is still coupled with probe (100) when cannula (1510) is inserted into probe (100). In particular, more proximal length will be exposed when cannula (1510) is fully inserted into probe (100) with tissue sample holder (300) removed from probe (100). It may therefore be desirable in some instances to provide separate depth indications on cannula (1510) to provide a visual indication associated with a proper insertion depth both with and without tissue sample holder (300) coupled with probe (100). FIG. 51 shows examples of such indicia, as do materials at the end of the appendix. In particular, FIG. 51 shows a first indicia (1516) and a second indicia (1518) on cannula (1510). First indicia (1516) is associated with insertion of cannula (1510) in lumen (151) in the absence of tissue sample holder (300); while second indicia (1518) is associated with insertion of cannula (1510) in lumen (151) via tissue sample holder (300).

In use, when tissue sample holder (300) is decoupled from probe (100) the user may insert cannula (1510) into opening (174) of cutter seal (170), and advance marker applier (1500) distally until indicia (1516) reaches the proximal face of cutter seal (1710). This will provide a visual indication to the user that lateral aperture (1514) has reached the longitudinal position associated with lateral aperture (114), such that the user may stop inserting cannula (1510) further into lumen (151). Similarly, when tissue sample holder (300) is coupled with probe (100) and the user inserts cannula (1510) into passage (313), the user may advance marker applier (1500) distally until indicia (1518) reaches the proximal face of manifold (310). This will provide a visual indication to the user that lateral aperture (1514) has reached the longitudinal position associated with lateral aperture (114), such that the user may stop inserting cannula (1510) further into lumen (151).

There may also be instances where various biopsy devices (10) have needles (110) of different lengths and/or gauge sizes. These different lengths and/or gauge sizes may also result in different distances between the proximal end of probe (100) and lateral aperture (114). To facilitate usability of marker applier (1500) with these different needle lengths and/or gauge sizes, cannula (1510) may include different sets of indicia (1516, 1518), with each pair of indicia (1516, 1518) being associated with a different needle length. For instance, one pair of indicia (1516, 1518) may be associated with a 8 gauge needle (110) while another pair of indicia (1516, 1518) is associate with a 10 gauge needle (110). Such different pairs of indicia (1516, 1518) may be color coded or otherwise coded to provide ready differentiation for easy identification of the proper indicia (1516, 1518). Still other suitable ways in which varying kinds of indicia may be incorporated into a cannula (1510) will be apparent to those of ordinary skill in the art in view of the teachings herein.

Figure 52:
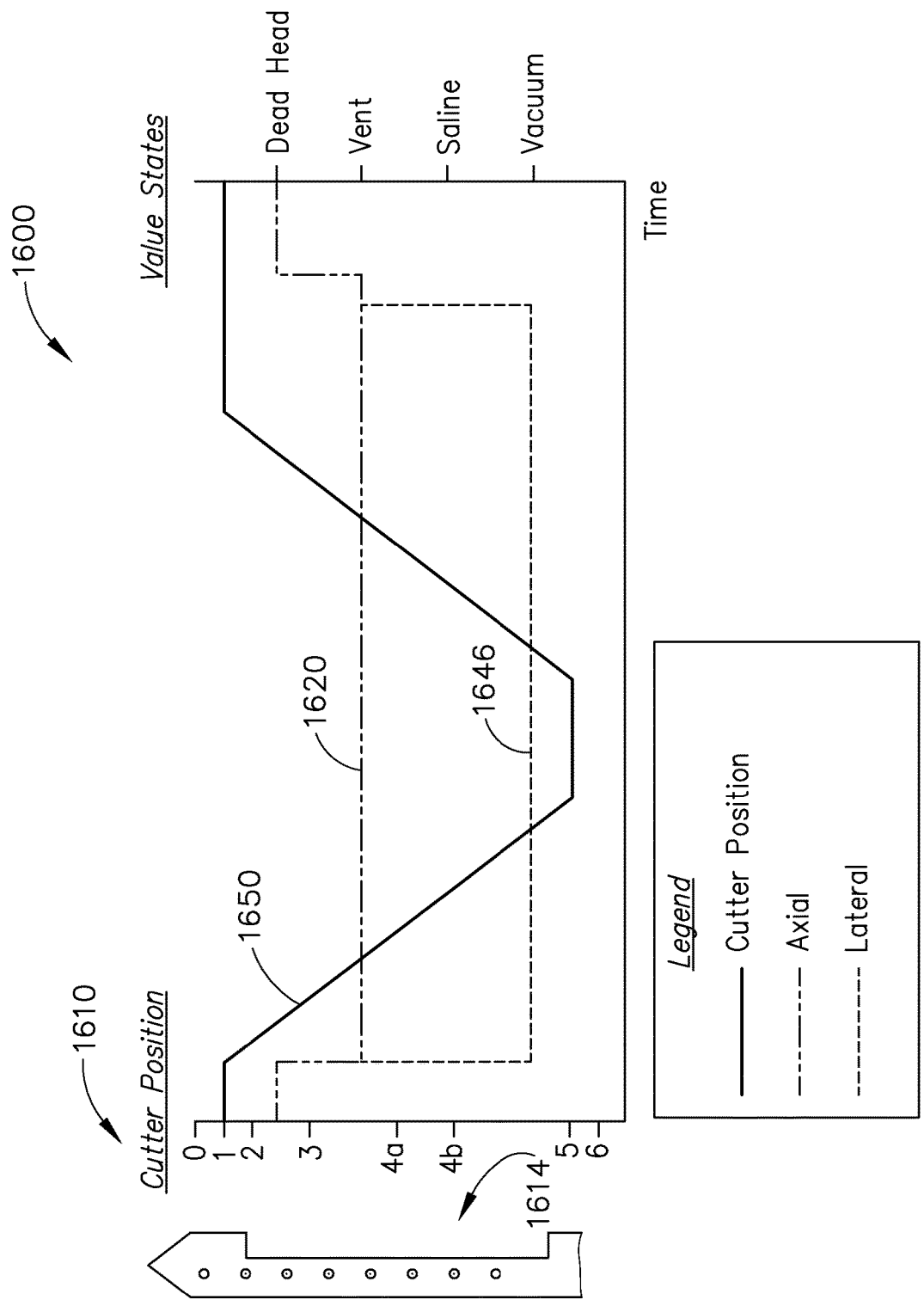
FIG. 52 depicts a graph showing various exemplary pneumatic states within the biopsy system of FIG. 1 during an exemplary marker applier cycle.

FIG. 52 depicts an exemplary pneumatic algorithm (1600) that may be carried out during the deployment of a marker at the biopsy site through device (10) (e.g. using marker applier (1500)). In particular, FIG. 52 shows movements of cutter (150) in relation to needle (110), which is represented by graphical representation (1610) including a graphical representation (1614) of lateral aperture (114). Movement of cutter (150) is shown in line (1650) for a full range of travel for cutter (150). Line (1620) represents pneumatic states of tube (20) during the marker sequence, thereby indicating the pneumatic states of lumen (151) in cutter (150). Line (1646) represents pneumatic states of tube (46) during the marker sequence, thereby indicating the pneumatic states of second lumen (192) of needle (110). The term "dead head" in FIG. 52 is intended to mean that the corresponding tube (20, 46) is sealed relative to atmosphere, and that neither vacuum nor saline is being provided to tube (20, 46) during that stage.

As shown in FIG. 52, both lumens (151, 192) are sealed in the "dead head" state after a tissue sample has been taken. During proximal retraction of cutter (150), vacuum is applied to second lumen (192) of needle (110) through tube (46) and venting is provided to lumen (151) of cutter (150) through tube (20). This lateral vacuum and axial venting continues as cutter (150) dwells at a proximal position with aperture (114) open. Both lumens (151, 192) remain in this state such that a marker may be deployed to the biopsy site through lateral aperture (114) after cutter (150) is retracted. This may help to prevent bodily fluids (e.g., blood, etc.) from entering or becoming trapped in marker applier (1500). After the marker is deployed by marker applier (1500), cutter (150) is advanced distally to reclose lateral aperture (114). At this stage, both lumens (151, 192) are vented to atmosphere to remove residual pressure therein. After venting, lumens (151, 192) are returned to the "dead head" state to seal lumens (151, 192). Both lumens (151, 192) remain in this state until the next biopsy sampling cycle begins.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A tissue sample holder kit, comprising: (a) a rotatable member, wherein the rotatable member includes a plurality of chambers; and (b) a first tissue sample tray including a plurality of tissue receiving features, wherein each tissue receiving feature is configured to removably fit within a corresponding chamber of the plurality of chambers of the rotatable member, wherein each tissue receiving feature is configured to receive a tissue sample.

Example 2

The tissue sample holder kit of any of the preceding or following examples, wherein the chambers comprise passages formed through the rotatable member.

Example 3

The tissue sample holder kit of any of the preceding or following examples, further comprising a second tissue sample tray including a plurality of tissue receiving features, wherein each tissue receiving feature is configured to removably fit within a corresponding chamber of the plurality of chambers of the rotatable member, wherein each tissue receiving feature is configured to receive a tissue sample.

Example 4

The tissue sample holder kit of Example 3, wherein the tissue receiving features of the second tissue sample tray are configured differently relative to the tissue receiving features of the first tissue sample tray.

Example 5

The tissue sample holder kit of Example 4, wherein the tissue receiving features of the first tissue sample tray comprise strips defined by sidewalls, wherein the sidewalls are substantially non-tapered.

Example 6

The tissue sample holder kit of Example 5, wherein the tissue receiving features of the second tissue sample tray comprise strips defined by sidewalls, wherein the sidewalls are substantially tapered.

Example 7

The tissue sample holder kit of any of the preceding or following examples, further comprising a biopsy device, wherein the rotatable member is configured to rotatably couple with the biopsy device.

Example 8

The tissue sample holder kit of Example 7, wherein the biopsy device comprises a needle and a cutter, wherein the tissue receiving features are configured to receive tissue samples severed by the cutter.

Example 9

The tissue sample holder kit of Example 8, wherein the rotatable member is rotatable to successively index the tissue receiving features relative to the cutter.

Example 10

The tissue sample holder kit of Example 8, wherein the cutter comprises a tube.

Example 11

A biopsy device comprising (a) a body; (b) a needle extending distally from the body, wherein the needle includes a tissue receiving feature; (c) a cutter movable relative to the needle, wherein the cutter is operable to sever tissue received in the tissue receiving feature; and (d) a user interface disposed on the body, wherein the user interface includes a plurality of user input features and a plurality of user feedback features.

Example 12

The biopsy device of any of the preceding or following examples, wherein the user input features comprise a plurality of buttons, wherein a first button of the plurality of buttons is operable to move the cutter relative to the needle, wherein a second button of the plurality of buttons is operable to move the needle relative to the body.

Example 13

The biopsy device of Example 12, wherein the first button is operable to trigger a tissue sampling sequence, wherein the tissue sampling sequence comprises movement of the cutter relative to the needle and a corresponding pneumatic algorithm, wherein the pneumatic algorithm includes communication of a vacuum to the cutter and communication of atmospheric air to a lumen of the needle during movement of the cutter.

Example 14

The biopsy device of Example 12, wherein the second button is operable to trigger a needle firing sequence, wherein the needle firing sequence includes motorized retraction of the needle relative to the body.

Example 15

The biopsy device of Example 14, wherein the needle firing sequence includes spring-biased distal firing of the needle relative to the body.

Example 16

The biopsy device of Example 14, wherein the needle firing sequence includes motorized distal advancement of the needle relative to the body.

Example 17

The biopsy device of Example 12, wherein a third button of the plurality of buttons is operable to communicate a vacuum to the needle and move the cutter relative to the needle without capturing a tissue sample.

Example 18

The biopsy device of Example 17, wherein the third button is configured to initiate a probe clearing sequence in response to a rapid press and release of the third button.

Example 19

The biopsy device of Example 18, wherein the third button is configured to initiate a partial retraction of the cutter relative to the needle in combination with a vacuum to the cutter in response to a sustained press on the third button.

Example 20

The biopsy device of Example 12, wherein a third button of the plurality of buttons is operable to move the cutter relative to the needle without providing a vacuum to the cutter or to the needle.

Example 21

The biopsy device of any of the preceding or following examples, wherein the user feedback features include a plurality of light sources associated with the user input features, wherein each light source is configured to remain illuminated to indicate availability of a control algorithm associated with the corresponding user input feature, wherein each light source is configured to flash during performance of the control algorithm associated with the corresponding user input feature.

Example 22

The biopsy device of any of the preceding or following examples, wherein the user feedback features include a graphical representation of the needle and a graphical representation of the cutter, wherein the graphical representation of the cutter is configured to move relative to the graphical representation of the needle in response to actual movement of the cutter relative to the needle.

Example 23

A controller for a biopsy device, wherein the biopsy device includes a tissue sample holder defining a plurality of tissue sample chambers, wherein the controller comprises: (a) a user interface including a graphical representation of the tissue sample holder, wherein the graphical representation of the tissue sample holder includes graphical representations of the tissue sample chambers; and (b) at least one user input operable to control one or more features of the biopsy device.

Example 24

The controller of any of the preceding or following examples, wherein the user interface is further configured to discretely illuminate each of the graphical representations of the tissue sample chambers to represent receipt of a tissue sample in the corresponding tissue sample chambers.

Example 25

The controller of any of the preceding or following examples, wherein the tissue sample holder is rotatable to successively capture tissue samples in the tissue sample chambers.

Example 26

The controller of Example 25, wherein the controller is operable to execute a control algorithm that comprises rotating the tissue sample holder to a position a first tissue sample chamber at a presentation position upon receipt of a first tissue sample in the first tissue sample chamber, then subsequently rotating the tissue sample holder to position a second tissue sample chamber for receipt of a second tissue sample.

Example 27

The controller of Example 26, wherein the at least one user input comprises an input operable to define the presentation position.

Example 28

The controller of Example 27, wherein the presentation position is selectable from a 12 o'clock position, a 3 o'clock position, a 6 o'clock position, and a 9 o'clock position.

Example 29

The controller of any of the preceding or following examples, wherein the at least one user input comprises an input operable to rotate the tissue sample holder in single chamber increments, to skip tissue sample chambers for receipt of tissue samples.

Example 30

The controller of any of the preceding or following examples, wherein the user interface is further configured to discretely illuminate each of the graphical representations of the tissue sample chambers to represent skipped tissue sample chambers.

Example 31

The controller of Example 30, wherein the user interface is further configured to discretely illuminate each of the graphical representations of the tissue sample chambers in a first color to represent skipped tissue sample chambers, and wherein the user interface is further configured to discretely illuminate each of the graphical representations of the tissue sample chambers in a second color to represent receipt of a tissue sample in the corresponding tissue sample chambers.

Example 32

The controller of any of the preceding or following examples, wherein the at least one user input comprises an input operable to return the tissue sample holder to a home position.

Example 33

A method of initializing a biopsy system, the method comprising: (a) performing an initialization process for needle arming features; (b) performing an initialization process for cutter actuation features; (c) performing an initialization process for tissue sample holder actuation features; (d) performing an initialization process for vacuum control features; and (e) priming a saline line.

Example 34

The method of any of the preceding or following examples, wherein the act of performing an initialization process for needle arming features comprises: (i) activating a motor until a needle translation feature reaches a hardstop position, (ii) determining whether a current limit associated with the motor has been exceeded en route to the hardstop position, and (iii) determining whether a maximum distance has been exceeded en route to the hardstop position.

Example 35

The method of Example 34, wherein the act of performing an initialization process for needle arming features further comprises: (i) activating the motor to move the needle translation feature from the hardstop position toward an initialized position, (ii) determining whether the motor stalls en route to the initialized position, (iii) determining whether a current limit associated with the motor has been exceeded en route to the initialized position, and (iii) stopping the needle translation feature at the initialized position.

Example 36

The method of any of the preceding or following examples, wherein the act of performing an initialization process for cutter actuation features comprises: (i) activating a motor until a cutter reaches a hardstop position, (ii) determining whether a maximum distance has been exceeded en route to the hardstop position, and (iii) determining whether a current limit associated with the motor has been exceeded en route to the hardstop position.

Example 37

The method of Example 36, wherein the act of performing an initialization process for cutter actuation features further comprises: (i) activating the motor to move the cutter from the hardstop position to an open position, (ii) determining whether the motor stalls en route to the open position, (iii) determining whether a current limit associated with the motor has been exceeded en route to the open position.

Example 38

The method of Example 37, wherein the act of performing an initialization process for cutter actuation features further comprises: (i) activating the motor to move the cutter from the open position to a closed position, (ii) determining whether the motor stalls en route to the closed position, (iii) determining whether a current limit associated with the motor has been exceeded en route to the closed position, and (iv) stopping the cutter at the closed position.

Example 39

The method of any of the preceding or following examples, wherein the act of performing an initialization process for tissue sample holder actuation features comprises: (i) storing an initial rotational position of a rotatable feature of a tissue sample holder, (ii) activating a motor to rotate the rotatable feature, (iii) determining whether motor stalls during rotation of the rotatable feature, (iv) determining whether the rotatable feature has completed three full revolutions during rotation of the rotatable feature, (v) determining whether a current limit associated with the motor has been exceeded during rotation of the rotatable feature, and (vi) detecting an index pulse associated with the rotatable feature.

Example 40

The method of Example 39, wherein the act of performing an initialization process for tissue sample holder actuation features comprises: (i) storing an offset position associated with the rotatable feature, (ii) continue rotating the rotatable member until the rotatable member reaches a slot closest to the initial position, based at least on the stored offset position, an index position, and the stored initial position.

Example 41

The method of any of the preceding or following examples, wherein the act of performing an initialization process for vacuum control features comprises: (i) activating a vacuum pump, (ii) measuring a series of vacuum levels, (iii) calculating a maximum vacuum value based on the measured values, and (iv) determining whether the maximum vacuum value is within a predetermined range.

Example 42

The method of any of the preceding or following examples, wherein the act of priming a saline line comprises: (i) providing saline to a first lumen while providing vacuum to a second lumen, (ii) venting the first and second lumens to atmosphere, and (iii) sealing the first and second lumens.

Example 43

A method of operating a biopsy device to acquire a tissue sample, wherein the biopsy device comprises a cutter and a needle, wherein the cutter defines a first lumen, wherein the needle defines a second lumen adjacent to the cutter, wherein the cutter is translatable relative to the needle, wherein the method comprises: (a) retracting the cutter proximally to a retracted position; (b) advancing the cutter from the retracted position to a distal position; (c) communicating vacuum to the first lumen during the act of retracting the cutter; (d) communicating vacuum to the second lumen during the act of retracting the cutter; (e) communicating vacuum to the first lumen during the act of advancing the cutter; (f) communicating vacuum to the second lumen for a first period of time during the act of advancing the cutter; and (g) communicating one or both of saline or atmospheric air to the second lumen for a second period of time during the act of advancing the cutter.

Example 44

The method of any of the preceding or following examples, further comprising transitioning from vacuum to atmospheric air to the second lumen upon transition from the first period of time to the second period of time.

Example 45

The method of any of the preceding or following examples, further comprising pulsing atmospheric air to the second lumen during the second period of time.

Example 46

The method of Example 45, further comprising pulsing saline to the second lumen during the second period of time.

Example 47

The method of Example 46, wherein the pulses of saline are provided between the pulses of atmospheric air.

Example 48

The method of any of the preceding or following examples, further comprising communicating vacuum to the first lumen for a third period of time after the cutter reaches the distal position.

Example 49

The method of Example 48, further comprising communicating atmospheric air to the first lumen for a fourth period of time after the cutter reaches the distal position.

Example 50

The method of Example 49, further comprising sealing the first lumen after expiry of the fourth period of time.

Example 51

The method of Example 49, further comprising communicating saline then atmospheric air to the second lumen during the third period of time.

Example 52

The method of Example 51, further comprising sealing the second lumen during the fourth period of time and after expiry of the fourth period of time.

Example 53

An apparatus, comprising a biopsy site marker applier, wherein the biopsy site marker applier comprises: (i) a cannula defining a marker deployment opening, (ii) at least one marker disposed in the cannula, and (iii) a pushrod operable to deploy the at least one marker through the marker deployment opening, wherein the cannula includes a first marking associated with insertion of the cannula in a biopsy device having a first configuration, wherein the cannula further includes a second marking associated with insertion of the cannula in a biopsy device having a second configuration.

Example 54

The apparatus of any of the preceding or following examples, wherein cannula has a closed distal end, wherein the marker deployment opening comprises a lateral aperture located proximal to the closed distal end.

Example 55

The apparatus of Example 54, wherein the first and second indicia are configured to position the lateral aperture of the cannula to a location adjacent to a corresponding lateral aperture of a biopsy device.

Example 56

The apparatus of any of the preceding or following examples, further comprising a biopsy device configured to receive the cannula.

Example 57

The apparatus of Example 56, wherein the biopsy device comprises a removable component, wherein the removable component includes a passage configured to receive the cannula.

Example 58

The apparatus of Example 57, wherein the removable component is configured to place the biopsy device in the first configuration when the removable component is coupled with the biopsy device; wherein the removable component is configured to place the biopsy device in the second configuration when the removable component is removed from the biopsy device.

Example 59

The apparatus of Example 57, wherein cannula has a closed distal end, wherein the marker deployment opening comprises a lateral aperture located proximal to the closed distal end, wherein the first and second indicia are configured to position the lateral aperture of the cannula to a location adjacent to a corresponding lateral aperture of a biopsy device, wherein the removable component is configured to increase the effective distance to the lateral aperture of the biopsy device.

Example 60

The apparatus of Example 57, wherein the removable component comprises a tissue sample holder.

Example 61

The apparatus of any of the preceding or following examples, wherein the cannula further includes a grip at the proximal end of the cannula, wherein the first indicia is proximate to the grip, wherein the second indicia is distal to the first indicia.

Example 62

The apparatus of any of the preceding or following examples, wherein the first and second indicia are color coded.

Example 63

A user interface for a biopsy device, wherein the biopsy device includes a tissue sample holder defining a plurality of tissue sample chambers, wherein the tissue sample holder is configured to rotate relative to the biopsy device, wherein the user interface comprises a graphical representation of the tissue sample holder, wherein the graphical representation of the tissue sample holder includes graphical representations of the tissue sample chambers, wherein the graphical representation of the tissue sample holder is configured to rotate to indicate the corresponding rotation of the tissue sample holder.

Example 64

The user interface of any of the preceding or following examples, wherein the biopsy device comprises a cutter having a cutter lumen, wherein the graphical representation of the tissue sample holder comprises a highlighted portion to indicate the corresponding position of the cutter lumen relative to the tissue sample chambers of the tissue sample holder.

Example 65

The user interface of the any of the preceding or following examples, wherein the graphical representations of the tissue sample chambers are configured to be filled with a first color to indicate that the corresponding tissue sample chamber is empty.

Example 66

The user interface of Example 65, wherein the biopsy device is operable to deposit a tissue sample within a tissue sample holder, wherein the graphical representations of the tissue sample chambers are configured to be filled with a second color to indicate that the biopsy device attempted to deposit a tissue sample in the corresponding tissue sample chamber.

Example 67

The user interface of any of the preceding or following examples, wherein the biopsy device is operable to collect a tissue sample, wherein the graphical representation of the tissue sample holder comprises a counter operable to indicate the number of tissue samples that the biopsy device attempts to collect.

Example 68

The user interface of Example 67, wherein the counter is positioned within a central portion of the graphical representation of the tissue sample holder.

Example 69

The user interface of Example 67, wherein the counter is configured to be displayed in a first color while the biopsy device attempts to collect a tissue sample.

Example 70

The user interface of Example 69, wherein the counter is configured to be displayed in a second color after the biopsy device attempts to collect a tissue sample.

Example 71

The user interface of any of the preceding or following examples, wherein the graphical representation of the tissue sample holder is configured to be reset.

Example 72

A method of operating a biopsy device to deploy a marker, wherein the biopsy device comprises a needle and a cutter, wherein the cutter defines a first lumen, wherein the needle defines a second lumen adjacent to the cutter, wherein the needle comprises a lateral aperture, wherein the cutter is translatable relative to the needle, wherein the method comprises the steps of: (a) retracting the cutter proximally to a retracted position such that the cutter is proximal to the lateral aperture of the needle; (b) communicating atmospheric air to the first lumen; (c) communicating vacuum to the second lumen; and (d) deploying a marker through the lateral aperture of the needle.

VIII. Conclusion

Additional features and functionalities that may be readily incorporated with the examples described above are shown in the Appendix attached hereto. Various suitable ways in which the teachings herein may be combined with the teachings in the Appendix will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy system, comprising:
   (a) a biopsy device, the biopsy device including:
      (i) a needle, and
      (ii) a cutter movable relative to the needle to sever a plurality of tissue samples,
   (b) a tissue sample holder including a plurality of chambers, the tissue sample holder being in fluid communication with the cutter of the biopsy device;
   (c) a control unit; and
   (d) a remote unit separate from the biopsy device, the remote unit including a visual indicator under control of the control unit, the visual indicator including at least one biopsy device status region, the visual indicator being adapted to convey to a user status information of the biopsy device by activating at least a portion of the at least one biopsy status region under control of the control unit, the at least one biopsy device status region including a tissue chamber occupancy indicator, the tissue chamber occupancy indicator including a visual representation of each chamber of the plurality of chambers of the tissue sample holder, the control unit being configured to drive the tissue chamber occupancy indicator to indicate which chambers of the plurality of chambers are occupied by severed tissue samples through the visual representation of each chamber of the plurality of chambers by changing illumination of each visual representation of each chamber of the plurality of chambers in response to receipt of a tissue sample in a corresponding chamber, the control unit being further operable to drive the tissue chamber occupancy indicator to indicate movement of the tissue sample holder by further changing illumination of each visual representation of each chamber of the plurality of chambers.

2. The biopsy system of claim 1, the tissue sample holder being operable to index each chamber of the plurality of chambers with the cutter for receiving the severed tissue samples.

3. The biopsy system of claim 2, the visual indicator being operable to activate a particular visual representation in response to signals received from the control unit indicating reception of the severed tissue samples into a corresponding chamber of the plurality of chambers of the tissue sample holder.

4. The biopsy system of claim 2, the visual indicator being operable to selectively adjust the correspondence between each visual representation of each chamber of the plurality of chambers and the plurality of chambers of the tissue sample holder to provide a graphical indication of movement of the tissue sample holder.

5. The biopsy system of claim 4, the graphical indication of movement of the tissue sample holder being configured to correspond to indexing of the plurality of chambers of the tissue sample holder with the cutter.

6. The biopsy system of claim 1, the visual indicator including a cutter position indicator, the cutter position indicator including a graphical representation of at least a portion of the needle.

7. The biopsy system of claim 1, the visual indicator including a cutter position indicator, the cutter position indicator including a graphical representation of at least a portion of the needle, the cutter position indicator being configured to visually depict the position of the cutter relative to the needle in response to signals received from the control unit.

8. The biopsy system of claim 1, the biopsy device further including a processing module, the visual indicator further including a cutter position indicator, the remote unit being configured to adjust the tissue chamber occupancy indicator when at least one tissue sample of the plurality of tissue samples is received within the tissue sample holder, the remote unit being further operable to adjust the cutter position indicator based on cutter position information received from the processing module to thereby convey the cutter position information to a user.

9. The biopsy system of claim 8, the visual indicator further including a vacuum status indicator, the vacuum status indicator being configured to visually indicate a level of vacuum to the user.

10. The biopsy system of claim 1, the visual indicator further including a vacuum status indicator and a cutter position indicator, the remote unit being configured to adjust the vacuum status indicator to convey a vacuum level to the user by activating at least a portion of the vacuum status indicator, the remote unit being further operable to adjust the cutter position indicator based on cutter position information received from the biopsy device to convey the cutter position information to the user by activating at least a portion of the cutter position indicator.

11. A biopsy system, comprising:
   (a) a needle;
   (b) a cutter movable relative to the needle to sever a tissue sample;

(c) a tissue sample holder in communication with the cutter, the tissue sample holder including a plurality of chambers configured to receive tissue samples captured by the cutter;
(d) a processing module; and
(e) a graphical user interface in communication with the processing module, the graphical user interface being configured to display a first indicator and a second indicator, the first indicator including a plurality of visual representations corresponding to each chamber of the plurality of chambers of the tissue sample holder, the processing module being configured to adjust illumination of each visual representation of the plurality of visual representations in response to receipt of the tissue sample in the tissue sample holder to visually indicate movement of each chamber of the plurality of chambers and occupancy of each chamber of the plurality of chambers with the tissue sample, the processing module being further configured to adjust the second indicator to provide information related to the cutter position relative to the needle to a user.

12. The biopsy system of claim 11, the tissue sample holder being configured to selectively index each chamber of the plurality of chambers with the cutter.

13. The biopsy system of claim 12, the processing module being configured to selectively alter a correspondence between the plurality of visual representations and the plurality of chambers of the tissue sample holder to convey movement of the tissue sample holder to the user.

14. A biopsy system, comprising:
(a) a needle;
(b) a cutter movable relative to the needle to sever a plurality of tissue samples;
(c) a tissue sample holder in communication with the cutter, the tissue sample holder including a plurality of chambers configured to receive the plurality of tissue samples severed by the cutter;
(d) a controller; and
(e) a graphical user interface in communication with the controller, the graphical user interface being configured to display a first indicator, a second indicator, and a third indicator, the controller being configured to adjust the first indicator to visually indicate a level of vacuum to a user, the controller being further configured to adjust the second indicator to visually indicate a cutter position relative to the needle to the user, the third indicator having a plurality of chamber representations, the plurality of chamber representations being configured to depict both occupancy of the plurality of chambers of the tissue sample holder with the plurality of tissue samples and movement of each chamber of the plurality of chambers relative to a reference point.

15. The biopsy system of claim 14, the tissue sample holder being configured to selectively index each chamber of the plurality of chambers with the cutter.

16. The biopsy system of claim 15, the controller being configured to activate one or more of the chamber representations to indicate which chambers are occupied by the plurality of tissue samples.

* * * * *